(12) United States Patent
Glucksmann et al.

(10) Patent No.: US 6,979,564 B2
(45) Date of Patent: Dec. 27, 2005

(54) 80090, HUMAN FUCOSYLTRANSFERASE NUCLEIC ACID MOLECULES AND USES THEREOF

(75) Inventors: Maria A. Glucksmann, Lexington, MA (US); Rachel Meyers, Newton, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 453 days.

(21) Appl. No.: 10/080,960

(22) Filed: Oct. 19, 2001

(65) Prior Publication Data

US 2002/0197695 A1 Dec. 26, 2002

Related U.S. Application Data

(60) Provisional application No. 60/242,040, filed on Oct. 20, 2000, provisional application No. 60/242,038, filed on Oct. 20, 2000, provisional application No. 60/241,992, filed on Oct. 20, 2000, and provisional application No. 60/242,637, filed on Oct. 23, 2000.

(51) Int. Cl.[7] .......................... C12N 9/10; C12N 1/20; C12N 15/00; C07H 21/04
(52) U.S. Cl. .................. 435/193; 435/69.1; 435/252.3; 435/320.1; 536/23.1; 536/23.2; 530/350
(58) Field of Search .............................. 435/193, 69.1, 435/252.3, 320.1; 536/23.1, 23.2; 530/350

(56) References Cited

U.S. PATENT DOCUMENTS

2002/0102604 A1 * 8/2002 Edwards et al. ............. 435/7.1
2003/0165831 A1    9/2003 Lee et al. ..................... 435/6

FOREIGN PATENT DOCUMENTS

| EP | 1 394 274 A2 | 3/2004 |
|---|---|---|
| WO | WO/0142451 | 6/2001 |
| WO | WO 03/029271 A2 | 4/2003 |

OTHER PUBLICATIONS

Seffernick et al. [J. Bacteriol. Apr. 2001, p. 2405–2410].*
Kelly, R. J., et al., "Sequence and Expression of a Candidate for the Human Secretor Blood Group α(1,2) Fucosyltransferase Gene (FUT2)", The Journal of Biological Chemistry 270(9):4640–4649 (1995).
Roos, C., et al., "Composition of Drosophila Melanogaster Proteome Involved in Fucosylated Glycan Metabolism", The Journal of Biological Chemistry 277(5):3168–3175 (2002).
Strausberg, R. L., et al., "*Homo sapiens* Fucosyltransferase 10 (alpha (1,3) fucosyltransferase), mRNA (cDNA clone MGC :74714 IMAGE: 5198060), complete cds.", Dec. 23, 2003 (sequence) GenBank [online] Bethesda, MD, USA: National Center for Biotechnology Information GenBank Accession No. BC063462.
Martinez–Duncker, I. et al., "*Homo sapiens* mRNA for alpha3–fucosyltransferase (FUT10 gene)", Sep. 4, 2003 (sequence) GenBank [online] Bethesda, MD, USA: National Center for Biotechnology Information GenBank Accession No. AJ582015.
Roos, C. et al.., "*Homo sapiens* Partial mRNA for Putative alpha 1,3–fucosyltransferase (FUT10 gene)", Feb. 26, 2002 (sequene) GenBank [online] Bethesda, MD, USA: National Center for Biotechnology Information GenBank Accession No. AJ431184.
Candelier, J. J., et al., "*Homo sapiens* mRNA for Putative alpha 1,3–fucosyltransferase (FUT10 gene)", Jan. 2, 2003 (sequence) GenBank [online] Bethesda, MD, USA: National Center for Biotechnology Information GenBank Accession No. AJ512465.
Candelier, J. J., et al., "*Homo sapiens* mRNA for Putative alpha3–fucosyltransferase (FUT10 gene)", Feb. 1, 2003 (sequence) GenBank [online] Bethesda, MD, USA: National Center for Biotechnology Information [retrieved on Jul. 19, 2004]. GenBank Accession No. AJ35838.
Candelier, J. J., et al., "*Homo sapiens* mRNA for Putative alpha3–fucosyltransferase (FUT10 gene), inactive short splice variant.", Feb. 1, 2003 (sequence) GenBank [online] Bethesda, MD, USA: National Center for Biotechnology Information GenBank Accession No. AJ535839.
Strausberg, R. L., et al., "FUT10 protein [*Homo sapiens*]", Dec. 23, 2003 (sequence) GenBank [online] Bethesda, MD, USA: National Center for Biotechnology Information GenBank Accession No. AAH63462.
Martinez–Duncker, I. et al., "alpha3–fucosyltransferase [*Homo sapiens*].", Sep. 4, 2003 (sequence) GenBank [online] Bethesda, MD, USA: National Center for Biotechnology Information GenBank Accession No. CAE46499.
Roos, C., et al., "Putative alpha 1,3–fucosyl transferase [*Homo sapiens*]", Feb. 26, 2002 (sequence) GenBank [online] Bethesda, MD, USA: National Center for Biotechnology Information GenBank Accession No. CAD24023.
Candelier, J. J., et al., "Putative alpha 1,3–fucosyltransferase [*Homo sapiens*]", Jan. 2, 2003 (sequence) GenBank [online] Bethesda, MD, USA: National Center for Biotechnology Information GenBank Accession No. CAD54669.

(Continued)

Primary Examiner—Tekchand Saidha
(74) Attorney, Agent, or Firm—Millennium Pharmaceuticals, Inc.

(57) ABSTRACT

The invention provides isolated nucleic acids molecules, designated 80090, 52874, 52880, 63497, or 33425 nucleic acid molecules, which encode novel fucosyltransferase, seven transmembrane receptor, or RhoGAP family members. The invention also provides antisense nucleic acid molecules, recombinant expression vectors containing 80090, 52874, 52880, 63497, or 33425 nucleic acid molecules, host cells into which the expression vectors have been introduced, and nonhuman transgenic animals in which an 80090, 52874, 52880, 63497, or 33425 gene has been introduced or disrupted. The invention still further provides isolated 80090, 52874, 52880, 63497, or 33425 proteins, fusion proteins, antigenic peptides and anti-80090, 52874, 52880, 63497, or 33425 antibodies. Diagnostic methods utilizing compositions of the invention are also provided.

12 Claims, 24 Drawing Sheets

OTHER PUBLICATIONS

Candelier, J. J., et al., "Putative alpha3–fucosyltransferase [*Homo sapiens*]", Feb. 1, 2003 (sequence) GenBank [online] Bethesda, MS, USA: National Center for Biotechnology Information GenBank Accession No. CAD59771.

Candelier, J. J., et al., "Putatuve alpha3–fucosyltransferase [*Homo sapiens*]" Feb. 1, 2003 (sequence) GenBank [online] Bethesda, MD, USA: National Center for Biotechnology Information GenBank Accession No. CAD59772.

Database EMBL 'Online! Nov. 11, 1999 Clark, et al.: "fe01b09.y1 Zebrafish WashU MPIMG EST Danio rerio cDNA clone Image: 3737561' similar to SW:FUT6_Human P51993 Alpha–(1,3)–Fucosyltransferase; mRNA sequence" Database Accession No. AW165373 XP002225370 Abstract.

Database EMBL 'Online! Sep. 28, 1998 Strausberg: "qa37a06.x1 Soares_NhHMPu_S1 *Homo sapiens* cDNA clone IMAGE:1688914 3', mRNA sequence" Retrieved from EBI Database Accession No. AI140437 XP002225371 Abstract.

Database EMBL 'Online! Apr. 28, 2000 Birren, et al. "Homo sapiens chromosome 8, clone RP11–722E23" retrieved from EBI Database Accession No. AC067638. XP002225372 Abstract.

Database EMBL 'Online! Jun. 14, 2001 Dumas, et al.: "Human secreted protein cDNA, SEQ ID NO:43" retrieved form EBI Database Accession No. AAH64764 XP002225373 Abstract.

Baboval et al. "Molecular Cloning of Rat Alpha 1, 3–Fucosyltransferase IX (Fuc–TIX) and Comparison of the Expression of Fuc–TIV and Fuc–TIXGenes During Rat Postnatal Cerebellum Development" [Abstract]at <http://www.ncbi.nim.nih.gov> (visited on Oct. 18, 2000).

Barrett et al. "The Structure of the GTPase–Activating Domain from p50rhoGAP" Nature 385:458–461 (1997).

Boguski et al. "Proteins Regulating Ras and Its Relatives" Nature 366:643–654 (1993).

Lopez–Ferrer et al. "Role of Fucosyltransferases in the Association Between Apomucin and Lewis Antigen Expression in Normal and Malignant Gastric Epithelium" [Abstract] at <http://www.ncbi.nlm.ni.gov> (visited on Oct. 18, 2000).

Musacchio et al. "Crystal Structure of the Breakpoint Cluster Region–Homology Domain from Phosphoinositide 3–Kinase p85 α Subunit" Proc. Natl. Acad. Sci. USA 93:14373–14378 (1996).

Rittinger et al. "Crystal Structure of a Small G Protein in Complex with the GTPase–Activating Protein rhoGAP" Nature 388:693–697 (1997).

Blast search for 33425 in dbEST database.
Blast search for 33425 in FastAlert_N.txt database.
Blast search for 33425 in FastAlert_P.txt database.
Blast search for 33425 in nuc database.
Blast search for 33425 in PATENT_2/gsnuc database.
Blast search for 33425 in protot database.
Blast search for 33425 in PATENT_2/gsprot database.
Blast search for 52874aa in FastAlert_P.txt database.
Blast search for 52874aa in protot database.
Blast search for 52874aa in PATENT_2/gsprot database.
Blast search for 52874nc in FastAlert_N.txt database.
Blast search for 52874nc in nuc database.
Blast search for 52880 in FastAlert_N.txt database.
Blast search for 52880 in MGP_human_gb.fasta database.
Blast search for 52880 in gsnuc database.
Blast search for 52880 in nuc database.
Blast search for 52880 in FastAlert_P.txt database.
Blast search for 52880 in protot database.
Blast search for 52880 in gsprot database.
Blast search for 52880 in PatentDbPreviewNuc database.
Blast search for 63497 in FastAlert_P.txt database.
Blast search for 63497 in nuc database.
Blast search for 63497 in FastAlert_N.txt database.
Blast search for 63497 in MGP_human_gb.fasta database.
Blast search for 63497 in gsnuc database.
Blast search for 63497 in protot database.
Blast search for 63497 in gsprot database.
Blast search for 63497 in PatentDbPreviewNuc database.
Blast search for 80090aa in FastAlert_P.txt database.
Blast search for 80090aa in protot database.
Blast search for 80090aa in PATENT_2/gsprot database.
Blast search for 80090nc in FastAlert_N.txt database.
Blast search for 80090nc in nuc database.
Blast search for 80090nc in PATENT_2/PatentDbPreviewNuc database.

* cited by examiner

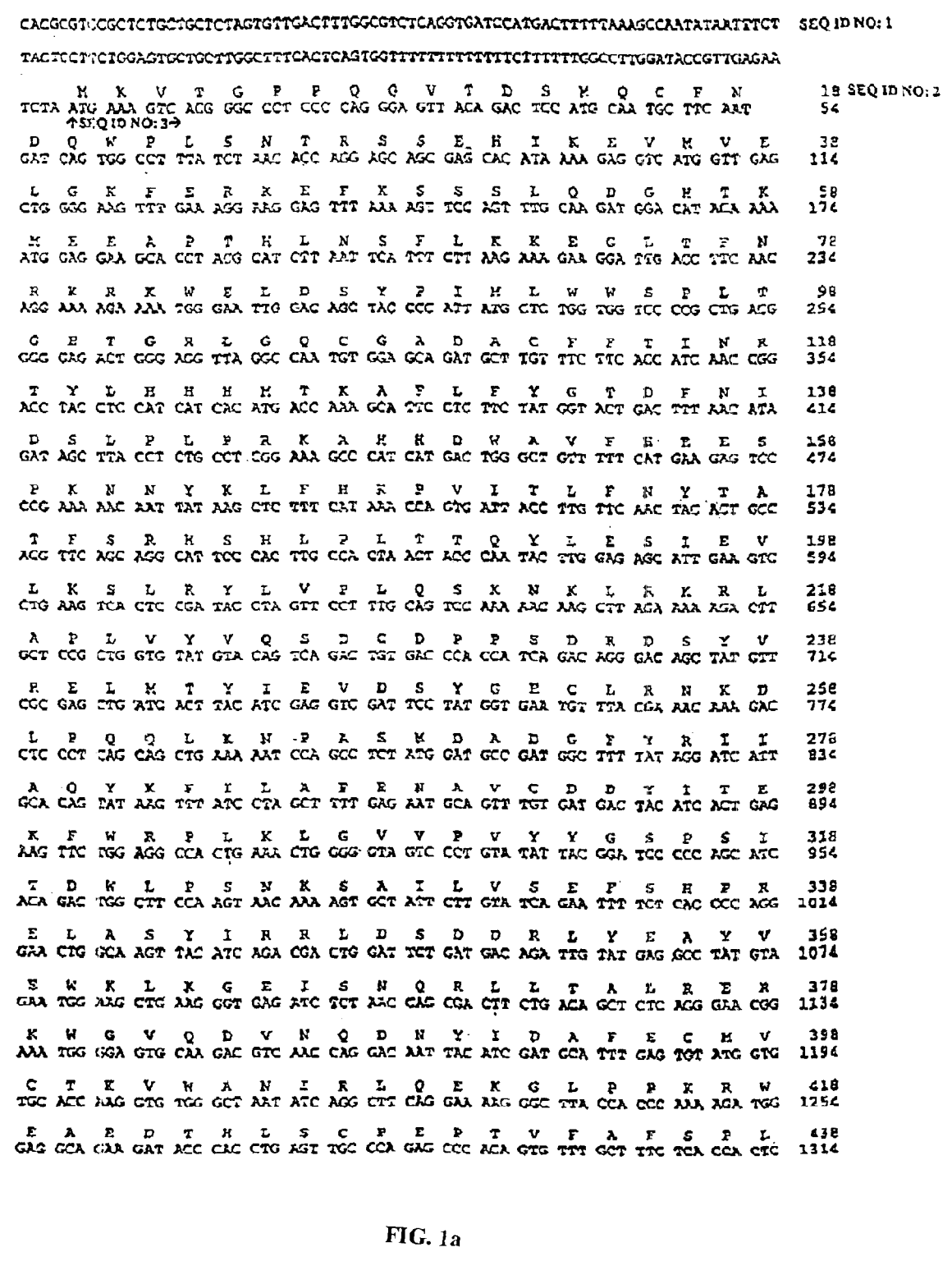

```
CACGCGTCCGCTCTGCTGCTCTAGTGTTGACTTTGGCGTCTCAGGTGATCCATGACTTTTTAAAGCCAATATAATTTCT  SEQ ID NO:1
TACTCCTTCTGGAGTGCTGCTTGGCTTTCACTCAGTGGTTTTTTTTTTTTCTTTTTTGGCCTTGGATACCGTTGAGAA
```

|  |  |  | M | K | V | T | G | P | P | Q | G | V | T | D | S | M | Q | C | F | N |  | 18 SEQ ID NO:2 |
|---|---|---|---|---|---|---|---|---|---|---|---|---|---|---|---|---|---|---|---|---|---|---|
|  |  | TCTA | ATG | AAA | GTC | ACG | GGC | CCT | CCC | CAG | GGA | GTT | ACA | GAC | TCC | ATG | CAA | TGC | TTC | AAT |  | 54 |
|  |  | ↑SEQ ID NO:3→ |

(Figure 1a — nucleotide and amino acid sequence listing; remaining codon/residue rows follow the same format through position 438 / 1314.)

FIG. 1a

```
    R   T   P   P   L   S   S   L   R   E   M   W   I   S   S   F   E   Q   S   K    458
   CGG ACT CCA CCT TTG AGC TCT TTG CGA GAG ATG TGG ATT TCC AGC TTT GAA CAA TCC AAG   1376

K   E   A   Q   A   L   R   W   L   V   D   R   N   Q   N   F   S   S   Q   E    478
   AAA GAA GCC CAG GCA CTA AGG TGG CTG GTT GAT AGG AAT CAA AAC TTT TCA TCT CAA GAG   1434

F   W   G   L   V   F   K   D   *                                                 487
   TTT TGG GGC CTA GTA TTC AAG GAC TGA                                                1461
                         ←SEQ ID NO:3↑
   TTTCAAAAATGATCAGAATGAAACAGAAAAAAAAAAAAAAAAAAAA
```

FIG. 1b

```
               *->lsdaflrllwrekllGllitvppLllaiaawigleeikewkksplyL    SEQ ID NO:16
                + +  +++ ++e     + +++            +g     e + +l
80090    35    VMVELGKFERKEF-KSSSLQ----          --DGHTKMEEAP-THLN-  67

SNDHELdVpiLlilSqapqGSrfptleenrillwtwpFndrgaPvppsrc
                + L ++ +-     r   l  +i lw+ p + q++   +  c
80090    68    --------SFLKKEGLTFNRKRKWELDSYPIMLWWSPLT--GETGRLGQC  107 slsydntarcrltanRsel..esAdavlFNAGHhrDlskgppmdlppeft
                + + c+ t nR  l++    a lF    'D  +  + +l
80090   108    -----GADACFFTINRTYLhhHMTKAFLF--YGTDFNIDSL-PL------  143 cvrarAedaDavllayednaaaaeaLatdfpRppgQpwVwaSmESPsnsg
                                                pR+    w  ++ ESP n
80090   144    -------------------------PRKAHHDWAVFHEESPKNN-     162

RFAVPGFKlNVLNqlqilldgyfNwtlSyradsDafhpYGylepltakar
                +  ++   +fN t ++ + s            ylc
80090   163    -----------YKLFHKPVITLFNYT

```
Query:   89  PI-MLWWS-PLTGETGRLGQCGADACFFTINRTYLHHHMTKAFLPYGTDFNIDSLPLPRK 146
             P+ ++WWS  ++      QCG  C T R+          + LFYG++      PLPR
Sbjct:   40  PVELVWWSRDMSWNYDVQRQCGIHTCRITNKRS--RRPWARGVLFYGSNIKTGDFPLPRN 97  SEQ ID NO:17

Query:  147  AHHDWAVPHEESPKNNYKLPHKPVITLFNYTATFSRHSHLPLTTQYLESIEVLKSLRYLV 206
             H  WA+ HEESP+N  + +K +  P++T+TFSR+S+LPLTT YL SELS  Y V
Sbjct:   98  EHQIWALLHEESPRNTPFVSNKEFLRHFHFTSFSRYSNLPLTTMYLPSGEALTSKDYYV 157

Query:  207  PLQSKNKLRKRLAP-LVYVQSDCDPPSDRDSYVRELMTYIEVDSYGECLRNKDLPQQLKN 265
              K+K   R +    +V++QSDCD  S R+ YV+ELM ++ +DSYG CLRN+DLP++ K+
Sbjct:  158  TFDGKSKYGYRPSTSVVFLQSDCDTMSGREDYVKELMKHLPIDSYGSCLRNRDLPERQKD 217
```

FIG. 4

```
Query:  221  LVYVQSDCDPPSDRDSYVRELMTYIEVDSYGECLRNKDLPQQLKNPASMDADGFYRIIAQ 280
             +  +V S+ +P  S R  Y ++L +++VD YG  R K LPQ                +++
Sbjct:   62  VAWVVSNWNPNSARVRYYQQLQKHLKVDVYGRSHRGKPLPQ---------GNMMETLSR 111  SEQ ID
                                                                            NO:18

Query:  281  YKFILAFENAVCDDYITEKFWR-PLKLGVVPVYYGSPSITDW---LPSNKSAILVSEFSH 336
             YKF LAFEN++   DYITEK WR L+ G VPV  G PS  ++    +P + + I V +F
Sbjct:  112  YKFYLAFENSMHPDYITEKLWRNALEAGAVPVVLG-PSRVNYERFIPPD-AFIHVDDFQS 169

Query:  337  PRELASYIRRLDSDDRLYEAYVEWKLKGEIS 367
             P+ELA Y++ LD +   Y Y+ WK + ++
Sbjct:  170  PKELAKYLKELDKNHAAYLKYLRWKYENPLN 200
```

FIG. 5

```
Query:    90 IMLWWSPLTGETGRLGQCGADACFFTINRTYLHHHMTKAF--LFYGTD--FNIDSLPLPR 145
             I+LW  P        +CG   C T +R+    H  KAP  +  D  ++ + L
Sbjct:   129 ILLWNEPSLVNAPAHVECG---CLVTTSRS----HNDKAFDAVVISADHPYSFEGLG-GV 180  SEQ ID
No:19

Query:   146 KAHHD-WAVFHEESPKNNYKLFHKPV--ITL--FNYTATFSRHSHLPLTTQYLESIEVLK 200
             K H D +AV+   + P  ++ +       P+    TL  FN  T T+    S L  T Y        + +
Sbjct:   181 KLHPDFYAVYAAKKPLSSTQ---NPLTNFTLPPFNLTMTYRLDSQLIWTDYYFSHTNLAR 237

Query:   201 SLRYLVPLQSKNKLRKRLAPLVY-VQSDCDPPSDRDSYVRELMTYIEVDSYGECLRNKDL 259
             L++      SK+       A V  ++S+         S       L Y+  +   + L
Sbjct:   238 RLKWF-RAPSKSFADOMPATTVLRLESEILKKS------RLAVYLVYEVNEKTLPESLY 289

Query:   260 PQQLKNPASMDA-DGFYRIIAQYKFILAFENAVCDDYITEKFWRPLKLGVVPVYYGSPSI 318
             ++L+  A +DA D          Y F+L FE +  C DY+   +       +VPV  G  ++
Sbjct:   290 MEELRKYADLDAHDNCLGTDDYHFMLIFETSACPDYVPPQMSMAMDKLLVPVLIGGGNL 349

Query:   319 TDWLPSNKSAILVSEFSHPRELASYIRRLDSDDRLYEAYVEW----KLKGEISNQRLLTA 374
             T+ +PS+   S I   +F+ P++L  +++ L ++    Y  Y  W        +L+          L +
Sbjct:   350 TNLVPSH-SYISSQDFATPQDLIIHLKDLANNQLEYRRYFWWHSIYRLRKTSQPYCALCS 408

Query:   375 LRERKWGVQDVNQDNY 390
             L ++    G  +V Q +Y
Sbjct:   409 LIQQSPGGHEVRQRSY 424
```

FIG. 6

```
                                                    M   N   V   S   F   A   H   L   H   F   A   G    12  SEQ ID NO:5
AGCTGCCTTTGCAGACTCTAACTCCAGCAGC ATG AAT GTG TCC TTT GCT CAC CTC CAC TTT GCC GGA    36  SEQ ID NO:4
                                ↑SEQ ID NO: 6↑
  G   Y   L   P   S   D   S   Q   D   W   R   T   I   I   P   A   L   L   V   A    32
GGC TAC CTG CCC TCT GAT TCC CAG GAC TGG AGA ACC ATC ATC CCG GCT CTC TTG GTG GCT    96

V   C   L   V   G   F   V   G   N   L   C   V   I   G   I   L   L   H   N   A    52
GTC TGC CTG GTG GGC TTC GTG GGA AAC CTG TGT GTG ATT GGC ATC CTC CTC CAC AAT GCT   156

W   K   G   K   P   S   M   I   H   S   L   I   L   N   L   S   L   A   D   L    72
TGG AAA GGA AAG CCA TCC ATG ATC CAC TCC CTG ATT CTG AAT CTC AGC CTG GCT GAT CTC   216

S   L   L   L   F   S   A   P   I   R   A   T   A   Y   S   K   S   V   W   D    92
TCC CTC CTG CTG TTT TCT GCA CCT ATC CGA GCT ACG GCG TAC TCC AAA AGT GTT TGG GAT   276

L   G   W   F   V   C   K   S   S   D   W   F   I   H   T   C   M   A   A   K   112
CTA GGC TGG TTT GTC TGC AAG TCC TCT GAC TGG TTT ATC CAC ACA TGC ATG GCA GCC AAG   336

S   L   T   I   V   V   V   A   K   V   C   F   M   Y   A   S   D   P   A   K   132
AGC CTG ACA ATC GTT GTG GTG GCC AAA GTA TGC TTC ATG TAT GCA AGT GAC CCA GCC AAG   396

Q   V   S   I   H   N   Y   T   I   W   S   V   L   V   A   I   W   T   V   A   152
CAA GTG AGT ATC CAC AAC TAC ACC ATC TGG TCA GTG CTG GTG GCC ATC TGG ACT GTG GCT   456

S   L   L   P   L   P   E   W   F   F   S   T   I   R   H   E   E   G   V   E   172
AGC CTG TTA CCC CTG CCG GAA TGG TTC TTT AGC ACC ATC AGG CAT CAT GAA GGT GTG GAA   516

M   C   L   V   D   V   P   A   V   A   E   E   F   M   S   H   F   G   K   L   192
ATG TGC CTC GTG GAT GTA CCA GCT GTG GCT GAA GAG TTT ATG TCG ATG TTT GGT AAG CTC   576

Y   P   L   L   A   F   G   L   P   L   F   F   A   S   F   Y   F   W   R   A   212
TAC CCA CTC CTG GCA TTT GGC CTT CCA TTA TTT TTT GCC AGC TTT TAT TTC TGG AGA GCT   636

Y   D   Q   C   K   K   R   G   T   K   T   Q   N   L   R   N   Q   I   R   S   232
TAT GAC CAA TGT AAA AAA CGA GGA ACT AAG ACT CAA AAT CTT AGA AAC CAG ATA CGC TCA   696

K   Q   V   T   V   M   L   L   S   I   A   I   I   S   A   L   L   W   L   P   252
AAG CAA GTC ACA GTG ATG CTG CTG AGC ATT GCC ATC ATC TCT GCT CTC TTG TGG CTC CCC   756

E   W   V   A   W   L   W   V   W   H   L   K   A   A   G   P   A   P   P   Q   272
GAA TGG GTA GCT TGG CTG TGG GTA TGG CAT CTG AAG GCT GCA GGC CCG GCC CCA CCA CAA   816

G   F   I   A   L   S   Q   V   L   M   F   S   I   S   S   A   N   P   L   I   292
GGT TTC ATA GCC CTG TCT CAA GTC TTG ATG TTT TCC ATC TCT TCA GCA AAT CCT CTC ATT   876

F   L   V   M   S   I   E   F   R   E   G   L   K   G   V   W   K   W   M   I   312
TTT CTT GTG ATG TCG GAA GAG TTC AGG GAA GGC TTG AAA GGT GTA TGG AAA TGG ATG ATA   936

T   K   K   P   P   T   V   S   E   S   Q   E   T   P   A   G   N   S   I   G   332
ACC AAA AAA CCT CCA ACT GTC TCA GAG TCT CAG GAA ACA CCA GCT GGC AAC TCA GAG GGT   996

L   P   D   K   V   P   S   P   E   S   P   A   S   I   P   E   K   E   K   P   352
CTT CCT GAC AAG GTC CCA TCT CCA GAA TCC CCA GCA TCC ATA CCA GAA AAA GAG AAA CCC  1056

S   S   P   S   G   G   K   G   K   T   E   K   A   E   I   P   I   L   P   D   372
AGC TCT CCC TCC TCT GGC AAA GGG AAA ACT GAG AAG GCA GAG ATT CCC ATC CTT CCT GAC  1116

V   E   Q   F   W   H   E   R   D   T   V   P   S   V   Q   L   K   S   T   N   392
GTA GAG CAG TTT TGG CAT GAG AGG GAC ACA GTC CCT TCT GTA CAA TTG AAG AGC ACC AAC  1176

P   T   D   C   G   S   S   G   N   S   A   W   Y   R   K   T   E   K   S   A   412
CCT ACA GAT TGT GGT AGC TCA GGT AAC TCA GCG TGG TAC CGC AAA ACT GAA AAA TCA GCA  1236

C   C   P   K   T   E   I   H   S   T   F   Y   F   Q   I   L   L   L   A   I   432
TGT TGC CCT AAG ACG GAA ATC CAT TCA ACA TTC TAC TTC CAG ATA CTG CTT CTA GCA ATT  1296

H   R   N   R   N   H   I   S   R   F   S   T   K   Q   L   L   L   G   L   Q   452
CAC AGA AAC AGA AAC CAC ATC TCA CGT TTC TCA ACT AAA CAA CTG CTT TTA GGA CTG CAG  1356
```

FIG. 7a

```
  I   K   F   R   F   S   V   F   P   *                         462
  CAC AAG TTC AGA TTT TCT GTC TTT CCT TAA                        1386
                          ←-SEQ ID NO:6→
  GTC
```

FIG. 7b

```
                   *->GNlLVilvilrtkkIr..tptnifilNLAvADLLflltlppwalyyl  SEQ ID NO:20
                      GNl Vi ++l +    ++++ + +ilNL++ADL +ll+  p+ ++++
        52874    40   GNLCVIGILLHNAWKGkpSMIHSLILNLSLADLSLLLFSAPIRATAY  86 vggsedWpfGsalCklvtaldvvnmyaSillLtaIS<-*
                   + W +G ++Ck +  ++ ++m  a  l++++  +
        52874    87  SK--SVWDLGWFVCKSSDWFIHTCMAAKSLTIVVVA    120
```

FIG. 9a

```
                   *->kvvillvWvlalllslPpllfswvktveegngtlnvnvtvClidfpe  SEQ ID NO:21
                      + v++++W++a ll lP  +fs+ +++e+ +      +Cl+d p
        52874    142  WSVLVAIWTVASLLPLPEWFFSTIRHHEGVE--------MCLVDVPA 180 estasvstwlrsyvllstlvgFllPllvilvcYtrIlrtlr.........
                   ++     ++++ + 1  l++F 1Pl++ +++ +r +   +++++++++
        52874    181  VA----EEFMSMFGKLYPLLAFGLPLFFASFYFWRAYDQCKkrgtktqnl 226

........kaaktllvvvvvFvlCWlPyfivllldtlc.lsiimsstCele
                   +++ ++++++ +ll + ++ +l+WlP ++++ ++ + +
        52874    227  rnqirskQVTVMLLSIAIISALLWLPEWVAWLWVWHLkAAGP-------- 268 rvlptallvtlwLayvNsclNPiIY<-*
                   + ++ ++ ++ +L ++ s  NP+I
        52874    269  APPQGFIALSQVLMFSISSANPLIF    293
```

FIG 9b

```
Query:  253  EWVAWLW-VWHLKAAGPAPPQGFIALSQVLMFSISSANPLIFLVMSEEFREGLKGVW--- 308
             EW WL+ V+H          F +S VL + S+ NP+++ +MS  FRE  K V
Sbjct.: 12   EWTEWLYDVYHY----------FHMVSGVLFYLSSAINPILYNLMSHRFREAFKNVLSSL 61  SEQ ID NO:22

Query:  309  --KWMITKKP-PTVS  320
               +W    KP P+ S
Sbjct.: 62   CKQWHSRHKPRPSFS  76
```

FIG. 10

```
Query:  208 YFWRAYDQC-KKRGTKTQNLRNQIRSKQVTVMXXXXXXXXXXXXWLPEWVAWLWVWHLKAA 266
            YF      C +KR  +T+   + R+ +VT+M            WLP W+   W ++A
Sbjct:  160 YFKIILKMCQRKRQMQTKRTATKKRTTKVTIMGLAIVISYTHCWLPFWIVQ---WSIEAN 216  SEQ ID NO:23

Query:  267 GPAPPQGFIALSQVLMFSI----SSANPLIFLVMSEEFREGLKGVWKWMITKKP 316
             + +     F++    S+ANP +++ +S+ F+    K + K + T KP
Sbjct:  217 LFEKSKYLLFCCTHFAFALQYINSAANPFLYVFLSDSFQ---KNIQKLLRTAKP 267
```

FIG. 11

```
Query:   16 PSDSQDWR--TIIPALL---VAVCLVGFVGNLCVIGILLHNAWKGKPSMI-HXXXXXXXX 69
            PSD+ +    T++  +L    + L+ F N+ + G++     W K +++ H
Sbjct:  115 PSDAPETYSDTVLSVVLGFYALLLLIAFASNILLAGVIKKYRWGMKMALLFHLCVTGALL 174  SEQ ID NO:24

Query:   70 XXXXXXXXXAP----IRATAYSKSVWDLGWFVCKSSDWFIHTCMAAKSLTIVVVAKVCF- 124
                       A    ++   S +V L F + W H   A + ++ +A CF
Sbjct:  175 SITNTLHLLASGYHLLKRQRNSSTV--LQSFAIIA--WVDHFIGFALLIFVMYLAIFCFK 230

Query:  125 MYASDPAKQVSI-HNYTIWSVLVAIWTVASLLPLPEWPFSTIRHHEGVEMCLVDPAVAE 183
               Y ++  + +    +Y ++V ++ W +A L+     FF    H   + C+  V AV+
Sbjct:  231 FYWNNKTRSIEWGRSYVLYAV-ISTWVIAFLIAGFTAFFQCDSHINSQDQCIQIVCAVSN 289

Query:  184 EFMSMFGKL 192
            F ++F +L
Sbjct:  290 IFSAIFTEL 298
```

FIG. 12

```
TACTCACTATAGGGCTCGAGCGGCCGCCCGGGCAGGTCTAGAATTCAGCGGCCGCTGAATTCTAGGCTGCTCTGGGCCT                    SEQ ID NO:7

TGCTAGCCGGCTCTGCACCTCCCAGAAGCCGTGGGCACGCCGCTCAGCTGCTCCATCGCCTCACTTTCCCAGGCTCGCG
                                                  M   G   P   G   E   A   L      7 SEQ ID NO:8
CCCGAAGCAGAGCCATGAGAACCCCAGGGTGCCTGGCGAGCCGCTAGCGCC ATG GGC CCG GGC GAG GCG CTG     21
                                             ↑SEQ ID NO: 9→
 L   A   G   L   L   V   M   V   L   A   V   A   L   L   S   N   A   L   V   L      27
CTG GCG GGT CTT CTG CTG ATG GTA CTG GCC GTG GCG CTG CTA TCC AAC GCA CTG CTG CTG      81

L   C   C   A   Y   S   A   E   L   R   T   R   A   S   G   V   L   L   V   N      47
CTT TGT TGC GCC TAC AGC GCT GAG CTC CGT ACT CGA GCC TCA GGC GTC CTC CTG GTG AAT     141

L   S   L   G   H   L   L   L   A   A   L   D   M   P   F   T   L   L   G   V      67
CTG TCG CTG GGC CAC CTG CTG CTG GCG GCG CTG GAC ATG CCC TTC ACG CTG CTC GGT GTG     201

M   R   G   R   T   P   S   A   P   G   A   C   Q   V   I   G   F   L   D   T      87
ATG CGC GGG CGG ACA CCG TCG GCG CCC GGC GCA TGC CAA GTC ATT GGC TTC CTG GAC ACC     261

F   L   A   S   N   A   A   L   S   V   A   A   L   S   A   D   Q   W   L   A     107
TTC CTG GCG TCC AAC GCG GCG CTG AGC GTG GCG GCG CTG AGC GCA GAC CAG TGG CTG GCA     321

V   G   F   P   L   R   Y   A   G   R   L   R   P   R   Y   A   G   L   L   L     127
GTG GGC TTC CCA CTC CGC TAC GCC GGA CGC CTG CGA CCG CGC TAT GCC GGC CTG CTG CTG     381

G   C   A   W   G   Q   S   L   A   F   S   G   A   A   L   G   C   S   W   L     147
GGC TGT GCC TGG GGA CAG TCG CTG GCC TTC TCA GGC GCT GCA CTT GGC TGC TCG TGG CTT     441

G   Y   S   S   A   F   A   S   C   S   L   R   P   P   E   P   E   R   P     167
GGC TAC AGC AGC GCC TTC GCG TCC TGT TCG CTG CGC CTG CCG CCC GAG CCT GAG CGT CCG     501

R   F   A   A   F   T   A   T   L   H   A   V   G   F   V   L   P   L   A   V     187
CGC TTC GCA GCC TTC ACC GCC ACG CTC CAT GCC GTG GGC TTC GTG CTG CCG CTG GCG GTG     561

L   C   L   T   S   L   Q   V   H   R   V   A   R   S   H   C   Q   R   M   D     207
CTC TGC CTC ACC TCG CTC CAG GTG CAC CGG GTG GCA CGC AGC CAC TGC CAG CGC ATG GAC     621

T   V   T   M   K   A   L   A   L   L   A   D   L   H   P   S   V   R   Q   R     227
ACT GTC ACC ATG AAG GCG CTC GCG CTG CTC GCC GAC CTG CAC CCC AGT GTG CGG CAG CGC     681

C   L   I   Q   Q   K   R   R   H   R   A   T   R   K   I   G   I   A   I     247
TGC CTC ATC CAG CAG AAG CGG CGC CGC CAC CGC GCC ACC AGG AAG ATT GGC ATT GCT ATT     741

A   T   F   L   I   C   F   A   P   Y   V   M   T   R   L   A   E   L   V   P     267
GCG ACC TTC CTC ATC TGC TTT GCC CCG TAT GTC ATG ACC AGG CTG GCG GAG CTC GTG CCC     801

F   V   T   V   N   A   Q   W   G   I   L   S   K   C   L   T   Y   S   K   A     287
TTC GTC ACC GTG AAC GCC CAG TGG GGC ATC CTC AGC AAG TGC CTG ACC TAC AGC AAG GCG     861

V   A   D   P   F   T   Y   S   L   L   R   R   P   F   R   Q   V   L   A   G     307
GTG GCC GAC CCG TTC ACG TAC TCT CTC CTC CGC CGG CCG TTC CGC CAA GTC CTG GCC GGC     921

M   V   H   R   L   L   K   R   T   P   R   P   A   S   T   H   D   S   S   L     327
ATG GTG CAC CGG CTG CTG AAG AGA ACC CCG CGC CCA GCA TCC ACC CAT GAC AGC TCT CTG     981

D   V   A   G   M   V   H   Q   L   L   K   R   T   P   R   P   A   S   T   H     347
GAT GTC GCC GGC ATG GTG CAC CAG CTG CTG AAG AGA ACC CCG CGC CCA GCG TCC ACC CAC    1041

N   G   S   V   D   T   E   N   D   S   C   L   Q   Q   T   H   *                 364
AAC GGC TCT GTG GAC ACA GAG AAT GAT TCC TGC CTG CAG CAG ACA CAC TGA                1092
                                                          ←SEQ ID NO:9↑
GGGCCTGGCAGGGCTCATCGCCCCACCTTCTAAGAAGCCCTGTGGAAAGA
```

FIG. 13

```
                    *->GNlLVilvilrtkklr.tptnifilNLAvADLLflltlppwalyylv  SEQ ID NO:25
                       N+LV+l   +++   lr++++ +++NL++  LL++++ +p++l+ ++
    52880    22      SNALVLLCCAYSAELRtRASGVLLVNLSLGHLLLAALDMPFTLLGVM 68 ggsedWpfGsalCklvtaldvvnmyaSillLtaISiDRYlAIvhPlryrr
                       g  + p +  C +  ++ld++      l+ +a+S D +lA+  Plry
    52880    69      RG--RTPSAPGACQVIGFLDTFLASNAALSVAALSADQWLAVGFPLRYAG 116 rrtsprrAkvvillvWvlalllslPpllfswvktveegngtlnvnvtvCl
                       r + pr A ++++++W +l++s   l+++   ++       +C+
    52880    117     RLR-PRYAGLLLGCAWGQSLAFSGAA-LGCSWLGYSSA-------FASCS 157 idfpeestasvstwlrsyvllstlvgFllPllvilvcYtrIlrtlr....
                       +   p  e+  ++   +++  ++  vgF+lPl v++ + +++ r++r++ +
    52880    158     LRLPPEP---ERPRFAAFTATLHAVGFVLPLAVLCLTSLQVHRVARshcq 204

..........................kaaktllvvvvvFvlCW
                       + ++ + +     + +++ +++  +++++++++a++ +++ + + +F++C+
    52880    205     rmdtvtmkalalladlhpsvrqrcliqqkrrrhRATRKIGIAIATFLICF 254 lPyfivllldtlc.lsiimsstCelervlptallvtlwLayvNsclNPiI
                       +Py + l + +       v   + +++ +L+y+ ++ +P+
    52880    255     APYVMTRLAELVPfVT-----------VNAQWGILSKCLTYSKAVADPFT 293

```
Query   134  SLAFSGAALGCSWLGYSSAFASCSXXXXXXXXXXXXFAAFTATLHAVGFVLPLAVLCLTSL 193
             +L F  AL  SWLG+   +ASC+            FA FT+  HA+ F+L  VLC T L
Sbjct   2    ALTFPATALALSWLGFHQLYASCTLCSRRPDERLRFAVFTSAFHALSFLLGFIVLCFTYL 61   SEQ ID NO:26

Query   194  QVHRVARSHCQRMDTVTMKALALLADLHPSVRQRCLIQQKRRPHRATRKIGIAIATFLIC 253
             +V +VAR HC+R+D +TM+ L LL D+HPSVR+RCL +QKRRR RAT+KI  I TFL+C
Sbjct   62   KVLKVARFHCKRIDVITMQTLVLLVDIHPSVRERCLEEQKRRRQRATKKISTFIGTFLVC 121

Query   254  FAPYVMTRLAELVPFVTVNAQWGILSKCLTYSKAVADPFTYSLLRRPFRQVLAGMVHRLL 313
             FAPYV+TRL EL      +++ WG+LSKCL YSKA +DPF YSLLR  +R+   +++R+
Sbjct   122  FAPYVITRLVELFSTAPIDSHWGVLSKCLAYSKAASDPFVYSLLRHQYRRSCKELLNRIF 181

Query   314  KR 315
             R
Sbjct   182  NR 183
```

FIG. 16

```
Query:  175 TLHAVGFVLPLAVL--CLTS--LQVHRVARSHCQRMDTVTMKALALLADLHPSVRQRCLI 230
             TL VGP++P V+   C    L VH  +  + D   + A      +
Sbjct:   28 TLFIVGFMIPCLVIIVCYACIPLTVIH-QKKKIRNHDNFQIAAAKGSSSSGGGSYMTTTC  86  SEQ ID NO:27

Query:  231 QQKRRRHRATRK-IGIAIATFLICFAPY----VMTRLAELVPFVTVNAQ---WGILSKCL 282
             +K R   RTK+ +    F IC+ P      V+ R+  +      N    W I S L
Sbjct:   87 TRKAREDRKTTKMLMVVFLCFAICYLPISILNVLKRVFGMFRHSEDNESVYWWHIFSHWL 146

Query:  283 TYSKAVADPFTYSLLRRPFRQVLAGMVHRLLKRTPRPAS 321
             Y+ +  +P  Y+ +   +R+    +  LLK   P S
Sbjct:  147 VYANSCINPIIYNFMNGKYRKAY-WKIFALLKFWGEPLS 184
```

FIG. 17

```
Query:  171 AFTATLHAVGFVLPLAVL-----CLTSLQVHRVARSHCQRMDTVTMKALALLADLHPSVR 225
             A+    L   F +P +V+      C+ +   H   R H   D++ +  ++ L L    R
Sbjct:   24 AYVVMLVVAVFFIPFSVMLYSYMCILNTVRHNAVRIH-NHPDSLCLSQVSKLG-LMSLQR  81  SEQ ID NO:28

Query:  226 QRCLIQQKRRRHRATRKIGIAIATFLICFAPY-VMTRLAELVPFVTVNAQWGILSKC--- 281
              +     + RA  I I    F +C+ P+ V + L+         + +S C
Sbjct:   82 PHQMSVDMSFKTRAFTTILILFVGFSLCWLPHSVYSLLSVFSKHFYYQHNFYEISTCVLW 141

Query:  282 LTYSKAVADPFTYSLLRRPFRQVLAGMVHRLLKRTPR-PAST 322
             L Y K+V +P  Y    + FR+    M+ +  K  P+ P T
Sbjct:  142 LCYLKSVFNPIIYCWRIKKFREACLEMMPKTFKILPQVPGRT 183
```

FIG. 18

```
Query:  221 HPSVRQRCLIQQKRRRHRATRKIGIAIATFLICFAPYVMTRLAELVPFVTVNAQWGILSK 280
             H  ++   CL+QQKR+   A+   G+A A      +P   R      F      W  L
Sbjct:    7 HKIIKAACLVQQKRQEFLASVARGVAPAD-----SPEAPRR-----SFAGGTWDWEYLG-  55  SEQ ID NO:29

Query:  281 CLTYSKAVADPFTYSLLRRPFRQVLAGMVHRLLKRTPRPASTHDSSLDV 329
                 + A+ F Y   RR RQ   G VH LL   P P    +S+LD+
Sbjct:   56 -FASPEEYAE-FQY---RRRHRQRRRGDVHSLLSNPPDPDEPSESTLDI  99
```

```
        *->llPllvilvcYtrIlrtlr....................kaaktl  SEQ ID NO:30
         +l+l  ++  +   +  +-++l+-++++  ++  ++++  +++ +++++a+   +
63497  189  VLCLGLMFWVSSSMVCILErhkqrvqhidrsdlspraspenRATQSI  235 lvvvvvFv<-*
        l++v++Fv
63497  236  LILVSTFV   243
```

FIG. 22

```
Query:    36  GCRLRSTDLIVKHLIVANFLALRCKGVPQTMAAFGVRYFLNALGCKLVFYLHEVGRGVSI  95
              G R R TDL +  L + + + L      G  TM F         CK + YLHR+ RG+S+
Sbjct:     5  GHRSRFTDLPIGLLSLVHLMMLLTMGFTAIMDMFMSWGRWDDTTCKSLIYLHRLLRGLSL  64   SEQ ID NO:31

Query:    96  GTTCLLSVFQVITVSSRKSRWAKLKEKAPKHUGFSVLLCWIVCMLVNIIPPMYVAGKHNY  155
              TTCLL+VFQ  IT+S R S   AK K K+P H+  + L  W++ M  +     +     N
Sbjct:    65  CTTCLLNVFQAITLSPRSSCLAKFHKSPHHISCAFLFLWVLYMSFSSHLLLSIIATPNL  124

Query:   156  TNITVNEDLGYCSGGGNNKIAQTLRAMLLSFPDVLCLGLMFWVSSSMUCILERHKQRVQH  215
              T+              CS   +   Q++ + LL+   DV +GLM   S  MV +L RH+++  QH
Sbjct:   125  TSNDFMYVTQSCSILPMSYSMQSMFSTLLAIRDVFLTGLMVLSSGYMVALLCPHRKQAQH  184

Query:   216  IDRSDLSPRASPENRATQSILILVSTP-VSSYTL-SCLFQVCMALLDNPNSLLVNTSALM  273
                +  + LSP+ASPE  RAT++ IL+L+S+F  V   Y  S +F     D P   +    ++
Sbjct:   185  LHSTSLSPKASPEQRATRTILMLMSSFFVLMYIFDSIVFCSRTMFKDGPTFYCIQI--IV  242

Query:   274  SVCFPTLSPFVLHSCDPSVYRF  295
              S + T+SPFV +  +  + +F
Sbjct:   243  SHSYATVSPFVFICTEKGIVKF  264
```

```
L   V   I   L   L   P   D   A   N   R   D   T   L   K   A   L   L   E   F   L    461
CTT GTC ATC CTC CTA CCT GAT GCA AAC AGG GAC ACA CTG AAG GCC CTT CTT GAA TTT CTC  1383

Q   R   V   I   D   N   K   E   N   K   M   T   V   M   N   V   A   M   V        481
CAA AGA GTA ATA GAT AAT AAA GAA AAA AAT AAA ATG ACA GTC ATG AAT GTA GCA ATG GTC  1443

M   A   P   N   L   F   M   C   H   A   L   G   L   K   S   S   E   Q   R   E    501
ATG GCC CCG AAT CTC TTT ATG TGT CAT GCA TTG GGA TTG AAG TCC AGT GAA CAG CGA GAA  1503

F   V   M   A   A   G   T   A   N   T   M   H   L   L   I   K   Y   Q   K   L    521
TTT GTA ATG GCA GCT GGG ACA GCA AAT ACC ATG CAC TTA TTG ATT AAG TAC CAA AAA CTT  1563

L   W   T   I   P   K   F   I   V   N   Q   V   R   K   Q   N   T   E   N   H    541
CTG TGG ACA ATT CCC AAG TTT ATT GTA AAC CAA GTG AGG AAG CAA AAC ACG GAA AAT CAT  1623

K   K   D   K   R   A   M   K   L   L   K   K   M   A   Y   D   R   E   K        561
AAA AAG GAT AAA AGA GCC ATG AAG AAA TTG CTG AAG AAA ATG GCT TAT GAC CGA GAA AAA  1683

Y   E   K   Q   D   K   S   T   N   D   A   D   V   P   Q   G   V   I   R   V    581
TAT GAA AAG CAA GAT AAG AGT ACA AAT GAT GCT GAC GTT CCT CAG GGA GTG ATT CGA GTG  1743

Q   A   P   H   L   S   K   V   S   M   A   I   Q   L   T   E   E   L   K   A    601
CAA GCT CCC CAT CTT TCG AAA GTT TCC ATG GCA ATA CAG CTA ACT GAA GAA CTA AAA GCC  1803

S   D   V   L   A   R   F   L   S   Q   E   S   G   V   A   Q   T   L   K   K    621
AGT GAT GTA CTT GCC AGG TTT CTC AGC CAA GAA AGT GGG GTT GCC CAG ACT CTC AAG AAA  1863

G   E   V   F   L   Y   E   I   G   G   N   I   G   E   R   C   L   D   D   D    641
GGA GAA GTT TTT TTG TAT GAA ATT GGA GGA AAT ATT GGG GAA CGC TGC CTT GAT GAT GAC  1923

T   Y   M   K   D   L   Y   Q   L   N   P   N   A   E   W   V   I   K   S   K    661
ACT TAC ATG AAG GAT TTA TAT CAG CTT AAC CCA AAT GCT GAG TGG GTT ATA AAG TCA AAG  1983

P   L   *                                                                         664
CCA TTG TAG                                                                       1992
← SEQ ID NO:15 ↑
AAGACTTAACAAGCTGCAGATAACCATGTGGACTTCTGTCATAATTCTTGCTGAGTCAAGAGTGTAAATAAAAGAAATT
GCAGGACTCATATTATTCAGTTGTACCCAAGTATTTAAAAATGACTCTCTTAAGCCTTAAAAAGTCATAGATTTGTGCT
GATGCCAGAATTATATTAATTATTATTAATGTTATTATTAGAAAAAAAATTTCTGGAGTGAGAGTAAAGAGGCTTAATT
AGTTGTGGGCAGTTTCATATGCTCTGTGAAATGTGTCCAGATGTGACATAGTTCTTTTTTTTTTAATATGTGGAAATC
TCTTCTCTTCCCATTCTTTTCTCCTAAAATCATATATACTGTAATATATGCTCTCTCACCTCTATTACCTCCTCACATC
TACCCTTTCCCAGTTAGGTTTGCTTTTTGACCAAAAAGATAACAAATACCAGGTATGGCAAGTTGTGAAGACAGCACAT
TAAAACATACCTAACTTCACAGTATTCCTGTCACCACAGAATGTTAGTATTCATCTCTTTGAATCATTTGCTCAAATAA
TAACATTCCACCTTTTCCTGCTGTATCACAGGAAGTGATTTGCATTTTTTTTCAGTTCATCTGACTTAAGTTCACAGAA
CGTATCAGCCGACCAAGAAAATAGGACTGTCAGAAGCTGCCAGTTATTACTGAACCATTAAATACTTATATACTAAGAA
TAAATAAAATATACCCATGTGAAATAATAATTGGATTATGGATAACAAGACAGTGAAAGCCAAAGCACTTTCTGTCTAC
TGTACTCTTCTAAATGGAATTTTAAAAGTCATAGCCTGGCTTTACGTGTTGTCATTATTAGCATTATAAATATGCATGAT
AGTATAATCCAGTAATGGTTGAAGAATGTATTTTACTTAAAGAGGGATTTTTTTTTTTAAGTCCTGAATAAGTCTACTG
GAAGAATTATTCTTCTGGGTGAAAAAGCTTTTGTTTGTGTTCTTATTTTAAATAACCGGAGTCAATTTATTAAAATGTT
CTTGAAAGTACTATTCCCAGGGATTTTATGCACAAACCATATTGTGACAAGAGATGAGCCTCTGTACTGTAAATAAGA
AATGAAGTAGAGAAATGTTAAATATTTTATGAGTTAGAATATAGTAAATAAAAGGTGATGTAAATGAATGCTGCACAA
ATGGTGTTCATGATACTTTTAGTAGTACTTTAGGAAAAACTACACATTCTCAGAAGCTCTTGATGTCTCTAATGAAGCG
GGGGAATGCTGTTAATGAGAACAGTCATAAAATTTTTAGCCATATAATTACAAGAACAGCCTGTGATATGATCACTTAAA
TGATTTTGTGGTGATTCGTGCCATTGCTTTTTTATTTAAAAGAAAAATTTTGTAATTAAATGCCTTTTTCTAAAAAAAA
```

```
                *->PiivekcveyIeklYPLaerGlqeEGIYRvsGsa....srvkeLrea  SEQ ID NO:32
                   P+i +k+++ Ie+       rGl++EG+ R++G a + ++++++eL ++
33425    343    PLIFQKLISRIEE------RGLETEGLLRIPGAAirikNLCQELEAK 383 fdkdgapdslelsekewfDvhvvaglLKlYLReLPePLipydlyeefira
                f ++  + + e+ ++       h  a+lLKl++ReLP+PL++ +  + f
33425    384    FYEG--TFNWESVKQ-----HDAASLLKLFIRELPQPLLSVEYLKAFQAV 426 akeqiedpderlralkellsSkLPrahynTLryLltHLnrvaeiyiensa
                 + ++   ++l+al+ l+  +LR+a+++TL++Ll++L+rv+      n +
33425    427    QN--LPTKKQQLQALNLLVI-LLPDANRDTLKALLEFLQRVID----NKE 469 vNkMnarNLAivFgPtLlrppdkesnd<-*
                +NkM++ N A v +P+L+   +  ++
33425    470    KNKMTVMNVAMVMAPNLFMCHA--LGL    494
```

FIG. 26

```
Query:   516  IKYQKLLWTIPKFIVNQVRKQNTENHXXXXX--XXXXXXXXXXYDREK-------YEKQ 565
              +KYQK+LW +P F++ QVR+ N                         +RE        +K
Sbjct:   1    LKYQKILWKVPSFLITQVRRMNEATMLLKKQLPSVRKLLRRKTLERETASPRTSKVLQKS 60  SEQ ID NO:33

Query:   566  DKSTNDADVPQGVIRVQAPHLSKVSMAIQLTEELKASDVLARF 608
              +    +DVP+GVIRV AP LSKVSMAIQL + KA D+LA+F
Sbjct:   61   PSARRMSDVPEGVIRVHAPLLSKVSMAIQLNNQTKAKDILAKF 103
```

FIG. 27

```
Query:   390 NWESVKQ-HDAASLLKLFIRELPQPLLSVE----YLKAFQA-VQNLPTKKXXXXXXXXXX 443
             N E  +  H  A LLK + RELP+PLL+ E    +++A +A V +   +
Sbjct:   16  NMEEYEDVHTVAGLLKQYFRELPEPLLTYELYEEFIEAAKAQVSDEDERMEALEMLKELI 75  SEQ ID NO:34

Query:   444 XXXPDANRDTLKALLEFLQRVIDNKEKNKMTVMNVAMVMAPNL 486
                P+ANR+TL+ LL+ L RV + E+NKM N+A+V P L
Sbjct:   76  KLLPEANRETLRYLLKHLSRVAQHSEENKMNAQNLAVVFGPTL 118
```

FIG. 28

```
Query:   399 AASLLKLFIRELPQPLLSVEYLKAFQAVQNLPTKKXXXXXXXXXXXXPDANRDTLKALL 458
             A SLLKLF+RELP+PLL+ + +  F+ V + P            P  NR  L  +L
Sbjct:    96 ACSLLKLFLRELPEPLLTTDLVARFEEVASHPKVTTQQAELQQLLEQLPKCNRTLLAWVL 155  SEQ ID NO:35

Query:   459 EFLQRVIDNKEKNKMTVMNVAMVMAPNLFM 488
                 VI + NK+   ++AM+++P L M
Sbjct:   156 LHFDAVIQQERHNKLNAQSLAMLLSPTLQM 185
```

FIG. 29

SEQUENCE LISTING

<160> NUMBER OF SEQ ID NOS: 37

<210> SEQ ID NO 1
<211> LENGTH: 1669
<212> TYPE: DNA
<213> ORGANISM: Homo sapiens
<220> FEATURE:
<221> NAME/KEY: CDS
<222> LOCATION: (163)...(1623)

<400> SEQUENCE: 1

```
cacgcgtccg ctctgctgct ctagtgttga ctttggcgtc tcaggtgatc catgactttt      60
taaagccaat ataatttctt actccttctg gagtgctgct tggctttcac tcagtggttt     120 ttttttttt cttttttggc cttggatacc gttgagaatc ta atg aaa gtc acg        174
                                              Met Lys Val Thr
                                                1
```

| | | |
|---|---|---|
| ggc cct ccc cag gga gtt aca gac tcc atg caa tgc ttc aat gat cag<br>Gly Pro Pro Gln Gly Val Thr Asp Ser Met Gln Cys Phe Asn Asp Gln<br>5                         10                   15                     20 | 222 |
| tgg cct tta tct aac acc agg agc agc gag cac ata aaa gag gtc atg<br>Trp Pro Leu Ser Asn Thr Arg Ser Ser Glu His Ile Lys Glu Val Met<br>                       25                  30                    35 | 270 |
| gtt gag ctg ggg aag ttt gaa agg aag gag ttt aaa agt tcc agt ttg<br>Val Glu Leu Gly Lys Phe Glu Arg Lys Glu Phe Lys Ser Ser Ser Leu<br>               40                   45                    50 | 318 |
| caa gat gga cat aca aaa atg gag gaa gca cct acg cat ctt aat tca<br>Gln Asp Gly His Thr Lys Met Glu Glu Ala Pro Thr His Leu Asn Ser<br>          55                  60                    65 | 366 |
| ttt ctt aag aaa gaa gga ttg acc ttc aac agg aaa aga aaa tgg gaa<br>Phe Leu Lys Lys Glu Gly Leu Thr Phe Asn Arg Lys Arg Lys Trp Glu<br>    70                  75                  80 | 414 |
| ttg gac agc tac ccc att atg ctc tgg tgg tcc ccg ctg acg ggg gag<br>Leu Asp Ser Tyr Pro Ile Met Leu Trp Trp Ser Pro Leu Thr Gly Glu<br>85                       90                  95                 100 | 462 |
| act ggg agg tta ggc caa tgt gga gca gat gct tgt ttc ttc acc atc<br>Thr Gly Arg Leu Gly Gln Cys Gly Ala Asp Ala Cys Phe Phe Thr Ile<br>                 105                  110                 115 | 510 |
| aac cgg acc tac ctc cat cat cac atg acc aaa gca ttc ctc ttc tat<br>Asn Arg Thr Tyr Leu His His His Met Thr Lys Ala Phe Leu Phe Tyr<br>          120                  125                  130 | 558 |
| ggt act gac ttt aac ata gat agc tta cct ctg cct cgg aaa gcc cat<br>Gly Thr Asp Phe Asn Ile Asp Ser Leu Pro Leu Pro Arg Lys Ala His<br>               135                  140                 145 | 606 |
| cat gac tgg gct gtt ttt cat gaa gag tcc ccg aaa aac aat tat aag<br>His Asp Trp Ala Val Phe His Glu Glu Ser Pro Lys Asn Asn Tyr Lys<br>       150                  155                  160 | 654 |
| ctc ttt cat aaa cca gtg att acc ttg ttc aac tac act gcc acg ttc<br>Leu Phe His Lys Pro Val Ile Thr Leu Phe Asn Tyr Thr Ala Thr Phe<br>165                       170                 175                 180 | 702 |
| agc agg cat tcc cac ttg cca cta act acc caa tac ttg gag agc att<br>Ser Arg His Ser His Leu Pro Leu Thr Thr Gln Tyr Leu Glu Ser Ile<br>               185                  190                 195 | 750 |
| gaa gtc ctg aag tca ctc cga tac cta gtt cct ttg cag tcc aaa aac<br>Glu Val Leu Lys Ser Leu Arg Tyr Leu Val Pro Leu Gln Ser Lys Asn<br>          200                  205                  210 | 798 |
| aag ctt aga aaa aga ctt gct ccg ctg gtg tat gta cag tca gac tgt<br>Lys Leu Arg Lys Arg Leu Ala Pro Leu Val Tyr Val Gln Ser Asp Cys<br>               215                  220                 225 | 846 |
| gac cca cca tca gac agg gac agc tat gtt cgc gag ctg atg act tac<br>Asp Pro Pro Ser Asp Arg Asp Ser Tyr Val Arg Glu Leu Met Thr Tyr<br>       230                  235                  240 | 894 |
| atc gag gtc gat tcc tat ggt gaa tgt tta cga aac aaa gac ctc cct<br>Ile Glu Val Asp Ser Tyr Gly Glu Cys Leu Arg Asn Lys Asp Leu Pro<br>245                       250                 255                 260 | 942 |
| cag cag ctg aaa aat cca gcc tct atg gat gcc gat ggc ttt tat agg<br>Gln Gln Leu Lys Asn Pro Ala Ser Met Asp Ala Asp Gly Phe Tyr Arg<br>               265                  270                 275 | 990 |
| atc att gca cag tat aag ttt atc cta gct ttt gag aat gca gtt tgt<br>Ile Ile Ala Gln Tyr Lys Phe Ile Leu Ala Phe Glu Asn Ala Val Cys<br>          280                  285                  290 | 1038 |
| gat gac tac atc act gag aag ttc tgg agg cca ctg aaa ctg ggg gta<br>Asp Asp Tyr Ile Thr Glu Lys Phe Trp Arg Pro Leu Lys Leu Gly Val<br>               295                  300                 305 | 1086 |
| gtc cct gta tat tac gga tcc ccc agc atc aca gac tgg ctt cca agt<br>Val Pro Val Tyr Tyr Gly Ser Pro Ser Ile Thr Asp Trp Leu Pro Ser | 1134 |

```
                310             315             320
aac aaa agt gct att ctt gta tca gaa ttt tct cac ccc agg gaa ctg    1182
Asn Lys Ser Ala Ile Leu Val Ser Glu Phe Ser His Pro Arg Glu Leu
325             330             335             340 gca agt tac atc aga cga ctg gat tct gat gac aga ttg tat gag gcc    1230
Ala Ser Tyr Ile Arg Arg Leu Asp Ser Asp Asp Arg Leu Tyr Glu Ala
                345             350             355 tat gta gaa tgg aag ctg aag ggt gag atc tct aac cag cga ctt ctg    1278
Tyr Val Glu Trp Lys Leu Lys Gly Glu Ile Ser Asn Gln Arg Leu Leu
            360             365             370 aca gct ctc agg gaa cgg aaa tgg gga gtg caa gac gtc aac cag gac    1326
Thr Ala Leu Arg Glu Arg Lys Trp Gly Val Gln Asp Val Asn Gln Asp
        375             380             385 aat tac atc gat gca ttt gag tgt atg gtg tgc acc aag gtg tgg gct    1374
Asn Tyr Ile Asp Ala Phe Glu Cys Met Val Cys Thr Lys Val Trp Ala
    390             395             400 aat atc agg ctt cag gaa aag ggc tta cca ccc aaa aga tgg gag gca    1422
Asn Ile Arg Leu Gln Glu Lys Gly Leu Pro Pro Lys Arg Trp Glu Ala
405             410             415             420 gaa gat acc cac ctg agt tgc cca gag ccc aca gtg ttt gct ttc tca    1470
Glu Asp Thr His Leu Ser Cys Pro Glu Pro Thr Val Phe Ala Phe Ser
                425             430             435 cca ctc cgg act cca cct ttg agc tct ttg cga gag atg tgg att tcc    1518
Pro Leu Arg Thr Pro Pro Leu Ser Ser Leu Arg Glu Met Trp Ile Ser
                440             445             450 agc ttt gaa caa tcc aag aaa gaa gcc cag gca cta agg tgg ctg gtt    1566
Ser Phe Glu Gln Ser Lys Lys Glu Ala Gln Ala Leu Arg Trp Leu Val
            455             460             465 gat agg aat caa aac ttt tca tct caa gag ttt tgg ggc cta gta ttc    1614
Asp Arg Asn Gln Asn Phe Ser Ser Gln Glu Phe Trp Gly Leu Val Phe
        470             475             480 aag gac tga tttcaaaaat gatcagaatg aaacagaaaa aaaaaaaaa             1663
Lys Asp  *
485 aaaaaa                                                              1669

<210> SEQ ID NO 2
<211> LENGTH: 486
<212> TYPE: PRT
<213> ORGANISM: Homo sapiens

<400> SEQUENCE: 2

Met Lys Val Thr Gly Pro Pro Gln Gly Val Thr Asp Ser Met Gln Cys
1               5                   10                  15

Phe Asn Asp Gln Trp Pro Leu Ser Asn Thr Arg Ser Ser Glu His Ile
            20                  25                  30

Lys Glu Val Met Val Glu Leu Gly Lys Phe Glu Arg Lys Glu Phe Lys
        35                  40                  45

Ser Ser Ser Leu Gln Asp Gly His Thr Lys Met Glu Glu Ala Pro Thr
    50                  55                  60

His Leu Asn Ser Phe Leu Lys Lys Glu Gly Leu Thr Phe Asn Arg Lys
65                  70                  75                  80

Arg Lys Trp Glu Leu Asp Ser Tyr Pro Ile Met Leu Trp Trp Ser Pro
                85                  90                  95

Leu Thr Gly Glu Thr Gly Arg Leu Gly Gln Cys Gly Ala Asp Ala Cys
            100                 105                 110

Phe Phe Thr Ile Asn Arg Thr Tyr Leu His His Met Thr Lys Ala
        115                 120                 125
```

```
Phe Leu Phe Tyr Gly Thr Asp Phe Asn Ile Asp Ser Leu Pro Leu Pro
    130                 135                 140

Arg Lys Ala His His Asp Trp Ala Val Phe His Glu Glu Ser Pro Lys
145                 150                 155                 160

Asn Asn Tyr Lys Leu Phe His Lys Pro Val Ile Thr Leu Phe Asn Tyr
                165                 170                 175

Thr Ala Thr Phe Ser Arg His Ser His Leu Pro Leu Thr Thr Gln Tyr
            180                 185                 190

Leu Glu Ser Ile Glu Val Leu Lys Ser Leu Arg Tyr Leu Val Pro Leu
        195                 200                 205

Gln Ser Lys Asn Lys Leu Arg Lys Arg Leu Ala Pro Leu Val Tyr Val
    210                 215                 220

Gln Ser Asp Cys Asp Pro Ser Asp Arg Asp Ser Tyr Val Arg Glu
225                 230                 235                 240

Leu Met Thr Tyr Ile Glu Val Asp Ser Tyr Gly Glu Cys Leu Arg Asn
                245                 250                 255

Lys Asp Leu Pro Gln Gln Leu Lys Asn Pro Ala Ser Met Asp Ala Asp
            260                 265                 270

Gly Phe Tyr Arg Ile Ile Ala Gln Tyr Lys Phe Ile Leu Ala Phe Glu
        275                 280                 285

Asn Ala Val Cys Asp Asp Tyr Ile Thr Glu Lys Phe Trp Arg Pro Leu
    290                 295                 300

Lys Leu Gly Val Val Pro Val Tyr Tyr Gly Ser Pro Ser Ile Thr Asp
305                 310                 315                 320

Trp Leu Pro Ser Asn Lys Ser Ala Ile Leu Val Ser Glu Phe Ser His
                325                 330                 335

Pro Arg Glu Leu Ala Ser Tyr Ile Arg Arg Leu Asp Ser Asp Asp Arg
            340                 345                 350

Leu Tyr Glu Ala Tyr Val Glu Trp Lys Leu Lys Gly Glu Ile Ser Asn
        355                 360                 365

Gln Arg Leu Leu Thr Ala Leu Arg Glu Arg Lys Trp Gly Val Gln Asp
    370                 375                 380

Val Asn Gln Asp Asn Tyr Ile Asp Ala Phe Glu Cys Met Val Cys Thr
385                 390                 395                 400

Lys Val Trp Ala Asn Ile Arg Leu Gln Glu Lys Gly Leu Pro Pro Lys
                405                 410                 415

Arg Trp Glu Ala Glu Asp Thr His Leu Ser Cys Pro Glu Pro Thr Val
            420                 425                 430

Phe Ala Phe Ser Pro Leu Arg Thr Pro Pro Leu Ser Ser Leu Arg Glu
        435                 440                 445

Met Trp Ile Ser Ser Phe Glu Gln Ser Lys Lys Glu Ala Gln Ala Leu
    450                 455                 460

Arg Trp Leu Val Asp Arg Asn Gln Asn Phe Ser Ser Gln Glu Phe Trp
465                 470                 475                 480

Gly Leu Val Phe Lys Asp
                485

<210> SEQ ID NO 3
<211> LENGTH: 1461
<212> TYPE: DNA
<213> ORGANISM: Homo sapiens

<400> SEQUENCE: 3
atgaaagtca cgggccctcc ccagggagtt acagactcca tgcaatgctt caatgatcag      60
```

-continued

```
tggcctttat ctaacaccag gagcagcgag cacataaaag aggtcatggt tgagctgggg      120
aagtttgaaa ggaaggagtt taaaagttcc agtttgcaag atggacatac aaaaatggag      180
gaagcaccta cgcatcttaa ttcatttctt aagaaagaag gattgacctt caacaggaaa      240
agaaaatggg aattggacag ctaccccatt atgctctggt ggtccccgct gacggggggag     300 actgggaggt taggccaatg tggagcagat gcttgtttct tcaccatcaa ccggacctac      360
ctccatcatc acatgaccaa agcattcctc ttctatggta ctgactttaa catagatagc      420
ttacctctgc ctcggaaagc ccatcatgac tgggctgttt tcatgaaga gtccccgaaa       480 aacaattata agctctttca taaaccagtg attaccttgt tcaactacac tgccacgttc      540
agcaggcatt cccacttgcc actaactacc caatacttgg agagcattga agtcctgaag      600
tcactccgat acctagttcc tttgcagtcc aaaaacaagc ttagaaaaag acttgctccg      660
ctggtgtatg tacagtcaga ctgtgaccca ccatcagaca gggacagcta tgttcgcgag      720
ctgatgactt acatcgaggt cgattcctat ggtgaatgtt tacgaaacaa agacctccct      780
cagcagctga aaaatccagc ctctatggat gccgatggct tttataggat cattgcacag      840
tataagttta tcctagcttt tgagaatgca gtttgtgatg actacatcac tgagaagttc      900
tggaggccac tgaaactggg ggtagtccct gtatattacg gatcccccag catcacagac      960
tggcttccaa gtaacaaaag tgctattctt gtatcagaat tttctcaccc cagggaactg     1020
gcaagttaca tcagacgact ggattctgat gacagattgt atgaggccta tgtagaatgg     1080
aagctgaagg gtgagatctc taaccagcga cttctgacag ctctcaggga acggaaatgg     1140
ggagtgcaag acgtcaacca ggacaattac atcgatgcat ttgagtgtat ggtgtgcacc     1200
aaggtgtggg ctaatatcag gcttcaggaa aagggcttac cacccaaaag atgggaggca     1260
gaagataccc acctgagttg cccagagccc acagtgtttg ctttctcacc actccggact     1320 ccaccttttga gctcttttgcg agagatgtgg atttccagct ttgaacaatc caagaaagaa    1380
gcccaggcac taaggtggct ggttgatagg aatcaaaact tttcatctca agagttttgg     1440
ggcctagtat tcaaggactg a                                               1461
```

<210> SEQ ID NO 4
<211> LENGTH: 1420
<212> TYPE: DNA
<213> ORGANISM: Homo sapiens
<220> FEATURE:
<221> NAME/KEY: CDS
<222> LOCATION: (32)...(1417)

<400> SEQUENCE: 4

```
agctgccttt gcagactcta actccagcag c atg aat gtg tcc ttt gct cac        52
                                  Met Asn Val Ser Phe Ala His
                                   1               5 ctc cac ttt gcc gga ggg tac ctg ccc tct gat tcc cag gac tgg aga      100
Leu His Phe Ala Gly Gly Tyr Leu Pro Ser Asp Ser Gln Asp Trp Arg
            10                  15                  20 acc atc atc ccg gct ctc ttg gtg gct gtc tgc ctg gtg ggc ttc gtg      148
Thr Ile Ile Pro Ala Leu Leu Val Ala Val Cys Leu Val Gly Phe Val
        25                  30                  35 gga aac ctg tgt gtg att ggc atc ctc ctc cac aat gct tgg aaa gga      196
Gly Asn Leu Cys Val Ile Gly Ile Leu Leu His Asn Ala Trp Lys Gly
 40                  45                  50                  55 aag cca tcc atg atc cac tcc ctg att ctg aat ctc agc ctg gct gat      244
Lys Pro Ser Met Ile His Ser Leu Ile Leu Asn Leu Ser Leu Ala Asp
                60                  65                  70
```

-continued

| | |
|---|---|
| ctc tcc ctc ctg ctg ttt tct gca cct atc cga gct acg gcg tac tcc<br>Leu Ser Leu Leu Leu Phe Ser Ala Pro Ile Arg Ala Thr Ala Tyr Ser<br>              75                  80                85 | 292 |
| aaa agt gtt tgg gat cta ggc tgg ttt gtc tgc aag tcc tct gac tgg<br>Lys Ser Val Trp Asp Leu Gly Trp Phe Val Cys Lys Ser Ser Asp Trp<br>            90                95               100 | 340 |
| ttt atc cac aca tgc atg gca gcc aag agc ctg aca atc gtt gtg gtg<br>Phe Ile His Thr Cys Met Ala Ala Lys Ser Leu Thr Ile Val Val Val<br>105                  110                115 | 388 |
| gcc aaa gta tgc ttc atg tat gca agt gac cca gcc aag caa gtg agt<br>Ala Lys Val Cys Phe Met Tyr Ala Ser Asp Pro Ala Lys Gln Val Ser<br>120                  125              130            135 | 436 |
| atc cac aac tac acc atc tgg tca gtg ctg gtg gcc atc tgg act gtg<br>Ile His Asn Tyr Thr Ile Trp Ser Val Leu Val Ala Ile Trp Thr Val<br>              140              145              150 | 484 |
| gct agc ctg tta ccc ctg ccg gaa tgg ttc ttt agc acc atc agg cat<br>Ala Ser Leu Leu Pro Leu Pro Glu Trp Phe Phe Ser Thr Ile Arg His<br>                155              160              165 | 532 |
| cat gaa ggt gtg gaa atg tgc ctc gtg gat gta cca gct gtg gct gaa<br>His Glu Gly Val Glu Met Cys Leu Val Asp Val Pro Ala Val Ala Glu<br>            170              175              180 | 580 |
| gag ttt atg tcg atg ttt ggt aag ctc tac cca ctc ctg gca ttt ggc<br>Glu Phe Met Ser Met Phe Gly Lys Leu Tyr Pro Leu Leu Ala Phe Gly<br>185                  190                195 | 628 |
| ctt cca tta ttt ttt gcc agc ttt tat ttc tgg aga gct tat gac caa<br>Leu Pro Leu Phe Phe Ala Ser Phe Tyr Phe Trp Arg Ala Tyr Asp Gln<br>200                  205              210            215 | 676 |
| tgt aaa aaa cga gga act aag act caa aat ctt aga aac cag ata cgc<br>Cys Lys Lys Arg Gly Thr Lys Thr Gln Asn Leu Arg Asn Gln Ile Arg<br>              220              225              230 | 724 |
| tca aag caa gtc aca gtg atg ctg ctg agc att gcc atc atc tct gct<br>Ser Lys Gln Val Thr Val Met Leu Leu Ser Ile Ala Ile Ile Ser Ala<br>            235                240              245 | 772 |
| ctc ttg tgg ctc ccc gaa tgg gta gct tgg ctg tgg gta tgg cat ctg<br>Leu Leu Trp Leu Pro Glu Trp Val Ala Trp Leu Trp Val Trp His Leu<br>            250              255              260 | 820 |
| aag gct gca ggc ccg gcc cca cca caa ggt ttc ata gcc ctg tct caa<br>Lys Ala Ala Gly Pro Ala Pro Pro Gln Gly Phe Ile Ala Leu Ser Gln<br>265                  270                275 | 868 |
| gtc ttg atg ttt tcc atc tct tca gca aat cct ctc att ttt ctt gtg<br>Val Leu Met Phe Ser Ile Ser Ser Ala Asn Pro Leu Ile Phe Leu Val<br>280                  285              290            295 | 916 |
| atg tcg gaa gag ttc agg gaa ggc ttg aaa ggt gta tgg aaa tgg atg<br>Met Ser Glu Glu Phe Arg Glu Gly Leu Lys Gly Val Trp Lys Trp Met<br>              300              305              310 | 964 |
| ata acc aaa aaa cct cca act gtc tca gag tct cag gaa aca cca gct<br>Ile Thr Lys Lys Pro Pro Thr Val Ser Glu Ser Gln Glu Thr Pro Ala<br>            315              320              325 | 1012 |
| ggc aac tca gag ggt ctt cct gac aag gtc cca tct cca gaa tcc cca<br>Gly Asn Ser Glu Gly Leu Pro Asp Lys Val Pro Ser Pro Glu Ser Pro<br>            330              335              340 | 1060 |
| gca tcc ata cca gaa aaa gag aaa ccc agc tct ccc tcc tct ggc aaa<br>Ala Ser Ile Pro Glu Lys Glu Lys Pro Ser Ser Pro Ser Ser Gly Lys<br>345                  350              355 | 1108 |
| ggg aaa act gag aag gca gag att ccc atc ctt cct gac gta gag cag<br>Gly Lys Thr Glu Lys Ala Glu Ile Pro Ile Leu Pro Asp Val Glu Gln<br>360                  365              370            375 | 1156 |
| ttt tgg cat gag agg gac aca gtc cct tct gta caa ttg aag agc acc<br>Phe Trp His Glu Arg Asp Thr Val Pro Ser Val Gln Leu Lys Ser Thr | 1204 |

-continued

```
                         380                 385                 390
aac cct aca gat tgt ggt agc tca ggt aac tca gcg tgg tac cgc aaa        1252
Asn Pro Thr Asp Cys Gly Ser Ser Gly Asn Ser Ala Trp Tyr Arg Lys
            395                 400                 405 act gaa aaa tca gca tgt tgc cct aag acg gaa atc cat tca aca ttc        1300
Thr Glu Lys Ser Ala Cys Cys Pro Lys Thr Glu Ile His Ser Thr Phe
        410                 415                 420 tac ttc cag ata ctg ctt cta gca att cac aga aac aga aac cac atc        1348
Tyr Phe Gln Ile Leu Leu Leu Ala Ile His Arg Asn Arg Asn His Ile
    425                 430                 435 tca cgt ttc tca act aaa caa ctg ctt tta gga ctg cag cac aag ttc        1396
Ser Arg Phe Ser Thr Lys Gln Leu Leu Leu Gly Leu Gln His Lys Phe
440                 445                 450                 455 aga ttt tct gtc ttt cct taa gtc                                         1420
Arg Phe Ser Val Phe Pro  *
                460
```

<210> SEQ ID NO 5
<211> LENGTH: 461
<212> TYPE: PRT
<213> ORGANISM: Homo sapiens

<400> SEQUENCE: 5

```
Met Asn Val Ser Phe Ala His Leu His Phe Ala Gly Gly Tyr Leu Pro
1               5                   10                  15

Ser Asp Ser Gln Asp Trp Arg Thr Ile Ile Pro Ala Leu Leu Val Ala
            20                  25                  30

Val Cys Leu Val Gly Phe Val Gly Asn Leu Cys Val Ile Gly Ile Leu
        35                  40                  45

Leu His Asn Ala Trp Lys Gly Lys Pro Ser Met Ile His Ser Leu Ile
    50                  55                  60

Leu Asn Leu Ser Leu Ala Asp Leu Ser Leu Leu Leu Phe Ser Ala Pro
65                  70                  75                  80

Ile Arg Ala Thr Ala Tyr Ser Lys Ser Val Trp Asp Leu Gly Trp Phe
                85                  90                  95

Val Cys Lys Ser Ser Asp Trp Phe Ile His Thr Cys Met Ala Ala Lys
            100                 105                 110

Ser Leu Thr Ile Val Val Ala Lys Val Cys Phe Met Tyr Ala Ser
        115                 120                 125

Asp Pro Ala Lys Gln Val Ser Ile His Asn Tyr Thr Ile Trp Ser Val
    130                 135                 140

Leu Val Ala Ile Trp Thr Val Ala Ser Leu Leu Pro Leu Pro Glu Trp
145                 150                 155                 160

Phe Phe Ser Thr Ile Arg His His Glu Gly Val Glu Met Cys Leu Val
                165                 170                 175

Asp Val Pro Ala Val Ala Glu Glu Phe Met Ser Met Phe Gly Lys Leu
            180                 185                 190

Tyr Pro Leu Leu Ala Phe Gly Leu Pro Leu Phe Phe Ala Ser Phe Tyr
        195                 200                 205

Phe Trp Arg Ala Tyr Asp Gln Cys Lys Lys Arg Gly Thr Lys Thr Gln
    210                 215                 220

Asn Leu Arg Asn Gln Ile Arg Ser Lys Gln Val Thr Val Met Leu Leu
225                 230                 235                 240

Ser Ile Ala Ile Ile Ser Ala Leu Leu Trp Leu Pro Glu Trp Val Ala
                245                 250                 255

Trp Leu Trp Val Trp His Leu Lys Ala Ala Gly Pro Ala Pro Pro Gln
```

-continued

```
                  260                 265                 270
Gly Phe Ile Ala Leu Ser Gln Val Leu Met Phe Ser Ile Ser Ser Ala
            275                 280                 285
Asn Pro Leu Ile Phe Leu Val Met Ser Glu Glu Phe Arg Glu Gly Leu
            290                 295                 300
Lys Gly Val Trp Lys Trp Met Ile Thr Lys Lys Pro Pro Thr Val Ser
305                 310                 315                 320
Glu Ser Gln Glu Thr Pro Ala Gly Asn Ser Glu Gly Leu Pro Asp Lys
                325                 330                 335
Val Pro Ser Pro Glu Ser Pro Ala Ser Ile Pro Glu Lys Glu Lys Pro
            340                 345                 350
Ser Ser Pro Ser Ser Gly Lys Gly Lys Thr Glu Lys Ala Glu Ile Pro
            355                 360                 365
Ile Leu Pro Asp Val Glu Gln Phe Trp His Glu Arg Asp Thr Val Pro
            370                 375                 380
Ser Val Gln Leu Lys Ser Thr Asn Pro Thr Asp Cys Gly Ser Ser Gly
385                 390                 395                 400
Asn Ser Ala Trp Tyr Arg Lys Thr Glu Lys Ser Ala Cys Cys Pro Lys
                405                 410                 415
Thr Glu Ile His Ser Thr Phe Tyr Phe Gln Ile Leu Leu Ala Ile
                420                 425                 430
His Arg Asn Arg Asn His Ile Ser Arg Phe Ser Thr Lys Gln Leu Leu
                435                 440                 445
Leu Gly Leu Gln His Lys Phe Arg Phe Ser Val Phe Pro
        450                 455                 460

<210> SEQ ID NO 6
<211> LENGTH: 1386
<212> TYPE: DNA
<213> ORGANISM: Homo sapiens

<400> SEQUENCE: 6
atgaatgtgt cctttgctca cctccacttt gccggagggt acctgccctc tgattcccag      60
gactggagaa ccatcatccc ggctctcttg gtggctgtct gcctggtggg cttcgtggga     120
aacctgtgtg tgattggcat cctcctccac aatgcttgga aggaaaagcc atccatgatc     180
cactccctga ttctgaatct cagcctggct gatctctccc tcctgctgtt ttctgcacct     240
atccgagcta cggcgtactc caaaagtgtt tgggatctag ctggtttgt ctgcaagtcc     300 tctgactggt ttatccacac atgcatggca gccaagagcc tgacaatcgt tgtggtggcc     360
aaagtatgct tcatgtatgc aagtgaccca gccaagcaag tgagtatcca aactacacc     420 atctggtcag tgctggtggc catctggact gtggctagcc tgttaccct gccggaatgg     480 ttctttagca ccatcaggca tcatgaaggt gtggaaatgt gcctcgtgga tgtaccagct     540
gtggctgaag agtttatgtc gatgtttggt aagctctacc cactcctggc atttggcctt     600
ccattatttt ttgccagctt ttatttctgg agagcttatg accaatgtaa aaaacgagga     660
actaagactc aaaatcttag aaaccagata cgctcaaagc aagtcacagt gatgctgctg     720
agcattgcca tcatctctgc tctccttgtg ctccccgaat gggtagcttg gctgtgggta     780
tggcatctga aggctgcagg cccggcccca ccacaaggtt tcatagccct gtctcaagtc     840
ttgatgtttt ccatctcttc agcaaatcct ctcattttc ttgtgatgtc ggaagagttc     900
agggaaggct tgaaaggtgt atggaaatgg atgataacca aaaaacctcc aactgtctca     960
gagtctcagg aaacaccagc tggcaactca gagggtcttc ctgacaaggt cccatctcca    1020
```

-continued

| | |
|---|---|
| gaatccccag catccatacc agaaaaagag aaacccagct ctccctcctc tggcaaaggg | 1080 |
| aaaactgaga aggcagagat tcccatcctt cctgacgtag agcagttttg gcatgagagg | 1140 |
| gacacagtcc cttctgtaca attgaagagc accaaccta cagattgtgg tagctcaggt | 1200 |
| aactcagcgt ggtaccgcaa aactgaaaaa tcagcatgtt gccctaagac ggaaatccat | 1260 |
| tcaacattct acttccagat actgcttcta gcaattcaca gaaacagaaa ccacatctca | 1320 |
| cgtttctcaa ctaaacaact gcttttagga ctgcagcaca agttcagatt ttctgtcttt | 1380 |
| ccttaa | 1386 |

<210> SEQ ID NO 7
<211> LENGTH: 1352
<212> TYPE: DNA
<213> ORGANISM: Homo sapiens
<220> FEATURE:
<221> NAME/KEY: CDS
<222> LOCATION: (210)...(1301)

<400> SEQUENCE: 7

| | |
|---|---|
| tactcactat agggctcgag cggccgcccg ggcaggtcta gaattcagcg gccgctgaat | 60 |
| tctaggctgc tctgggcctt gctagccggc tctgcacctc ccagaagccg tgggcacgcc | 120 |
| gctcagctgc tccatcgcct cactttccca ggctcgcgcc cgaagcagag ccatgagaac | 180 |
| cccagggtgc ctggcgagcc gctagcgcc atg ggc ccc ggc gag gcg ctg ctg | 233 |
|  Met Gly Pro Gly Glu Ala Leu Leu | |
|  1 5 | |
| gcg ggt ctt ctg gtg atg gta ctg gcc gtg gcg ctg cta tcc aac gca | 281 |
| Ala Gly Leu Leu Val Met Val Leu Ala Val Ala Leu Leu Ser Asn Ala | |
|  10 15 20 | |
| ctg gtg ctg ctt tgt tgc gcc tac agc gct gag ctc cgt act cga gcc | 329 |
| Leu Val Leu Leu Cys Cys Ala Tyr Ser Ala Glu Leu Arg Thr Arg Ala | |
|  25 30 35 40 | |
| tca ggc gtc ctc ctg gtg aat ctg tcg ctg ggc cac ctg ctg ctg gcg | 377 |
| Ser Gly Val Leu Leu Val Asn Leu Ser Leu Gly His Leu Leu Leu Ala | |
|  45 50 55 | |
| gcg ctg gac atg ccc ttc acg ctg ctc ggt gtg atg cgc ggg cgg aca | 425 |
| Ala Leu Asp Met Pro Phe Thr Leu Leu Gly Val Met Arg Gly Arg Thr | |
|  60 65 70 | |
| ccg tcg gcg ccc ggc gca tgc caa gtc att ggc ttc ctg gac acc ttc | 473 |
| Pro Ser Ala Pro Gly Ala Cys Gln Val Ile Gly Phe Leu Asp Thr Phe | |
|  75 80 85 | |
| ctg gcg tcc aac gcg gcg ctg agc gtg gcg gcg ctg agc gca gac cag | 521 |
| Leu Ala Ser Asn Ala Ala Leu Ser Val Ala Ala Leu Ser Ala Asp Gln | |
|  90 95 100 | |
| tgg ctg gca gtg ggc ttc cca ctg cgc tac gcc gga cgc ctg cga ccg | 569 |
| Trp Leu Ala Val Gly Phe Pro Leu Arg Tyr Ala Gly Arg Leu Arg Pro | |
| 105 110 115 120 | |
| cgc tat gcc ggc ctg ctg ctg ggc tgt gcc tgg gga cag tcg ctg gcc | 617 |
| Arg Tyr Ala Gly Leu Leu Leu Gly Cys Ala Trp Gly Gln Ser Leu Ala | |
|  125 130 135 | |
| ttc tca ggc gct gca ctt ggc tgc tcg tgg ctt ggc tac agc agc gcc | 665 |
| Phe Ser Gly Ala Ala Leu Gly Cys Ser Trp Leu Gly Tyr Ser Ser Ala | |
|  140 145 150 | |
| ttc gcg tcc tgt tcg ctg cgc ctg ccg ccc gag cct gag cgt ccg cgc | 713 |
| Phe Ala Ser Cys Ser Leu Arg Leu Pro Pro Glu Pro Glu Arg Pro Arg | |
|  155 160 165 | |
| ttc gca gcc ttc acc gcc acg ctc cat gcc gtg ggc ttc gtg ctg ccg | 761 |
| Phe Ala Ala Phe Thr Ala Thr Leu His Ala Val Gly Phe Val Leu Pro | |
|  170 175 180 | |

```
ctg gcg gtg ctc tgc ctc acc tcg ctc cag gtg cac cgg gtg gca cgc      809
Leu Ala Val Leu Cys Leu Thr Ser Leu Gln Val His Arg Val Ala Arg
185                 190                 195                 200 agc cac tgc cag cgc atg gac act gtc acc atg aag gcg ctc gcg ctg      857
Ser His Cys Gln Arg Met Asp Thr Val Thr Met Lys Ala Leu Ala Leu
                205                 210                 215 ctc gcc gac ctg cac ccc agt gtg cgg cag cgc tgc ctc atc cag cag      905
Leu Ala Asp Leu His Pro Ser Val Arg Gln Arg Cys Leu Ile Gln Gln
                220                 225                 230 aag cgg cgc cgc cac cgc gcc acc agg aag att ggc att gct att gcg      953
Lys Arg Arg Arg His Arg Ala Thr Arg Lys Ile Gly Ile Ala Ile Ala
            235                 240                 245 acc ttc ctc atc tgc ttt gcc ccg tat gtc atg acc agg ctg gcg gag     1001
Thr Phe Leu Ile Cys Phe Ala Pro Tyr Val Met Thr Arg Leu Ala Glu
        250                 255                 260 ctc gtg ccc ttc gtc acc gtg aac gcc cag tgg ggc atc ctc agc aag     1049
Leu Val Pro Phe Val Thr Val Asn Ala Gln Trp Gly Ile Leu Ser Lys
265                 270                 275                 280 tgc ctg acc tac agc aag gcg gtg gcc gac ccg ttc acg tac tct ctg     1097
Cys Leu Thr Tyr Ser Lys Ala Val Ala Asp Pro Phe Thr Tyr Ser Leu
                285                 290                 295 ctc cgc cgg ccg ttc cgc caa gtc ctg gcc ggc atg gtg cac cgg ctg     1145
Leu Arg Arg Pro Phe Arg Gln Val Leu Ala Gly Met Val His Arg Leu
                300                 305                 310 ctg aag aga acc ccg cgc cca gca tcc acc cat gac agc tct ctg gat     1193
Leu Lys Arg Thr Pro Arg Pro Ala Ser Thr His Asp Ser Ser Leu Asp
            315                 320                 325 gtg gcc ggc atg gtg cac cag ctg ctg aag aga acc ccg cgc cca gcg     1241
Val Ala Gly Met Val His Gln Leu Leu Lys Arg Thr Pro Arg Pro Ala
        330                 335                 340 tcc acc cac aac ggc tct gtg gac aca gag aat gat tcc tgc ctg cag     1289
Ser Thr His Asn Gly Ser Val Asp Thr Glu Asn Asp Ser Cys Leu Gln
345                 350                 355                 360 cag aca cac tga gggcctggca gggctcatcg ccccccacctt ctaagaagcc         1341
Gln Thr His * ctgtggaaag a                                                        1352

<210> SEQ ID NO 8
<211> LENGTH: 363
<212> TYPE: PRT
<213> ORGANISM: Homo sapiens

<400> SEQUENCE: 8

Met Gly Pro Gly Glu Ala Leu Leu Ala Gly Leu Leu Val Met Val Leu
 1               5                  10                  15

Ala Val Ala Leu Leu Ser Asn Ala Leu Val Leu Leu Cys Cys Ala Tyr
                20                  25                  30

Ser Ala Glu Leu Arg Thr Arg Ala Ser Gly Val Leu Leu Val Asn Leu
            35                  40                  45

Ser Leu Gly His Leu Leu Leu Ala Ala Leu Asp Met Pro Phe Thr Leu
        50                  55                  60

Leu Gly Val Met Arg Gly Arg Thr Pro Ser Ala Pro Gly Ala Cys Gln
65                  70                  75                  80

Val Ile Gly Phe Leu Asp Thr Phe Leu Ala Ser Asn Ala Ala Leu Ser
                85                  90                  95

Val Ala Ala Leu Ser Ala Asp Gln Trp Leu Ala Val Gly Phe Pro Leu
            100                 105                 110
```

```
Arg Tyr Ala Gly Arg Leu Arg Pro Arg Tyr Ala Gly Leu Leu Leu Gly
            115                 120                 125
Cys Ala Trp Gly Gln Ser Leu Ala Phe Ser Gly Ala Ala Leu Gly Cys
        130                 135                 140
Ser Trp Leu Gly Tyr Ser Ser Ala Phe Ala Ser Cys Ser Leu Arg Leu
145                 150                 155                 160
Pro Pro Glu Pro Glu Arg Pro Arg Phe Ala Ala Phe Thr Ala Thr Leu
                165                 170                 175
His Ala Val Gly Phe Val Leu Pro Leu Ala Val Leu Cys Leu Thr Ser
            180                 185                 190
Leu Gln Val His Arg Val Ala Arg Ser His Cys Gln Arg Met Asp Thr
        195                 200                 205
Val Thr Met Lys Ala Leu Ala Leu Leu Ala Asp Leu His Pro Ser Val
210                 215                 220
Arg Gln Arg Cys Leu Ile Gln Gln Lys Arg Arg His Arg Ala Thr
225                 230                 235                 240
Arg Lys Ile Gly Ile Ala Ile Ala Thr Phe Leu Ile Cys Phe Ala Pro
                245                 250                 255
Tyr Val Met Thr Arg Leu Ala Glu Leu Val Pro Phe Val Thr Val Asn
            260                 265                 270
Ala Gln Trp Gly Ile Leu Ser Lys Cys Leu Thr Tyr Ser Lys Ala Val
        275                 280                 285
Ala Asp Pro Phe Thr Tyr Ser Leu Leu Arg Arg Pro Phe Arg Gln Val
290                 295                 300
Leu Ala Gly Met Val His Arg Leu Leu Lys Arg Thr Pro Arg Pro Ala
305                 310                 315                 320
Ser Thr His Asp Ser Ser Leu Asp Val Ala Gly Met Val His Gln Leu
                325                 330                 335
Leu Lys Arg Thr Pro Arg Pro Ala Ser Thr His Asn Gly Ser Val Asp
            340                 345                 350
Thr Glu Asn Asp Ser Cys Leu Gln Gln Thr His
        355                 360

<210> SEQ ID NO 9
<211> LENGTH: 1092
<212> TYPE: DNA
<213> ORGANISM: Homo sapiens

<400> SEQUENCE: 9
atgggccccg gcgaggcgct gctggcgggt cttctggtga tggtactggc cgtggcgctg      60
ctatccaacg cactggtgct gctttgttgc gcctacagcg ctgagctccg tactcgagcc     120
tcaggcgtcc tcctggtgaa tctgtcgctg gccacctgc tgctggcggc gctggacatg     180
cccttcacgc tgctcggtgt gatgcgcggg cggacaccgt cggcgcccgg cgcatgccaa     240
gtcattggct tcctggacac cttcctggcg tccaacgcgg cgctgagcgt gcggcgcctg     300
agcgcagacc agtggctggc agtgggcttc ccactgcgct acgccggacg cctgcgaccg     360
cgctatgccg gctgctgct gggctgtgcc tggggacagt cgctggcctt ctcaggcgct     420
gcacttggct gctcgtggct tggctacagc agcgccttcg cgtcctgttc gctgcgcctg     480
ccgcccgagc tgagcgtcc gcgcttcgca gccttcaccg ccacgctcca tgccgtgggc     540
ttcgtgctgc cgctggcggt gctctgcctc acctcgctcc aggtgcaccg ggtggcacgc     600
agccactgcc agcgcatgga cactgtcacc atgaaggcgc tcgcgctgct cgccgacctg     660 cacccccagtg tgcggcagcg ctgcctcatc agcagaaagc ggcgccgcca ccgcgccacc     720
```

```
aggaagattg gcattgctat tgcgaccttc ctcatctgct ttgccccgta tgtcatgacc      780
aggctggcgg agctcgtgcc cttcgtcacc gtgaacgccc agtggggcat cctcagcaag      840
tgcctgacct acagcaaggc ggtggccgac ccgttcacgt actctctgct ccgccggccg      900
ttccgccaag tcctggccgg catggtgcac cggctgctga agagaacccc gcgcccagca      960
tccacccatg acagctctct ggatgtggcc ggcatggtgc accagctgct gaagagaacc     1020
ccgcgcccag cgtccaccca aacggctct gtggacacag agaatgattc ctgcctgcag      1080
cagacacact ga                                                         1092

<210> SEQ ID NO 10
<211> LENGTH: 1178
<212> TYPE: DNA
<213> ORGANISM: Homo sapiens
<220> FEATURE:
<221> NAME/KEY: CDS
<222> LOCATION: (152)...(1057)

<400> SEQUENCE: 10
ctgtgacttt aagtatttct aagggcagag caatgggagg tggagaatgc tgggttgcag       60
gtgacactat aaacgtagat catgcctcct atttccatgc aggacctccc agccctgaag      120
acaaacatca gtgacagaca tcagtggcag a atg gcc tcc cgg tat gtg gca         172
                                  Met Ala Ser Arg Tyr Val Ala
                                    1               5 gtg gga atg atc tta tca cag acc gtg gtg gga gtc ctg ggg agc ttc        220
Val Gly Met Ile Leu Ser Gln Thr Val Val Gly Val Leu Gly Ser Phe
            10                  15                  20 tct gtt ctt ctc cat tat ctc tcc ttt tac tgc act ggg tgc agg tta        268
Ser Val Leu Leu His Tyr Leu Ser Phe Tyr Cys Thr Gly Cys Arg Leu
    25                  30                  35 agg tcc aca gat ttg att gtt aag cac ctg att gta gcc aac ttc tta        316
Arg Ser Thr Asp Leu Ile Val Lys His Leu Ile Val Ala Asn Phe Leu
40                  45                  50                  55 gct ctc cgc tgt aaa gga gtc ccc cag aca atg gca gct ttt ggg gtt        364
Ala Leu Arg Cys Lys Gly Val Pro Gln Thr Met Ala Ala Phe Gly Val
                60                  65                  70 aga tat ttt ctc aat gct ctt ggg tgc aaa ctt gtt ttc tat ctc cat        412
Arg Tyr Phe Leu Asn Ala Leu Gly Cys Lys Leu Val Phe Tyr Leu His
            75                  80                  85 aga gtg ggc agg gga gtg tcc att ggc acc acc tgc ctc ttg agt gtc        460
Arg Val Gly Arg Gly Val Ser Ile Gly Thr Thr Cys Leu Leu Ser Val
        90                  95                 100 ttc cag gtg atc acg gtc agc tcc agg aaa tcc agg tgg gca aaa ctt        508
Phe Gln Val Ile Thr Val Ser Ser Arg Lys Ser Arg Trp Ala Lys Leu
    105                 110                 115 aaa gag aaa gcc ccc aag cat gtt ggc ttt tct gtt ctc ctg tgc tgg        556
Lys Glu Lys Ala Pro Lys His Val Gly Phe Ser Val Leu Leu Cys Trp
120                 125                 130                 135 atc gtg tgc atg ttg gta aac atc atc ttt ccc atg tat gtg gct ggc        604
Ile Val Cys Met Leu Val Asn Ile Ile Phe Pro Met Tyr Val Ala Gly
                140                 145                 150 aaa tgg aac tac aca aac atc aca gtg aac gag gat ttg gga tac tgt        652
Lys Trp Asn Tyr Thr Asn Ile Thr Val Asn Glu Asp Leu Gly Tyr Cys
            155                 160                 165 tct ggg gga ggc aac aac aaa atc gca cag aca ctg cgt gca atg ttg        700
Ser Gly Gly Gly Asn Asn Lys Ile Ala Gln Thr Leu Arg Ala Met Leu
        170                 175                 180 tta tca ttc cct gat gtg ttg tgt ctg ggg ctc atg ttc tgg gtc agc        748
Leu Ser Phe Pro Asp Val Leu Cys Leu Gly Leu Met Phe Trp Val Ser
```

-continued

```
Leu Ser Phe Pro Asp Val Leu Cys Leu Gly Leu Met Phe Trp Val Ser
    185                 190                 195 agc tcc atg gtt tgc ata ctg cac agg cac aag cag cgg gtc cag cac    796
Ser Ser Met Val Cys Ile Leu His Arg His Lys Gln Arg Val Gln His
200                 205                 210                 215 att gat agg agc gat ctc tcc ccc aga gcc tcc cca gag aac aga gct    844
Ile Asp Arg Ser Asp Leu Ser Pro Arg Ala Ser Pro Glu Asn Arg Ala
                220                 225                 230 acg cag agc atc ctc atc ctg gtg agc acc ttt gtg tct tct tac act    892
Thr Gln Ser Ile Leu Ile Leu Val Ser Thr Phe Val Ser Ser Tyr Thr
                235                 240                 245 ctc tcc tgc ctt ttc caa gtt tgt atg gct ctt ttg gat aat ccc aat    940
Leu Ser Cys Leu Phe Gln Val Cys Met Ala Leu Leu Asp Asn Pro Asn
            250                 255                 260 agt tta ctg gtg aac act tca gcc tta atg agt gta tgt ttc cca act    988
Ser Leu Leu Val Asn Thr Ser Ala Leu Met Ser Val Cys Phe Pro Thr
        265                 270                 275 ctc agc ccc ttt gtt ctc atg agc tgt gac ccc agt gta tac agg ttt   1036
Leu Ser Pro Phe Val Leu Met Ser Cys Asp Pro Ser Val Tyr Arg Phe
280                 285                 290                 295 tgt ttt gcc tgg aaa aga tga caagatctcc taacctcatc ataaacatgt      1087
Cys Phe Ala Trp Lys Arg  *
                300 acattgtata tatttgctca tggttcaatt gatgacttac tcttctgtgc cgcaacctgc  1147 ccgggcggcc gctcgagccc tatagtgagt a                                 1178

<210> SEQ ID NO 11
<211> LENGTH: 301
<212> TYPE: PRT
<213> ORGANISM: Homo sapiens

<400> SEQUENCE: 11

Met Ala Ser Arg Tyr Val Ala Val Gly Met Ile Leu Ser Gln Thr Val
1               5                   10                  15

Val Gly Val Leu Gly Ser Phe Ser Val Leu Leu His Tyr Leu Ser Phe
            20                  25                  30

Tyr Cys Thr Gly Cys Arg Leu Arg Ser Thr Asp Leu Ile Val Lys His
        35                  40                  45

Leu Ile Val Ala Asn Phe Leu Ala Leu Arg Cys Lys Gly Val Pro Gln
    50                  55                  60

Thr Met Ala Ala Phe Gly Val Arg Tyr Phe Leu Asn Ala Leu Gly Cys
65                  70                  75                  80

Lys Leu Val Phe Tyr Leu His Arg Val Gly Arg Gly Val Ser Ile Gly
                85                  90                  95

Thr Thr Cys Leu Leu Ser Val Phe Gln Val Ile Thr Val Ser Ser Arg
            100                 105                 110

Lys Ser Arg Trp Ala Lys Leu Lys Glu Lys Ala Pro Lys His Val Gly
        115                 120                 125

Phe Ser Val Leu Leu Cys Trp Ile Val Cys Met Leu Val Asn Ile Ile
    130                 135                 140

Phe Pro Met Tyr Val Ala Gly Lys Trp Asn Tyr Thr Asn Ile Thr Val
145                 150                 155                 160

Asn Glu Asp Leu Gly Tyr Cys Ser Gly Gly Asn Asn Lys Ile Ala
                165                 170                 175

Gln Thr Leu Arg Ala Met Leu Leu Ser Phe Pro Asp Val Leu Cys Leu
            180                 185                 190
```

| Gly | Leu | Met | Phe | Trp | Val | Ser | Ser | Met | Val | Cys | Ile | Leu | His | Arg |
| | | 195 | | | | 200 | | | | 205 | | | | |

| His | Lys | Gln | Arg | Val | Gln | His | Ile | Asp | Arg | Ser | Asp | Leu | Ser | Pro | Arg |
| 210 | | | | | 215 | | | | | 220 | | | | | |

| Ala | Ser | Pro | Glu | Asn | Arg | Ala | Thr | Gln | Ser | Ile | Leu | Ile | Leu | Val | Ser |
| 225 | | | | | 230 | | | | | 235 | | | | | 240 |

| Thr | Phe | Val | Ser | Tyr | Thr | Leu | Ser | Cys | Leu | Phe | Gln | Val | Cys | Met |
| | | | | 245 | | | | | 250 | | | | | 255 |

| Ala | Leu | Leu | Asp | Asn | Pro | Asn | Ser | Leu | Leu | Val | Asn | Thr | Ser | Ala | Leu |
| | | | 260 | | | | | 265 | | | | | 270 | | |

| Met | Ser | Val | Cys | Phe | Pro | Thr | Leu | Ser | Pro | Phe | Val | Leu | Met | Ser | Cys |
| | | 275 | | | | | 280 | | | | | 285 | | | |

| Asp | Pro | Ser | Val | Tyr | Arg | Phe | Cys | Phe | Ala | Trp | Lys | Arg |
| | | 290 | | | | | 295 | | | | 300 | |

<210> SEQ ID NO 12
<211> LENGTH: 906
<212> TYPE: DNA
<213> ORGANISM: Homo sapiens

<400> SEQUENCE: 12

```
atggcctccc ggtatgtggc agtgggaatg atcttatcac agaccgtggt gggagtcctg      60
gggagcttct ctgttcttct ccattatctc tcctttttact gcactgggtg caggttaagg    120
tccacagatt tgattgttaa gcacctgatt gtagccaact tcttagctct ccgctgtaaa    180
ggagtccccc agacaatggc agcttttggg gttagatatt ttctcaatgc tcttgggtgc    240
aaacttgttt tctatctcca tagagtgggc aggggagtgt ccattggcac cacctgcctc    300
ttgagtgtct tccaggtgat cacggtcagc tccaggaaat ccaggtgggc aaaacttaaa    360
gagaaagccc ccaagcatgt tggcttttct gttctcctgt gctggatcgt gtgcatgttg    420
gtaaacatca tctttcccat gtatgtggct ggcaaatgga actacacaaa catcacagtg    480
aacgaggatt tgggatactg ttctggggga ggcaacaaca aaatcgcaca gacactgcgt    540
gcaatgttgt tatcattccc tgatgtgttg tgtctggggc tcatgttctg ggtcagcagc    600
tccatggttt gcatactgca caggcacaag cagcgggtcc agcacattga taggagcgat    660
ctctccccca gagcctcccc agagaacaga gctacgcaga gcatcctcat cctggtgagc    720
acctttgtgt cttcttacac tctctcctgc ctttttccaag tttgtatggc tcttttggat    780
aatcccaata gttactggt gaacacttca gccttaatga gtgtatgttt cccaactctc    840
agccccttttg ttctcatgag ctgtgacccc agtgtataca ggttttgttt tgcctggaaa    900
agatga                                                               906
```

<210> SEQ ID NO 13
<211> LENGTH: 3492
<212> TYPE: DNA
<213> ORGANISM: Homo sapiens
<220> FEATURE:
<221> NAME/KEY: CDS
<222> LOCATION: (73)...(2064)

<400> SEQUENCE: 13

```
tgccaggcga gacaggaact tctttcccct tctctgtgtc aggatcgcag aaagtatgtc       60
ccttctctca cc atg agc tgg ctc tcc agt tcc cag gga gtg gta cta aca      111
              Met Ser Trp Leu Ser Ser Ser Gln Gly Val Val Leu Thr
                1               5                  10 gcc tac cac ccc agc ggc aag gac cag gcc gtc ggg aac agc cat gca       159
```

```
Ala Tyr His Pro Ser Gly Lys Asp Gln Ala Val Gly Asn Ser His Ala
     15                  20                  25 aag gca ggg gag gaa gcc acc tcg agt cgc aga tat ggc cag tac act      207
Lys Ala Gly Glu Glu Ala Thr Ser Ser Arg Arg Tyr Gly Gln Tyr Thr
 30                  35                  40                  45 atg aac cag gaa agc acc acc atc aaa gtt atg gag aag cct cca ttt      255
Met Asn Gln Glu Ser Thr Thr Ile Lys Val Met Glu Lys Pro Pro Phe
                 50                  55                  60 gat cga tca att tcc cag gat tct ttg gat gaa cta tct atg gaa gac      303
Asp Arg Ser Ile Ser Gln Asp Ser Leu Asp Glu Leu Ser Met Glu Asp
                 65                  70                  75 tat tgg ata gaa cta gaa aac atc aag aaa tct agt gaa aac agc caa      351
Tyr Trp Ile Glu Leu Glu Asn Ile Lys Lys Ser Ser Glu Asn Ser Gln
         80                  85                  90 gaa gat caa gag gtg gtt gtt gtc aaa gag cct gat gag gga gaa ttg      399
Glu Asp Gln Glu Val Val Val Val Lys Glu Pro Asp Glu Gly Glu Leu
         95                 100                 105 gaa gaa gag tgg ctt aaa gag gcc ggt tta tcc aat ctc ttc gga gag      447
Glu Glu Glu Trp Leu Lys Glu Ala Gly Leu Ser Asn Leu Phe Gly Glu
110                 115                 120                 125 tct gct gga gat cca cag gaa agc att gtg ttt tta tca aca ttg acg      495
Ser Ala Gly Asp Pro Gln Glu Ser Ile Val Phe Leu Ser Thr Leu Thr
                130                 135                 140 cgg acc cag gca gca gca gtt cag aag cga gta gag acg gtc tcc cag      543
Arg Thr Gln Ala Ala Ala Val Gln Lys Arg Val Glu Thr Val Ser Gln
                145                 150                 155 acc ttg aga aaa aaa aac aaa cag tac cag att cct gac gtc aga gac      591
Thr Leu Arg Lys Lys Asn Lys Gln Tyr Gln Ile Pro Asp Val Arg Asp
        160                 165                 170 ata ttt gct caa cag aga gaa tca aaa gaa aca gct cca ggt ggc act      639
Ile Phe Ala Gln Gln Arg Glu Ser Lys Glu Thr Ala Pro Gly Gly Thr
        175                 180                 185 gaa tcg cag tca ctt aga aca aat gaa aac aaa tac caa gga aga gat      687
Glu Ser Gln Ser Leu Arg Thr Asn Glu Asn Lys Tyr Gln Gly Arg Asp
190                 195                 200                 205 gac gag gca tct aac ctt gtt ggt gaa gag aag ctg atc cca cct gag      735
Asp Glu Ala Ser Asn Leu Val Gly Glu Glu Lys Leu Ile Pro Pro Glu
                210                 215                 220 gag acg cct gcc cct gaa aca gac atc aac ctg gag gta tca ttt gcc      783
Glu Thr Pro Ala Pro Glu Thr Asp Ile Asn Leu Glu Val Ser Phe Ala
                225                 230                 235 gag caa gca ctc aat cag aaa gag agc tcc aag gag aaa atc cag aag      831
Glu Gln Ala Leu Asn Gln Lys Glu Ser Ser Lys Glu Lys Ile Gln Lys
                240                 245                 250 agc aaa ggc gat gat gcc aca tta cct agt ttc aga ttg cca aaa gac      879
Ser Lys Gly Asp Asp Ala Thr Leu Pro Ser Phe Arg Leu Pro Lys Asp
        255                 260                 265 aaa acg ggt acc aca agg att ggt gac ctc gca ccc cag gac atg aag      927
Lys Thr Gly Thr Thr Arg Ile Gly Asp Leu Ala Pro Gln Asp Met Lys
270                 275                 280                 285 aaa gtt tgc cat tta gcc cta att gag ctg act gcc ctc tat gat gta      975
Lys Val Cys His Leu Ala Leu Ile Glu Leu Thr Ala Leu Tyr Asp Val
                290                 295                 300 ttg ggt att gag ctg aaa caa caa aaa gct gtg aaa atc aaa aca aaa     1023
Leu Gly Ile Glu Leu Lys Gln Gln Lys Ala Val Lys Ile Lys Thr Lys
                305                 310                 315 gat tct ggt ctt ttt tgc gtt cca ttg aca gcg cta tta gaa caa gat     1071
Asp Ser Gly Leu Phe Cys Val Pro Leu Thr Ala Leu Leu Glu Gln Asp
        320                 325                 330
```

```
cag agg aaa gta cca gga atg cga ata ccc ttg atc ttt caa aaa ctg      1119
Gln Arg Lys Val Pro Gly Met Arg Ile Pro Leu Ile Phe Gln Lys Leu
    335                 340                 345 att tct cga att gaa gag aga ggt ttg gaa aca gaa ggc ctc tta cgg      1167
Ile Ser Arg Ile Glu Glu Arg Gly Leu Glu Thr Glu Gly Leu Leu Arg
350                 355                 360                 365 atc cct gga gct gcc att aga atc aag aat ctt tgc caa gaa cta gaa      1215
Ile Pro Gly Ala Ala Ile Arg Ile Lys Asn Leu Cys Gln Glu Leu Glu
                370                 375                 380 gca aag ttt tat gaa ggg act ttt aat tgg gaa agt gtc aaa cag cat      1263
Ala Lys Phe Tyr Glu Gly Thr Phe Asn Trp Glu Ser Val Lys Gln His
            385                 390                 395 gat gcc gcc agc ctg ctg aag ctc ttc att cgg gag ttg ccc cag cca      1311
Asp Ala Ala Ser Leu Leu Lys Leu Phe Ile Arg Glu Leu Pro Gln Pro
        400                 405                 410 ctg ctc agt gtg gag tat ctc aaa gcc ttt cag gct gtc cag aat ctt      1359
Leu Leu Ser Val Glu Tyr Leu Lys Ala Phe Gln Ala Val Gln Asn Leu
    415                 420                 425 cca acc aag aag cag caa cta cag gct ttg aac ctt ctt gtc atc ctc      1407
Pro Thr Lys Lys Gln Gln Leu Gln Ala Leu Asn Leu Leu Val Ile Leu
430                 435                 440                 445 cta cct gat gca aac agg gac aca ctg aag gcc ctt ctt gaa ttt ctc      1455
Leu Pro Asp Ala Asn Arg Asp Thr Leu Lys Ala Leu Leu Glu Phe Leu
                450                 455                 460 caa aga gta ata gat aat aaa gaa aaa aat aaa atg aca gtc atg aat      1503
Gln Arg Val Ile Asp Asn Lys Glu Lys Asn Lys Met Thr Val Met Asn
            465                 470                 475 gta gca atg gtc atg gcc ccg aat ctc ttt atg tgt cat gca ttg gga      1551
Val Ala Met Val Met Ala Pro Asn Leu Phe Met Cys His Ala Leu Gly
        480                 485                 490 ttg aag tcc agt gaa cag cga gaa ttt gta atg gca gct ggg aca gca      1599
Leu Lys Ser Ser Glu Gln Arg Glu Phe Val Met Ala Ala Gly Thr Ala
    495                 500                 505 aat acc atg cac tta ttg att aag tac caa aaa ctt ctg tgg aca att      1647
Asn Thr Met His Leu Leu Ile Lys Tyr Gln Lys Leu Leu Trp Thr Ile
510                 515                 520                 525 ccc aag ttt att gta aac caa gtg agg aag caa aac acg gaa aat cat      1695
Pro Lys Phe Ile Val Asn Gln Val Arg Lys Gln Asn Thr Glu Asn His
                530                 535                 540 aaa aag gat aaa aga gcc atg aag aaa ttg ctg aag aaa atg gct tat      1743
Lys Lys Asp Lys Arg Ala Met Lys Lys Leu Leu Lys Lys Met Ala Tyr
            545                 550                 555 gac cga gaa aaa tat gaa aag caa gat aag agt aca aat gat gct gac      1791
Asp Arg Glu Lys Tyr Glu Lys Gln Asp Lys Ser Thr Asn Asp Ala Asp
        560                 565                 570 gtt cct cag gga gtg att cga gtg caa gct ccc cat ctt tcg aaa gtt      1839
Val Pro Gln Gly Val Ile Arg Val Gln Ala Pro His Leu Ser Lys Val
    575                 580                 585 tcc atg gca ata cag cta act gaa gaa cta aaa gcc agt gat gta ctt      1887
Ser Met Ala Ile Gln Leu Thr Glu Glu Leu Lys Ala Ser Asp Val Leu
590                 595                 600                 605 gcc agg ttt ctc agc caa gaa agt ggg gtt gcc cag act ctc aag aaa      1935
Ala Arg Phe Leu Ser Gln Glu Ser Gly Val Ala Gln Thr Leu Lys Lys
                610                 615                 620 gga gaa gtt ttt ttg tat gaa att gga gga aat att ggg gaa cgc tgc      1983
Gly Glu Val Phe Leu Tyr Glu Ile Gly Gly Asn Ile Gly Glu Arg Cys
            625                 630                 635 ctt gat gat gac act tac atg aag gat tta tat cag ctt aac cca aat      2031
Leu Asp Asp Asp Thr Tyr Met Lys Asp Leu Tyr Gln Leu Asn Pro Asn
        640                 645                 650
```

-continued

```
gct gag tgg gtt ata aag tca aag cca ttg tag aagacttaac aagctgcaga    2084
Ala Glu Trp Val Ile Lys Ser Lys Pro Leu  *
    655                 660 taaccatgtg gacttctgtc ataattcttg ctgagtcaag agtgtaaata aaagaaatgg    2144
caggactcat attattcagt tgtacccaag tatttaaaaa tgactctctt aagccttaaa    2204
aagtcataga tttgtgctgc tgccagaatt atattaatta ttattaatgt tattattaga    2264
aaaaaaattt ctggagtgag agtaaagagg cttaattagt ttgtgggcag ttttcatatg    2324
ctctgtgaaa tgtgtccaga tgtgacatag tttttttttt ttaatatgtg gaaatgtctt    2384
ctcttcccat tcttttctcc taaaatcata tatactgtaa tatatgctct ctcacctcta    2444
ttacctcctc acatctaccc tttcccagtt aggtttgctt tttgaccaaa agataacaa     2504 ataccaggta tggcaagttg tgaagacagc acattaaaac atacctaatt tcacagtatt    2564
cctgtcacga cagaatgtta gtattcatct ctttgaatca tttgctcaaa taataacatt    2624 ccacctttc ctgctgtatc acaggaagtg atttgcattt tttttcagtt catctgactt     2684
atgttcacag aaccgtatca gcgaccaaga aataggact gtcagaagct gccagttatt     2744
actgaaccat taaatactta tatactaaga ataaataaaa tatacccatg tgaaataata    2804
attggattat ggataacaag agagtgaaag ccaaagcact ttctgtctac tgtactcttc    2864
taaatggaat tttaaaagtc atagctggct ttacgtgttg tcattattag cattataaat    2924
atgcatgata gtataatcca gtaatggttg aagaatgtat tttacttaaa gagggatttt    2984 ttttttttaag tcctgaataa gtctactgga agaattattc ttctgggtga aaaagctttt   3044
gtttgtgttc ttatttttaaa taatcggagt caatttatta aaatgttctt gaaagtacta   3104
ttcccaggga ttttaatgca caaaccatat tgtgacaaga gatgagcctc tgtactgtaa    3164
ataagaaatg aagtagagaa atgttaaata ttttatgagt ttagaatata gtaaataaaa    3224
ggtgatgtaa atgaatgctg cacaaacggt gttcatgata cttttagtag tactttagga   3284
aaaactacac attctcagaa gctcttgatg tctctaatga agggggggaa tgctgttaat    3344
gagaacagtc ataaattttt agcatataat tacaagaaca gcctgtggat atgatcactt    3404
aaatgatttt gtggtgattc gtgccattgc tttttatttt aaaagaaaat tttgtaatta    3464
aatgcctttt tctaaaaaaa aaaaaaaa                                       3492
```

<210> SEQ ID NO 14
<211> LENGTH: 663
<212> TYPE: PRT
<213> ORGANISM: Homo sapiens

<400> SEQUENCE: 14

```
Met Ser Trp Leu Ser Ser Ser Gln Gly Val Val Leu Thr Ala Tyr His
 1               5                  10                  15

Pro Ser Gly Lys Asp Gln Ala Val Gly Asn Ser His Ala Lys Ala Gly
                20                  25                  30

Glu Glu Ala Thr Ser Ser Arg Arg Tyr Gly Gln Tyr Thr Met Asn Gln
            35                  40                  45

Glu Ser Thr Thr Ile Lys Val Met Glu Lys Pro Pro Phe Asp Arg Ser
        50                  55                  60

Ile Ser Gln Asp Ser Leu Asp Glu Leu Ser Met Glu Asp Tyr Trp Ile
 65                  70                  75                  80

Glu Leu Glu Asn Ile Lys Lys Ser Ser Glu Asn Ser Gln Glu Asp Gln
                85                  90                  95
```

-continued

```
Glu Val Val Val Lys Glu Pro Asp Glu Gly Glu Leu Glu Glu Glu
            100                 105                 110

Trp Leu Lys Glu Ala Gly Leu Ser Asn Leu Phe Gly Glu Ser Ala Gly
        115                 120                 125

Asp Pro Gln Glu Ser Ile Val Phe Leu Ser Thr Leu Thr Arg Thr Gln
    130                 135                 140

Ala Ala Ala Val Gln Lys Arg Val Glu Thr Val Ser Gln Thr Leu Arg
145                 150                 155                 160

Lys Lys Asn Lys Gln Tyr Gln Ile Pro Asp Val Arg Asp Ile Phe Ala
                165                 170                 175

Gln Gln Arg Glu Ser Lys Glu Thr Ala Pro Gly Gly Thr Glu Ser Gln
            180                 185                 190

Ser Leu Arg Thr Asn Glu Asn Lys Tyr Gln Gly Arg Asp Asp Glu Ala
        195                 200                 205

Ser Asn Leu Val Gly Glu Glu Lys Leu Ile Pro Pro Glu Glu Thr Pro
    210                 215                 220

Ala Pro Glu Thr Asp Ile Asn Leu Glu Val Ser Phe Ala Glu Gln Ala
225                 230                 235                 240

Leu Asn Gln Lys Glu Ser Ser Lys Glu Lys Ile Gln Lys Ser Lys Gly
                245                 250                 255

Asp Asp Ala Thr Leu Pro Ser Phe Arg Leu Pro Lys Asp Lys Thr Gly
            260                 265                 270

Thr Thr Arg Ile Gly Asp Leu Ala Pro Gln Asp Met Lys Lys Val Cys
        275                 280                 285

His Leu Ala Leu Ile Glu Leu Thr Ala Leu Tyr Asp Val Leu Gly Ile
    290                 295                 300

Glu Leu Lys Gln Gln Lys Ala Val Lys Ile Lys Thr Lys Asp Ser Gly
305                 310                 315                 320

Leu Phe Cys Val Pro Leu Thr Ala Leu Leu Glu Gln Asp Gln Arg Lys
                325                 330                 335

Val Pro Gly Met Arg Ile Pro Leu Ile Phe Gln Lys Leu Ile Ser Arg
            340                 345                 350

Ile Glu Glu Arg Gly Leu Glu Thr Glu Gly Leu Leu Arg Ile Pro Gly
        355                 360                 365

Ala Ala Ile Arg Ile Lys Asn Leu Cys Gln Glu Leu Glu Ala Lys Phe
    370                 375                 380

Tyr Glu Gly Thr Phe Asn Trp Glu Ser Val Lys Gln His Asp Ala Ala
385                 390                 395                 400

Ser Leu Leu Lys Leu Phe Ile Arg Glu Leu Pro Gln Pro Leu Leu Ser
                405                 410                 415

Val Glu Tyr Leu Lys Ala Phe Gln Ala Val Gln Asn Leu Pro Thr Lys
            420                 425                 430

Lys Gln Gln Leu Gln Ala Leu Asn Leu Leu Val Ile Leu Leu Pro Asp
        435                 440                 445

Ala Asn Arg Asp Thr Leu Lys Ala Leu Leu Glu Phe Leu Gln Arg Val
    450                 455                 460

Ile Asp Asn Lys Glu Lys Asn Lys Met Thr Val Met Asn Val Ala Met
465                 470                 475                 480

Val Met Ala Pro Asn Leu Phe Met Cys His Ala Leu Gly Leu Lys Ser
                485                 490                 495

Ser Glu Gln Arg Glu Phe Val Met Ala Ala Gly Thr Ala Asn Thr Met
            500                 505                 510

His Leu Leu Ile Lys Tyr Gln Lys Leu Leu Trp Thr Ile Pro Lys Phe
```

---continued

```
               515                 520                 525
Ile Val Asn Gln Val Arg Lys Gln Asn Thr Glu Asn His Lys Lys Asp
        530                 535                 540

Lys Arg Ala Met Lys Lys Leu Leu Lys Lys Met Ala Tyr Asp Arg Glu
545                 550                 555                 560

Lys Tyr Glu Lys Gln Asp Lys Ser Thr Asn Asp Ala Asp Val Pro Gln
                565                 570                 575

Gly Val Ile Arg Val Gln Ala Pro His Leu Ser Lys Val Ser Met Ala
                580                 585                 590

Ile Gln Leu Thr Glu Gly Leu Lys Ala Ser Asp Val Leu Ala Arg Phe
            595                 600                 605

Leu Ser Gln Glu Ser Gly Val Ala Gln Thr Leu Lys Lys Gly Glu Val
        610                 615                 620

Phe Leu Tyr Glu Ile Gly Gly Asn Ile Gly Glu Arg Cys Leu Asp Asp
625                 630                 635                 640

Asp Thr Tyr Met Lys Asp Leu Tyr Gln Leu Asn Pro Asn Ala Glu Trp
                645                 650                 655

Val Ile Lys Ser Lys Pro Leu
                660
```

<210> SEQ ID NO 15
<211> LENGTH: 1992
<212> TYPE: DNA
<213> ORGANISM: Homo sapiens

<400> SEQUENCE: 15

| | | | | | |
|---|---|---|---|---|---|
| atgagctggc | tctccagttc | ccagggagtg | gtactaacag | cctaccaccc | cagcggcaag | 60 |
| gaccaggccg | tcgggaacag | ccatgcaaag | gcaggggagg | aagccacctc | gagtcgcaga | 120 |
| tatggccagt | acactatgaa | ccaggaaagc | accaccatca | agttatggaa | gaagcctcca | 180 |
| tttgatcgat | caatttccca | ggattctttg | gatgaactat | ctatggaaga | ctattggata | 240 |
| gaactagaaa | acatcaagaa | atctagtgaa | acagccaag | aagatcaaga | ggtggttgtt | 300 |
| gtcaaagagc | ctgatgaggg | agaattggaa | gaagagtggc | ttaaagaggc | cggtttatcc | 360 |
| aatctcttcg | gagagtctgc | tggagatcca | caggaaagca | ttgtgttttt | atcaacattg | 420 |
| acgcggaccc | aggcagcagc | agttcagaag | cgagtagaga | cggtctccca | gaccttgaga | 480 |
| aaaaaaaaca | aacagtacca | gattcctgac | gtcagagaca | tatttgctca | acagagagaa | 540 |
| tcaaagaaa | cagctccagg | tggcactgaa | tcgcagtcac | ttagaacaaa | tgaaaacaaa | 600 |
| taccaaggaa | gagatgacga | ggcatctaac | cttgttggtg | aagagaagct | gatcccacct | 660 |
| gaggagacgc | ctgcccctga | acagacatc | aacctggagg | tatcatttgc | cgagcaagca | 720 |
| ctcaatcaga | aagagagctc | caaggagaaa | atccagaaga | gcaaaggcga | tgatgccaca | 780 |
| ttacctagtt | tcagattgcc | aaaagacaaa | acgggtacca | aaggattgg | tgacctcgca | 840 |
| ccccaggaca | tgaagaaagt | ttgccattta | gccctaattg | agctgactgc | cctctatgat | 900 |
| gtattgggta | ttgagctgaa | acaacaaaaa | gctgtgaaaa | tcaaaacaaa | agattctggt | 960 |
| cttttttgcg | ttccattgac | agcgctatta | gaacaagatc | agaggaaagt | accaggaatg | 1020 |
| cgaataccct | tgatctttca | aaaactgatt | tctcgaattg | aagagagagg | tttggaaaca | 1080 |
| gaaggcctct | tacggatccc | tggagctgcc | attagaatca | agaatctttg | ccaagaacta | 1140 |
| gaagcaaagt | tttatgaagg | acttttaat | tgggaaagtg | tcaaacagca | tgatgccgcc | 1200 |
| agcctgctga | agctcttcat | tcgggagttg | ccccagccac | tgctcagtgt | ggagtatctc | 1260 |

-continued

```
aaagcctttc aggctgtcca gaatcttcca accaagaagc agcaactaca ggctttgaac      1320
cttcttgtca tcctcctacc tgatgcaaac agggacacac tgaaggccct tcttgaattt      1380
ctccaaagag taatagataa taaagaaaaa aataaaatga cagtcatgaa tgtagcaatg      1440
gtcatggccc cgaatctctt tatgtgtcat gcattgggat tgaagtccag tgaacagcga      1500
gaatttgtaa tggcagctgg gacagcaaat accatgcact tattgattaa gtaccaaaaa      1560
cttctgtgga caattcccaa gtttattgta aaccaagtga ggaagcaaaa cacggaaaat      1620
cataaaaagg ataaagagc catgaagaaa ttgctgaaga aaatggctta tgaccgagaa       1680
aaatatgaaa agcaagataa gagtacaaat gatgctgacg ttcctcaggg agtgattcga      1740
gtgcaagctc cccatctttc gaaagtttcc atggcaatac agctaactga agaactaaaa      1800
gccagtgatg tacttgccag gtttctcagc caagaaagtg gggttgccca gactctcaag      1860
aaaggagaag tttttttgta tgaaattgga ggaaatattg gggaacgctg ccttgatgat      1920
gacacttaca tgaaggattt atatcagctt aacccaaatg ctgagtgggt tataaagtca      1980
aagccattgt ag                                                          1992
```

<210> SEQ ID NO 16
<211> LENGTH: 502
<212> TYPE: PRT
<213> ORGANISM: Artificial Sequence
<220> FEATURE:
<223> OTHER INFORMATION: Consensus amino acid sequence

<400> SEQUENCE: 16

```
Leu Ser Asp Ala Phe Leu Arg Leu Leu Trp Arg Glu Lys Leu Leu Gly
 1               5                  10                  15

Leu Leu Ile Thr Val Pro Pro Leu Leu Leu Ala Ile Ala Ala Trp Ile
            20                  25                  30

Gly Leu Glu Glu Ile Lys Glu Trp Lys Lys Ser Pro Leu Tyr Leu Ser
        35                  40                  45

Asn Asp His Glu Leu Asp Val Pro Ile Leu Leu Ile Leu Ser Gln Ala
    50                  55                  60

Pro Gln Gly Ser Arg Phe Pro Thr Leu Glu Glu Asn Arg Ile Leu Leu
65                  70                  75                  80

Trp Thr Trp Pro Phe Asn Asp Arg Gly Ala Pro Val Pro Pro Ser Arg
                85                  90                  95

Cys Ser Leu Ser Tyr Asp Asn Thr Ala Arg Cys Arg Leu Thr Ala Asn
           100                 105                 110

Arg Ser Glu Leu Glu Ser Ala Asp Ala Val Leu Phe Asn Ala Gly His
       115                 120                 125

His Arg Asp Leu Ser Lys Gly Pro Pro Met Asp Leu Pro Pro Glu Phe
   130                 135                 140

Thr Gln Val Arg Ala Arg Ala Glu Asp Ala Asp Ala Val Leu Leu Ala
145                 150                 155                 160

Tyr Glu Asp Asn Ala Ala Ala Glu Ala Leu Ala Thr Asp Phe Pro
               165                 170                 175

Arg Pro Pro Gly Gln Pro Trp Val Trp Ala Ser Met Glu Ser Pro Ser
           180                 185                 190

Asn Ser Gly Arg Phe Ala Val Pro Gly Phe Lys Ile Asn Val Leu Asn
       195                 200                 205

Gly Leu Gln Ile Leu Leu Asp Gly Tyr Phe Asn Trp Thr Leu Ser Tyr
   210                 215                 220

Arg Ala Asp Ser Asp Ala Phe His Pro Tyr Gly Tyr Leu Glu Pro Leu
```

```
225                 230                 235                 240

Thr Ala Lys Ala Arg Lys Arg Gly Phe Lys Val Gln Ser Gln Val Val
                245                 250                 255

Glu Ala Pro Leu Asn Leu Ser Ala Lys Ala Lys Leu Ala Ala Trp Val
            260                 265                 270

Val Ser Asn Cys Asn Thr Arg Ser Lys Arg Glu Arg Phe Tyr Lys Gln
        275                 280                 285

Leu Lys Lys His Leu Gln Val Asp Val Tyr Gly Arg Val Ala Asn Pro
    290                 295                 300

Leu Pro Leu Lys Ser Gly Cys Ser Lys Gly Val Glu Leu Ile Glu Thr
305                 310                 315                 320

Leu Ser Gln Tyr Lys Phe Tyr Leu Ala Phe Glu Asn Ser Gln His Glu
                325                 330                 335

Asp Tyr Val Thr Glu Lys Leu Trp Lys Asn Ala Leu Gln Ala Gly Thr
            340                 345                 350

Ile Pro Val Val Leu Gly Pro Ser Arg Ala Val Tyr Glu Asp Phe Val
        355                 360                 365

Pro Pro Lys Ser Phe Ile His Val Asp Asp Phe Lys Ser Ala Lys Glu
    370                 375                 380

Leu Ala Asp Tyr Leu Leu Tyr Leu Asp Lys Asn Pro Thr Ala Tyr Leu
385                 390                 395                 400

Asp Met Leu Tyr Glu Asn Pro Leu Asn Thr Leu Asp Gly Lys Ala Tyr
                405                 410                 415

Phe Tyr Gln Asp Leu Ser Phe Lys Lys Ile Leu Asp Phe Phe Lys Thr
            420                 425                 430

Ile Leu Glu Asn Asp Thr Ile Tyr His Lys Tyr Ser Glu Tyr Phe Glu
        435                 440                 445

Trp Arg Glu Asp Leu Arg Val Arg Leu Phe Ser Trp Asp Ala Leu Arg
    450                 455                 460

Val Leu Glu Tyr Asp Glu Gly Phe Cys Arg Val Cys Arg Leu Leu Gln
465                 470                 475                 480

Lys Ala Pro Asp Leu Leu Glu Leu Ser Arg Tyr Lys Thr Ile Pro Asn
                485                 490                 495

Leu Ala Lys Trp Phe Gln
            500

<210> SEQ ID NO 17
<211> LENGTH: 178
<212> TYPE: PRT
<213> ORGANISM: Artificial Sequence
<220> FEATURE:
<223> OTHER INFORMATION: Consensus amino acid sequence

<400> SEQUENCE: 17

Pro Val Glu Leu Val Trp Trp Ser Arg Asp Met Ser Trp Asn Tyr Asp
1               5                   10                  15

Val Gln Arg Gln Cys Gly Ile His Thr Cys Arg Ile Thr Asn Lys Arg
                20                  25                  30

Ser Arg Arg Pro Trp Ala Arg Gly Val Leu Phe Tyr Gly Ser Asn Ile
            35                  40                  45

Lys Thr Gly Asp Phe Pro Leu Pro Arg Asn Glu His Gln Ile Trp Ala
    50                  55                  60

Leu Leu His Glu Glu Ser Pro Arg Asn Thr Pro Phe Val Ser Asn Lys
65                  70                  75                  80

Glu Phe Leu Arg His Phe His Phe Thr Ser Thr Phe Ser Arg Tyr Ser
```

```
                85                  90                  95
Asn Leu Pro Leu Thr Thr Met Tyr Leu Pro Ser Gly Glu Ala Leu Thr
            100                 105                 110

Ser Lys Asp Tyr Tyr Val Thr Phe Asp Gly Lys Ser Lys Tyr Gly Tyr
            115                 120                 125

Arg Pro Ser Thr Ser Val Val Phe Leu Gln Ser Asp Cys Asp Thr Met
            130                 135                 140

Ser Gly Arg Glu Asp Tyr Val Lys Glu Leu Met Lys His Leu Pro Ile
145                 150                 155                 160

Asp Ser Tyr Gly Ser Cys Leu Arg Asn Arg Asp Leu Pro Glu Arg Gln
                165                 170                 175

Lys Asp

<210> SEQ ID NO 18
<211> LENGTH: 139
<212> TYPE: PRT
<213> ORGANISM: Artificial Sequence
<220> FEATURE:
<223> OTHER INFORMATION: Consensus amino acid sequence

<400> SEQUENCE: 18

Val Ala Trp Val Val Ser Asn Trp Asn Pro Asn Ser Ala Arg Val Arg
 1               5                  10                  15

Tyr Tyr Gln Gln Leu Gln Lys His Leu Lys Val Asp Val Tyr Gly Arg
                20                  25                  30

Ser His Arg Gly Lys Pro Leu Pro Gln Gly Asn Met Met Glu Thr Leu
            35                  40                  45

Ser Arg Tyr Lys Phe Tyr Leu Ala Phe Glu Asn Ser Met His Pro Asp
        50                  55                  60

Tyr Ile Thr Glu Lys Leu Trp Arg Asn Ala Leu Glu Ala Gly Ala Val
 65                 70                  75                  80

Pro Val Val Leu Gly Pro Ser Arg Val Asn Tyr Glu Arg Phe Ile Pro
                85                  90                  95

Pro Asp Ala Phe Ile His Val Asp Asp Phe Gln Ser Pro Lys Glu Leu
            100                 105                 110

Ala Lys Tyr Leu Lys Glu Leu Asp Lys Asn His Ala Ala Tyr Leu Lys
        115                 120                 125

Tyr Leu Arg Trp Lys Tyr Glu Asn Pro Leu Asn
    130                 135

<210> SEQ ID NO 19
<211> LENGTH: 296
<212> TYPE: PRT
<213> ORGANISM: Artificial Sequence
<220> FEATURE:
<223> OTHER INFORMATION: Consensus amino acid sequence

<400> SEQUENCE: 19

Ile Leu Leu Trp Asn Glu Pro Ser Leu Val Asn Ala Pro Ala His Val
 1               5                  10                  15

Glu Cys Gly Cys Leu Val Thr Thr Ser Arg Ser His Asn Asp Lys Ala
                20                  25                  30

Phe Asp Ala Val Val Ile Ser Ala Asp His Pro Tyr Ser Phe Glu Gly
            35                  40                  45

Leu Gly Gly Val Lys Leu His Pro Asp Phe Tyr Ala Val Tyr Ala Ala
        50                  55                  60

Lys Lys Pro Leu Ser Ser Thr Gln Asn Pro Leu Thr Asn Phe Thr Leu
```

```
                65                  70                  75                  80
            Pro Pro Phe Asn Leu Thr Met Thr Tyr Arg Leu Asp Ser Gln Leu Ile
                            85                  90                  95
            Trp Thr Asp Tyr Tyr Phe Ser His Thr Asn Leu Ala Arg Arg Leu Lys
                            100                 105                 110
            Trp Phe Arg Ala Pro Ser Lys Ser Phe Ala Asp Asp Met Pro Ala Thr
                            115                 120                 125
            Thr Val Leu Arg Leu Glu Ser Glu Ile Leu Lys Lys Ser Arg Leu Ala
                            130                 135                 140
            Val Tyr Leu Val Tyr Glu Val Asn Glu Lys Thr Leu Pro Glu Ser Leu
            145                 150                 155                 160
            Tyr Met Glu Glu Leu Arg Lys Tyr Ala Asp Leu Asp Ala His Asp Asn
                            165                 170                 175
            Cys Leu Gly Thr Asp Asp His Tyr His Phe Met Leu Ile Phe Glu Thr
                            180                 185                 190
            Ser Ala Cys Pro Asp Tyr Val Pro Pro Gln Met Ser Met Ala Met Asp
                            195                 200                 205
            Lys Leu Leu Val Pro Val Leu Ile Gly Gly Gly Asn Leu Thr Asn Leu
                            210                 215                 220
            Val Pro Ser His Ser Tyr Ile Ser Ser Gln Asp Phe Ala Thr Pro Gln
            225                 230                 235                 240
            Asp Leu Ile Ile His Leu Lys Asp Leu Ala Asn Asn Gln Leu Glu Tyr
                            245                 250                 255
            Arg Arg Tyr Phe Trp Trp His Ser Ile Tyr Arg Leu Arg Lys Thr Ser
                            260                 265                 270
            Gln Pro Tyr Cys Ala Leu Cys Ser Leu Ile Gln Gln Ser Pro Gly Gly
                            275                 280                 285
            His Glu Val Arg Gln Arg Ser Tyr
                            290                 295

<210> SEQ ID NO 20
<211> LENGTH: 81
<212> TYPE: PRT
<213> ORGANISM: Artificial Sequence
<220> FEATURE:
<223> OTHER INFORMATION: Consensus amino acid sequence

<400> SEQUENCE: 20

Gly Asn Leu Leu Val Ile Leu Val Ile Leu Arg Thr Lys Lys Leu Arg
            1               5                   10                  15
            Thr Pro Thr Asn Ile Phe Ile Leu Asn Leu Ala Val Ala Asp Leu Leu
                            20                  25                  30
            Phe Leu Leu Thr Leu Pro Pro Trp Ala Leu Tyr Tyr Leu Val Gly Gly
                            35                  40                  45
            Ser Glu Asp Trp Pro Phe Gly Ser Ala Leu Cys Lys Leu Val Thr Ala
                            50                  55                  60
            Leu Asp Val Val Asn Met Tyr Ala Ser Ile Leu Leu Thr Ala Ile
            65                  70                  75                  80
            Ser

<210> SEQ ID NO 21
<211> LENGTH: 155
<212> TYPE: PRT
<213> ORGANISM: Artificial Sequence
<220> FEATURE:
<223> OTHER INFORMATION: Consensus amino acid sequence
```

```
<400> SEQUENCE: 21

Lys Val Val Ile Leu Leu Val Trp Val Leu Ala Leu Leu Ser Leu
1               5                   10                  15

Pro Pro Leu Leu Phe Ser Trp Val Lys Thr Val Glu Glu Gly Asn Gly
            20                  25                  30

Thr Leu Asn Val Asn Val Thr Val Cys Leu Ile Asp Phe Pro Glu Glu
            35                  40                  45

Ser Thr Ala Ser Val Ser Thr Trp Leu Arg Ser Tyr Val Leu Leu Ser
    50                  55                  60

Thr Leu Val Gly Phe Leu Leu Pro Leu Val Ile Leu Val Cys Tyr
65                  70                  75                  80

Thr Arg Ile Leu Arg Thr Leu Arg Lys Ala Ala Lys Thr Leu Leu Val
                85                  90                  95

Val Val Val Val Phe Val Leu Cys Trp Leu Pro Tyr Phe Ile Val Leu
                100                 105                 110

Leu Leu Asp Thr Leu Cys Leu Ser Ile Ile Met Ser Ser Thr Cys Glu
            115                 120                 125

Leu Glu Arg Val Leu Pro Thr Ala Leu Leu Val Thr Leu Trp Leu Ala
130                 135                 140

Tyr Val Asn Ser Cys Leu Asn Pro Ile Ile Tyr
145                 150                 155

<210> SEQ ID NO 22
<211> LENGTH: 65
<212> TYPE: PRT
<213> ORGANISM: Artificial Sequence
<220> FEATURE:
<223> OTHER INFORMATION: Consensus amino acid sequence

<400> SEQUENCE: 22

Glu Trp Thr Glu Trp Leu Tyr Asp Val Tyr His Tyr Phe His Met Val
1               5                   10                  15

Ser Gly Val Leu Phe Tyr Leu Ser Ser Ala Ile Asn Pro Ile Leu Tyr
            20                  25                  30

Asn Leu Met Ser His Arg Phe Arg Glu Ala Phe Lys Asn Val Leu Ser
            35                  40                  45

Ser Leu Cys Lys Gln Trp His Ser Arg His Lys Pro Arg Pro Ser Phe
    50                  55                  60

Ser
65

<210> SEQ ID NO 23
<211> LENGTH: 108
<212> TYPE: PRT
<213> ORGANISM: Artificial Sequence
<220> FEATURE:
<223> OTHER INFORMATION: Consensus amino acid sequence

<400> SEQUENCE: 23

Tyr Phe Lys Ile Ile Leu Lys Met Cys Gln Arg Lys Arg Gln Met Gln
1               5                   10                  15

Thr Lys Arg Thr Ala Thr Lys Lys Arg Thr Thr Lys Val Thr Ile Met
            20                  25                  30

Gly Leu Ala Ile Val Ile Ser Tyr Thr His Cys Trp Leu Pro Phe Trp
            35                  40                  45

Ile Val Gln Trp Ser Ile Glu Ala Asn Leu Phe Glu Lys Ser Lys Tyr
    50                  55                  60
```

```
Leu Leu Phe Cys Cys Thr His Phe Ala Phe Ala Leu Gln Tyr Ile Asn
65                  70                  75                  80

Ser Ala Ala Asn Pro Phe Leu Tyr Val Phe Leu Ser Asp Ser Phe Gln
                85                  90                  95

Lys Asn Ile Gln Lys Leu Leu Arg Thr Ala Lys Pro
            100                 105

<210> SEQ ID NO 24
<211> LENGTH: 183
<212> TYPE: PRT
<213> ORGANISM: Artificial Sequence
<220> FEATURE:
<223> OTHER INFORMATION: Consensus amino acid sequence

<400> SEQUENCE: 24

Pro Ser Asp Ala Pro Glu Thr Tyr Ser Asp Thr Val Leu Ser Val Val
1               5                   10                  15

Leu Gly Phe Tyr Ala Leu Leu Leu Ile Ala Phe Ala Ser Asn Ile
            20                  25                  30

Leu Leu Ala Gly Val Ile Lys Lys Tyr Arg Trp Gly Met Lys Met Ala
        35                  40                  45

Leu Leu Phe His Leu Cys Val Thr Gly Ala Leu Leu Ser Ile Thr Asn
50                  55                  60

Thr Leu His Leu Ala Ser Gly Tyr His Leu Leu Lys Arg Gln Arg
65                  70                  75                  80

Asn Ser Ser Thr Val Leu Gln Ser Phe Ala Ile Ile Ala Trp Val Asp
            85                  90                  95

His Phe Ile Gly Phe Ala Leu Leu Ile Phe Val Met Tyr Leu Ala Ile
            100                 105                 110

Phe Cys Phe Lys Phe Tyr Trp Asn Asn Lys Thr Arg Ser Ile Glu Trp
            115                 120                 125

Gly Arg Ser Tyr Val Leu Tyr Ala Ile Ser Thr Trp Val Ile Ala Phe
130                 135                 140

Leu Ile Ala Gly Phe Thr Ala Phe Phe Gln Cys Asp Ser His Ile Asn
145                 150                 155                 160

Ser Gln Asp Gln Cys Ile Gln Ile Val Cys Ala Val Ser Asn Ile Phe
                165                 170                 175

Ser Ala Ile Phe Thr Glu Leu
            180

<210> SEQ ID NO 25
<211> LENGTH: 259
<212> TYPE: PRT
<213> ORGANISM: Artificial Sequence
<220> FEATURE:
<223> OTHER INFORMATION: Consensus amino acid sequence

<400> SEQUENCE: 25

Gly Asn Leu Leu Val Ile Leu Val Ile Leu Arg Thr Lys Lys Leu Arg
1               5                   10                  15

Thr Pro Thr Asn Ile Phe Ile Leu Asn Leu Ala Val Ala Asp Leu Leu
            20                  25                  30

Phe Leu Leu Thr Leu Pro Pro Trp Ala Leu Tyr Tyr Leu Val Gly Gly
        35                  40                  45

Ser Glu Asp Trp Pro Phe Gly Ser Ala Leu Cys Lys Leu Val Thr Ala
    50                  55                  60

Leu Asp Val Val Asn Met Tyr Ala Ser Ile Leu Leu Leu Thr Ala Ile
65                  70                  75                  80
```

```
Ser Ile Asp Arg Tyr Leu Ala Ile Val His Pro Leu Arg Tyr Arg Arg
                85                  90                  95

Arg Arg Thr Ser Pro Arg Arg Ala Lys Val Val Ile Leu Leu Val Trp
            100                 105                 110

Val Leu Ala Leu Leu Leu Ser Leu Pro Pro Leu Leu Phe Ser Trp Val
        115                 120                 125

Lys Thr Val Glu Glu Gly Asn Gly Thr Leu Asn Val Asn Val Thr Val
    130                 135                 140

Cys Leu Ile Asp Phe Pro Glu Glu Ser Thr Ala Ser Val Ser Thr Trp
145                 150                 155                 160

Leu Arg Ser Tyr Val Leu Leu Ser Thr Leu Val Gly Phe Leu Leu Pro
                165                 170                 175

Leu Leu Val Ile Leu Val Cys Tyr Thr Arg Ile Leu Arg Thr Leu Arg
                180                 185                 190

Lys Ala Ala Lys Thr Leu Leu Val Val Val Val Phe Val Leu Cys
                195                 200                 205

Trp Leu Pro Tyr Phe Ile Val Leu Leu Leu Asp Thr Leu Cys Leu Ser
    210                 215                 220

Ile Ile Met Ser Ser Thr Cys Glu Leu Glu Arg Val Leu Pro Thr Ala
225                 230                 235                 240

Leu Leu Val Thr Leu Trp Leu Ala Tyr Val Asn Ser Cys Leu Asn Pro
                245                 250                 255

Ile Ile Tyr

<210> SEQ ID NO 26
<211> LENGTH: 182
<212> TYPE: PRT
<213> ORGANISM: Artificial Sequence
<220> FEATURE:
<223> OTHER INFORMATION: Consensus amino acid sequence

<400> SEQUENCE: 26

Ala Leu Thr Phe Pro Ala Thr Ala Leu Ala Leu Ser Trp Leu Gly Phe
1               5                   10                  15

His Gln Leu Tyr Ala Ser Cys Thr Leu Cys Ser Arg Arg Pro Asp Glu
            20                  25                  30

Arg Leu Arg Phe Ala Val Phe Ser Ala Phe His Ala Leu Ser Phe
        35                  40                  45

Leu Leu Ser Phe Ile Val Leu Cys Phe Thr Tyr Leu Lys Val Leu Lys
    50                  55                  60

Val Ala Arg Phe His Cys Lys Arg Ile Asp Val Ile Thr Met Gln Thr
65                  70                  75                  80

Leu Val Leu Leu Val Asp Ile His Pro Ser Val Arg Glu Arg Cys Leu
                85                  90                  95

Glu Glu Gln Lys Arg Arg Gln Arg Ala Thr Lys Lys Ile Ser Thr
            100                 105                 110

Phe Ile Gly Thr Phe Leu Val Cys Phe Ala Pro Tyr Val Ile Thr Arg
        115                 120                 125

Leu Val Glu Leu Phe Ser Thr Ala Pro Ile Asp Ser His Trp Gly Val
    130                 135                 140

Leu Ser Lys Cys Leu Ala Tyr Ser Lys Ala Ala Ser Asp Pro Phe Val
145                 150                 155                 160

Tyr Ser Leu Leu Arg His Gln Tyr Arg Arg Ser Cys Lys Glu Leu Leu
                165                 170                 175
```

Asn Arg Ile Phe Asn Arg
            180

<210> SEQ ID NO 27
<211> LENGTH: 157
<212> TYPE: PRT
<213> ORGANISM: Artificial Sequence
<220> FEATURE:
<223> OTHER INFORMATION: Consensus amino acid sequence

<400> SEQUENCE: 27

Thr Leu Phe Ile Val Gly Phe Met Ile Pro Cys Leu Val Ile Ile Val
 1               5                  10                  15

Cys Tyr Ala Cys Ile Phe Leu Thr Val His His Gln Lys Lys Lys Ile
            20                  25                  30

Arg Asn His Asp Asn Phe Gln Ile Ala Ala Lys Gly Ser Ser Ser
        35                  40                  45

Ser Gly Gly Gly Ser Tyr Met Thr Thr Thr Cys Thr Arg Lys Ala Arg
    50                  55                  60

Glu Asp Arg Lys Thr Thr Lys Met Leu Met Val Val Phe Leu Cys Phe
65                  70                  75                  80

Ala Ile Cys Tyr Leu Pro Ile Ser Ile Leu Asn Val Leu Lys Arg Val
                85                  90                  95

Phe Gly Met Phe Arg His Ser Glu Asp Asn Glu Ser Val Tyr Trp Trp
            100                 105                 110

His Ile Phe Ser His Trp Leu Val Tyr Ala Asn Ser Cys Ile Asn Pro
        115                 120                 125

Ile Ile Tyr Asn Phe Met Asn Gly Lys Tyr Arg Lys Ala Tyr Trp Lys
    130                 135                 140

Ile Phe Ala Leu Leu Lys Phe Trp Gly Glu Pro Leu Ser
145                 150                 155

<210> SEQ ID NO 28
<211> LENGTH: 160
<212> TYPE: PRT
<213> ORGANISM: Artificial Sequence
<220> FEATURE:
<223> OTHER INFORMATION: Consensus amino acid sequence

<400> SEQUENCE: 28

Ala Tyr Val Val Met Leu Val Val Ala Val Phe Phe Ile Pro Phe Ser
 1               5                  10                  15

Val Met Leu Tyr Ser Tyr Met Cys Ile Leu Asn Thr Val Arg His Asn
            20                  25                  30

Ala Val Arg Ile His Asn His Pro Asp Ser Leu Cys Leu Ser Gln Val
        35                  40                  45

Ser Lys Leu Gly Leu Met Ser Leu Gln Arg Pro His Gln Met Ser Val
    50                  55                  60

Asp Met Ser Phe Lys Thr Arg Ala Phe Thr Thr Ile Leu Ile Leu Phe
65                  70                  75                  80

Val Gly Phe Ser Leu Cys Trp Leu Pro His Ser Val Tyr Ser Leu Leu
                85                  90                  95

Ser Val Phe Ser Lys His Phe Tyr Gln His Asn Phe Tyr Glu Ile
            100                 105                 110

Ser Thr Cys Val Leu Trp Leu Cys Tyr Leu Lys Ser Val Phe Asn Pro
        115                 120                 125

Ile Ile Tyr Cys Trp Arg Ile Lys Lys Phe Arg Glu Ala Cys Leu Glu
    130                 135                 140

```
Met Met Pro Lys Thr Phe Lys Ile Leu Pro Gln Val Pro Gly Arg Thr
145                 150                 155                 160
```

<210> SEQ ID NO 29
<211> LENGTH: 93
<212> TYPE: PRT
<213> ORGANISM: Artificial Sequence
<220> FEATURE:
<223> OTHER INFORMATION: Consensus amino acid sequence

<400> SEQUENCE: 29

```
His Lys Ile Ile Lys Ala Ala Cys Leu Val Gln Gln Lys Arg Gln Glu
1               5                   10                  15

Phe Leu Ala Ser Val Ala Arg Gly Val Ala Pro Ala Asp Ser Pro Glu
            20                  25                  30

Ala Pro Arg Arg Ser Phe Ala Gly Gly Thr Trp Asp Trp Glu Tyr Leu
        35                  40                  45

Gly Phe Ala Ser Pro Glu Glu Tyr Ala Glu Phe Gln Tyr Arg Arg Arg
50                  55                  60

His Arg Gln Arg Arg Gly Asp Val His Ser Leu Leu Ser Asn Pro
65                  70                  75                  80

Pro Asp Pro Asp Glu Pro Ser Glu Ser Thr Leu Asp Ile
                85                  90
```

<210> SEQ ID NO 30
<211> LENGTH: 33
<212> TYPE: PRT
<213> ORGANISM: Artificial Sequence
<220> FEATURE:
<223> OTHER INFORMATION: Consensus amino acid sequence

<400> SEQUENCE: 30

```
Leu Leu Pro Leu Leu Val Ile Leu Val Cys Tyr Thr Arg Ile Leu Arg
1               5                   10                  15

Thr Leu Arg Lys Ala Ala Lys Thr Leu Leu Val Val Val Val Val Phe
            20                  25                  30

Val
```

<210> SEQ ID NO 31
<211> LENGTH: 260
<212> TYPE: PRT
<213> ORGANISM: Artificial Sequence
<220> FEATURE:
<223> OTHER INFORMATION: Consensus amino acid sequence

<400> SEQUENCE: 31

```
Gly His Arg Ser Arg Pro Thr Asp Leu Pro Ile Gly Leu Leu Ser Leu
1               5                   10                  15

Val His Leu Met Met Leu Leu Thr Met Gly Phe Ile Ala Thr Met Asp
            20                  25                  30

Met Phe Met Ser Trp Gly Arg Trp Asp Asp Thr Thr Cys Lys Ser Leu
        35                  40                  45

Ile Tyr Leu His Arg Leu Leu Arg Gly Leu Ser Leu Cys Thr Thr Cys
50                  55                  60

Leu Leu Asn Val Phe Gln Ala Ile Thr Leu Ser Pro Arg Ser Ser Cys
65                  70                  75                  80

Leu Ala Lys Phe Lys His Lys Ser Pro His His Ile Ser Cys Ala Phe
                85                  90                  95

Leu Phe Leu Trp Val Leu Tyr Met Ser Phe Ser Ser His Leu Leu Leu
```

```
                100                 105                 110
Ser Ile Ile Ala Thr Pro Asn Leu Thr Ser Asn Asp Phe Met Tyr Val
            115                 120                 125

Thr Gln Ser Cys Ser Ile Leu Pro Met Ser Tyr Ser Met Gln Ser Met
130                 135                 140

Phe Ser Thr Leu Leu Ala Ile Arg Asp Val Phe Leu Ile Gly Leu Met
145                 150                 155                 160

Val Leu Ser Ser Gly Tyr Met Val Ala Leu Leu Cys Arg His Arg Lys
                165                 170                 175

Gln Ala Gln His Leu His Ser Thr Ser Leu Ser Pro Lys Ala Ser Pro
            180                 185                 190

Glu Gln Arg Ala Thr Arg Thr Ile Leu Met Leu Met Ser Ser Phe Phe
            195                 200                 205

Val Leu Met Tyr Ile Phe Asp Ser Ile Val Phe Cys Ser Arg Thr Met
            210                 215                 220

Phe Lys Asp Gly Pro Thr Phe Tyr Cys Ile Gln Ile Val Ser His
225                 230                 235                 240

Ser Tyr Ala Thr Val Ser Pro Phe Val Phe Ile Cys Thr Glu Lys His
                245                 250                 255

Ile Val Lys Phe
            260

<210> SEQ ID NO 32
<211> LENGTH: 170
<212> TYPE: PRT
<213> ORGANISM: Artificial Sequence
<220> FEATURE:
<223> OTHER INFORMATION: Consensus amino acid

<400> SEQUENCE: 32

Pro Ile Ile Val Glu Lys Cys Val Glu Tyr Ile Glu Lys Leu Tyr Pro
1               5                   10                  15

Leu Ala Glu Arg Gly Leu Gln Glu Glu Gly Ile Tyr Arg Val Ser Gly
            20                  25                  30

Ser Ala Ser Arg Val Lys Glu Leu Arg Glu Ala Phe Asp Lys Asp Gly
            35                  40                  45

Ala Pro Asp Ser Leu Glu Leu Ser Glu Lys Glu Trp Phe Asp Val His
50                  55                  60

Val Val Ala Gly Leu Leu Lys Leu Tyr Leu Arg Glu Leu Pro Glu Pro
65                  70                  75                  80

Leu Ile Pro Tyr Asp Leu Tyr Glu Glu Phe Ile Arg Ala Ala Lys Glu
                85                  90                  95

Gln Ile Glu Asp Pro Asp Glu Arg Leu Arg Ala Leu Lys Glu Leu Leu
            100                 105                 110

Ser Ser Lys Leu Pro Arg Ala His Tyr Asn Thr Leu Arg Tyr Leu Leu
            115                 120                 125

Thr His Leu Asn Arg Val Ala Glu Ile Tyr Ile Glu Asn Ser Ala Val
            130                 135                 140

Asn Lys Met Asn Ala Arg Asn Leu Ala Ile Val Phe Gly Pro Thr Leu
145                 150                 155                 160

Leu Arg Pro Pro Asp Lys Glu Ser Asn Asp
                165                 170

<210> SEQ ID NO 33
<211> LENGTH: 103
<212> TYPE: PRT
```

<213> ORGANISM: Artificial Sequence
<220> FEATURE:
<223> OTHER INFORMATION: Consensus amino acid sequence

<400> SEQUENCE: 33

```
Leu Lys Tyr Gln Lys Ile Leu Trp Lys Val Pro Ser Phe Leu Ile Thr
 1               5                  10                  15

Gln Val Arg Arg Met Asn Glu Ala Thr Met Leu Leu Lys Lys Gln Leu
            20                  25                  30

Pro Ser Val Arg Lys Leu Leu Arg Arg Lys Thr Leu Glu Arg Glu Thr
        35                  40                  45

Ala Ser Pro Lys Thr Ser Lys Val Leu Gln Lys Ser Pro Ser Ala Arg
    50                  55                  60

Arg Met Ser Asp Val Pro Glu Gly Val Ile Arg Val His Ala Pro Leu
65                  70                  75                  80

Leu Ser Lys Val Ser Met Ala Ile Gln Leu Asn Asn Gln Thr Lys Ala
                85                  90                  95

Lys Asp Ile Leu Ala Lys Phe
            100
```

<210> SEQ ID NO 34
<211> LENGTH: 103
<212> TYPE: PRT
<213> ORGANISM: Artificial Sequence
<220> FEATURE:
<223> OTHER INFORMATION: Consensus amino acid sequence

<400> SEQUENCE: 34

```
Asn Met Glu Glu Tyr Glu Asp Val His Thr Val Ala Gly Leu Leu Lys
 1               5                  10                  15

Gln Tyr Phe Arg Glu Leu Pro Glu Pro Leu Leu Thr Tyr Glu Leu Tyr
            20                  25                  30

Glu Glu Phe Ile Glu Ala Ala Lys Ala Gln Val Ser Asp Glu Asp Glu
        35                  40                  45

Arg Met Glu Ala Leu Glu Met Leu Lys Glu Leu Ile Lys Leu Leu Pro
    50                  55                  60

Glu Ala Asn Arg Glu Thr Leu Arg Tyr Leu Leu Lys His Leu Ser Arg
65                  70                  75                  80

Val Ala Gln His Ser Glu Glu Asn Lys Met Asn Ala Gln Asn Leu Ala
                85                  90                  95

Val Val Phe Gly Pro Thr Leu
            100
```

<210> SEQ ID NO 35
<211> LENGTH: 90
<212> TYPE: PRT
<213> ORGANISM: Artificial Sequence
<220> FEATURE:
<223> OTHER INFORMATION: Consensus amino acid sequence

<400> SEQUENCE: 35

```
Ala Cys Ser Leu Leu Lys Leu Phe Leu Arg Glu Leu Pro Glu Pro Leu
 1               5                  10                  15

Leu Thr Thr Asp Leu Val Ala Arg Phe Glu Glu Val Ala Ser His Pro
            20                  25                  30

Lys Val Thr Thr Gln Gln Ala Glu Leu Gln Gln Leu Leu Glu Gln Leu
        35                  40                  45

Pro Lys Cys Asn Arg Thr Leu Leu Ala Trp Val Leu Leu His Phe Asp
    50                  55                  60
```

-continued

```
Ala Val Ile Gln Gln Glu Arg His Asn Lys Leu Asn Ala Gln Ser Leu
 65                  70                  75                  80

Ala Met Leu Leu Ser Pro Thr Leu Gln Met
                 85                  90

<210> SEQ ID NO 36
<211> LENGTH: 79
<212> TYPE: PRT
<213> ORGANISM: Artificial Sequence
<220> FEATURE:
<223> OTHER INFORMATION: Consensus amino acid sequence
<220> FEATURE:
<221> NAME/KEY: VARIANT
<222> LOCATION: (1)...(79)
<223> OTHER INFORMATION: Xaa = Any Amino Acid

<400> SEQUENCE: 36

Gly Ser Thr Ala Leu Ile Val Met Phe Tyr Trp Cys Gly Ser Thr Ala
  1               5                  10                  15

Asn Cys Pro Asp Glu Glu Asp Pro Lys Arg His Xaa Xaa Leu Ile Val
             20                  25                  30

Met Asn Gln Gly Ala Xaa Xaa Leu Ile Val Met Phe Thr Gly Ser Thr
         35                  40                  45

Ala Asn Cys Leu Ile Val Met Phe Tyr Trp Ser Thr Ala Cys Asp Glu
     50                  55                  60

Asn His Arg Phe Tyr Trp Cys Ser His Xaa Xaa Leu Ile Val Met
 65                  70                  75

<210> SEQ ID NO 37
<211> LENGTH: 50
<212> TYPE: PRT
<213> ORGANISM: Artificial Sequence
<220> FEATURE:
<223> OTHER INFORMATION: Consensus amino acid sequence
<220> FEATURE:
<221> NAME/KEY: VARIANT
<222> LOCATION: (1)...(50)
<223> OTHER INFORMATION: Xaa = Any Amino Acid

<400> SEQUENCE: 37

Leu Ile Val Met Phe Trp Ala Cys Pro Gly Ala Cys Xaa Xaa Xaa Ser
  1               5                  10                  15

Ala Cys Lys Ser Thr Ala Leu Ile Met Arg Gly Ser Ala Cys Pro Asn
             20                  25                  30

Val Ser Thr Ala Cys Pro Xaa Xaa Asp Glu Asn Phe Ala Pro Xaa Xaa
             35                  40                  45

Ile Tyr
 50
```

80090, HUMAN FUCOSYLTRANSFERASE NUCLEIC ACID MOLECULES AND USES THEREOF

This application claims benefit of priority from U.S. Applications Ser. No. 60/242,040 filed 20 Oct. 2000, Ser. No. 60/242,038 filed 20 Oct. 2000, Ser. No. 60/241,992 filed 20 Oct. 2000, and Ser. No. 60/242,637 filed 23 Oct. 2000, which are hereby incorporated by reference in their entirety.

BACKGROUND OF THE INVENTION

In general, transferases catalyze the transfer of one molecular group from one molecule to another. For instance, such molecular groups include phosphate, amino, methyl, acetyl, acyl, phosphatidyl, phosphoribosyl, among other groups. One particular transferase, fucosyltransferase, transfers a fucosyl group from one molecule to another.

Fucosyltransferases catalyze the transfer of fucose from GDP-Fuc to Gal in an α1,2-linkage and to GlcNAc in an α1,3-, α1,4-, or α1,6-linkage. Since known fucosyltransferases utilize the same nucleotide sugar, it is believed that their specificity resides in the recognition of the acceptor and in the type of linkage formed. On the basis of protein sequence similarities, these enzymes have been classified into four distinct families: (1) the alpha-2-fucosyltransferases, (2) the alpha-3-fucosyltransferases, (3) the mammalian alpha-6-fucosyltransferases, and (4) the bacterial alpha-6-fucosyltransferases. Conserved structural features, as well as a consensus peptide motif have been identified in the catalytic domains of all alpha-2 and alpha-6-fucosyltranferases, from prokaryotic and eukaryotic origin. Based on these sequence similarities, alpha-2 and alpha-6-fucosyltranferases have been grouped into one superfamily. In addition, a few amino acids were found strictly conserved in this superfamily, and two of these residues have been reported to be essential for enzyme activity for a human alpha-2-fucosyltransferase. The alpha-3-fucosyltransferases constitute a distinct family as they lack the consensus peptide, but some regions display similarities with the alpha-2 and alpha-6-fucosyltranferases. All these observations strongly suggest that the fucosyltransferases share some common structural and/or catalytic features.

Fucosyltransferases are thought to be involved in the synthesis of ABO blood group antigens and in tumor cell adhesion, among other physiological phenomena. See, e.g., Koda et al. (1997) *J. Biol. Chem.* 272:7501–7505; and Weston et al. (1999) *Cancer Res.* 59:2127–2135. For example, α(1,2)fucosyltransferase forms the H blood group antigen and catalyzes the transfer of fucose in the α(1,2) linkage to the terminal galactose of a precursor molecule. In addition, facosyltransferases have been found to be associated with particular mucins, the coregulation of which is lost in gastric tumors in comparison to normal gastric epithelial cells. Lopez-Ferrer, A., et al. (2000) *Gut* 47(3):349–56.

Given the important biological roles and properties of fucosyltransferases, there exists a need for the identification and characterization of novel fucosyltransferase genes and proteins as well as for the discovery of binding agents (e.g., ligands) and modulators of these nucleic acids and polypeptides for use in regulating a variety of normal and/or pathological cellular processes.

G-protein coupled receptors (GPCRs) are proteins that mediate signal transduction of a diverse number of ligands through heterotrimeric G proteins (see, e.g., Strader (1994) *Annu. Rev. Biochem.* 63:101–132). GPCRs are a component of many modular cell signaling systems involving, e.g., G proteins, intracellular enzymes and channels. Upon ligand binding to a GPCR, intracellular signal molecules, e.g., G proteins, can be activated or turned off. These GPCR-coupled G proteins can modulate the activity of different intracellular effector molecules, e.g., enzymes and ion channels (see, e.g., Gutkind (1998) *J. Biol. Chem.* 273: 1839–1842; Selbie (1998) *Trends Pharmacol. Sci.* 19:87–93).

GPCR polypeptides typically include seven transmembrane domains, including an intracellular domain and an extracellular ligand binding domain. The intracellular domain(s) bind G proteins, which represent a family of heterotrimeric proteins comprising of α, β and γ subunits. G proteins typically bind guanine nucleotides. Following ligand binding to the GPCR, a conformational change is transmitted from the extracellular GPCR ligand binding domain to the intracellular domain-bound G protein. This causes the G protein α-subunit to exchange a bound GDP molecule for a GTP molecule and to dissociate from the βγ-subunits. The GTP-bound form of the α-subunit typically functions as an effector-modulating moiety, leading to the production of second messengers, such as, e.g., cyclic AMP (e.g., by activation of adenylate cyclase), diacylglycerol or inositol phosphates.

GPCRs are of critical importance in cell signaling systems, including the endocrine system, the central nervous system and peripheral physiological processes. The GPCR genes and gene-products can also be causative agents of disease (see, e.g., Spiegel (1993) *J. Clin. Invest.* 92:1119–1125); McKusick (1993) *J. Med. Genet.* 30:1–26). Given the important biological roles and properties of GPCRs, there exists a need for the identification and characterization of novel GPCR genes and proteins as well as for the discovery of binding agents (e.g., ligands) and modulators of these nucleic acids and polypeptides for use in regulating a variety of normal and/or pathological cellular processes. Since RAlc may be the cognate receptor for specific endogenous ligand, the 52874 and 52880 proteins may similarly recognize an endogenous ligand.

One type of receptor family is the seven transmembrane domain (7TM) receptor family. This receptor family is characterized structurally by the presence of seven hydrophobic, membrane-spanning regions, as well as an intracellular domain and an extracellular ligand binding domain. Members of the 7TM receptor family typically are G-protein coupled receptors (GPCRs). G-protein coupled receptors are proteins that mediate signal transduction of a diverse number of ligands through heterotrimeric G proteins (see, e.g., Strader (1994) *Annu. Rev. Biochem.* 63:101–132). GPCRs are a component of many modular cell signaling systems involving, e.g., G proteins, intracellular enzymes and channels. Upon ligand binding to a GPCR, intracellular signal molecules, e.g., G proteins, can be activated or turned off. These GPCR-coupled G proteins can modulate the activity of different intracellular effector molecules, e.g., enzymes and ion channels (see, e.g., Gutkind (1998) *J. Biol. Chem.* 273: 1839–1842; Selbie (1998) *Trends Pharmacol. Sci.* 19:87–93).

The intracellular domain(s) of GPCRs bind G proteins, which represent a family of heterotrimeric proteins comprising of α, β and γ subunits. G proteins typically bind guanine nucleotides. Following ligand binding to the GPCR, a conformational change is transmitted from the extracellular GPCR ligand binding domain to the intracellular domain-bound G protein. This causes the G protein α-subunit to exchange a bound GDP molecule for a GTP molecule and to dissociate from the βγ-subunits. The GTP-bound form of the α-subunit typically functions as an effector-modulating moiety, leading to the production of second messengers, such as, e.g., cyclic AMP (e.g., by activation of adenylate cyclase), diacylglycerol or inositol phosphates.

Seven TM receptors, such as GPCRs, are of critical importance in cell signaling systems, including the endocrine system, the central nervous system and peripheral physiological processes. GPCRs are the receptors of different families of neuropeptides, and neuropeptides are involved in nociception. The GPCR genes and gene-products can also be causative agents of disease (see, e.g., Spiegel (1993) *J. Clin. Invest.* 92:1119–1125); McKusick (1993) *J. Med. Genet.* 30:1–26). Given the important biological roles and properties of 7TMs, there exists a need for the identification and characterization of novel 7TM genes and proteins as well as for the discovery of binding agents (e.g., ligands) and modulators of these nucleic acids and polypeptides for use in regulating a variety of normal and/or pathological cellular processes.

Members of the Rho family of small G proteins transduce signals from plasma-membrane receptors and control cell adhesion, motility and shape by actin cytoskeleton formation. Like all other GTPases, Rho proteins act as molecular switches, with an active GTP-bound form and an inactive GDP-bound form. The active conformation is promoted by guanine-nucleotide exchange factors, and the inactive state by GTPase-activating proteins (GAPs) which stimulate the intrinsic GTPase activity of small G proteins. GAPs promote GTP hydrolysis, which switches the G-protein to the inactive state.

RhoGAP domains are found in a wide variety of large, multi-functional proteins. Barrett, T., et al. (1997) *Nature* 385(6615):458–61. A number of structures are known for this family. Please see Musacchio, A., et al. (1996) *Proc Natl Acad Sci* 93(25):14373–8; Rittinger, K., et al. (1997) 388 (6643):693–7; and Boguski, M. S., et al. (1993) *Nature* 366(6456):643–54, all of which are incorporated herein by reference. The RhoGAP domain is composed of several alpha helices. This domain is also known as the breakpoint cluster region-homology (BH) domain. In addition to their GAP domains, the rhoGAP proteins may contain SH2, SH3, Ser/Thr kinase, and pleckstrin homology domains as well as proline-rich regions. Several of these domains are known to mediate protein-protein interactions. With the exception of the chimerins that are found in the brain, rhoGAPs are ubiquitously expressed and so require tight regulation to prevent permanent deactivation of Rho-family GTPases. The coupling of protein-protein interaction domains to rhoGAP activity probably provides an indirect means of regulation through control of its subcellular location.

Given the important biological roles and properties of rhoGAPs, there exists a need for the identification and characterization of novel rhoGAP genes and proteins as well as for the discovery of binding agents (e.g., ligands) and modulators of these nucleic acids and polypeptides for use in regulating a variety of normal and/or pathological cellular processes.

SUMMARY OF THE INVENTION

The present invention is based, in part, on the discovery of a novel fucosyltransferase, referred to herein as "80090". The nucleotide sequence of a cDNA encoding 80090 is shown in SEQ ID NO:1, and the amino acid sequence of an 80090 polypeptide is shown in SEQ ID NO:2. In addition, the nucleotide sequences of the coding region are depicted in SEQ ID NO:3.

In addition, the present invention is also based, in part, on the discovery of novel human G protein-coupled receptors, referred to herein as "52874" and "52880". The nucleotide sequence of a cDNA encoding 52874 is shown in SEQ ID NO:4, and the amino acid sequence of a 52874 polypeptide is shown in SEQ ID NO:5. In addition, the nucleotide sequence of the coding region is depicted in SEQ ID NO:6. The nucleotide sequence of a cDNA encoding 52880 is shown in SEQ ID NO:7, and the amino acid sequence of a 52880 polypeptide is shown in SEQ ID NO:8. In addition, the nucleotide sequence of the coding region is depicted in SEQ ID NO:9.

In addition, the present invention is also based, in part, on the discovery of a novel seven transmembrane domain (7TM) receptor, with similarities to the rhodopsin family of 7TM receptors, and nucleic acids encoding these receptors, referred to herein collectively as "7TMRs," or by the individual clone name "63497". The nucleotide sequence of a cDNA encoding 63497 is shown in SEQ ID NO:10, and the amino acid sequence of a 63497 polypeptide is shown in SEQ ID NO:11. In addition, the nucleotide sequence of the coding region is depicted in SEQ ID NO:12.

In addition, the present invention is also based, in part, on the discovery of a novel human rhoGAP, referred to herein as "33425". The nucleotide sequence of a cDNA encoding 33425 is shown in SEQ ID NO:13, and the amino acid sequence of a 33425 polypeptide is shown in SEQ ID NO:14. In addition, the nucleotide sequence of the coding region is depicted in SEQ ID NO:15.

Accordingly, in one aspect, the invention features a nucleic acid molecule which encodes an 80090, 52874, 52880, 63497, or 33425 protein or polypeptide, e.g., a biologically active portion of the 80090, 52874, 52880, 63497, or 33425 protein. In a preferred embodiment, the isolated nucleic acid molecule encodes a polypeptide having the amino acid sequence of SEQ ID NO:2, 5, 8, 11, or 14. In other embodiments, the invention provides an isolated 80090, 52874, 52880, 63497, or 33425 nucleic acid molecule having the nucleotide sequence shown in SEQ ID NO:1, 3, 4, 6, 7, 9, 10, 12, 13 or 15. In still other embodiments, the invention provides nucleic acid molecules that are substantially identical (e.g., naturally occurring allelic variants) to the nucleotide sequence shown in SEQ ID NO:1, 3, 4, 6, 7, 9, 10, 12, 13 or 15. In other embodiments, the invention provides a nucleic acid molecule which hybridizes under stringent hybridization conditions to a nucleic acid molecule comprising the nucleotide sequence of SEQ ID NO:1, 3, 4, 6, 7, 9, 10, 12, 13 or 15, wherein the nucleic acid encodes a full length 80090, 52874, 52880, 63497, or 33425 protein or an active fragment thereof.

In a related aspect, the invention further provides nucleic acid constructs which include an 80090, 52874, 52880, 63497, or 33425 nucleic acid molecule described herein. In certain embodiments, the nucleic acid molecules of the invention are operatively linked to native or heterologous regulatory sequences. Also included, are vectors and host cells containing the 80090, 52874, 52880, 63497, or 33425 nucleic acid molecules of the invention e.g., vectors and host cells suitable for producing 80090, 52874, 52880, 63497, or 33425 nucleic acid molecules and polypeptides.

In another related aspect, the invention provides nucleic acid fragments suitable as primers or hybridization probes for the detection of 80090, 52874, 52880, 63497, or 33425-encoding nucleic acids.

In still another related aspect, isolated nucleic acid molecules that are antisense to an 80090, 52874, 52880, 63497, or 33425 encoding nucleic acid molecule are provided.

In another aspect, the invention features 80090, 52874, 52880, 63497, or 33425 polypeptides, and biologically active or antigenic fragments thereof that are useful, e.g., as reagents or targets in assays applicable to treatment and diagnosis of 80090, 52874, 52880, 63497, or 33425-mediated or related disorders. In another embodiment, the invention provides 80090, 52874, 52880, 63497, or 33425 polypeptides having an 80090, 52874, 52880, 63497, or 33425 activity. Preferred polypeptides are 80090 proteins including at least one fucosyltransferase domain, 52874, 52880, or 63497 proteins including at least one 7 transmembrane domain, and 33425 proteins including at least one RhoGAP domain, and, preferably, having an 80090, 52874, 52880, 63497, or 33425 activity, e.g., an 80090, 52874, 52880, 63497, or 33425 activity as described herein.

In other embodiments, the invention provides 80090, 52874, 52880, 63497, or 33425 polypeptides, e.g., an 80090, 52874, 52880, 63497, or 33425 polypeptide having the amino acid sequence shown in SEQ ID NO:2, 5, 8, 11 or 14; an amino acid sequence that is substantially identical to the amino acid sequence shown in SEQ ID NO:2, 5, 8, 11 or 14; or an amino acid sequence encoded by a nucleic acid molecule having a nucleotide sequence which hybridizes under stringent hybridization conditions to a nucleic acid molecule comprising the nucleotide sequence of SEQ ID NO:1, 3, 4, 6, 7, 9, 10, 12, 13 or 15, wherein the nucleic acid encodes a full length 80090, 52874, 52880, 63497, or 33425 protein or an active fragment thereof.

In a related aspect, the invention further provides nucleic acid constructs which include an 80090, 52874, 52880, 63497, or 33425 nucleic acid molecule described herein.

In a related aspect, the invention provides 80090, 52874, 52880, 63497, or 33425 polypeptides or fragments operatively linked to non-80090, 52874, 52880, 63497, or 33425 polypeptides to form fusion proteins.

In another aspect, the invention features antibodies and antigen-binding fragments thereof, that react with, or more preferably specifically bind 80090, 52874, 52880, 63497, or 33425 polypeptides.

In another aspect, the invention provides methods of screening for compounds that modulate the expression or activity of the 80090, 52874, 52880, 63497, or 33425 polypeptides or nucleic acids.

In still another aspect, the invention provides a process for modulating 80090, 52874, 52880, 63497, or 33425 polypeptide or nucleic acid expression or activity, e.g. using the screened compounds. In certain embodiments, the methods involve treatment of conditions related to aberrant activity or expression of the 80090, 52874, 52880, 63497, or 33425 polypeptides or nucleic acids, such as conditions involving aberrant or deficient cellular proliferation or differentiation.

The invention also provides assays for determining the activity of or the presence or absence of 80090, 52874, 52880, 63497, or 33425 polypeptides or nucleic acid molecules in a biological sample, including for disease diagnosis.

In further aspect the invention provides assays for determining the presence or absence of a genetic alteration in an 80090, 52874, 52880, 63497, or 33425 polypeptide or nucleic acid molecule, including for disease diagnosis.

BRIEF DESCRIPTION OF THE DRAWINGS

FIGS. 1A–B depicts a cDNA sequence (SEQ ID NO:1) and predicted amino acid sequence (SEQ ID NO:2) of human 80090. The methionine-initiated open reading frame of human 80090 (without the 5' and 3' untranslated regions) extends from nucleotide position 1 to position 1461 of SEQ ID NO:3, including the terminal codon.

FIG. 3 depicts an alignment of the glycosyltransferase family 10 (fucosyltransferase) domain of human 80090 with a consensus amino acid sequence derived from a hidden Markov model (HMM) from PFAM. The upper sequences are the consensus amino acid sequences (SEQ ID NO:16), while the lower amino acid sequences correspond to amino acids 35–395 of SEQ ID NO:2.

FIG. 4 depicts a BLAST alignment of human 80090 with a consensus amino acid sequence derived from a ProDomain No. PD313476, "CG4435" (Release 2001.1; Corpet et at. (1999), *Nucl. Acids Res.* 27:263–267 and Gouzy et al. (1999) *Computers and Chemistry* 23:333–340). The lower sequence is amino acid residues 40–217 of the 229 amino acid consensus sequence (SEQ ID NO: 17), while the upper amino acid sequence corresponds to the "CG4435" domain of human 80090, amino acid residues 89–265 of SEQ ID NO:2.

FIG. 5 depicts a BLAST alignment of human 80090 with a consensus amino acid sequence derived from a ProDomain No. PD002778, "Transferase fucosyltransferase glycosyltransferase alpha-12-fucosyltransferase galactoside transmembrance glycoprotein 3-L-signal-anchor golgi" (Release 2001.1; Corpet et at. (1999), *Nucl. Acids Res.* 27:263–267 and Gouzy et al. (1999) *Computers and Chemistry* 23:333–340). The lower sequence is amino acid residues 62–200 of the 227 amino acid consensus sequence (SEQ ID NO: 18), while the upper amino acid sequence corresponds to the "Transferase fucosyltransferase glycosyltransferase alpha-12-fucosyltransferase galactoside transmembrane glycoprotein 3-L-signal-anchor golgi" domain of human 80090, amino acid residues 221–367 of SEQ ID NO:2.

FIG. 6 depicts a BLAST alignment of human 80090 with a consensus amino acid sequence derived from a ProDomain No. PD323544, "CG9169" (Release 2001.1; Corpet et at. (1999), *Nucl. Acids Res.* 27:263–267 and Gouzy et al. (1999) *Computers and Chemistry* 23:333–340). The lower sequence is amino acid residues 129–424 of the 445 amino acid consensus sequence (SEQ ID NO:19), while the upper amino acid sequence corresponds to the "CG9169" domain of human 80090, amino acid residues 90–390 of SEQ ID NO:2.

FIGS. 7A–B depicts a cDNA sequence (SEQ ID NO:4) and predicted amino acid sequence (SEQ ID NO:5) of human 52874. The methionine-initiated open reading frame of human 52874 (without the 5' and 3' untranslated regions)

extends from nucleotide position 1 to position 1386 of SEQ ID NO:6, including the terminal codon.

Figure 8:
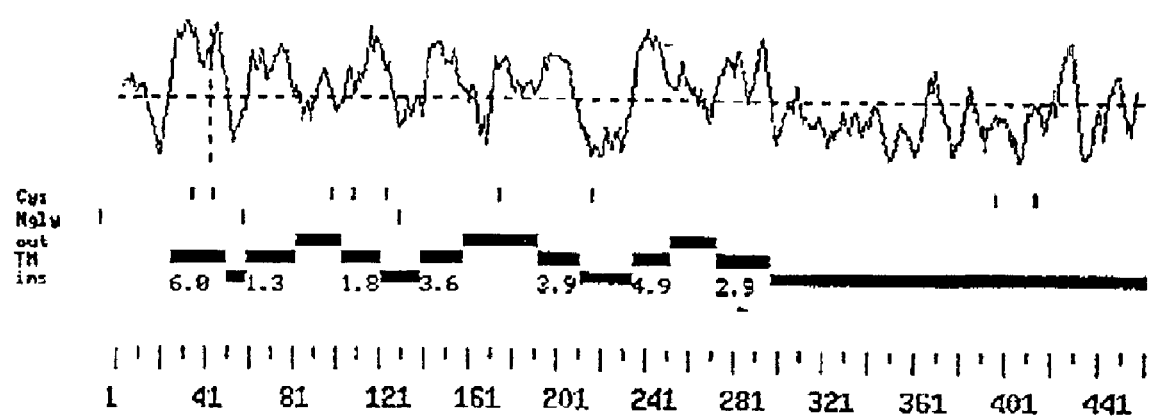

FIG. 8 depicts a hydropathy plot of human 52874. Relatively hydrophobic residues are shown above the dashed horizontal line, and relatively hydrophilic residues are below the dashed horizontal line. The cysteine residues (cys) and N-glycosylation sites (Ngly) are indicated by short vertical lines just below the hydropathy trace. The location of the transmembrane domains and the extracellular and intracellular portions are also indicated. The numbers corresponding to the amino acid sequence of human 52874 are indicated. Polypeptides of the invention include fragments which include: all or part of a hydrophobic sequence, e.g., a sequence above the dashed line, e.g., the sequence from about amino acid 60 to 75, 140 to 155, and from about 240 to 260 of SEQ ID NO:5; all or part of a hydrophilic sequence, e.g., a sequence below the dashed line, e.g., the sequence from about amino acid 210 to 230, 320 to 340 and from about 390 to 410 of SEQ ID NO:5; or a sequence which includes a Cys, or a glycosylation site.

FIGS. 9A–B depict an alignment of the 7 transmembrane receptor (rhodopsin family) domain of human 52874 with a consensus amino acid sequence derived from a hidden Markov model (HMM) from PFAM. The upper sequences are the consensus amino acid sequences (SEQ ID NOs:20 and 21), while the lower amino acid sequences correspond to amino acids 40–120 and 142–293 of SEQ ID NO:5.

FIG. 10 depicts a BLAST alignment of human 52874 with a consensus amino acid sequence derived from a ProDomain No. PD032606, "Receptor neurotensin coupled G-protein type transmembrane lipoprotein levocabastine-palmitate phosphorylation" (Release 2001.1; Corpet et at. (1999), Nucl. Acids Res. 27:263–267 and Gouzy et al. (1999) Computers and Chemistry 23:333–340). The lower sequence is amino acid residues 12–76 of the 84 amino acid consensus sequence (SEQ ID NO:22), while the upper amino acid sequence corresponds to the "Receptor neurotensin coupled G-protein type transmembrane lipoprotein levocabastine-palmitate phosphorylation" domain of human 52874, amino acid residues 253–320 of SEQ ID NO:5.

FIG. 11 depicts a BLAST alignment of human 52874 with a consensus amino acid sequence derived from a ProDomain No. PD128109, "Similar somatostatin receptors" (Release 2001.1; Corpet et at. (1999), Nucl. Acids Res. 27:263–267 and Gouzy et al. (1999) Computers and Chemistry 23:333–340). The lower sequence is amino acid residues 160–267 of the 305 amino acid consensus sequence (SEQ ID NO:23), while the upper amino acid sequence corresponds to the "Similar somatostatin receptors" domain of human 52874, amino acid residues 208–316 of SEQ ID NO:5.

FIG. 12 depicts a BLAST alignment of human 52874 with a consensus amino acid sequence derived from a ProDomain No. PD145471, "C01G12.7" (Release 2001.1; Corpet et at. (1999), Nucl. Acids Res. 27:263–267 and Gouzy et al. (1999) Computers and Chemistry 23:333–340). The lower sequence is amino acid residues 115–298 of the 599 amino acid consensus sequence (SEQ ID NO:24), while the upper amino acid sequence corresponds to the "C01G12.7" domain of human 52874, amino acid residues 16–192 of SEQ ID NO:5.

FIG. 13 depicts a cDNA sequence (SEQ ID NO:7) and predicted amino acid sequence (SEQ ID NO:8) of human 52880. The methionine-initiated open reading frame of human 52880 (without the 5' and 3' untranslated regions) extends from nucleotide position 1 to position 1092 of SEQ ID NO:9, including the terminal codon.

Figure 14:
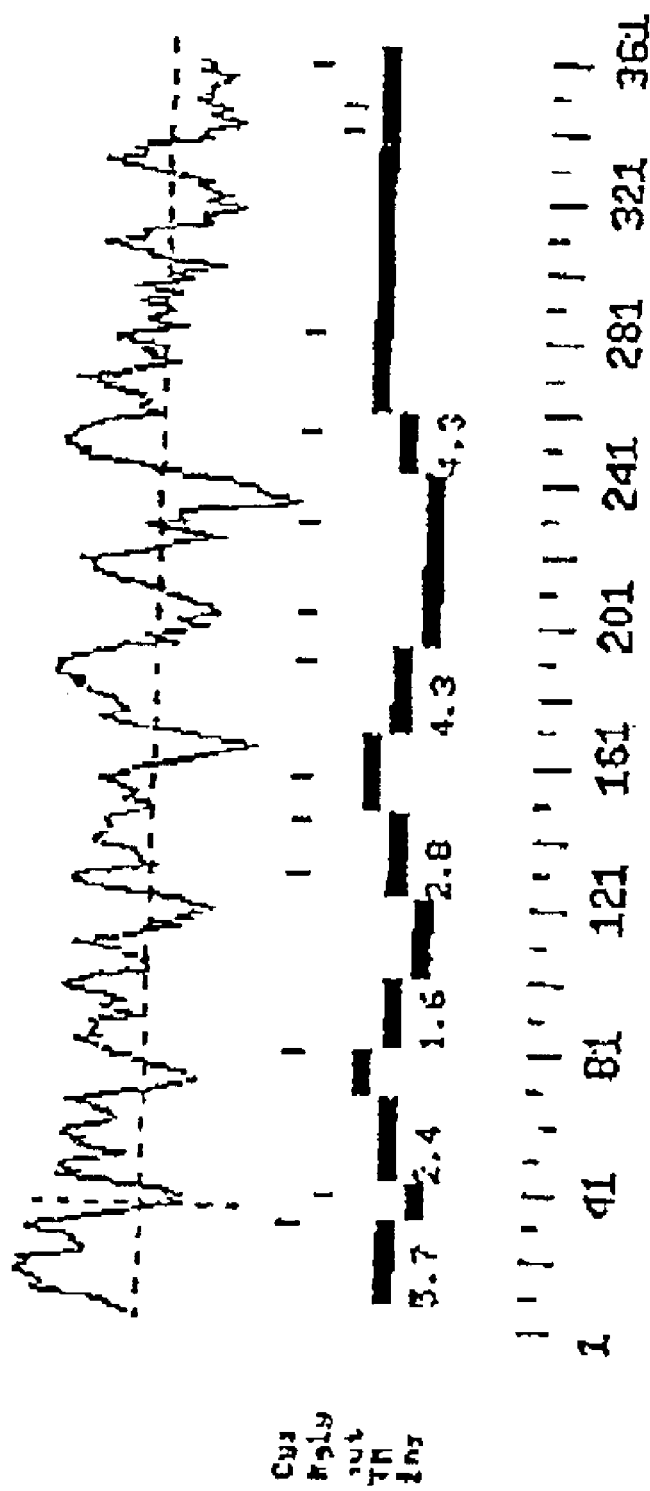

FIG. 14 depicts a hydropathy plot of human 52880. Relatively hydrophobic residues are shown above the dashed horizontal line, and relatively hydrophilic residues are below the dashed horizontal line. The cysteine residues (cys) and N-glycosylation sites (Ngly) are indicated by short vertical lines just below the hydropathy trace. The location of the transmembrane domains and the extracellular and intracellular portions are also indicated. The numbers corresponding to the amino acid sequence of human 52880 are indicated. Polypeptides of the invention include fragments which include: all or part of a hydrophobic sequence, e.g., a sequence above the dashed line, e.g., the sequence from about amino acid 45 to 65, 170 to 190, and from about 245 to 255 of SEQ ID NO:8; all or part of a hydrophilic sequence, e.g., a sequence below the dashed line, e.g., the sequence from about amino acid 230 to 240, 312 to 322 and from about 340 to 350 of SEQ ID NO:8; or a sequence which includes a Cys, or a glycosylation site.

FIG. 15 depicts an alignment of the 7 transmembrane receptor (rhodopsin family) domain of human 52880 with a consensus amino acid sequence derived from a hidden Markov model (HMM) from PFAM. The upper sequences are the consensus amino acid sequences (SEQ ID NO:25), while the lower amino acid sequences correspond to amino acids 22–294 of SEQ ID NO:8.

FIG. 16 depicts a BLAST alignment of human 52880 with a consensus amino acid sequence derived from a ProDomain No. PD310793, "Receptor orphan GPR26 protein-coupled" (Release 2001.1; Corpet et at. (1999), Nucl. Acids Res. 27:263–267 and Gouzy et al. (1999) Computers and Chemistry 23:333–340). The lower sequence is amino acid residues 2–183 of the 205 amino acid consensus sequence (SEQ ID NO:26), while the upper amino acid sequence corresponds to the "Receptor orphan GPR26 protein-coupled" domain of human 52880, amino acid residues 134–315 of SEQ ID NO:8.

FIG. 17 depicts a BLAST alignment of human 52880 with a consensus amino acid sequence derived from a ProDomain No. PD155019, "Receptor type hypocretin EG:22E5.10 EG:22E5.11 transmembrane coupled orexin G-protein" (Release 2001.1; Corpet et at. (1999), Nucl. Acids Res. 27:263–267 and Gouzy et al. (1999) Computers and Chemistry 23:333–340). The lower sequence is amino acid residues 28–184 of the 227 amino acid consensus sequence (SEQ ID NO:27), while the upper amino acid sequence corresponds to the "Receptor type hypocretin EG:22E5.10 EG:22E5.11 transmembrane coupled orexin G-protein" domain of human 52880, amino acid residues 175–321 of SEQ ID NO:8.

FIG. 18 depicts a BLAST alignment of human 52880 with a consensus amino acid sequence derived from a ProDomain No. PD032094, "Receptor acid lysophosphatidic high-affinity homolog transmembrane novel rhodopsin similar" (Release 2001.1; Corpet et at. (1999), Nucl. Acids Res. 27:263–267 and Gouzy et al. (1999) Computers and Chemistry 23:333–340). The lower sequence is amino acid residues 24–183 of the 202 amino acid consensus sequence (SEQ ID NO:28), while the upper amino acid sequence corresponds to the "Receptor acid lysophosphatidic high-affinity homolog transmembrane novel rhodopsin similar" domain of human 52880, amino acid residues 171–322 of SEQ ID NO:8.

FIG. 19 depicts a BLAST alignment of human 52880 with a consensus amino acid sequence derived from a ProDomain No. PD322057, "NT2RM2000452 FLJ10317 Fis cDNA" (Release 2001.1; Corpet et at. (1999), Nucl. Acids Res.

27:263–267 and Gouzy et al. (1999) *Computers and Chemistry* 23:333–340). The lower sequence is amino acid residues 7–99 of the 388 amino acid consensus sequence (SEQ ID NO:29), while the upper amino acid sequence corresponds to the "NT2RM2000452 FLJ10317 Fis cDNA" domain of human 52880, amino acid residues 221–329 of SEQ ID NO:8.

Figure 20:
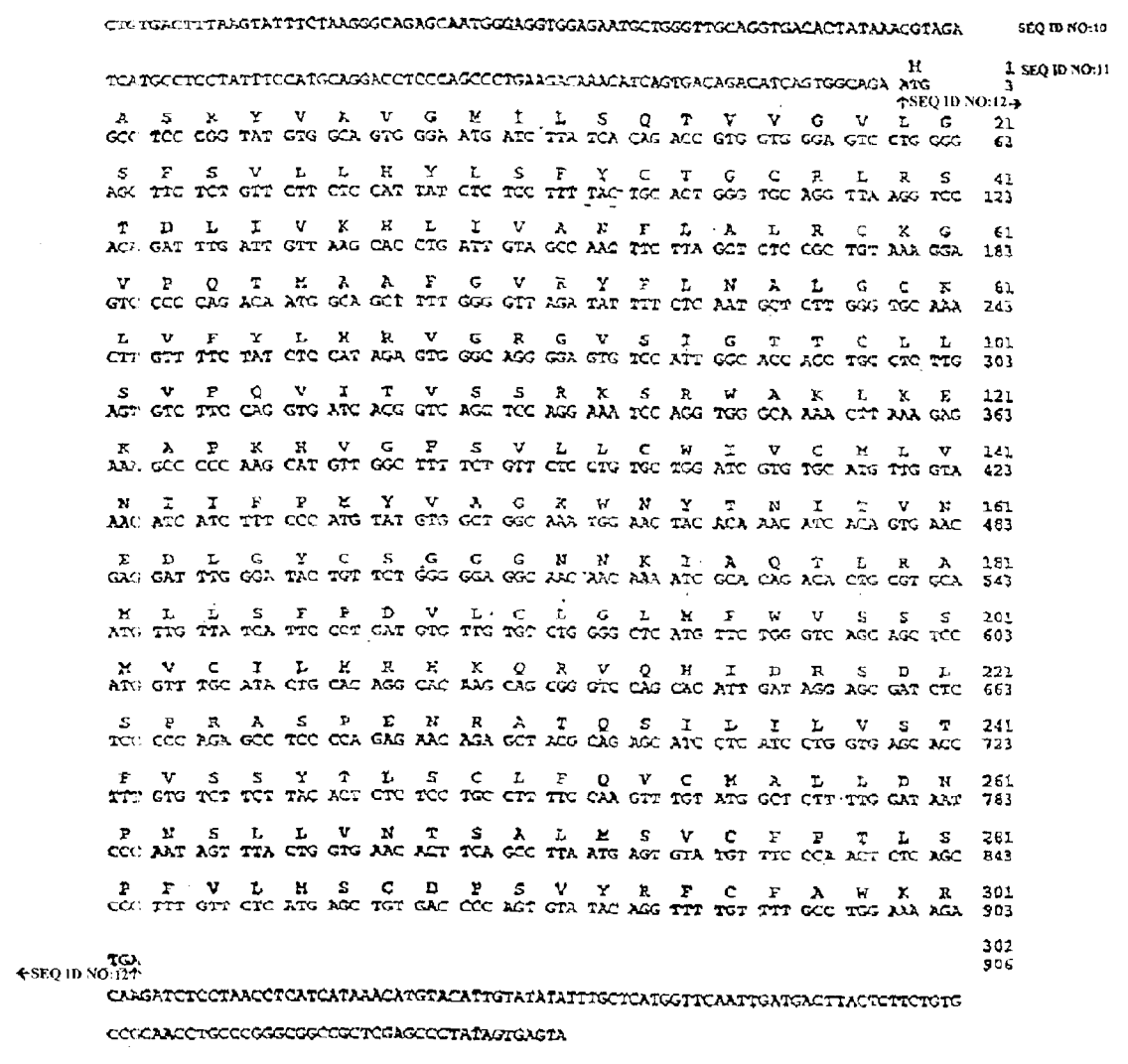

FIG. 20 depicts a cDNA sequence (SEQ ID NO:10) and predicted amino acid sequence (SEQ ID NO:11) of human 63497. The methionine-initiated open reading frame of human 63497 (without the 5' and 3' untranslated regions) extends from nucleotide position 1 to position 906 of SEQ ID NO:12, including the terminal codon.

Figure 21:
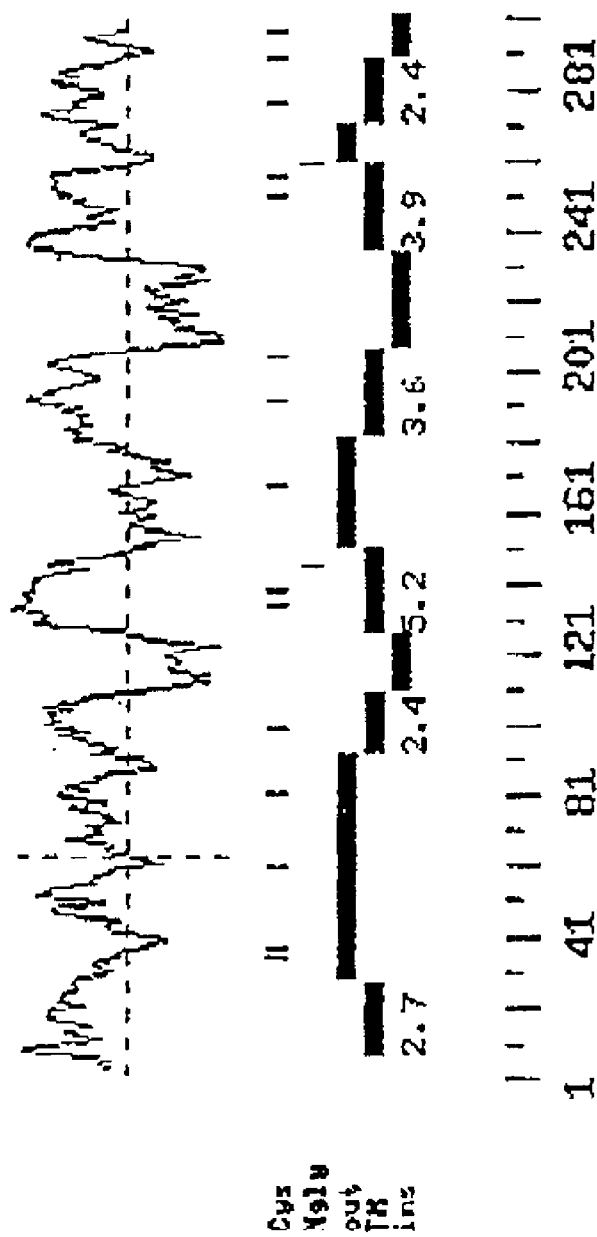

FIG. 21 depicts a hydropathy plot of human 63497. Relatively hydrophobic residues are shown above the dashed horizontal line, and relatively hydrophilic residues are below the dashed horizontal line. The cysteine residues (cys) and N-glycosylation sites (Ngly) are indicated by short vertical lines just below the hydropathy trace. The location of the transmembrane domains and the extracellular and intracellular portions are also indicated. The numbers corresponding to the amino acid sequence of human 63497 are indicated. Polypeptides of the invention include fragments which include: all or part of a hydrophobic sequence, e.g., a sequence above the dashed line, e.g., the sequence from about amino acid 65 to 80, 130 to 145, and from about 180 to 200 of SEQ ID NO:11; all or part of a hydrophilic sequence, e.g., a sequence below the dashed line, e.g., the sequence from about amino acid 110 to 120, and from about 210 to 230 of SEQ ID NO:11; or a sequence which includes a Cys, or a glycosylation site.

FIG. 22 depicts an alignment of the 7 transmembrane receptor (rhodopsin family) domain of human 63497 with a consensus amino acid sequence derived from a hidden Markov model (HMM) from PFAM. The upper sequences are the consensus amino acid sequences (SEQ ID NO:30), while the lower amino acid sequences correspond to amino acids 189–243 of SEQ ID NO:11.

FIG. 23 depicts a BLAST alignment of human 63497 with a consensus amino acid sequence derived from a ProDomain No. PD009900, "Receptor pheromone G-protein vomeronasal coupled M24 VN1 VN3 VN2 VN4" (Release 2001.1; Corpet et at. (1999), *Nucl. Acids Res.* 27:263–267 and Gouzy et al. (1999) *Computers and Chemistry* 23:333–340). The lower sequence is amino acid residues 5–264 of the 274 amino acid consensus sequence (SEQ ID NO:3 1), while the upper amino acid sequence corresponds to the "Receptor pheromone G-protein vomeronasal coupled M24 VN1 VN3 VN2 VN4" domain of human 63497, amino acid residues 36–295 of SEQ ID NO:11.

Figure 24A:
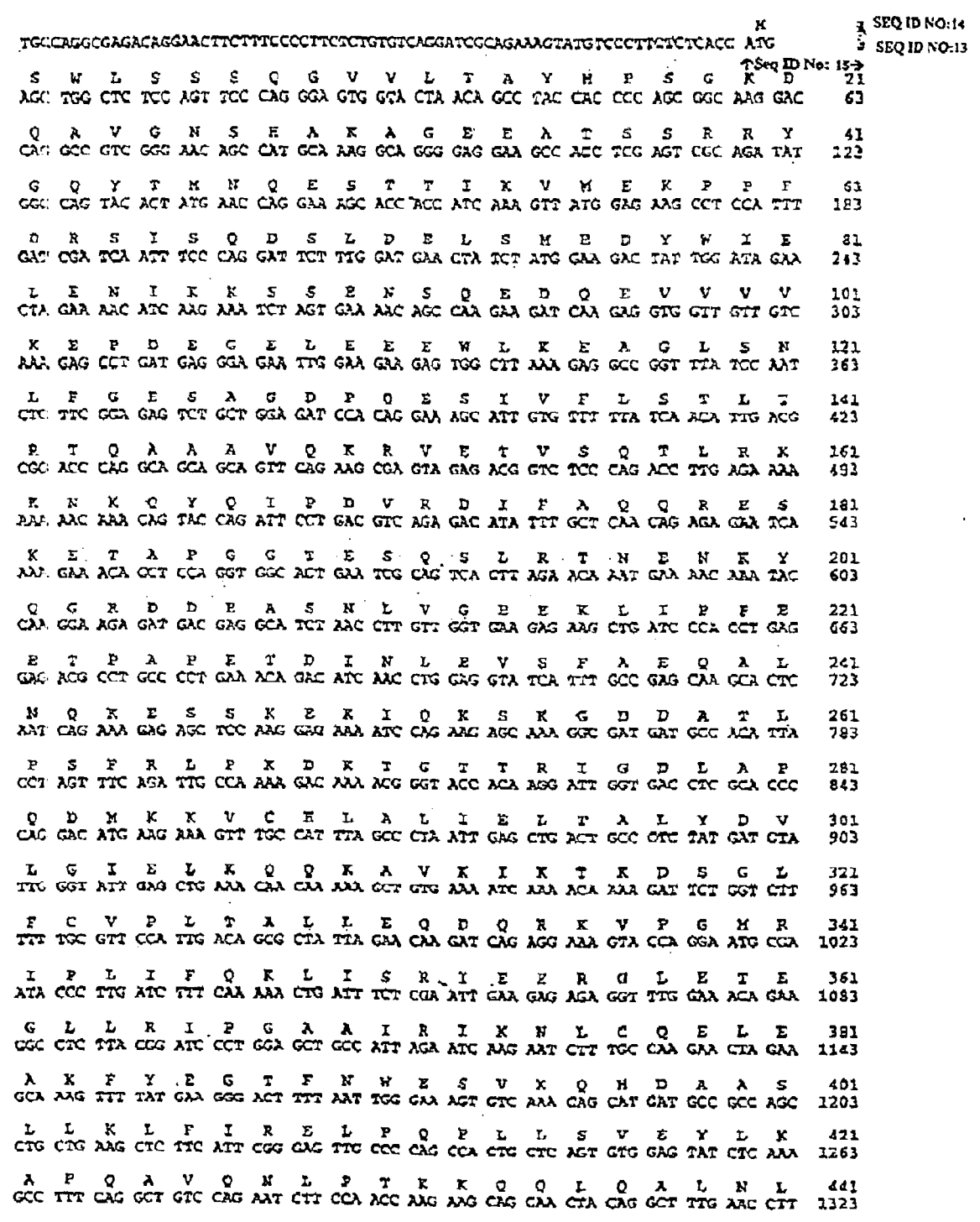

FIGS. 24A–C depicts a cDNA sequence (SEQ ID NO:13) and predicted amino acid sequence (SEQ ID NO:14) of human 33425. The methionine-initiated open reading frame of human 33425 (without the 5' and 3' untranslated regions) extends from nucleotide position 1 to position 1992 of SEQ ID NO: 15, including the terminal codon.

Figure 25:
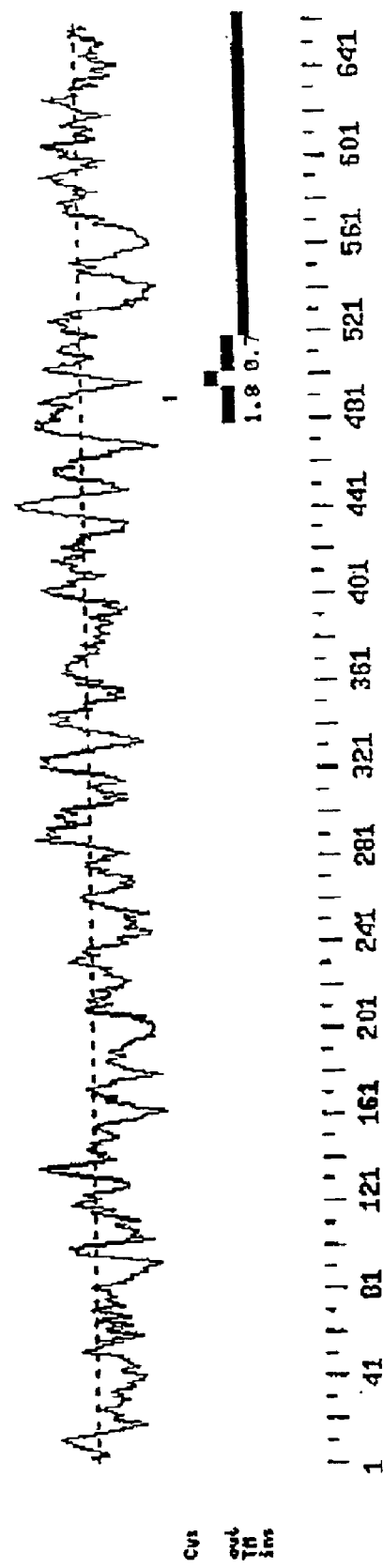

FIG. 25 depicts a hydropathy plot of human 33425. Relatively hydrophobic residues are shown above the dashed horizontal line, and relatively hydrophilic residues are below the dashed horizontal line. The cysteine residues (cys) are indicated by short vertical lines just below the hydropathy trace. The location of the transmembrane domains and the extracellular and intracellular portions are also indicated. The numbers corresponding to the amino acid sequence of human 33425 are indicated. Polypeptides of the invention include fragments which include: all or part of a hydrophobic sequence, e.g., a sequence above the dashed line, e.g., the sequence from about amino acid 290 to 300, 320 to 328, and from about 480 to 490 of SEQ ID NO:14; all or part of a hydrophilic sequence, e.g., a sequence below the dashed line, e.g., the sequence from about amino acid 180 to 200, 380 to 395 and from about 555 to 570 of SEQ ID NO:14; or a sequence which includes a Cys.

FIG. 26 depicts an alignment of the rhoGAP domain of human 33425 with a consensus amino acid sequence derived from a hidden Markov model (HMM) from PFAM. The upper sequences are the consensus amino acid sequences (SEQ ID NO:32), while the lower amino acid sequences correspond to amino acids 343–494 of SEQ ID NO:14.

FIG. 27 depicts a BLAST alignment of human 33425 with a consensus amino acid sequence derived from a ProDomain No. PD301916, "Similar NT2RM2000363 cluster Fis FLJ10312 weakly cDNA breakpoint" (Release 2001.1; Corpet et at. (1999), *Nucl. Acids Res.* 27:263–267 and Gouzy et al. (1999) *Computers and Chemistry* 23:333–340). The lower sequence is amino acid residues 1–103 of the 153 amino acid consensus sequence (SEQ ID NO:33), while the upper amino acid sequence corresponds to the "Similar NT2RM2000363 cluster Fis FLJ10312 weakly cDNA breakpoint" domain of human 33425, amino acid residues 516–608 of SEQ ID NO:14.

FIG. 28 depicts a BLAST alignment of human 33425 with a consensus amino acid sequence derived from a ProDomain No. PD000780, "GTPase activating similar GTPase-activating activation domain Fis zinc cDNA subunit" (Release 2001.1; Corpet et at. (1999), *Nucl. Acids Res.* 27:263–267 and Gouzy et al. (1999) *Computers and Chemistry* 23:333–340). The lower sequence is amino acid residues 16–118 of the 161 amino acid consensus sequence (SEQ ID NO:34), while the upper amino acid sequence corresponds to the "GTPase activating similar GTPase-activating activation domain Fis zinc cDNA subunit" domain of human 33425, amino acid residues 390–486 of SEQ ID NO:14.

FIG. 29 depicts a BLAST alignment of human 33425 with a consensus amino acid sequence derived from a ProDomain No. PD215173, "RLIP" (Release 2001.1; Corpet et at. (1999), *Nucl. Acids Res.* 27:263–267 and Gouzy et al. (1999) *Computers and Chemistry* 23:333–340). The lower sequence is amino acid residues 96–185 of the 186 amino acid consensus sequence (SEQ ID NO:35), while the upper amino acid sequence corresponds to the "RLIP" domain of human 33425, amino acid residues 399–488 of SEQ ID NO:14.

Other features and advantages of the invention will be apparent from the following detailed description, and from the claims.

DETAILED DESCRIPTION

Human 80090

The human 80090 sequence (FIG. 1; SEQ ID NO:1), which is approximately 1669 nucleotides long including untranslated regions, contains a predicted methionine-initiated coding sequence of about 1461 nucleotides (nucleotides 163–1623 of SEQ ID NO:1; SEQ ID NO:3), including the terminal codon. The coding sequence encodes a 486 amino acid protein (SEQ ID NO:2).

This mature protein form is approximately 486 amino acid residues in length (from about amino acid 1 to amino 486 of SEQ ID NO:2). Human 80090 contains the following regions or other structural features:

One glycosyltransferase family 10 (fucosyltransferase) domain located at about amino acid residues 35–395;

One predicted transmembrane domain which extends from about amino acid residues 306–322 of SEQ ID NO:2;

Four predicted N-glycosylation sites (PS00001) located at about amino acid residues 117–120, 175–178, 325–328 and 473–476 of SEQ ID NO:2;

Eight predicted protein kinase C phosphorylation sites (PS00005) located at about amino acid residues 101–103, 158–160, 201–203, 232–234, 297–299, 324–326, 445–447 and 457–459 of SEQ ID NO:2;

Twelve predicted casein kinase II phosphorylation sites (PS00006) located at about amino acid residues 51–54, 57–60, 226–229, 232–235, 243–246, 249–252, 317–320, 426–429, 445–448, 452–455, 457–460 and 475–478 of SEQ ID NO:2;

Two predicted tyrosine kinase phosphorylation sites (PS00007) located at about amino acid residues 80–88 and 346–354 of SEQ ID NO:2; and Four predicted N-myristoylation sites (PS00008) located at about amino acid residues 9–14, 74–79, 105–110 and 133–138 of SEQ ID NO:2.

For general information regarding PFAM identifiers, PS prefix, and PF prefix domain identification numbers, refer to Sonnhammer et al. (1997) *Protein* 28:405–420.

The 80090 protein contains a significant number of structural characteristics in common with members of the fucosyltransferase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

As used herein, the term "fucosyltransferase family" includes a molecule which is involved in the transfer of fucose from GDP-fucose to either galactose in an alpha1,2- linkage or to GlcNAc in alpha1,3-, alpha1,4-, or alpha1,6- linkages.

An 80090 polypeptide can include a "fucosyltransferase domain" or regions homologous with a "fucosyltransferase domain."

As used herein, an "80090 activity", "biological activity of 80090" or "functional activity of 80090", refers to an activity exerted by an 80090 protein, polypeptide or nucleic acid molecule on, e.g., an 80090-responsive cell or on an 80090 substrate, e.g., a protein substrate, as determined in vivo or in vitro. In one embodiment, an 80090 activity is a direct activity, such as an association with an 80090 target molecule "binding molecule" or "substrate". A "target molecule" or "binding partner" or "substrate" is a molecule with which an 80090 protein binds or interacts in nature, e.g., a molecule in which the 80090 protein activates a fucosyltransferase activity.

An 80090 polypeptide can have one or more of the following activities: the ability to transfer a fucosyl moiety from one molecule to another; regulating antigen synthesis; interacting with mucin; regulating tumor cell adhesion or tumor growth; or it is an agonist, e.g., a positive or negative agonist, or an antagonist of an 80090 activity described herein, e.g., a fucosyltransferase activity.

To identify the presence of a "fucosyltransferase" domain in an 80090 protein sequence, and make the determination that a polypeptide or protein of interest has a particular profile, the amino acid sequence of the protein can be searched against a database of HMMs (e.g., the Pfam database, release 2.1) using the default parameters. For example, the hmmsf program, which is available as part of the HMMER package of search programs, is a family specific default program for MILPAT0063, and a score of 15 is the default threshold score for determining a hit. Alternatively, the threshold score for determining a hit can be lowered (e.g., to 8 bits). A description of the Pfam database can be found in Sonhammer et al. (1997) Proteins 28(3):405–420, and a detailed description of HMMs can be found, for example, in Gribskov et al.(1990) Meth. Enzymol. 183:146–159; Gribskov et al.(1987) Proc. Natl. Acad. Sci. USA 84:4355–4358; Krogh et al.(1994) J. Mol. Biol. 235:1501–1531; and Stultz et al.(1993) Protein Sci. 2:305–314, the contents of which are incorporated herein by reference. A search was performed against the HMM database resulting in the identification of a fucosyltransferase domain in the amino acid sequence of human 80090 at about residues 35–395 of SEQ ID NO:2 (see FIG. 1).

An 80090 polypeptide can include a fucosyltransferase domain or regions homologous with a fucosyltransferase domain. As used herein, the fucosyltransferase domain includes an amino acid sequence of about 200–500 amino acid residues in length. Preferably, an fucosyltransferase protein domain includes at least about 250–450 amino acids, more preferably about 300–400 amino acids, or about 350–375 amino acids. The fucosyltransferase domain (HMM) has been assigned the PFAM Accession PF00852. An alignment of the fucosyltransferase domain (amino acids 35–395 of SEQ ID NO:2) of human 80090 with a consensus amino acid sequence derived from a hidden Markov model is depicted in FIG. 3.

In a preferred embodiment 80090 polypeptide or protein has a "fucosyltransferase domain" or a region which includes at least about 200–500 more preferably about 250–450 or 300–400 amino acid residues and has at least about 50%, 60%, 70% 80% 90% 95%, 99%, or 100% homology with a "fucosyltransferase domain," e.g., the fucosyltransferase domain of human 80090 (e.g., residues 35–395 of SEQ ID NO:2).

For further identification of domains in an 80090 protein sequence, and make the determination that a polypeptide or protein of interest has a particular profile, the amino acid sequence of the protein can be searched against a database of domains, e.g., the ProDom database (Corpet et al. (1999), *Nucl. Acids Res.* 27:263–267). The ProDom protein domain database consists of an automatic compilation of homologous domains. Current versions of ProDom are built using recursive PSI-BLAST searches (Altschul SF et al. (1997) *Nucleic Acids Res.* 25:3389–3402; Gouzy et al. (1999) *Computers and Chemistry* 23:333–340) of the SWISS-PROT 38 and TREMBL protein databases. The database automatically generates a consensus sequence for each domain.

A BLAST search was performed against the HMM database resulting in the identification of a region homologous to ProDom family PD313476 ("CG4435" SEQ ID NO:17, ProDomain Release 2001.1; Corpet et at. (1999), *Nucl. Acids Res.* 27:263–267 and Gouzy et al. (1999) *Computers and Chemistry* 23:333–340). An alignment of the "CG4435" domain (amino acids 89–265 of SEQ ID NO:2) of human 80090 with a consensus amino acid sequence (SEQ ID NO:17) derived from a hidden Markov model is depicted in FIG. 4. The consensus sequence for SEQ ID NO:17 is 42% identical over amino acids 89–265 of SEQ ID NO:2 as shown in FIG. 4.

A BLAST search was performed against the HMM database resulting in the identification of a region homologous to ProDom family PD002778 ("Transferase fucosyltransferase glycosyltransferase alpha-12-fucosyltransferase galactoside transmembrance glycoprotein 3-L-signal-anchor golgi" SEQ ID NO:18, ProDomain Release 2001.1; Corpet et at. (1999), *Nucl. Acids Res.* 27:263–267 and Gouzy et al. (1999) *Computers and Chemistry* 23:333–340). An alignment of the "Transferase fucosyltransferase glycosyltransferase alpha-12-fucosyltransferase galactoside transmembrance glycoprotein 3-L-signal-anchor golgi" domain (amino acids 221–367 of SEQ ID NO:2) of human 80090 with a consensus amino acid sequence (SEQ ID NO:18) derived from a hidden Markov model is depicted in FIG. 5. The consensus sequence for SEQ ID NO:18 is 36% identical over amino acids 221–367 of SEQ ID NO:2 as shown in FIG. 5.

A BLAST search was performed against the HMM database resulting in the identification of a region homologous to ProDom family PD323544 ("CG9169" SEQ ID NO:19, ProDomain Release 2001.1; Corpet et at. (1999), *Nucl. Acids Res.* 27:263–267 and Gouzy et al. (1999) *Computers and Chemistry* 23:333–340). An alignment of the "CG9169" domain (amino acids 90–390 of SEQ ID NO:2) of human 80090 with a consensus amino acid sequence (SEQ ID NO:19) derived from a hidden Markov model is depicted in FIG. 6. The consensus sequence for SEQ ID NO:19 is 24% identical over amino acids 90–390 of SEQ ID NO:2 as shown in FIG. 6.

A BLAST search was performed against the HMM database resulting in the identification of a region homologous to ProDom family PD323544 ("CG9169" SEQ ID NO:19, ProDomain Release 2001.1; Corpet et at. (1999), *Nucl. Acids Res.* 27:263–267 and Gouzy et al. (1999) *Computers and Chemistry* 23:333–340). An alignment of the "CG9169" domain (amino acids 90–390 of SEQ ID NO:2) of human 80090 with a consensus amino acid sequence (SEQ ID NO:19) derived from a hidden Markov model is depicted in FIG. 6. The consensus sequence for SEQ ID NO:19 is 24% identical over amino acids 90–390 of SEQ ID NO:2 as shown in FIG. 6.

An 80090 polypeptide can include at least one "transmembrane domain" or region homologous with a "transmembrane domain". As used herein, the term "transmembrane domain" includes an amino acid sequence of about 10 to 40 amino acid residues in length and spans the plasma membrane. Transmembrane domains are rich in hydrophobic residues, e.g., at least 50%, 60%, 70%, 80%, 90%, 95% or more of the amino acids of a transmembrane domain are hydrophobic, e.g., leucines, isoleucines, tyrosines, or tryptophans. Transmembrane domains typically have alpha-helical structures and are described in, for example, Zagotta, W. N. et al., (1996) *Annual Rev. Neurosci.* 19:235–263, the contents of which are incorporated herein by reference.

Figure 2:
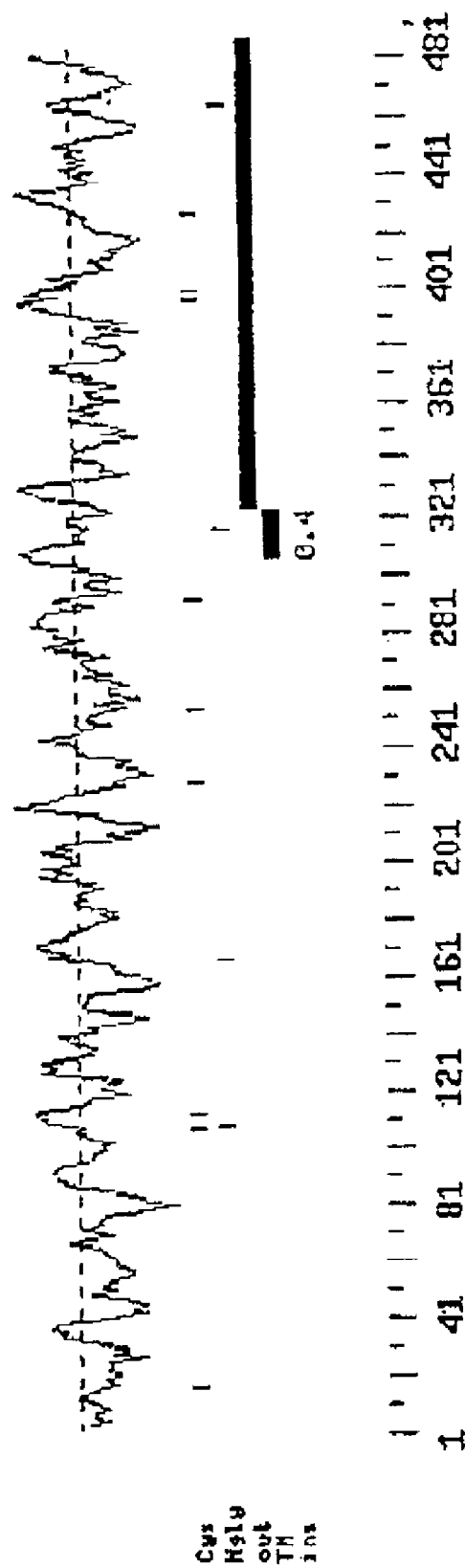
FIG. 2 depicts a hydropathy plot of human 80090. Relatively hydrophobic residues are shown above the dashed horizontal line, and relatively hydrophilic residues are below the dashed horizontal line. The cysteine residues (cys) and N-glycosylation sites (Ngly) are indicated by short vertical lines just below the hydropathy trace. The location of the transmembrane domains and the extracellular and intracellular portions are also indicated. The numbers corresponding to the amino acid sequence of human 80090 are indicated. Polypeptides of the invention include fragments which include: all or part of a hydrophobic sequence, e.g., a sequence above the dashed line, e.g., the sequence from about amino acid 167 to 175, 280 to 288, and from about 392 to 400 of SEQ ID NO:2; all or part of a hydrophilic sequence, e.g., a sequence below the dashed line, e.g., the sequence from about amino acid 15 to 30, 250 to 270 and from about 410 to 425 of SEQ ID NO:2; or a sequence which includes a Cys, or a glycosylation site.

In a preferred embodiment, an 80090 polypeptide or protein has at least one "transmembrane domain" or a region which includes at least about 12 to 35 more preferably about 14 to 30 or 15 to 25 amino acid residues and has at least about 60%, 70% 80% 90% 95%, 99%, or 100% homology with a "transmembrane domain," e.g., the transmembrane domains of human 80090 (e.g., residues 306 to 322 of SEQ ID NO:2). The transmembrane domain of human 80090 is visualized in the hydropathy plot (FIG. 2) as regions of about 15 to 25 amino acids where the hydropathy trace is mostly above the horizontal line.

To identify the presence of a "transmembrane" domain in an 80090 protein sequence, and make the determination that a polypeptide or protein of interest has a particular profile, the amino acid sequence of the protein can be analyzed by a transmembrane prediction method that predicts the secondary structure and topology of integral membrane proteins based on the recognition of topological models (MEMSAT, Jones et al., (1994) *Biochemistry* 33:3038–3049).

An 80090 polypeptide can include at least one, preferably two "non-transmembrane regions." As used herein, the term "non-transmembrane region" includes an amino acid sequence not identified as a transmembrane domain. The non-transmembrane regions in 80090 are located at about amino acids 1–305 and 323–486 of SEQ ID NO:2.

The non-transmembrane regions of 80090 include at least one cytoplasmic region. When located at the N-terminus, the cytoplasmic region is referred to herein as the "N-terminal cytoplasmic domain." As used herein, an "N-terminal cytoplasmic domain" includes an amino acid sequence having about 1 to 400, preferably about 1 to 350, more preferably about 1 to 310, or even more preferably about 1 to 305 amino acid residues in length and is located inside of a cell or within the cytoplasm of a cell. The C-terminal amino acid residue of an "N-terminal cytoplasmic domain" is adjacent to an N-terminal amino acid residue of a transmembrane domain in an 80090 protein. For example, an N-terminal cytoplasmic domain is located at about amino acid residues 1 to 305 of SEQ ID NO:2.

In a preferred embodiment, a polypeptide or protein has an N-terminal cytoplasmic domain or a region which includes at least about 5, preferably about 1 to 350, and more preferably about 1 to 305 amino acid residues and has at least about 60%, 70% 80% 90% 95%, 99%, or 100% homology with an "N-terminal cytoplasmic domain," e.g., the N-terminal cytoplasmic domain of human 80090 (e.g., residues 1 to 305 of SEQ ID NO:2).

In a preferred embodiment, an 80090 family member can include at least one fucosyltransferase family domain (PFAM Accession Number PF00852). Furthermore, an 80090 family member can include at least one, two, three, and preferably four N-glycosylation site (PS00001); at least one, two, three, four, five, six, seven, and preferably eight protein kinase C phosphorylation sites (PS00005); at least one, two, three, four, five, six, seven, eight, nine, ten, eleven, and preferably twelve casein kinase II phosphorylation sites (PS00006); at least one, and preferably two tyrosine kinase phosphorylation sites (PS00007); and at least one, two, three, and preferably four N-myristoylation sites (PS00008).

As the 80090 polypeptides of the invention may modulate 80090-mediated activities, they may be useful for developing novel diagnostic and therapeutic agents for 80090-mediated or related disorders, as described below.

Based on the above-described sequence similarities, the 80090 molecules of the present invention are predicted to have similar biological activities as fucosyltransferase family members. Thus, the 80090 molecules can act as novel diagnostic targets and therapeutic agents for modulating an immune response, e.g., controlling immunological disorders such as autoimmune disorders, or cell proliferation, e.g., controlling cancer such as gastric tumors.

Human 52874

The human 52874 sequence (FIGS. 7A–B; SEQ ID NO:4), which is approximately 1420 nucleotides long including untranslated regions, contains a predicted methionine-initiated coding sequence of about 1386 nucleotides (nucleotides 32–1417 of SEQ ID NO:4; SEQ ID NO:6), including the terminal codon. The coding sequence encodes a 461 amino acid protein (SEQ ID NO:5).

In one embodiment, a 52874 molecule may include a signal sequence. As used herein, a "signal sequence" refers to a peptide of about 10–80 amino acid residues in length which occurs at the N-terminus of secretory and integral membrane proteins and which contains a majority of hydrophobic amino acid residues. For example, a signal sequence contains at least about 20–65 amino acid residues, more preferably about 41 amino acid residues, and has at least about 40–70%, preferably about 50–65%, and more preferably about 55–60% hydrophobic amino acid residues (e.g., alanine, valine, leucine, isoleucine, phenylalanine, tyrosine, tryptophan, or proline). Such a "signal sequence", also referred to in the art as a "signal peptide", serves to direct a protein containing such a sequence to a lipid bilayer. For example, in one embodiment, a 52874 protein contains a signal sequence of about amino acids 1–41 of SEQ ID NO:5. The "signal sequence" is cleaved during processing of the mature protein. In this embodiment, the mature 52874 protein corresponds to amino acids 42–461 of SEQ ID NO:5.

Therefore, the mature protein form is approximately 461 amino acid residues in length (from about amino acid 1 to amino acid 461 of SEQ ID NO:5) or, if a signal sequence is present and then cleaved off, is approximately 420 amino acids in length (from about amino acid 42 to amino acid 461 of SEQ ID NO:5). Human 52874 contains the following regions or other structural features: predicted transmembrane domains which extend from about amino acid residue 25–49, 59–81, 103–120, 139–157, 192–210, 235–251, and 273–296 of SEQ ID NO:5; or if a signal sequence is present and then cleaved off, predicted transmembrane domains extend from about amino acid residue 18–40, 62–79, 98–116, 151–169, 194–210, and 232–255 of the mature protein of SEQ ID NO:5 (i.e., the mature protein having amino acids 42–461 of SEQ ID NO:5).

The mature protein form is approximately 461 or 420 amino acid residues in length (from about amino acid 1 to amino acid 461 or amino acid 42 to amino acid 461 of SEQ ID NO:5). Human 52874 contains the following regions or other structural features:

two predicted seven transmembrane (7TM) family domains located at about amino acids 40–120 and 142–293 of SEQ ID NO:5. The seven transmembrane domains show homology to members of the rhodopsin family;

three predicted N-glycosylation sites (PS00001) located at about amino acids 2–5, 66–69, and 138–141 of SEQ ID NO:5;

one predicted glycosaminoglycan attachment site (PS00002) located at about amino acids 357–360 of SEQ ID NO:5;

one predicted cAMP- and cGMP-dependent protein kinase phosphorylation site (PS00004) located at about amino acids 218–221 of SEQ ID NO:5;

six predicted protein kinase C phosphorylation sites (PS00005) located at about amino acids 164–166, 313–315, 357–359, 362–364, 408–410, and 443–445 of SEQ ID NO:5;

four predicted casein kinase II phosphorylation sites (PS00006) located at about amino acids 68–71, 89–92, 318–321, and 345–348 of SEQ ID NO:5; and three predicted N-myristoylation sites (PS00008) located at about amino acids 170–175, 328–333, and 397–402 of SEQ ID NO:5.

For general information regarding PFAM identifiers, PS prefix, and PF prefix domain identification numbers, refer to Sonnhammer et al. (1997) *Protein* 28:405–420.

Human 52880

The human 52880 sequence (FIG. 13; SEQ ID NO:7), which is approximately 1352 nucleotides long including untranslated regions, contains a predicted methionine-initiated coding sequence of about 1092 nucleotides (nucleotides 210–1301 of SEQ ID NO:7; SEQ ID NO:9), including the terminal codon. The coding sequence encodes a 363 amino acid protein (SEQ ID NO:8).

In one embodiment, a 52880 molecule may include a signal sequence. As used herein, a "signal sequence" refers to a peptide of about 10–60 amino acid residues in length which occurs at the N-terminus of secretory and integral membrane proteins and which contains a majority of hydrophobic amino acid residues. For example, a signal sequence contains at least about 20–50 amino acid residues, more preferably about 33 amino acid residues, and has at least about 40–70%, preferably about 50–65%, and more preferably about 55–60% hydrophobic amino acid residues (e.g., alanine, valine, leucine, isoleucine, phenylalanine, tyrosine, tryptophan, or proline). Such a "signal sequence", also referred to in the art as a "signal peptide", serves to direct a protein containing such a sequence to a lipid bilayer. For example, in one embodiment, a 52880 protein contains a signal sequence of about amino acids 1–33 of SEQ ID NO:8. The "signal sequence" is cleaved during processing of the mature protein. In this embodiment, the mature 52880 protein corresponds to amino acids 34–363 of SEQ ID NO:8.

Therefore, the mature protein form is approximately 363 amino acid residues in length (from about amino acid 1 to amino acid 363 of SEQ ID NO:8) or, if a signal sequence is present and then cleaved off, is approximately 330 amino acids in length (from about amino acid 34 to amino acid 363 of SEQ ID NO:8). Human 52880 contains the following regions or other structural features: predicted transmembrane domains which extend from about amino acid residue 7–31, 43–67, 81–100, 123–147, 169–193 and 243–259 of SEQ ID NO:8; or if a signal sequence is present and then cleaved off, predicted transmembrane domains extend from about amino acid residue 10–34, 48–67, 90–114, 136–160, and 210–226 of the mature protein of SEQ ID NO:8 (i.e., the mature protein having amino acids 34–363 of SEQ ID NO:8).

The mature protein form is approximately 363 or 330 amino acid residues in length (from about amino acid 1 to amino acid 363 or amino acid 34 to amino acid 363 of SEQ ID NO:8). Human 52880 contains the following regions or other structural features:

one predicted seven transmembrane (7TM) family domain located at about amino acids 22–294 of SEQ ID NO:8. The seven transmembrane domains show homology to members of the rhodopsin family;

three predicted N-glycosylation sites (PS00001) located at about amino acids 47–50, 348–351, and 355–358 of SEQ ID NO:8;

six predicted protein kinase C phosphorylation sites (PS00005) located at about amino acids 157–159, 210–212, 223–225, 240–242, 316–318, and 340–342 of SEQ ID NO:8;

three predicted casein kinase II phosphorylation sites (PS00006) located at about amino acids 321–324, 325–328, and 353–356 of SEQ ID NO:8;

one predicted tyrosine kinase phosphorylation site (PS00007) located at about amino acids 286–294 of SEQ ID NO:8;

six predicted N-myristoylation sites (PS00008) located at about amino acids 66–71, 124–129, 132–137, 139–144, 244–249, 349–354 of SEQ ID NO:8; and two predicted prokaryotic membrane lipoprotein lipid attachment sites (PS00013) located at about amino acids 134–144 and 146–156 of SEQ ID NO:8.

For general information regarding PFAM identifiers, PS prefix, and PF prefix domain identification numbers, refer to Sonnhammer et al. (1997) *Protein* 28:405–420.

Human 63497

The human 63497 sequence (FIG. 20; SEQ ID NO:10), which is approximately 1178 nucleotides long including untranslated regions, contains a predicted methionine-initiated coding sequence of about 906 nucleotides (nucleotides 152–1057 of SEQ ID NO:10; SEQ ID NO:12), including the terminal codon. The coding sequence encodes a 301 amino acid protein (SEQ ID NO:11).

In one embodiment, a 63497 molecule may include a signal sequence. As used herein, a "signal sequence" refers to a peptide of about 10–80 amino acid residues in length which occurs at the N-terminus of secretory and integral membrane proteins and which contains a majority of hydrophobic amino acid residues. For example, a signal sequence contains at least about 30–70 amino acid residues, more preferably about 61 amino acid residues, and has at least about 40–70%, preferably about 50–65%, and more preferably about 55–60% hydrophobic amino acid residues (e.g., alanine, valine, leucine, isoleucine, phenylalanine, tyrosine, tryptophan, or proline). Such a "signal sequence", also referred to in the art as a "signal peptide", serves to direct a protein containing such a sequence to a lipid bilayer. For example, in one embodiment, a 63497 protein contains a signal sequence of about amino acids 1–61 of SEQ ID NO:11. The "signal sequence" is cleaved during processing of the mature protein. In this embodiment, the mature 63497 protein corresponds to amino acids 62–301 of SEQ ID NO:11.

Therefore, the mature protein form is approximately 301 amino acid residues in length (from about amino acid 1 to amino acid 301 of SEQ ID NO:11) or, if a signal sequence is present and then cleaved off, is approximately 240 amino acids in length (from about amino acid 62 to amino acid 301 of SEQ ID NO:11). Human 63497 contains the following regions or other structural features: predicted transmembrane domains which extend from about amino acid residue 7–27, 92–109, 127–150, 182–206, 235–259, and 271–288 of SEQ ID NO:11; or if a signal sequence is present and then cleaved off, predicted transmembrane domains extend from about amino acid residue 31–48, 66–89, 121–145, 174–198, and 210–227 of the mature protein of SEQ ID NO:11 (i.e., the mature protein having amino acids 62–301 of SEQ ID NO:11).

The mature protein form is approximately 301 or 240 amino acid residues in length (from about amino acid 1 to amino acid 301 or amino acid 62 to amino acid 301 of SEQ ID NO:11). Human 63497 contains the following regions or other structural features:

one predicted seven transmembrane (7TM) family domain located at about amino acids 189–243 of SEQ ID NO:11. The seven transmembrane domains show homology to members of the rhodopsin family;

two predicted N-glycosylation sites (PS00001) located at about amino acids 154–157 and 268–271 of SEQ ID NO:11;

one predicted glycosaminoglycan attachment site (PS00002) located at about amino acids 168–171 of SEQ ID NO:11;

three predicted protein kinase C phosphorylation sites (PS00005) located at about amino acids 110–112, 178–180, and 222–224 of SEQ ID NO:11;

two predicted casein kinase II phosphorylation sites (PS00006) located at about amino acids 159–162 and 185–188 of SEQ ID NO:11;

five predicted N-myristoylation sites (PS00008) located at about amino acids 9–14, 18–23, 61–66, 92–97, and 169–174 of SEQ ID NO:11;

one predicted prokaryotic membrane lipoprotein lipid attachment site (PS00013) located at about amino acids 278–288 of SEQ ID NO:11; and one predicted leucine zipper pattern site (PS00029) located at about amino acids 251–272.

For general information regarding PFAM identifiers, PS prefix, and PF prefix domain identification numbers, refer to Sonnhammer et al. (1997) *Protein* 28:405–420.

The 52874, 52880, or 63497 protein contains a significant number of structural characteristics in common with members of the 7TM family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

As used herein, the term "seven transmembrane domain receptor" or "7TM" or "7TMR" refers to a family of proteins that preferably comprise an N-terminal extracellular domain, seven transmembrane domains (also referred to as membrane-spanning domains), three extracellular domains (also referred to as extracellular loops), three cytoplasmic domains (also referred to as cytoplasmic loops), and a C-terminal cytoplasmic domain (also referred to as a cytoplasmic tail).

As used herein, the term "G protein-coupled receptor" or "GPCR" refers to a family of proteins that preferably comprise an N-terminal extracellular domain, seven transmembrane domains (also referred to as membrane-spanning domains), three extracellular domains (also referred to as extracellular loops), three cytoplasmic domains (also referred to as cytoplasmic loops), and a C-terminal cytoplasmic domain (also referred to as a cytoplasmic tail). Members of the GPCR family also share certain conserved amino acid residues, some of which have been determined to be critical to receptor function and/or G protein signaling. For example, GPCRs usually contain the following features including a conserved asparagine residue in the first transmembrane domain.

Based on structural similarities, members of the 7TMR family have been classified into various subfamilies, including: Subfamily I which comprises receptors typified by rhodopsin and the beta2-adrenergic receptor and currently contains over 200 unique members (reviewed by Dohlman et al. (1991) *Annu. Rev. Biochem.* 60:653–688); Subfamily II, which includes the parathyroid hormone/calcitonin/secretin receptor family (Juppner et al. (1991) *Science* 254:1024–1026; Lin et al. (1991) *Science* 254:1022–1024); Subfamily III, which includes the metabotropic glutamate receptor family in mammals, such as the GABA receptors (Nakanishi et al. (1992) *Science* 258: 597–603); Subfamily IV, which includes the cAMP receptor family that is known to mediate the chemotaxis and development of *D. discoideum* (Klein et al. (1988) *Science* 241:1467–1472); and Subfamily V, which includes the fungal mating pheromone receptors such as STE2 (reviewed by Kurjan I et al. (1992) *Annu. Rev. Biochem.* 61:1097–1129). Within each family, distinct, highly conserved motifs have been identified. These motifs have been suggested to be critical for the structural integrity of the receptor, as well as for coupling to G proteins.

Based on the results from the HMM analysis (HMMER Version 2.1.1), the 52874, 52880, and 63497 polypeptides appears to belong to the rhodopsin subfamily of 7TMRs (family 1).

As used herein, a "52874, 52880, or 63497 activity", "biological activity of 52874, 52880, or 63497" or "functional activity of 52874, 52880, or 63497", refers to an activity exerted by a 52874, 52880, or 63497 protein, polypeptide or nucleic acid molecule on e.g., a 52874-, 52880-, or 63497-responsive cell or on a 52874, 52880, or 63497 substrate, e.g., a protein substrate, as determined in vivo or in vitro. In one embodiment, a 52874, 52880, or 63497 activity is a direct activity, such as an association with a 52874, 52880, or 63497 target molecule. A "target molecule" or "binding partner" is a molecule with which a 52874, 52880, or 63497 protein binds or interacts in nature. A 52874, 52880, or 63497 activity can also be an indirect activity, e.g., a cellular signaling activity mediated by interaction of the 52874, 52880, or 63497 receptor with a 52874, 52880, or 63497 ligand.

The 52874, 52880, or 63497 molecules of the present invention are predicted to have similar biological activities as 7TM receptor family members, e.g., G-protein coupled receptor family members. For example, the 52874, 52880, or 63497 proteins of the present invention can have one or more of the following activities: (1) regulating, sensing and/or transmitting an extracellular signal into a cell, (for example, a heart cell, a bone cell (e.g., an osteoclast or an osteoblast), a hematopoietic cell, a neural cell); (2) interacting with (e.g., binding to) an extracellular signal or a cell surface receptor; (3) mobilizing an intracellular molecule that participates in a signal transduction pathway (e.g., adenylate cyclase or phosphatidylinositol 4,5-bisphosphate ($PIP_2$), inositol 1,4,5-triphosphate ($IP_3$)); (4) regulating polarization of the plasma membrane; (5) controlling production or secretion of molecules; (6) altering the structure of a cellular component; (7) modulating cell proliferation, e.g., synthesis of DNA; and (8) modulating cell migration, cell differentiation; and cell survival. Thus, the 52874, 52880, or 63497 molecules can act as novel diagnostic targets and therapeutic agents for controlling G-protein coupled receptor-related disorders. Other activities, as described below, include the ability to modulate function, survival, morphology, proliferation and/or differentiation of cells of tissues in which 52874, 52880, or 63497 molecules are expressed.

Many available therapeutic drugs in use today target GPCRs, as they mediate vital physiological responses, including vasodilation, heart rate, bronchodilation, endocrine secretion, and gut peristalsis. See, eg., Lefkowitz et al., Ann. Rev. Biochem. 52:159 (1983). For example, ligands to beta adrenergic receptors are used in the treatment of anaphylaxis, shock, hypertension, hypotension, asthma and other conditions. Additionally, spontaneous activation of GPCRs occurs, where a GPCR cellular response is generated in the absence of a ligand. Increased spontaneous activity can be decreased by antagonists of the GPCR (a process known as inverse agonism); such methods are therapeutically important where diseases cause an increase in spontaneous GPCR activity. Thus, modulation of the activity of the 52874, 52880, or 63497 molecules of the invention may be beneficial in modulating a variety of physiological responses, such as vasodilation, heart rate, bronchodilation, endocrine secretion or gut peristalsis. Moreover, downmodulation of the 52874, 52880, or 63497 molecules of the invention can be beneficial in conditions characterized by increased spontaneous activity of 52874, 52880, or 63497. Furthermore, the 52874, 52880, or 63497 molecules of the invention are members of the rhodopsin family of 7TM receptors. Rhodopsin is a visual pigment which is a sensor for recognizing optical information and a membrane protein widely distributed in vertebrate and invertebrate species. Rhodopsin is useful as a material for photosensor or optical information recognition elements. Thus, the 52874, 52880, or 63497 molecules of the invention also may prove useful as materials for photosensor or optical information recognition elements.

The response mediated by a 52874, 52880, or 63497 receptor protein depends on the type of cell. For example, in some cells, binding of a ligand to the receptor protein may stimulate an activity such as release of compounds, gating of a channel, cellular adhesion, migration, differentiation, etc., through phosphatidylinositol or cyclic AMP metabolism and turnover while in other cells, the binding of the ligand will produce a different result. Regardless of the cellular activity/ response modulated by the receptor protein, GPCRs of the 7TM family interacts with G proteins to produce one or more secondary signals, in a variety of intracellular signal transduction pathways, e.g., through phosphatidylinositol or cyclic AMP metabolism and turnover, in a cell. As used herein, a "signaling transduction pathway" refers to the modulation (e.g., stimulation or inhibition) of a cellular function/activity upon the binding of a ligand to the GPCR (52874, 52880, or 63497 protein). Examples of such functions include mobilization of intracellular molecules that participate in a signal transduction pathway, e.g., phosphatidylinositol 4,5-bisphosphate ($PIP_2$), inositol 1,4,5-triphosphate ($IP_3$) and adenylate cyclase.

As used herein, "phosphatidylinositol turnover and metabolism" refers to the molecules involved in the turnover and metabolism of phosphatidylinositol 4,5-bisphosphate ($PIP_2$) as well as to the activities of these molecules. $PIP_2$ is a phospholipid found in the cytosolic leaflet of the plasma membrane. Binding of ligand to the receptor activates, in some cells, the plasma-membrane enzyme phospholipase C that in turn can hydrolyze $PIP_2$ to produce 1,2-diacylglycerol (DAG) and inositol 1,4,5-triphosphate ($IP_3$). Once formed $IP_3$ can diffuse to the endoplasmic reticulum surface where it can bind an $IP_3$ receptor, e.g., a calcium channel protein containing an $IP_3$ binding site. $IP_3$ binding can induce opening of the channel, allowing calcium ions to be released into the cytoplasm. $IP_3$ can also be phosphorylated by a specific kinase to form inositol 1,3,4,5-tetraphosphate ($IP_4$), a molecule which can cause calcium entry into the cytoplasm from the extracellular medium. $IP_3$ and $IP_4$ can subsequently be hydrolyzed very rapidly to the inactive products inositol 1,4-biphosphate ($IP_2$) and inositol 1,3,4-triphosphate, respectively. These inactive products can be recycled by the cell to synthesize $PIP_2$. The other second messenger produced by the hydrolysis of $PIP_2$, namely 1,2-diacylglycerol (DAG), remains in the cell membrane where it can serve to activate the enzyme protein kinase C. Protein kinase C is usually found soluble in the cytoplasm of the cell, but upon an increase in the intracellular calcium concentration, this enzyme can move to the plasma membrane where it can be activated by DAG. The activation of protein kinase C in different cells results in various cellular responses such as the phosphorylation of glycogen synthase, or the phosphorylation of various transcription factors, e.g., NF-kB. The language "phosphatidylinositol activity", as used herein, refers to an activity of $PIP_2$ or one of its metabolites.

Another signaling pathway in which the receptor may participate is the cAMP turnover pathway. As used herein, "cyclic AMP turnover and metabolism" refers to the molecules involved in the turnover and metabolism of cyclic AMP (cAMP) as well as to the activities of these molecules. Cyclic AMP is a second messenger produced in response to ligand-induced stimulation of certain G protein coupled receptors. In the cAMP signaling pathway, binding of a ligand to a GPCR can lead to the activation of the enzyme adenyl cyclase, which catalyzes the synthesis of cAMP. The newly synthesized cAMP can in turn activate a cAMP-dependent protein kinase. This activated kinase can phosphorylate a voltage-gated potassium channel protein, or an associated protein, and lead to the inability of the potassium channel to open during an action potential. The inability of the potassium channel to open results in a decrease in the outward flow of potassium, which normally repolarizes the membrane of a neuron, leading to prolonged membrane depolarization.

To identify the presence of a 7 transmembrane receptor profile in a 52874, 52880, or 63497 receptor, and make the determination that a polypeptide or protein of interest has a particular profile, the amino acid sequence of the protein can be searched against the Pfam database of HMMs (e.g., the Pfam database, release 2.1) using the default parameters. For example, the hmmsf program, which is available as part of the HMMER package of search programs, is a family specific default program for PF00001 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28:405–420 and a detailed description of HMMs can be found, for example, in Gribskov et al. (1990) *Meth. Enzymol.* 183:146–159; Gribskov et al. (1987) *Proc. Natl. Acad. Sci. USA* 84:4355–4358; Krogh et al. (1994) *J. Mol. Biol.* 235:1501–1531; and Stultz et al. (1993) *Protein Sci.* 2:305–314, the contents of which are incorporated herein by reference. Alternatively, the seven transmembrane domain can be predicted based on stretches of hydrophobic amino acids forming α-helices (SOUSI server). For example, using a SOUSI server, two 7 TM receptor domain profiles were identified in the amino acid sequence of SEQ ID NO:5 (e.g., amino acids 40–120 and 142–293 of SEQ ID NO:5), one 7TM receptor domain profile in the amino acid sequence of SEQ ID NO: 8 (e.g., amino acids 22–294 of SEQ ID NO:8), and one 7TM receptor domain profile in the amino acid sequence of SEQ ID NO:11 (e.g., amino acids 189–243 of SEQ ID NO:11). Accordingly, 52874, 52880, or 63497 proteins having at least 50–60% homology, preferably about 60–70%, more preferably about 70–80%, or about 80–90% homology with the 7 transmembrane receptor profile of human 52874, 52880, or 63497 are within the scope of the invention.

In one embodiment, a 52874, 52880, or 63497 protein includes at least one "7 transmembrane receptor" domain or regions homologous with a "7 transmembrane receptor" domain. As used herein, the term "7 transmembrane receptor" domain includes an amino acid sequence having at least about 10–350 amino acid residues in length and having a bit score for the alignment of the sequence to the 7tm_1 family Hidden Markov Model (HMM) of at least 8. Preferably, a "7 transmembrane receptor family" domain includes at least about 50–350 amino acid residues, more preferably about 75–300 amino acid residues, or at least about 80–280 amino acids in length and having a bit score for the alignment of the sequence to the "7 transmembrane receptor family" domain (HMM) of at least 12 or greater. The "7 transmembrane receptor family" domain (HMM) has been assigned the PFAM Accession PF00001. An alignment of the "7 transmembrane receptor family" domain (amino acids 40–120 and 142–293 of SEQ ID NO:5, 22–294 of SEQ ID NO:8 and 189–243 of SEQ ID NO:11) of human 52874, 52880, or 63497 with a consensus amno acid sequence derived from a hidden Markov model is depicted in FIGS. 9A–B, 15, and 22.

Preferably, the 7 transmembrane receptor family domain includes the following amino acid consensus sequence having Prosite signatures as PS00237 or PS50262, or sequences homologous thereto: [GSTALIVMFYWC]-[GSTANCPDE]-{EDPKRH}-x(2)-[LIVMNQGA]-x(2)-[LIVMFT]-[GSTANC]-[LIVMFYWSTAC]-[DENH]-R-[FYWCSH]-X(2)-[LIVM] (SEQ ID NO:36). In addition, the 7 transmembrane receptor family domain may include the following amino acid consensus sequence having Prosite signature PS00238, or sequences homologous thereto: [LIVMFWAC]-[PGAC]-x(3)-[SAC]-K-[STALIMR]-[GSACPNV]-[STACP]-x(2)-[DENF]-[AP]-x(2)-[IY] (SEQ ID NO:37). In the above conserved motifs, and other motifs described herein, the standard IUPAC one-letter code for the amino acids is used. Each element in the pattern is separated by a dash (-); square brackets ([ ]) indicate the particular residues that are accepted at that position; x indicates that any residue is accepted at that position; and numbers in parentheses (( )) indicate the number of residues represented by the accompanying amino acid.

In a preferred embodiment, 52874, 52880, or 63497 polypeptide or protein has a "7 transmembrane receptor domain" or a region which includes at least about x amino acid residues and has at least about 60%, 70%, 80%, 90%, 95%, 99%, or 100% homology with a "7 transmembrane receptor domain," e.g., the 7 transmembrane receptor domain of human 52874 (e.g. amino acid residues 40–120 and 142–293 of SEQ ID NO:5) or human 52880 (e.g. amino acid residues 22–294 of SEQ ID NO:8) or human 63497 (e.g., amino acid residues 189–243 of SEQ ID NO:11).

For further identification of domains in a 52874, 52880, or 63497 protein sequence, and make the determination that a polypeptide or protein of interest has a particular profile, the amino acid sequence of the protein can be searched against a database of domains, e.g., the ProDom database (Corpet et al. (1999), *Nucl. Acids Res.* 27:263–267). The ProDom protein domain database consists of an automatic compilation of homologous domains. Current versions of ProDom are built using recursive PSI-BLAST searches (Altschul SF et al. (1997) *Nucleic Acids Res.* 25:3389–3402; Gouzy et al. (1999) 23:333–340) of the SWISS-PROT 38 and TREMBL protein databases. The database automatically generates a consensus sequence for each domain.

A BLAST search was performed against the HMM database resulting in the identification of regions homologous to ProDom family PD032606 ("Receptor neurotensin coupled G-protein type transmembrane lipoprotein levocabastine-palmitate phosphorylation" SEQ ID NO:22, ProDomain Release 2001.1; Corpet et at. (1999), *Nucl. Acids Res.* 27:263–267 and Gouzy et al. (1999) *Computers and Chemistry* 23:333–340). An alignment of the "Receptor neurotensin coupled G-protein type transmembrane lipoprotein levocabastine-palmitate phosphorylation" domain (amino acids 253–320 of SEQ ID NO:5) of human 52874 with consensus amino acid sequences (SEQ ID NO:22) derived from a hidden Markov model is depicted in FIG. 10. The consensus sequence for SEQ ID NO:22 is 33% identical over amino acids 253–320 of SEQ ID NO:5 as shown in FIG. 10.

A BLAST search was performed against the HMM database resulting in the identification of regions homologous to ProDom family PD128109 ("Similar somatostatin receptors" SEQ ID NO:23, ProDomain Release 2001.1; Corpet et at. (1999), *Nucl. Acids Res.* 27:263–267 and Gouzy et al. (1999) *Computers and Chemistry* 23:333–340). An alignment of the "Similar somatostatin receptors" domain (amino acids 208–316 of SEQ ID NO:5) of human 52874 with consensus amino acid sequences (SEQ ID NO:23) derived from a hidden Markov model is depicted in FIG. 11. The consensus sequence for SEQ ID NO:23 is 24% identical over amino acids 208–316 of SEQ ID NO:5 as shown in FIG. 11.

A BLAST search was performed against the HMM database resulting in the identification of regions homologous to ProDom family PD145471 ("C01G12.7" SEQ ID NO:24, ProDomain Release 2001.1; Corpet et at. (1999), *Nucl. Acids Res.* 27:263–267 and Gouzy et al. (1999) *Computers and Chemistry* 23:333–340). An alignment of the "C01G12.7" domain (amino acids 16–192 of SEQ ID NO:5) of human 52874 with consensus amino acid sequences (SEQ ID NO:24) derived from a hidden Markov model is depicted in FIG. 12. The consensus sequence for SEQ ID NO:24 is 20% identical over amino acids 16–192 of SEQ ID NO:5 as shown in FIG. 12.

A BLAST search was performed against the HMM database resulting in the identification of regions homologous to ProDom family PD310793 ("Receptor orphan GPR26 protein-coupled" SEQ ID NO:26, ProDomain Release 2001.1; Corpet et al. (1999), *Nucl. Acids Res.* 27:263–267 and Gouzy et al. (1999) *Computers and Chemistry* 23:333–340). An alignment of the "Receptor orphan GPR26 protein-coupled" domain (amino acids 134–315 of SEQ ID NO:8) of human 52880 with consensus amino acid sequences (SEQ ID NO:26) derived from a hidden Markov model is depicted in FIG. 16. The consensus sequence for SEQ ID NO:26 is 51% identical over amino acids 134–315 of SEQ ID NO:8 as shown in FIG. 16.

A BLAST search was performed against the HMM database resulting in the identification of regions homologous to ProDom family PD155019 ("Receptor type hypocretin EG:22E5.10 EG:22E5.11 transmembrane coupled orexin G-protein" SEQ ID NO:27, ProDomain Release 2001.1; Corpet et at. (1999), *Nucl. Acids Res.* 27:263–267 and Gouzy et al. (1999) *Computers and Chemistry* 23:333–340). An alignment of the "Receptor type hypocretin EG:22E5.10 EG:22E5.11 transmembrane coupled orexin G-protein" domain (amino acids 175–321 of SEQ ID NO:8) of human 52880 with consensus amino acid sequences (SEQ ID NO:27) derived from a hidden Markov model is depicted in FIG. 17. The consensus sequence for SEQ ID NO:27 is 23% identical over amino acids 175–321 of SEQ ID NO:8 as shown in FIG. 17.

A BLAST search was performed against the HMM database resulting in the identification of regions homologous to ProDom family PD032094 ("Receptor acid lysophosphatidic high-affinity homolog transmembrane novel thodopsin similar" SEQ ID NO:28, ProDomain Release 2001.1; Corpet et at. (1999), *Nucl. Acids Res.* 27:263–267 and Gouzy et al. (1999) *Computers and Chemistry* 23:333–340). An alignment of the "Receptor acid lysophosphatidic high-affinity homolog transmembrane novel thodopsin similar" domain (amino acids 171–322 of SEQ ID NO:8) of human 52880 with consensus amino acid sequences (SEQ ID NO:28) derived from a hidden Markov model is depicted in FIG. 18. The consensus sequence for SEQ ID NO:28 is 22% identical over amino acids 171–322 of SEQ ID NO:8 as shown in FIG. 18.

A BLAST search was performed against the HMM database resulting in the identification of regions homologous to ProDom family PD322057 ("NT2RM2000452 FLJ10317 Fis cDNA" SEQ ID NO:29, ProDomain Release 2001.1; Corpet et at. (1999), *Nucl. Acids Res.* 27:263–267 and Gouzy et al. (1999) *Computers and Chemistry* 23:333–340). An alignment of the "NT2RM2000452 FLJ10317 Fis cDNA" domain (amino acids 221–329 of SEQ ID NO:8) of human 52880 with consensus amino acid sequences (SEQ ID NO:29) derived from a hidden Markov model is depicted in FIG. 19. The consensus sequence for SEQ ID NO:29 is 30% identical over amino acids 221–329 of SEQ ID NO:8 as shown in FIG. 19.

A BLAST search was performed against the HMM database resulting in the identification of regions homologous to ProDom family PD009900 ("Receptor pheromone G-protein vomeronasal coupled M24 VN1 VN3 VN2 VN4" SEQ ID NO:31, ProDomain Release 2001.1; Corpet et at. (1999), *Nucl. Acids Res.* 27:263–267 and Gouzy et al. (1999) *Computers and Chemistry* 23:333–340). An alignment of the "Receptor pheromone G-protein vomeronasal coupled M24 VN1 VN3 VN2 VN4" domain (amino acids 36–295 of SEQ ID NO:11) of human 63497 with consensus amino acid sequences (SEQ ID NO:31) derived from a hidden Markov model is depicted in FIG. 23. The consensus sequence for SEQ ID NO:31 is 34% identical over amino acids 36–295 of SEQ ID NO:11 as shown in FIG. 23.

A 52874, 52880, or 63497 polypeptide can include at least one, two, three, four, five, six, or seven "transmembrane domains" or regions homologous with "transmembrane domains". As used herein, the term "transmembrane domain" includes an amino acid sequence of about 10 to 40 amino acid residues in length and spans the plasma membrane. Transmembrane domains are rich in hydrophobic residues, e.g., at least 50%, 60%, 70%, 80%, 90%, 95% or more of the amino acids of a transmembrane domain are hydrophobic, e.g., leucines, isoleucines, tyrosines, or tryptophans. Transmembrane domains typically have alpha-helical structures and are described in, for example, Zagotta, W. N. et al., (1996) *Annual Rev. Neurosci.* 19:235–263, the contents of which are incorporated herein by reference.

In a preferred embodiment, a 52874, 52880, or 63497 polypeptide or protein has at least one, two, three, four, five, six, or seven "transmembrane domains" or regions which include at least about 12 to 35 more preferably about 14 to 30 or 15 to 25 amino acid residues and has at least about 60%, 70% 80% 90% 95%, 99%, or 100% homology with a "transmembrane domain," e.g., the transmembrane domains of human 52874, 52880, or 63497 (e.g., residues 25–49, 59–81, 103–120, 139–157, 192–210, 235–251, and 273–296 of SEQ ID NO:5; or 18–40, 62–79, 98–116, 151–169, 194–210, and 232–255 of the mature protein of SEQ ID NO:5; or 7–31, 43–67, 81–100, 123–147, 169–193 and 243–259 of SEQ ID NO:8; or 10–34, 48–67, 90–114, 136–160, and 210–226 of the mature protein of SEQ ID NO:8; or 7–27, 92–109, 127–150, 182–206, 235–259, and 271–288 of SEQ ID NO:11 or 31–48, 66–89, 121–145, 174–198, and 210–227 of mature SEQ ID NO:11). The transmembrane domains of human 52874, 52880, or 63497 are visualized in the hydropathy plots (FIGS. 8, 14, and 21) as regions of about 15 to 25 amino acids where the hydropathy trace is mostly above the horizontal line.

To identify the presence of a "transmembrane" domain in a 52874, 52880, or 63497 protein sequence, and make the determination that a polypeptide or protein of interest has a particular profile, the amino acid sequence of the protein can be analyzed by a transmembrane prediction method that predicts the secondary structure and topology of integral membrane proteins based on the recognition of topological models (MEMSAT, Jones et al., (1994) *Biochemistry* 33:3038–3049).

A 52874, 52880, or 63497 polypeptide can include at least one, two, three, four, five, six, seven, or eight "non-transmembrane regions." As used herein, the term "non-transmembrane region" includes an amino acid sequence not identified as a transmembrane domain. The non-transmembrane regions in 52874, 52880, or 63497 are located at about amino acids 1–24, 50–58, 82–102, 121–138, 158–191, 211–234, 252–272, and 297–461 of SEQ ID NO:5 or 1–17, 41–61, 80–97, 117–150, 170–193, 211–231, and 256–420 of mature SEQ ID NO:5; or 1–6, 32–42, 68–80, 101–122, 148–168, 194–242, and 260–363 of SEQ ID NO:8; or 1–9, 35–47, 68–89, 115–135, 161–209, and 227–330 of mature SEQ ID NO:8; or 1–6, 28–91, 110–126, 151–181, 207–234, 260–270, and 289–301 of SEQ ID NO:11 or 1–30, 49–65, 90–120, 146–173, 199–209, and 228–240 of mature SEQ ID NO:11.

The non-transmembrane regions of 52874, 52880, or 63497 include at least one, two, three, or four cytoplasmic regions. When located at the N-terminus, the cytoplasmic region is referred to herein as the "N-terminal cytoplasmic domain." As used herein, an "N-terminal cytoplasmic domain" includes an amino acid sequence having about 1 to 50, preferably about 1 to 40, more preferably about 1 to 30, or even more preferably about 1 to 20 amino acid residues in length and is located inside of a cell or within the cytoplasm of a cell. The C-terminal amino acid residue of an "N-terminal cytoplasmic domain" is adjacent to an N-terminal amino acid residue of a transmembrane domain in a 52874, 52880, or 63497 protein. For example, an N-terminal cytoplasmic domain is located at about amino acid residues 1 to 17 of mature SEQ ID NO:5, residues 1–9 of mature SEQ ID NO:8, and residues 1–6 of SEQ ID NO:11.

In a preferred embodiment, a polypeptide or protein has an N-terminal cytoplasmic domain or a region which includes at least about 5, preferably about 1 to 50, and more preferably about 1 to 20 amino acid residues and has at least about 60%, 70% 80% 90% 95%, 99%, or 100% homology with an "N-terminal cytoplasmic domain," e.g., the N-terminal cytoplasmic domain of human 52874, 52880, or 63497 (e.g., residues 1–17 of mature SEQ ID NO:5, residues 1–9 of mature SEQ ID NO:8, and residues 1–6 of SEQ ID NO:11).

In another embodiment, a cytoplasmic region of a 52874, 52880, or 63497 protein can include the C-terminus and can be a "C-terminal cytoplasmic domain," also referred to herein as a "C-terminal cytoplasmic tail." As used herein, a "C-terminal cytoplasmic domain" includes an amino acid sequence having a length of at least about 10, preferably about 20 to 80, more preferably about 50 to70 amino acid residues and is located inside of a cell or within the cytoplasm of a cell. The N-terminal amino acid residue of a "C-terminal cytoplasmic domain" is adjacent to a C-terminal amino acid residue of a transmembrane domain in a 52874, 52880, or 63497 protein. For example, a C-terminal cytoplasmic domain is located at about amino acid residues 297–461 of SEQ ID NO:5 or residues 256–420 of mature SEQ ID NO:5; or residues 289–301 of SEQ ID NO:11, or residues 228–240 of mature SEQ ID NO:11.

In a preferred embodiment, a 52874, 52880, or 63497 polypeptide or protein has a C-terminal cytoplasmic domain or a region which includes at least about 5, preferably about 8 to 80, and more preferably about 10 to 70 amino acid residues and has at least about 60%, 70% 80% 90% 95%, 99%, or 100% homology with a C-terminal cytoplasmic domain," e.g., the C-terminal cytoplasmic domain of human 52874, 52880, or 63497 (e.g., residues 297–461 of SEQ ID NO:5 or residues 256–420 of mature SEQ ID NO:5 or residues 289–301 of SEQ ID NO:11, or residues 228–240 of mature SEQ ID NO:11).

In another embodiment, a 52874, 52880, or 63497 protein includes at least one, two, or three cytoplasmic loops. As used herein, the term "loop" includes an amino acid sequence that resides outside of a phospholipid membrane, having a length of at least about 4, preferably about 5 to 80, more preferably about 6 to 50 amino acid residues, and has an amino acid sequence that connects two transmembrane domains within a protein or polypeptide. Accordingly, the N-terminal amino acid of a loop is adjacent to a C-terminal amino acid of a transmembrane domain in a 52874, 52880, or 63497 molecule, and the C-terminal amino acid of a loop is adjacent to an N-terminal amino acid of a transmembrane domain in a 52874, 52880, or 63497 molecule. As used herein, a "cytoplasmic loop" includes a loop located inside of a cell or within the cytoplasm of a cell. For example, a "cytoplasmic loop" can be found at about amino acid residues 50–58, 121–138, and 211–234 of SEQ ID NO:5 or 80–97, and 170–193 of mature SEQ ID NO:5; or 32–42, 101–122, and 194–242 of SEQ ID NO:8 or 68–89 and 161–209 of mature SEQ ID NO:8, or residues 110–126, and 207–234 of SEQ ID NO:11, or residues 49–65, and 146–173 of mature SEQ ID NO:11.

In a preferred embodiment, a 52874, 52880, or 63497 polypeptide or protein has a cytoplasmic loop or a region which includes at least about 4, preferably about 5 to 80, and more preferably about 6 to 50 amino acid residues and has at least about 60%, 70% 80% 90% 95%, 99%, or 100% homology with a cytoplasmic loop," e.g., a cytoplasmic loop of human 52874, 52880, or 63497 (e.g., residues 50–58, 121–138, and 211–234 of SEQ ID NO:5 or 80–97, and 170–193 of mature SEQ ID NO:5; or 32–42, 101–122, and 194–242 of SEQ ID NO:8 or 68–89 and 161–209 of mature SEQ ID NO:8, or residues 110–126, and 207–234 of SEQ ID NO:11, or residues 49–65, and 146–173 of mature SEQ ID NO:11).

In another embodiment, a 52874, 52880, or 63497 protein includes at least one, two, or three non-cytoplasmic loops. As used herein, a "non-cytoplasmic loop" includes an amino acid sequence located outside of a cell or within an intracellular organelle. Non-cytoplasmic loops include extracellular domains (i.e., outside of the cell) and intracellular domains (i.e., within the cell). When referring to membrane-bound proteins found in intracellular organelles (e.g., mitochondria, endoplasmic reticulum, peroxisomes microsomes, vesicles, endosomes, and lysosomes), non-cytoplasmic loops include those domains of the protein that reside in the lumen of the organelle or the matrix or the intermembrane space. For example, a "non-cytoplasmic loop" can be found at about amino acid residues 82–102, 158–191, and 252–272 of SEQ ID NO:5 or 41–61, 117–150, and 211–231 of mature SEQ ID NO:5; or 68–80 and 146–168 of SEQ ID NO:8 or 35–47 and 115–135 of mature SEQ ID NO:8, or residues 28–91, 151–181, and 260–270 of SEQ ID NO:11, or residues 90–120, and 199–209 of mature SEQ ID NO:11.

In a preferred embodiment, a 52874, 52880, or 63497 polypeptide or protein has at least one non-cytoplasmic loop or a region which includes at least about 4, preferably about 5 to 50, more preferably about 6 to 40 amino acid residues and has at least about 60%, 70% 80% 90% 95%, 99%, or 100% homology with a "non-cytoplasmic loop," e.g., at least one non-cytoplasmic loop of human 52874, 52880, or 63497 (e.g., residues 82–102, 158–191, and 252–272 of SEQ ID NO:5 or 41–61, 117–150, and 211–231 of mature SEQ ID NO:5; or 68–80 and 146–168 of SEQ ID NO:8 or 35–47 and 115–135 of mature SEQ ID NO:8, or residues 28–91, 151–181, and 260–270 of SEQ ID NO:11, or residues 90–120, and 199–209 of mature SEQ ID NO:11).

In a preferred embodiment, a 52874 family member can include at least one, preferably two seven transmembrane receptor family domains (PFAM Accession Number PF00001). Furthermore, a 52874 family member can include at least one, two, and preferably three N-glycosylation sites (PS00001); at least one glycosaminoglycan attachment site (PS00002); at least one cAMP- and cGMP-dependent protein kinase phosphorylation sites (PS00004); at least one, two, three, four, five, and preferably six protein kinase C phosphorylation sites (PS00005); at least one, two, three, and preferably four casein kinase II phosphorylation sites (PS00006); and at least one, two, and preferably three N-myristoylation sites (PS00008).

In a preferred embodiment, a 52880 family member can include at least one seven transmembrane receptor family domain (PFAM Accession Number PF00001). Furthermore, a 52880 family member can include at least one, two, and preferably three N-glycosylation sites (PS00001); at least one, two, three, four, five, and preferably six protein kinase C phosphorylation sites (PS00005); at least one, two, and preferably three casein kinase II phosphorylation sites (PS00006); at least one tyrosine kinase phosphorylation site (PS00007); at least one, two, three, four, five, and preferably six N-myristoylation sites (PS00008); at least one, and preferably two prokaryotic membrane lipoprotein lipid attachment site (PS00013).

In a preferred embodiment, a 63497 family member can include at least one seven transmembrane receptor family domains (PFAM Accession Number PF00001). Furthermore, a 63497 family member can include at least one, and preferably two N-glycosylation sites (PS00001); at least one glycosaminoglycan attachment site (PS00002); at least one, two, and preferably three protein kinase C phosphorylation sites (PS00005); at least one, and preferably two casein kinase II phosphorylation sites (PS00006); at least one, two, three, four, and preferably five N-myristoylation sites (PS00008); at least one prokaryotic membrane lipoprotein lipid attachment site (PS00013); and at least one leucine zipper pattern site (PS00029).

As the 52874, 52880, or 63497 polypeptides of the invention may modulate 52874-, 52880-, or 63497-mediated activities, they may be useful as of for developing novel diagnostic and therapeutic agents for 52874-, 52880-, or 63497-mediated or related disorders, as described below.

Based on the above-described sequence similarities, the 52874, 52880, or 63497 molecules of the present invention are predicted to have similar biological activities as seven transmembrane receptor family members. Thus, the 52874, 52880, or 63497 molecules can act as novel diagnostic targets and therapeutic agents for controlling one or more of cellular proliferative and/or differentiative disorders, heart disorders, cardiovascular disorders, including endothelial cell disorders, hematopoietic disorders, blood vessel disorders, brain disorders, pain and metabolic disorders, hormonal disorders and platelet disorders.

Human 33425

The human 33425 sequence (FIGS. 24A–C; SEQ ID NO:13), which is approximately 3492 nucleotides long including untranslated regions, contains a predicted methionine-initiated coding sequence of about 1992 nucleotides (nucleotides 73–2764 of SEQ ID NO:13; SEQ ID NO:15), including the terminal codon. The coding sequence encodes a 663 amino acid protein (SEQ ID NO:14).

This mature protein form is approximately 663 amino acid residues in length (from about amino acid 1 to amino 663 of SEQ ID NO:2). Human 33425 contains the following regions or other structural features:

one RhoGAP family domain located at about amino acids 343–494 of SEQ ID NO:14;

one predicted cAMP- and cGMP-dependent protein kinase phosphorylation site (PS00004) located at about amino acids 86–89 of SEQ ID NO:14;

twelve predicted protein kinase C phosphorylation sites (PS00005) located at about amino acids 18–20, 37–39, 52–54, 158–160, 193–195, 246–248, 263–265, 273–275, 393–395, 431–433, 453–455, and 618–620 of SEQ ID NO:14;

ten predicted casein kinase II phosphorylation sites (PS00006) located at about amino acids 18–21, 69–72, 74–77, 92–95, 126–129, 235–238, 246–249, 254–257, 351–354, and 568–571 of SEQ ID NO:14;

four predicted tyrosine kinase phosphorylation sites (PS00007) lcoated at about amino acids 195–201, 554–562, 620–627, and 636–643 of SEQ ID NO:14; and seven predicted N-myristoylation sites (PS00008) located at about amino acids 9–14, 25–30, 187–192, 493–498, 507–512, 614–619, and 630–635 of SEQ ID NO:14.

For general information regarding PFAM identifiers, PS prefix, and PF prefix domain identification numbers, refer to Sonnhammer et al. (1997) *Protein* 28:405–420.

The 33425 protein contains a significant number of structural characteristics in common with members of the rhoGAP family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

As used herein, the term "rhoGAP" refers to a protein or polypeptide which is capable of, binding to one or more of the Rho family of G proteins, stimulating intrinsic GTPase activity, promoting GTP hydrolysis, and/or promoting an inactive state of Rho proteins. As referred to herein, rhoGAPs preferably include a catalytic domain of about 100–250 amino acid residues in length, preferably about 100–200 amino acid residues in length, or more preferably about 140–160 amino acid residues in length. The stimulation of GTP hydrolysis of small GTP-binding proteins by rhoGAPs is highly specific for members of the Rho family of GTPases and not members of other families. Please see Musacchio, supra.

A rhoGAP domain may include about 1–10 conserved amino acid residues that correspond to at least one amino acid residue of Pro 343, Arg 365, Lys 404, Leu 410, Pro 411, Pro 412, Pro 447, Asn 471, Pro 484 and Leu 486. These 10 residues are identically conserved in six rhoGap family members, namely p50rhoGAP, p190, bcr, chimerin, 3BP-1 and the p85 subunit of phosphatidylinositase-3-OH kinase (p85), reported in Barrett, T., et al. (1997) *Nature* 385(6615): 458–61, which is incorporated herein by reference. Seven of the 10 are proline or leucine and are important for the structural integrity of the molecule.

In addition, a rhoGAP domain may include 1–5 additional conserved amino acid residues that correspond to at least one amino acid residue, which is Gly 362, Leu 413, Leu 458, Met 473 or Asn 477. These five additional conserved amino acid residues are identical in five of the six rhoGAP family members reported in Barrett, supra which members promote GTP hydrolysis, but are not identical to corresponding amino acid residues of p85 which lacks GAP activity, thus suggesting that protein-binding and GAP functions are separate activities. It has been suggested that an amino acid residue of p50rhoGAP that corresponds to Arg 365 plays an important role in GAP function and likely is involved in G-protein binding to GAPs or plays a role in transition-state stabilization. Barrett, supra, and Rittinger, supra. Based on these sequence similarities, the 33425 molecules of the present invention are predicted to have similar biological activities as rhoGAP family members.

RhoGAPs stimulate the intrinsic GTPase activity of small G proteins and switches the G protein to an inactive state. Typically, rhoGAPs play a role in diverse cellular processes. Thus, the molecules of the present invention may be involved in one or more of: 1) binding to one or more of the Rho family of G proteins; 2) stimulating GTPase activity; 3) promoting GTP hydrolysis; 4) activating intrinsic activity of G proteins; 5) promoting an inactive state of Rho protein; 6) regulating signal transduction; 7) regulating cell adhesion, motility and shape; 8) modulating cellular proliferation; 9) modulating actin cytoskleleton formation; 10) regulating the JNK signaling pathway; 11) activating kinase cascades; and 12) the ability to antagonize or inhibit, competitively or noncompetitively, any of 1–11.

A 33425 polypeptide can include a "rhoGAP domain" or regions homologous with an "rhoGAP domain".

As used herein, the term "rhoGAP domain" includes an amino acid sequence of about 50–300 amino acid residues in length and having a bit score for the alignment of the sequence to the rhoGAP domain (HMM) of at least 8. Preferably, a rhoGAP domain includes at least about 100–250 amino acids, more preferably about 100–200 amino acid residues, or about 140–160 amino acids and has a bit score for the alignment of the sequence to the rhoGAP domain (HMM) of at least 16, 25, 50, 100 or greater. The rhoGAP domain (HMM) has been assigned the PFAM Accession PF00620. An alignment of the rhoGAP domain (amino acids 343–494 of SEQ ID NO:14) of human 33425 with a consensus amino acid sequence derived from a hidden Markov model is depicted in FIG. 26.

In a preferred embodiment 33425 polypeptide or protein has a "rhoGAP domain" or a region which includes at least about 100–250 more preferably about 100–200 or 140–160 amino acid residues and has at least about 60%, 70%, 80%, 90%, 95%, 99%, or 100% homology with an "rhoGAP domain," e.g., the rhoGAP domain of human 33425 (e.g., amino acid residues 343–494 of SEQ ID NO:14).

To identify the presence of an "rhoGAP" domain in a 33425 protein sequence, and make the determination that a polypeptide or protein of interest has a particular profile, the amino acid sequence of the protein can be searched against a database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al., (1997) *Proteins* 28(3):405–420 and a detailed description of HMMs can be found, for example, in Gribskov et al., (1990) *Meth. Enzymol*. 183:146–159; Gribskov et al., (1987) *Proc. Natl. Acad. Sci. USA* 84:4355–4358; Krogh et al., (1994) *J. Mol. Biol*. 235:1501–1531; and Stultz et al., (1993) *Protein Sci*. 2:305–314, the contents of which are incorporated herein by reference.

An additional method to identify the presence of a "RhoGAP" domain in a 33425 protein sequence, and make the determination that a polypeptide or protein of interest has a particular profile, the amino acid sequence of the protein can be searched against a SMART database (Simple Modular Architecture Research Tool) of HMMs as described in Schultz et al. (1998), *Proc. Natl. Acad. Sci. USA* 95:5857 and Schultz et al. (2000) *Nucl. Acids Res* 28:231. The database contains domains identified by profiling with the hidden Markov models of the HMMer2 search program (R. Durbin et al. (1998) *Biological sequence analysis: probabilistic models of proteins and nucleic acids*. Cambridge University Press.). The database also is extensively annotated and monitored by experts to enhance accuracy. A search was performed against the HMM database resulting in the identification of a "RhoGAP_3" domain in the amino acid sequence of human 33425 at about residues 340 to 520 of SEQ ID NO:14 (see FIGS. 24A–C).

For further identification of domains in a 33425 protein sequence, and make the determination that a polypeptide or protein of interest has a particular profile, the amino acid sequence of the protein can be searched against a database of domains, e.g., the ProDom database (Corpet et al. (1999), *Nucl. Acids Res*. 27:263–267). The ProDom protein domain database consists of an automatic compilation of homologous domains. Current versions of ProDom are built using recursive PSI-BLAST searches (Altschul SF et al. (1997) *Nucleic Acids Res*. 25:3389–3402; Gouzy et al. (1999) *Computers and Chemistry* 23:333–340) of the SWISS-PROT 38 and TREMBL protein databases. The database automatically generates a consensus sequence for each domain.

A BLAST search was performed against the HMM database resulting in the identification of a region homologous to ProDom family PD301916 ("Similar NT2RM2000363 cluster Fis FLJ10312 weakly cDNA breakpoint" SEQ ID NO:33, ProDomain Release 2001.1; Corpet et at. (1999), *Nucl. Acids Res*. 27:263–267 and Gouzy et al. (1999) *Computers and Chemistry* 23:333–340). An alignment of the "Similar NT2RM2000363 cluster Fis FLJ10312 weakly cDNA breakpoint" domain (amino acids 516–608 of SEQ ID NO:14) of human 33425 with a consensus amino acid sequence (SEQ ID NO:33) derived from a hidden Markov model is depicted in FIG. 27. The consensus sequence for SEQ ID NO:33 is 39% identical over amino acids 516–608 of SEQ ID NO:14 as shown in FIG. 27.

A BLAST search was performed against the HMM database resulting in the identification of a region homologous to ProDom family PD000780 ("GTPase activating similar GTPase-activating activation domain Fis zinc cDNA subunit" SEQ ID NO:34, ProDomain Release 2001.1; Corpet et at. (1999), *Nucl. Acids Res*. 27:263–267 and Gouzy et al. (1999) *Computers and Chemistry* 23:333–340). An alignment of the "GTPase activating similar GTPase-activating activation domain Fis zinc cDNA subunit" domain (amino acids 390–486 of SEQ ID NO:14) of human 33425 with a consensus amino acid sequence (SEQ ID NO:34) derived from a hidden Markov model is depicted in FIG. 28. The consensus sequence for SEQ ID NO:34 is 36% identical over amino acids 390–486 of SEQ ID NO:14 as shown in FIG. 28.

A BLAST search was performed against the HMM database resulting in the identification of a region homologous to ProDom family PD215173 ("RLIP" SEQ ID NO:35, Pro-Domain Release 2001.1; Corpet et at. (1999), *Nucl. Acids Res.* 27:263–267 and Gouzy et al. (1999) *Computers and Chemistry* 23:333–340). An alignment of the "RLIP" domain (amino acids 399–488 of SEQ ID NO:14) of human 33425 with a consensus amino acid sequence (SEQ ID NO:35) derived from a hidden Markov model is depicted in FIG. 29. The consensus sequence for SEQ ID NO:35 is 34% identical over amino acids 399–488 of SEQ ID NO:14 as shown in FIG. 29.

A 33425 polypeptide can include at least one, preferably two "transmembrane domains" or regions homologous with "transmembrane domains". As used herein, the term "transmembrane domain" includes an amino acid sequence of about 10 to 40 amino acid residues in length and spans the plasma membrane. Transmembrane domains are rich in hydrophobic residues, e.g., at least 50%, 60%, 70%, 80%, 90%, 95% or more of the amino acids of a transmembrane domain are hydrophobic, e.g., leucines, isoleucines, tyrosines, or tryptophans. Transmembrane domains typically have alpha-helical structures and are described in, for example, Zagotta, W. N. et al., (1996) *Annual Rev. Neurosci.* 19:235–263, the contents of which are incorporated herein by reference.

In a preferred embodiment, a 33425 polypeptide or protein has at least one, preferably two "transmembrane domains" or regions which includes at least about 12 to 35 more preferably about 14 to 30 or 15 to 25 amino acid residues and has at least about 60%, 70% 80% 90% 95%, 99%, or 100% homology with a "transmembrane domain," e.g., the transmembrane domains of human 33425 (e.g., residues 478–494 and 502–518 of SEQ ID NO:14). The transmembrane domain of human 33425 is visualized in the hydropathy plot (FIG. 25) as regions of about 15 to 25 amino acids where the hydropathy trace is mostly above the horizontal line.

To identify the presence of a "transmembrane" domain in a 33425 protein sequence, and make the determination that a polypeptide or protein of interest has a particular profile, the amino acid sequence of the protein can be analyzed by a transmembrane prediction method that predicts the secondary structure and topology of integral membrane proteins based on the recognition of topological models (MEMSAT, Jones et al., (1994) *Biochemistry* 33:3038–3049).

A 33425 polypeptide can include at least one, two, preferably three "non-transmembrane regions." As used herein, the term "non-transmembrane region" includes an amino acid sequence not identified as a transmembrane domain. The non-transmembrane regions in 33425 are located at about amino acids 1–477, 495–501, and 519–663 of SEQ ID NO:14.

The non-transmembrane regions of 33425 include at least one, preferably two cytoplasmic regions. When located at the N-terminus, the cytoplasmic region is referred to herein as the "N-terminal cytoplasmic domain." As used herein, an "N-terminal cytoplasmic domain" includes an amino acid sequence having about 1 to 600, preferably about 1 to 500, more preferably about 1 to 480, or even more preferably about 1 to 478 amino acid residues in length and is located inside of a cell or within the cytoplasm of a cell. The C-terminal amino acid residue of an "N-terminal cytoplasmic domain" is adjacent to an N-terminal amino acid residue of a transmembrane domain in a 33425 protein. For example, an N-terminal cytoplasmic domain is located at about amino acid residues 1 to 477 of SEQ ID NO:14.

In a preferred embodiment, a polypeptide or protein has an N-terminal cytoplasmic domain or a region which includes at least about 5, preferably about 1 to 600, and more preferably about 1 to 500 amino acid residues and has at least about 60%, 70% 80% 90% 95%, 99%, or 100% homology with an "N-terminal cytoplasmic domain," e.g., the N-terminal cytoplasmic domain of human 33425 (e.g., residues 1 to 477 of SEQ ID NO:14).

In another embodiment, a cytoplasmic region of a 33425 protein can include the C-terminus and can be a "C-terminal cytoplasmic domain," also referred to herein as a "C-terminal cytoplasmic tail." As used herein, a "C-terminal cytoplasmic domain" includes an amino acid sequence having a length of at least about 5, preferably about 100 to 200, more preferably about 125 to 150 amino acid residues and is located inside of a cell or within the cytoplasm of a cell. The N-terminal amino acid residue of a "C-terminal cytoplasmic domain" is adjacent to a C-terminal amino acid residue of a transmembrane domain in a 33425 protein. For example, a C-terminal cytoplasmic domain is located at about amino acid residues 519 to 663 of SEQ ID NO:14.

In a preferred embodiment, a 33425 polypeptide or protein has a C-terminal cytoplasmic domain or a region which includes at least about 5, preferably about 100 to 200, and more preferably about 125 to 150 amino acid residues and has at least about 60%, 70% 80% 90% 95%, 99%, or 100% homology with a C-terminal cytoplasmic domain," e.g., the C-terminal cytoplasmic domain of human 33425 (e.g., residues 519 to 663 of SEQ ID NO:14).

In another embodiment, a 33425 protein includes at least one non-cytoplasmic loop. As used herein, a "non-cytoplasmic loop" includes an amino acid sequence located outside of a cell or within an intracellular organelle. Non-cytoplasmic loops include extracellular domains (i.e., outside of the cell) and intracellular domains (i.e., within the cell). When referring to membrane-bound proteins found in intracellular organelles (e.g., mitochondria, endoplasmic reticulum, peroxisomes microsomes, vesicles, endosomes, and lysosomes), non-cytoplasmic loops include those domains of the protein that reside in the lumen of the organelle or the matrix or the intermembrane space. For example, a "non-cytoplasmic loop" can be found at about amino acid residues 495–501 of SEQ ID NO:14.

In a preferred embodiment, a 33425 polypeptide or protein has at least one non-cytoplasmic loop or a region which includes at least about 4, preferably about 5 to 10, more preferably about 6 to 8 amino acid residues and has at least about 60%, 70% 80% 90% 95%, 99%, or 100% homology with a "non-cytoplasmic loop," e.g., at least one non-cytoplasmic loop of human 33425 (e.g., residues 495–501 of SEQ ID NO:14).

In a preferred embodiment, a 33425 family member can include at least one RhoGAP family domain (PFAM Accession Number PF00620). Furthermore, a 33425 family member can include at least one cAMP- and cGMP-dependent protein kinase phosphorylation site (PS00004); at least one, two, three, four, five, six, seven, eight, nine, ten, eleven and preferably twelve protein kinase C phosphorylation sites (PS00005); at least one, two, three, four, five, six, seven, eight, nine, and preferably ten casein kinase II phosphorylation sites (PS00006); at least one, two, three, and preferably four tyrosine kinase phosphorylation sites (PS00007); and at least one, two, three, four, five, six, and preferably seven N-myristoylation sites (PS00008).

As the 33425 polypeptides of the invention may modulate 33425-mediated activities, they may be useful for developing novel diagnostic and therapeutic agents for 33425-mediated or related disorders, as described below.

As used herein, a "33425 activity", "biological activity of 33425" or "functional activity of 33425", refers to an activity exerted by a 33425 protein, polypeptide or nucleic acid molecule on e.g., a 33425-responsive cell or on a 33425 substrate, e.g., a lipid or protein substrate, as determined in vivo or in vitro. In one embodiment, a 33425 activity is a direct activity, such as an association with a 33425 target molecule. A "target molecule" or "binding partner" is a molecule with which a 33425 protein binds or interacts in nature, e.g., a lipid to which the 33425 protein attaches an acyl chain. A 33425 activity can also be an indirect activity, e.g., a cellular signaling activity mediated by interaction of the 33425 protein with a 33425 ligand. For example, the 33425 proteins of the present invention can have one or more of the following activities: 1) binding to one or more of the Rho family of G proteins; 2) stimulating GTPase activity; 3) promoting GTP hydrolysis; 4) activating intrinsic activity of G proteins; 5) promoting an inactive state of Rho protein; 6) regulating signal transduction; 7) regulating cell adhesion, motility and shape; 8) modulating cellular proliferation; 9) modulating actin cytoskleleton formation; 10) regulating the JNK signalling pathway; 11) activating kinase cascades; and 12) the ability to antagonize or inhibit, competitively or noncompetitively, any of 1–11.

Based on the above-described sequence similarities, the 33425 molecules of the present invention are predicted to have similar biological activities as RhoGAP family members. Thus, the 33425 molecules can act as novel diagnostic targets and therapeutic agents for controlling one or more of cellular proliferative and/or differentiative disorders, heart disorders, cardiovascular disorders, including endothelial cell disorders, hematopoietic disorders, blood vessel disorders, brain disorders, pain and metabolic disorders, liver disorders and platelet disorders.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

The 80090, 52874, 52880, 63497, or 33425 nucleic acid and protein of the invention can be used to treat and/or diagnose a variety of proliferative disorders. E.g., such disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L., (1991) *Crit. Rev. in Oncol./Hemotol.* 11:267–97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Stemberg disease.

Disorders involving the immune system include autoimmune disorders or immune deficiency disorders, e.g., congenital X-linked infantile hypogammaglobulinemia, transient hypogammaglobulinemia, common variable immunodeficiency, selective IgA deficiency, chronic mucocutaneous candidiasis, or severe combined immunodeficiency.

Examples of disorders involving the heart or "cardiovascular disorder" include, but are not limited to, a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of cardiovascular disorders include but are not limited to, hypertension, atherosclerosis, coronary artery spasm, coronary artery disease, arrhythmias, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, disorders involving cardiac transplantation, and congestive heart failure.

A cardiovasular disease or disorder also includes an endothelial cell disorder. As used herein, an "endothelial cell disorder" includes a disorder characterized by aberrant, unregulated, or unwanted endothelial cell activity, e.g., proliferation, migration, angiogenesis, or vascularization; or aberrant expression of cell surface adhesion molecules or genes associated with angiogenesis, e.g., TIE-2, FLT and FLK. Endothelial cell disorders include tumorigenesis, tumor metastasis, psoriasis, diabetic retinopathy, endometriosis, Grave's disease, ischemic disease (e.g., atherosclerosis), and chronic inflammatory diseases (e.g., rheumatoid arthritis).

Examples of hematopoietic disorders include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicella-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Diseases of metabolic imbalance include, but are not limited to, obesity, anorexia nervosa, cachexia, lipid disorders, and diabetes. Examples of pain disorders include, but are not limited to, pain response elicited during various forms of tissue injury, e.g., inflammation, infection, and ischemia, usually referred to as hyperalgesia (described in, for example, Fields, H. L., (1987) *Pain*, New York:McGraw-Hill); pain associated with muscoloskeletal disorders, e.g., joint pain; tooth pain; headaches; pain associated with surgery; pain related to irritable bowel syndrome; or chest pain.

Disorders of the present invention also include hormonal disorders, such as conditions or diseases in which the production and/or regulation of hormones in an organism is aberrant. Examples of such disorders and diseases include type I and type II diabetes mellitus, pituitary disorders (e.g., growth disorders), thyroid disorders (e.g., hypothyroidism or hyperthyroidism), and reproductive or fertility disorders (e.g., disorders which affect the organs of the reproductive system, e.g., the prostate gland, the uterus, or the vagina; disorders which involve an imbalance in the levels of a reproductive hormone in a subject; disorders affecting the ability of a subject to reproduce; and disorders affecting secondary sex characteristic development, e.g., adrenal hyperplasia).

Disorders which may be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolsim, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein may be useful for the early detection and treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, venoocclusive disease, portal vein thrombosis or Budd-Chiari syndrome.

The 80090, 52874, 52880, 63497, or 33425 protein, fragments thereof, and derivatives and other variants of the sequence in SEQ ID NO:2, 5, 8, 11 or 14 are collectively referred to as "polypeptides or proteins of the invention" or "80090, 52874, 52880, 63497, or 33425 polypeptides or proteins". Nucleic acid molecules encoding such polypeptides or proteins are collectively referred to as "nucleic acids of the invention" or "80090, 52874, 52880, 63497, or 33425 nucleic acids." 80090, 52874, 52880, 63497, or 33425 molecules refer to 80090, 52874, 52880, 63497, or 33425 nucleic acids, polypeptides, and antibodies.

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Stringent conditions are known to those skilled in the art and can be found in *Current Protocols in Molecular Biology*, John Wiley & Sons, N.Y. (1989), 6.3.1–6.3.6. Aqueous and nonaqueous methods are described in that reference and either can be used. A preferred, example of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions are hybridization in 6× sodium chloride/sodium citrate (SSC) at about 45° C., followed by one or more washes in 0.2×SSC, 0.1% SDS at 60° C. Preferably, stringent hybridization conditions are hybridization in 6× sodium chloride/sodium citrate (SSC) at about 45° C., followed by one or more washes in 0.2×SSC, 0.1% SDS at 65° C. Particularly preferred stringency conditions (and the conditions that should be used if the practitioner is uncertain about what conditions should be applied to determine if a molecule is within a hybridization limitation of the invention) are 0.5M Sodium Phosphate, 7% SDS at 65° C., followed by one or more washes at 0.2×SSC, 1% SDS at 65° C. Preferably, an isolated nucleic acid molecule of the invention that hybridizes under stringent conditions to the sequence of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15, corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules which include an open reading frame encoding an 80090, 52874, 52880, 63497, or 33425 protein, preferably a mammalian 80090, 52874, 52880, 63497, or 33425 protein, and can further include non-coding regulatory sequences, and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of 80090, 52874, 52880, 63497, or 33425 protein having less than about 30%, 20%, 10% and more preferably 5% (by dry weight), of non-80090, 52874, 52880, 63497, or 33425 protein (also referred to herein as a "contaminating protein"), or of chemical precursors or non-80090, 52874, 52880, 63497, or 33425 chemicals. When the 80090, 52874, 52880, 63497, or 33425 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 80090, 52874, 52880, 63497, or 33425 (e.g., the sequence of SEQ ID NO:1, 3, 4, 6, 7, 9, 10, 12, 13 or 15) without abolishing or more preferably, without substantially altering a biological activity, whereas an "essential" amino acid residue results in such a change. For example, amino acid residues that are conserved among the polypeptides of the present invention, e.g., those present in the fucosyltransferase, 7TM receptor, or RhoGAP domains, are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in an 80090, 52874, 52880, 63497, or 33425 protein is preferably replaced with another amino acid residue from the same side chain family. Alternatively, in another embodiment, mutations can be introduced randomly along all or part of an 80090, 52874, 52880, 63497, or 33425 coding sequence, such as by saturation mutagenesis, and the resultant mutants can be screened for 80090, 52874, 52880, 63497, or 33425 biological activity to identify mutants that retain activity. Following mutagenesis of SEQ ID NO:1, 3, 4, 6, 7, 9, 10, 12, 13 or 15, the encoded protein can be expressed recombinantly and the activity of the protein can be determined.

As used herein, a "biologically active portion" of an 80090, 52874, 52880, 63497, or 33425 protein includes a fragment of an 80090, 52874, 52880, 63497, or 33425 protein which participates in an interaction between an 80090, 52874, 52880, 63497, or 33425 molecule and a non-80090, 52874, 52880, 63497, or 33425 molecule. Biologically active portions of an 80090, 52874, 52880, 63497, or 33425 protein include peptides comprising amino acid sequences sufficiently homologous to or derived from the amino acid sequence of the 80090, 52874, 52880, 63497, or 33425 protein, e.g., the amino acid sequence shown in SEQ ID NO:2, 5, 8, 11 or 14, which include less amino acids than the fall length 80090, 52874, 52880, 63497, or 33425 proteins, and exhibit at least one activity of an 80090, 52874, 52880, 63497, or 33425 protein. Typically, biologically active portions comprise a domain or motif with at least one activity of the 80090, 52874, 52880, 63497, or 33425 protein, e.g., fucosyltransferase, 7TM receptor, or RhoGAP domain activity. A biologically active portion of an 80090, 52874, 52880, 63497, or 33425 protein can be a polypeptide which is, for example, 10, 25, 50, 100, 200 or more amino acids in length. Biologically active portions of an 80090, 52874, 52880, 63497, or 33425 protein can be used as targets for developing agents which modulate an 80090, 52874, 52880, 63497, or 33425 mediated activity, e.g., fucosyltransferase, 7TM receptor, or RhoGAP domain activity.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to the 80090 amino acid sequence of SEQ ID NO:2 having 486 amino acid residues, at least 146, preferably at least 194, more preferably at least 243, even more preferably at least 292, and even more preferably at least 340, 389, 437 or 486 amino acid residues are aligned, or when aligning a second sequence to the 52874 amino acid sequence of SEQ ID NO:5 having 461 amino acid residues, at least 138, preferably at least 184, more preferably at least 231, even more preferably at least 277, and even more preferably at least 323, 369, 415 or 461 amino acid residues are aligned, or when aligning a second sequence to the 52880 amino acid sequence of SEQ ID NO:8 having 363 amino acid residues, at least 109, preferably at least 145, more preferably at least 182, even more preferably at least 218, and even more preferably at least 254, 290, 327 or 363 amino acid residues are aligned, or when aligning a second sequence to the 63497 amino acid sequence of SEQ ID NO:11 having 301 amino acid residues, at least 90, preferably at least 120, more preferably at least 151, even more preferably at least 181, and even more preferably at least 211, 241, 271 or 301 amino acid residues are aligned, or when aligning a second sequence to the 33425 amino acid sequence of SEQ ID NO:14 having 663 amino acid residues, at least 199, preferably at least 265, more preferably at least 332, even more preferably at least 398, and even more preferably at least 464, 530, 597 or 663 amino acid residues are aligned. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) is using a Blossum 62 scoring matrix with a gap open penalty of 12, a gap extend penalty of 4, and a frameshift gap penalty of 5.

The percent identity between two amino acid or nucleotide sequences can be determined using the algorithm of E. Meyers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990) *J. Mol. Biol.* 215:403–10. BLAST nucleotide searches can be performed with the NBLAST program, score=100, wordlength=12 to obtain nucleotide sequences homologous to 80090, 52874, 52880, 63497, or 33425 nucleic acid molecules of the invention. BLAST protein searches can be performed with the XBLAST program, score=50, wordlength=3 to obtain amino acid sequences homologous to 80090, 52874, 52880, 63497, or 33425 protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used.

Particular 80090, 52874, 52880, 63497, or 33425 polypeptides of the present invention have an amino acid sequence substantially identical to the amino acid sequence of SEQ ID NO:2, 5, 8, 11 or 14. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%. 91%, 92%, 93%, 94%, 95%, 96%, 97%, 98% or 99% identity to SEQ ID NO:2, 5, 8, 11 or 14 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity to SEQ ID NO:1, 3, 4, 6, 7, 9, 10, 12, 13 or 15 are termed substantially identical.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject", as used herein, can refer to a mammal, e.g., a human, or to an experimental or animal or disease model. The subject can also be a non-human animal, e.g., a horse, cow, goat, or other domestic animal.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

Various aspects of the invention are described in further detail below.

Isolated Nucleic Acid Molecules

In one aspect, the invention provides, an isolated or purified, nucleic acid molecule that encodes an 80090, 52874, 52880, 63497, or 33425 polypeptide described herein, e.g., a full length 80090, 52874, 52880, 63497, or 33425 protein or a fragment thereof, e.g., a biologically active portion of 80090, 52874, 52880, 63497, or 33425 protein. Also included is a nucleic acid fragment suitable for use as a hybridization probe, which can be used, e.g., to identify a nucleic acid molecule encoding a polypeptide of the invention, 80090, 52874, 52880, 63497, or 33425 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1, SEQ ID NO:4, SEQ ID NO:7, SEQ ID NO:10, OR SEQ ID NO:13, or a portion of any of these nucleotide sequences. In one embodiment, the nucleic acid molecule includes sequences encoding the human 80090, 52874, 52880, 63497, or 33425 protein (i.e., "the coding region", from nucleotides 163–1623 of SEQ ID NO:1, 32–1417 of SEQ ID NO:4, 210–1301 of SEQ ID NO:7, 152–1057 of SEQ ID NO:10, and 73–2764 of SEQ ID NO:13, including the terminal codon), as well as 5' untranslated sequences (nucleotides 1–162 of SEQ ID NO:1, 1–31 of SEQ ID NO:4, 1–209 of SEQ ID NO:7, 1–151 of SEQ ID NO:10, and 1–72 of SEQ ID NO:13). Alternatively, the nucleic acid molecule can include only the coding region of SEQ ID NO:1, SEQ ID NO:4, SEQ ID NO:7, SEQ ID NO:10, or SEQ ID NO:13 (e.g., nucleotides 163–1623 of SEQ ID NO:1, 32–1417 of SEQ ID NO:4, 210–1301 of SEQ ID NO:7, 152–1057 of SEQ ID NO:10, and 73–2764 of SEQ ID NO:13, corresponding to SEQ ID NO:3, 6, 9, 12, and 15) and, e.g., no flanking sequences which normally accompany the subject sequence. In another embodiment, the nucleic acid molecule encodes a sequence corresponding to the mature protein of SEQ ID NO:2, 5, 8, 11 or 14.

In another embodiment, an isolated nucleic acid molecule of the invention includes a nucleic acid molecule which is a complement of the nucleotide sequence shown in SEQ ID NO:1, 3, 4, 6, 7, 9, 10, 12, 13 or 15, or a portion of any of these nucleotide sequences. In other embodiments, the nucleic acid molecule of the invention is sufficiently complementary to the nucleotide sequence shown in SEQ ID NO:1, 3, 4, 6, 7, 9, 10, 12, 13 or 15, such that it can hybridize to the nucleotide sequence shown in SEQ ID NO:1, 3, 4, 6, 7, 9, 10, 12, 13 or 15, thereby forming a stable duplex.

In one embodiment, an isolated nucleic acid molecule of the present invention includes a nucleotide sequence which is at least about 60%, 65%, 70%, 75%, 80%, 85%, 90%, 91%, 92%, 93%, 94%, 95%, 96%, 97%, 98%, 99%, or more homologous to the nucleotide sequence shown in SEQ ID NO:1, 3, 4, 6, 7, 9, 10, 12, 13 or 15. In the case of an isolated nucleic acid molecule which is longer than or equivalent in length to the reference sequence, e.g., SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15, the comparison is made with the full length of the reference sequence. Where the isolated nucleic acid molecule is shorter than the reference sequence, e.g., shorter than SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15, the comparison is made to a segment of the reference sequence of the same length (excluding any loop required by the homology calculation).

80090, 52874, 52880, 63497, or 33425 Nucleic Acid Fragments

A nucleic acid molecule of the invention can include only a portion of the nucleic acid sequence of SEQ ID NO:1, 3, 4, 6, 7, 9, 10, 12, 13 or 15. For example, such a nucleic acid molecule can include a fragment which can be used as a probe or primer or a fragment encoding a portion of an 80090, 52874, 52880, 63497, or 33425 protein, e.g., an immunogenic or biologically active portion of an 80090, 52874, 52880, 63497, or 33425 protein. A fragment can comprise: nucleotides 265–1347 of SEQ ID NO:1, 149–391 of SEQ ID NO:4, 455–910 of SEQ ID NO:4, 273–1091 of SEQ ID NO:7, 716–880 of SEQ ID NO:10, or 1099–1554 of SEQ ID NO:13, which encodes an fucosyltransferase, 7TM receptor, or RhoGAP domain of human 80090, 52874, 52880, 63497, or 33425. The nucleotide sequence determined from the cloning of the 80090, 52874, 52880, 63497, or 33425 gene allows for the generation of probes and primers designed for use in identifying and/or cloning other 80090, 52874, 52880, 63497, or 33425 family members, or fragments thereof, as well as 80090, 52874, 52880, 63497, or 33425 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 150 amino acids in length. Fragments also include nucleic acid sequences corresponding to specific amino acid sequences described above or fragments thereof. Nucleic acid fragments should not be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, the nucleic acid fragment can include a fucosyltransferase, 7TM receptor, or RhoGAP domain. In a preferred embodiment the fragment is at least, 50, 100, 200, 300, 400, 500, 600, 700, or 900 base pairs in length.

80090, 52874, 52880, 63497, or 33425 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:1, 3, 4, 6, 7, 9, 10, 12, 13 or 15, or of a naturally occurring allelic variant or mutant of SEQ ID NO:1, 3, 4, 6, 7, 9, 10, 12, 13 or 15.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes a fucosyltransferase, 7TM receptor, or RhoGAP domain (e.g., about amino acid residues 35–395 of SEQ ID NO:2, 40–120 and 142–293 of SEQ ID NO:5, 22–294 of SEQ ID NO:8, 189–243 of SEQ ID NO:11, or 343–494 of SEQ ID NO:14).

In another embodiment a set of primers is provided, e.g., primers suitable for use in a PCR, which can be used to amplify a selected region of an 80090, 52874, 52880, 63497, or 33425 sequence, e.g., a region described herein. The primers should be at least 5, 10, or 50 base pairs in length and less than 100, or less than 200, base pairs in length. The primers should be identical, or differs by one base from a sequence disclosed herein or from a naturally occurring variant. E.g., primers suitable for amplifying all or a portion of any of the following regions are provided: a fucosyltransferase, 7TM receptor, or RhoGAP domain (e.g., about amino acid residues 35–395 of SEQ ID NO:2, 40–120 and 142–293 of SEQ ID NO:5, 22–294 of SEQ ID NO:8, 189–243 of SEQ ID NO:11, or 343–494 of SEQ ID NO:14).

A nucleic acid fragment can encode an epitope bearing region of a polypeptide described herein.

A nucleic acid fragment encoding a "biologically active portion of an 80090, 52874, 52880, 63497, or 33425 polypeptide" can be prepared by isolating a portion of the nucleotide sequence of SEQ ID NO:1, 3, 4, 6, 7, 9, 10, 12, 13 or 15, which encodes a polypeptide having an 80090, 52874, 52880, 63497, or 33425 biological activity (e.g., the biological activities of the 80090, 52874, 52880, 63497, or 33425 proteins as described herein), expressing the encoded portion of the 80090, 52874, 52880, 63497, or 33425 protein (e.g., by recombinant expression in vitro) and assessing the activity of the encoded portion of the 80090, 52874, 52880, 63497, or 33425 protein. For example, a nucleic acid fragment encoding a biologically active portion of 80090, 52874, 52880, 63497, or 33425 includes a fucosyltransferase, 7TM receptor, or RhoGAP domain (e.g., about amino acid residues 35–395 of SEQ ID NO:2, 40–120 and 142–293 of SEQ ID NO:5, 22–294 of SEQ ID NO:8, 189–243 of SEQ ID NO:11, or 343–494 of SEQ ID NO:14). A nucleic acid fragment encoding a biologically active portion of an 80090, 52874, 52880, 63497, or 33425 polypeptide, may comprise a nucleotide sequence which is greater than 300–1200 or more nucleotides in length.

In preferred embodiments, nucleic acids include a nucleotide sequence which is about 300, 400, 500, 600, 700, 800, 900, 1000, 1100, 1200, 1300, 1400 nucleotides in length and hybridizes under stringent hybridization conditions to a nucleic acid molecule of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15.

80090, 52874, 52880, 63497, or 33425 Nucleic Acid Variants

The invention further encompasses nucleic acid molecules that differ from the nucleotide sequence shown in SEQ ID NO:1, 3, 4, 6, 7, 9, 10, 12, 13 or 15. Such differences can be due to degeneracy of the genetic code (and result in a nucleic acid which encodes the same 80090, 52874, 52880, 63497, or 33425 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:2, 5, 8, 11 or 14. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non preferred, for a particular expression system. E.g., the nucleic acid can be one in which at least one colon, at preferably at least 10%, or 20% of the codons has been altered such that the sequence is optimized for expression in *E. coli*, yeast, human, insect, or CHO cells.

Nucleic acid variants can be naturally occurring, such as allelic variants (same locus), homologs (different locus), and orthologs (different organism) or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:1, 3, 4, 6, 7, 9, 10, 12, 13 or 15, e.g., as follows: by at least one but less than 10, 20, 30, or 40 nucleotides; at least one but less than 1%, 5%, 10% or 20% of the in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the amino acid sequence shown in SEQ ID NO:2, 5, 8, 11 or 14 or a fragment of this sequence. Such nucleic acid molecules can readily be obtained as being able to hybridize under stringent conditions, to the nucleotide sequence shown in SEQ ID NO:3, 6, 9, 12, or 15 or a fragment of this sequence. Nucleic acid molecules corresponding to orthologs, homologs, and allelic variants of the 80090, 52874, 52880, 63497, or 33425 cDNAs of the invention can further be isolated by mapping to the same chromosome or locus as the 80090, 52874, 52880, 63497, or 33425 gene. Preferred variants include those that are correlated with fucosyltransferase, 7TM receptor, or RhoGAP activity.

Allelic variants of 80090, 52874, 52880, 63497, or 33425, e.g., human 80090, 52874, 52880, 63497, or 33425, include both functional and non-functional proteins. Functional allelic variants are naturally occurring amino acid sequence variants of the 80090, 52874, 52880, 63497, or 33425 protein within a population that maintain the ability to modulate the phosphorylation state of itself or another protein or polypeptide. Functional allelic variants will typically contain only conservative substitution of one or more amino acids of SEQ ID NO:2, 5, 8, 11 or 14, or substitution, deletion or insertion of non-critical residues in non-critical regions of the protein. Non-functional allelic variants are naturally-occurring amino acid sequence variants of the 80090, 52874, 52880, 63497, or 33425, e.g., human 80090, 52874, 52880, 63497, or 33425, protein within a population that do not have the ability to attach an acyl chain to a lipid precursor. Non-functional allelic variants will typically contain a non-conservative substitution, a deletion, or insertion, or premature truncation of the amino acid sequence of SEQ ID NO:2, 5, 8, 11 or 14, or a substitution, insertion, or deletion in critical residues or critical regions of the protein.

Moreover, nucleic acid molecules encoding other 80090, 52874, 52880, 63497, or 33425 family members and, thus, which have a nucleotide sequence which differs from the 80090, 52874, 52880, 63497, or 33425 sequences of SEQ ID NO:1, 3, 4, 6, 7, 9, 10, 12, 13 or 15 are intended to be within the scope of the invention.

Antisense Nucleic Acid Molecules, Ribozymes and Modified 80090, 52874, 52880, 63497, or 33425 Nucleic Acid Molecules In another aspect, the invention features, an isolated nucleic acid molecule which is antisense to 80090, 52874, 52880, 63497, or 33425. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 80090, 52874, 52880, 63497, or 33425 coding strand, or to only a portion thereof (e.g., the coding region of human 80090, 52874, 52880, 63497, or 33425 corresponding to SEQ ID NO:3). In another embodiment, the antisense nucleic acid molecule is antisense to a "noncoding region" of the coding strand of a nucleotide sequence encoding 80090, 52874, 52880, 63497, or 33425 (e.g., the 5' and 3' untranslated regions).

An antisense nucleic acid can be designed such that it is complementary to the entire coding region of 80090, 52874, 52880, 63497, or 33425 mRNA, but more preferably is an oligonucleotide which is antisense to only a portion of the coding or noncoding region of 80090, 52874, 52880, 63497, or 33425 mRNA. For example, the antisense oligonucleotide can be complementary to the region surrounding the translation start site of 80090, 52874, 52880, 63497, or 33425 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding an 80090, 52874, 52880, 63497, or 33425 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., (1987) *Nucleic Acids. Res.* 15:6625–6641). The antisense nucleic acid molecule can also comprise a 2'-o-methylribonucleotide (Inoue et al., (1987) *Nucleic Acids Res.* 15:6131–6148) or a chimeric RNA-DNA analogue (Inoue et al., (1987) *FEBS Lett.* 215:327–330).

In still another embodiment, an antisense nucleic acid of the invention is a ribozyme. A ribozyme having specificity for an 80090, 52874, 52880, 63497, or 33425-encoding nucleic acid can include one or more sequences complementary to the nucleotide sequence of an 80090, 52874, 52880, 63497, or 33425 cDNA disclosed herein (i.e., SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15), and a sequence having known catalytic sequence responsible for mRNA cleavage (see U.S. Pat. No. 5,093,246 or Haselhoff and Gerlach, (1988) *Nature* 334:585–591). For example, a derivative of a Tetrahymena L-19 IVS RNA can be constructed in which the nucleotide sequence of the active site is complementary to the nucleotide sequence to be cleaved in an 80090, 52874, 52880, 63497, or 33425-encoding mRNA. See, e.g., Cech et al. U.S. Pat. No. 4,987,071; and Cech et al. U.S. Pat. No. 5,116,742. Alternatively, 80090, 52874, 52880, 63497, or 33425 mRNA can be used to select a catalytic RNA having a specific ribonuclease activity from a pool of RNA molecules. See, e.g., Bartel, D. and Szostak, J. W. (1993) *Science* 261:1411–1418.

80090, 52874, 52880, 63497, or 33425 gene expression can be inhibited by targeting nucleotide sequences complementary to the regulatory region of the 80090, 52874, 52880, 63497, or 33425 (e.g., the 80090, 52874, 52880, 63497, or 33425 promoter and/or enhancers) to form triple helical structures that prevent transcription of the 80090, 52874, 52880, 63497, or 33425 gene in target cells. See generally, Helene, C., (1991) *Anticancer Drug Des.* 6(6): 569–84; Helene, C. et al., (1992) *Ann. N.Y. Acad. Sci.* 660:27–36; and Maher, L. J., (1992) *Bioassays* 14(12): 807–15. The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or calorimetric.

A 80090, 52874, 52880, 63497, or 33425 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al., (1996) *Bioorganic & Medicinal Chemistry* 4 (1): 5–23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al., (1996) supra; Perry-O'Keefe et al., *Proc. Natl. Acad. Sci.* 93: 14670–675.

PNAs of 80090, 52874, 52880, 63497, or 33425 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 80090, 52874, 52880, 63497, or 33425 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B., (1996) supra)); or as probes or primers for DNA sequencing or hybridization (Hyrup B. et al., (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al., (1989) *Proc. Natl. Acad. Sci. USA* 86:6553–6556; Lemaitre et al., (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al., (1988) *Bio-Techniques* 6:958–976) or intercalating agents. (See, e.g., Zon, (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to an 80090, 52874, 52880, 63497, or 33425 nucleic acid of the invention, two complementary regions one having a fluorophore and one a quencher such that the molecular beacon is useful for quantitating the presence of the 80090, 52874, 52880, 63497, or 33425 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated 80090, 52874, 52880, 63497, or 33425 Polypeptides

In another aspect, the invention features, an isolated 80090, 52874, 52880, 63497, or 33425 protein, or fragment, e.g., a biologically active portion, for use as immunogens or antigens to raise or test (or more generally to bind) anti-80090, 52874, 52880, 63497, or 33425 antibodies. 80090, 52874, 52880, 63497, or 33425 protein can be isolated from cells or tissue sources using standard protein purification techniques. 80090, 52874, 52880, 63497, or 33425 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and postranslational events. The polypeptide can be expressed in systems, e.g., cultured cells, which result in substantially the same postranslational modifications present when expressed the polypeptide is expressed in a native cell, or in systems which result in the alteration or omission of postranslational modifications, e.g., gylcosylation or cleavage, present when expressed in a native cell.

In a preferred embodiment, a 80090 polypeptide has one or more of the following characteristics:

(i) it has the ability to promote transfer of a fucose group from one molecule to another;

(ii) it has a molecular weight (e.g., a deduced molecular weight, preferably ignoring any contribution of post translational modifications), amino acid composition, or other physical characteristic of the fucosyltransferase of SEQ ID NO:2;

(iii) it has an overall sequence similarity of at least 60%, more preferably at least 70, 80, 90, or 95%, with a polypeptide of SEQ ID NO:2;

(iv) it has a fucosyltransferase domain which is preferably about 70%, 80%, 90% or 95% identical with amino acid residues 35–395 of SEQ ID NO:2; and (v) it has at least 3, preferably 6, and most preferably 90 of the cysteines found in the amino acid sequence of the native protein.

In preferred embodiments, 52874, 52880 and/or 63497 polypeptides have one or more of the following characteristics:

(i) it has the ability to regulate, sense and/or transmit an extracellular signal into a cell;

(ii) it has the ability to interact with (e.g., bind to) an extracellular signal or a cell surface receptor;

(iii) it has the ability to mobilize an intracellular molecule that participates in a signal transduction pathway (e.g., adenylate cyclase or phosphatidylinositol 4,5-bisphosphate (PIP$_2$), inositol 1,4,5-triphosphate (IP$_3$));

(iv) it has the ability to regulate polarization of the plasma membrane;

(v) it has the ability to modulate cell proliferation, cell migration, differentiation and/or cell survival.

In a preferred embodiment, a 33425 polypeptide has one or more of the following characteristics:

(i) it promotes the inactive state of rho proteins;

(ii) it binds to one or more of the Rho family of G proteins;

(iii) it stimulates GTPase activity;

(iv) it promotes GTP hydrolysis;

(v) it activates intrinsic activity of G proteins;

(vi) it has a molecular weight, e.g., a deduced molecular weight, amino acid composition or other physical characteristic of the polypeptide of SEQ ID NO:14;

(vii) it has an overall sequence similarity of at least 50%, preferably at least 60%, more preferably at least 70, 80, 90, or 95%, with a polypeptide of SEQ ID NO:14;

(viii) it has a rhoGAP domain which preferably has an overall sequence similarity of about 70%, 80%, 90% or 95% with amino acid residues 343–494 of SEQ ID NO:14; or (ix) it has at least 70%, preferably 80%, and most preferably 95% of the cysteines found in the amino acid sequence of the native protein.

In a preferred embodiment the 80090, 52874, 52880, 63497, or 33425 protein, or fragment thereof, differs from the corresponding sequence in SEQ ID NO:2, 5, 8, 11 or 14. In one embodiment it differs by at least one but by less than 15, 10 or 5 amino acid residues. In another it differs from the corresponding sequence in SEQ ID NO:2, 5, 8, 11 or 14 by at least one residue but less than 20%, 15%, 10% or 5% of the residues in it differ from the corresponding sequence in SEQ ID NO:2, 5, 8, 11 or 14. (If this comparison requires alignment the sequences should be aligned for maximum homology. "Looped" out sequences from deletions or insertions, or mismatches, are considered differences.) The differences are, preferably, differences or changes at a non-essential residue or a conservative substitution. In a preferred embodiment the differences are not in the facosyltransferase, 7TM receptor, or RhoGAP domain. In another preferred embodiment one or more differences are in non-active site residues, e.g. outside of the fucosyltransferase, 7TM receptor, or RhoGAP domain.

Other embodiments include a protein that contain one or more changes in amino acid sequence, e.g., a change in an amino acid residue which is not essential for activity. Such 80090, 52874, 52880, 63497, or 33425 proteins differ in amino acid sequence from SEQ ID NO:2, 5, 8, 11 or 14, yet retain biological activity.

In one embodiment, a biologically active portion of an 80090, 52874, 52880, 63497, or 33425 protein includes a fucosyltransferase, 7TM receptor, or RhoGAP domain. In another embodiment, a biologically active portion of an 80090, 52874, 52880, 63497, or 33425 protein includes a protein kinase C phosphorylation domain. Moreover, other biologically active portions, in which other regions of the protein are deleted, can be prepared by recombinant techniques and evaluated for one or more of the functional activities of a native 80090, 52874, 52880, 63497, or 33425 protein.

In a preferred embodiment, the 80090, 52874, 52880, 63497, or 33425 protein has an amino acid sequence shown in SEQ ID NO:2, 5, 8, 11 or 14. In other embodiments, the 80090, 52874, 52880, 63497, or 33425 protein is substantially identical to SEQ ID NO:2, 5, 8, 11 or 14. In yet another embodiment, the 80090, 52874, 52880, 63497, or 33425 protein is substantially identical to SEQ ID NO:2, 5, 8, 11 or 14 and retains the functional activity of the protein of SEQ ID NO:2, 5, 8, 11 or 14, as described in detail above. Accordingly, in another embodiment, the 80090, 52874, 52880, 63497, or 33425 protein is a protein which includes an amino acid sequence at least about 60%, 65%, 70%, 75%, 80%, 85%, 90%, 95%, 98% or more identical to SEQ ID NO:2, 5, 8, 11 or 14.

80090, 52874, 52880, 63497, or 33425 Chimeric or Fusion Proteins

In another aspect, the invention provides 80090, 52874, 52880, 63497, or 33425 chimeric or fusion proteins. As used herein, an 80090, 52874, 52880, 63497, or 33425 "chimeric protein" or "fusion protein" includes an 80090, 52874, 52880, 63497, or 33425 polypeptide linked to a non-80090, 52874, 52880, 63497, or 33425 polypeptide. A "non-80090, 52874, 52880, 63497, or 33425 polypeptide" refers to a polypeptide having an amino acid sequence corresponding to a protein which is not substantially homologous to the 80090, 52874, 52880, 63497, or 33425 protein, e.g., a protein which is different from the 80090, 52874, 52880, 63497, or 33425 protein and which is derived from the same or a different organism. The 80090, 52874, 52880, 63497, or 33425 polypeptide of the fusion protein can correspond to all or a portion e.g., a fragment described herein of an 80090, 52874, 52880, 63497, or 33425 amino acid sequence. In a preferred embodiment, an 80090, 52874, 52880, 63497, or 33425 fusion protein includes at least one (or two) biologically active portion of an 80090, 52874, 52880, 63497, or 33425 protein. The non-80090, 52874, 52880, 63497, or 33425 polypeptide can be fused to the N-terminus or C-terminus of the 80090, 52874, 52880, 63497, or 33425 polypeptide.

The fusion protein can include a moiety which has a high affinity for a ligand. For example, the fusion protein can be a GST-80090, 52874, 52880, 63497, or 33425 fusion protein in which the 80090, 52874, 52880, 63497, or 33425 sequences are fused to the C-terminus of the GST sequences. Such fusion proteins can facilitate the purification of recombinant 80090, 52874, 52880, 63497, or 33425. Alternatively, the fusion protein can be an 80090, 52874, 52880, 63497, or 33425 protein containing a heterologous signal sequence at its N-terminus. In certain host cells (e.g., mammalian host cells), expression and/or secretion of 80090, 52874, 52880, 63497, or 33425 can be increased through use of a heterologous signal sequence.

Fusion proteins can include all or a part of a serum protein, e.g., a portion of an immunoglobulin (e.g., IgG, IgA, or IgE), e.g., an Fc region and/or the hinge C1 and C2 sequences of an immunoglobulin or human serum albumin.

The 80090, 52874, 52880, 63497, or 33425 fusion proteins of the invention can be incorporated into pharmaceutical compositions and administered to a subject in vivo. The 80090, 52874, 52880, 63497, or 33425 fusion proteins can be used to affect the bioavailability of an 80090, 52874, 52880, 63497, or 33425 substrate. 80090, 52874, 52880, 63497, or 33425 fusion proteins may be useful therapeutically for the treatment of disorders caused by, for example, (i) aberrant modification or mutation of a gene encoding an 80090, 52874, 52880, 63497, or 33425 protein; (ii) mis-regulation of the 80090, 52874, 52880, 63497, or 33425 gene; and (iii) aberrant post-translational modification of an 80090, 52874, 52880, 63497, or 33425 protein.

Moreover, the 80090, 52874, 52880, 63497, or 33425-fusion proteins of the invention can be used as immunogens to produce anti-80090, 52874, 52880, 63497, or 33425 antibodies in a subject, to purify 80090, 52874, 52880, 63497, or 33425 ligands and in screening assays to identify molecules which inhibit the interaction of 80090, 52874, 52880, 63497, or 33425 with an 80090, 52874, 52880, 63497, or 33425 substrate.

Expression vectors are commercially available that already encode a fusion moiety (e.g., a GST polypeptide). A 80090, 52874, 52880, 63497, or 33425-encoding nucleic acid can be cloned into such an expression vector such that the fusion moiety is linked in-frame to the 80090, 52874, 52880, 63497, or 33425 protein.

Variants of 80090, 52874, 52880, 63497, or 33425 Proteins

In another aspect, the invention also features a variant of an 80090, 52874, 52880, 63497, or 33425 polypeptide, e.g., which functions as an agonist (mimetics) or as an antagonist. Variants of the 80090, 52874, 52880, 63497, or 33425 proteins can be generated by mutagenesis, e.g., discrete point mutation, the insertion or deletion of sequences or the truncation of an 80090, 52874, 52880, 63497, or 33425 protein. An agonist of the 80090, 52874, 52880, 63497, or 33425 proteins can retain substantially the same, or a subset, of the biological activities of the naturally occurring form of an 80090, 52874, 52880, 63497, or 33425 protein. An antagonist of an 80090, 52874, 52880, 63497, or 33425 protein can inhibit one or more of the activities of the naturally occurring form of the 80090, 52874, 52880, 63497, or 33425 protein by, for example, competitively modulating an 80090, 52874, 52880, 63497, or 33425-mediated activity of an 80090, 52874, 52880, 63497, or 33425 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 80090, 52874, 52880, 63497, or 33425 protein.

Variants of an 80090, 52874, 52880, 63497, or 33425 protein can be identified by screening combinatorial libraries of mutants, e.g., truncation mutants, of an 80090, 52874, 52880, 63497, or 33425 protein for agonist or antagonist activity.

Libraries of fragments e.g., N terminal, C terminal, or internal fragments, of an 80090, 52874, 52880, 63497, or 33425 protein coding sequence can be used to generate a variegated population of fragments for screening and subsequent selection of variants of an 80090, 52874, 52880, 63497, or 33425 protein.

Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property. Recursive ensemble mutagenesis (REM), a new technique which enhances the frequency of functional mutants in the libraries, can be used in combination with the screening assays to identify 80090, 52874, 52880, 63497, or 33425 variants (Arkin and Yourvan, (1992) *Proc. Natl. Acad. Sci. USA* 89:7811–7815; Delgrave et al., (1993) *Protein Engineering* 6(3):327–331).

Cell based assays can be exploited to analyze a variegated 80090, 52874, 52880, 63497, or 33425 library. For example, a library of expression vectors can be transfected into a cell line, e.g., a cell line, which ordinarily responds to 80090, 52874, 52880, 63497, or 33425 in a substrate-dependent manner. The transfected cells are then contacted with 80090, 52874, 52880, 63497, or 33425 and the effect of the expression of the mutant on signaling by the 80090, 52874, 52880, 63497, or 33425 substrate can be detected, e.g., by measuring fucosyltransferase, 7TM receptor, or RhoGAP activity. Plasmid DNA can then be recovered from the cells which score for inhibition, or alternatively, potentiation of signaling by the 80090, 52874, 52880, 63497, or 33425 substrate, and the individual clones further characterized.

In another aspect, the invention features a method of making an 80090, 52874, 52880, 63497, or 33425 polypeptide, e.g., a peptide having a non-wild type activity, e.g., an antagonist, agonist, or super agonist of a naturally occurring 80090, 52874, 52880, 63497, or 33425 polypeptide, e.g., a naturally occurring 80090, 52874, 52880, 63497, or 33425 polypeptide. The method includes: altering the sequence of an 80090, 52874, 52880, 63497, or 33425 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of an 80090, 52874, 52880, 63497, or 33425 polypeptide a biological activity of a naturally occurring 80090, 52874, 52880, 63497, or 33425 polypeptide. The method includes: altering the sequence, e.g., by substitution or deletion of one or more residues, of an 80090, 52874, 52880, 63497, or 33425 polypeptide, e.g., altering the sequence of a non-conserved region, or a domain or residue described herein, and testing the altered polypeptide for the desired activity.

Anti-80090, 52874, 52880, 63497, or 33425 Antibodies

In another aspect, the invention provides an anti-80090, 52874, 52880, 63497, or 33425 antibody. The term "antibody" as used herein refers to an immunoglobulin molecule or immunologically active portion thereof, i.e., an antigen-binding portion. Examples of immunologically active portions of immunoglobulin molecules include F(ab) and F(ab')$_2$ fragments which can be generated by treating the antibody with an enzyme such as pepsin.

The antibody can be a polyclonal, monoclonal, recombinant, e.g., a chimeric or humanized, fully human, non-human, e.g., murine, or single chain antibody. In a preferred embodiment it has effector function and can fix complement. The antibody can be coupled to a toxin or imaging agent.

A full-length 80090, 52874, 52880, 63497, or 33425 protein or, antigenic peptide fragment of 80090, 52874, 52880, 63497, or 33425 can be used as an immunogen or can be used to identify anti-80090, 52874, 52880, 63497, or 33425 antibodies made with other immunogens, e.g., cells, membrane preparations, and the like. The antigenic peptide of 80090, 52874, 52880, 63497, or 33425 should include at least 8 amino acid residues of the amino acid sequence shown in SEQ ID NO:2, 5, 8, 11 or 14 and encompasses an epitope of 80090, 52874, 52880, 63497, or 33425. Preferably, the antigenic peptide includes at least 10 amino acid residues, more preferably at least 15 amino acid residues, even more preferably at least 20 amino acid residues, and most preferably at least 30 amino acid residues.

Fragments of 80090, 52874, 52880, 63497, or 33425 can be used as immunogens or used to characterize the specificity of an antibody or antibodies against what are believed to be hydrophilic regions of the 80090, 52874, 52880, 63497, or 33425 protein. Similarly, a fragment of 80090, 52874, 52880, 63497, or 33425 can be used to make an antibody against what is believed to be a hydrophobic region of the 80090, 52874, 52880, 63497, or 33425 protein; a fragment of 80090, 52874, 52880, 63497, or 33425 can be used to make an antibody against the fucosyltransferase, 7TM receptor, or RhoGAP region of the 80090, 52874, 52880, 63497, or 33425 protein. Hydophobicity and hydrophilicity can be determined by using a Kyte-Dolittle plot as described herein.

Antibodies reactive with, or specific for, any of these regions, or other regions or domains described herein are provided.

In a preferred embodiment the antibody fails to bind an Fc receptor, e.g. it is a type which does not support Fc receptor binding or has been modified, e.g., by deletion or other mutation, such that is does not have a functional Fc receptor binding region.

Preferred epitopes encompassed by the antigenic peptide are regions of 80090, 52874, 52880, 63497, or 33425 are located on the surface of the protein, e.g., hydrophilic regions, as well as regions with high antigenicity. For example, an Emini surface probability analysis of the human 80090, 52874, 52880, 63497, or 33425 protein sequence can be used to indicate the regions that have a particularly high probability of being localized to the surface of the 80090, 52874, 52880, 63497, or 33425 protein and are thus likely to constitute surface residues useful for targeting antibody production.

In a preferred embodiment the antibody binds an epitope on any domain or region on 80090, 52874, 52880, 63497, or 33425 proteins described herein.

Chimeric, humanized, but most preferably, completely human antibodies are desirable for applications which include repeated administration, e.g., therapeutic treatment (and some diagnostic applications) of human patients.

Additionally, chimeric, humanized, and completely human antibodies are also within the scope of the invention. Chimeric, humanized, but most preferably, completely human antibodies are desirable for applications which include repeated administration, e.g., therapeutic treatment of human patients, and some diagnostic applications.

Chimeric and humanized monoclonal antibodies, comprising both human and non-human portions, can be made using standard recombinant DNA techniques. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) *Int. Rev. Immunol.* 13:65–93); and U.S. Pat. Nos. 5,625,126; 5,633,425; 5,569,825; 5,661,016; and 5,545,806. In addition, companies such as Abgenix, Inc. (Fremont, Calif.) and Medarex, Inc. (Princeton, N.J.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) *Bio/Technology* 12:899–903).

The anti-80090, 52874, 52880, 63497, or 33425 antibody can be a single chain antibody. A single-chain antibody (scFV) can be engineered (see, for example, Colcher, D. et al. (1999) *Ann. N Y Acad. Sci.* 880:263–80; and Reiter, Y. (1996) *Clin. Cancer Res.* 2:245–52). The single chain antibody can be dimerized or multimerized to generate multivalent antibodies having specificities for different epitopes of the same target 80090, 52874, 52880, 63497, or 33425 protein.

In a preferred embodiment, the antibody has reduced or no ability to bind an Fc receptor. For example, it is an isotype or subtype, fragment or other mutant, which does not support binding to an Fc receptor, e.g., it has a mutagenized or deleted Fc receptor binding region. An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

An anti-80090, 52874, 52880, 63497, or 33425 antibody (e.g., monoclonal antibody) can be used to isolate 80090, 52874, 52880, 63497, or 33425 by standard techniques, such as affinity chromatography or immunoprecipitation. Moreover, an anti-80090, 52874, 52880, 63497, or 33425 antibody can be used to detect 80090, 52874, 52880, 63497, or 33425 protein (e.g., in a cellular lysate or cell supernatant) in order to evaluate the abundance and pattern of expression of the protein. Anti-80090, 52874, 52880, 63497, or 33425 antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

In preferred embodiments, an antibody can be made by immunizing with a purified 80090, 52874, 52880, 63497, or 33425 antigen, or a fragment thereof, e.g., a fragment described herein, a membrane associated antigen, tissues, e.g., crude tissue preparations, whole cells, preferably living cells, lysed cells, or cell fractions, e.g., membrane fractions.

Antibodies which bind only a native 80090, 52874, 52880, 63497, or 33425 protein, only denatured or otherwise non-native 80090, 52874, 52880, 63497, or 33425 protein, or which bind both, are within the invention. Antibodies with linear or conformational epitopes are within the invention. Conformational epitopes sometimes can be identified by identifying antibodies which bind to native but not denatured 80090, 52874, 52880, 63497, or 33425 protein.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include an 80090, 52874, 52880, 63497, or 33425 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 80090, 52874, 52880, 63497, or 33425 proteins, mutant forms of 80090, 52874, 52880, 63497, or 33425 proteins, fusion proteins, and the like).

The recombinant expression vectors of the invention can be designed for expression of 80090, 52874, 52880, 63497, or 33425 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S., (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 80090, 52874, 52880, 63497, or 33425 activity assays, (e.g., direct assays or competitive assays described in detail below), or to generate antibodies specific for 80090, 52874, 52880, 63497, or 33425 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six (6) weeks).

To maximize recombinant protein expression in *E. coli* is to express the protein in host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

The 80090, 52874, 52880, 63497, or 33425 expression vector can be a yeast expression vector, a vector for expression in insect cells, e.g., a baculovirus expression vector or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al., (1987) *Genes Dev.* 1:268–277), lymphoid-specific promoters (Calame and Eaton, (1988) *Adv. Immunol.* 43:235–275), in particular promoters of T cell receptors (Winoto and Baltimore, (1989) *EMBO J.* 8:729–733) and immunoglobulins (Banetji et al., (1983) *Cell* 33:729–740; Queen and Baltimore, (1983) *Cell* 33:741–748), neuron-specific promoters (e.g., the neurofilament promoter; Byrne and Ruddle, (1989) *Proc. Natl. Acad.*

Sci. USA 86:5473–5477), pancreas-specific promoters (Edlund et al., (1985) Science 230:912–916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss, (1990) Science 249:374–379) and the α-fetoprotein promoter (Campes and Tilghman, (1989) Genes Dev. 3:537–546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub, H. et al., Antisense RNA as a molecular tool for genetic analysis, Reviews—Trends in Genetics, Vol. 1(1) 1986.

Another aspect the invention provides a host cell which includes a nucleic acid molecule described herein, e.g., an 80090, 52874, 52880, 63497, or 33425 nucleic acid molecule within a recombinant expression vector or an 80090, 52874, 52880, 63497, or 33425 nucleic acid molecule containing sequences which allow it to homologously recombine into a specific site of the host cell's genome. The terms "host cell" and "recombinant host cell" are used interchangeably herein. Such terms refer not only to the particular subject cell but rather also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an 80090, 52874, 52880, 63497, or 33425 protein can be expressed in bacterial cells such as E. coli, insect cells, yeast or mammalian cells (such as Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation A host cell of the invention can be used to produce (i.e., express) an 80090, 52874, 52880, 63497, or 33425 protein. Accordingly, the invention further provides methods for producing an 80090, 52874, 52880, 63497, or 33425 protein using the host cells of the invention. In one embodiment, the method includes culturing the host cell of the invention (into which a recombinant expression vector encoding an 80090, 52874, 52880, 63497, or 33425 protein has been introduced) in a suitable medium such that an 80090, 52874, 52880, 63497, or 33425 protein is produced. In another embodiment, the method further includes isolating an 80090, 52874, 52880, 63497, or 33425 protein from the medium or the host cell.

In another aspect, the invention features, a cell or purified preparation of cells which include an 80090, 52874, 52880, 63497, or 33425 transgene, or which otherwise misexpress 80090, 52874, 52880, 63497, or 33425. The cell preparation can consist of human or non-human cells, e.g., rodent cells, e.g., mouse or rat cells, rabbit cells, or pig cells. In preferred embodiments, the cell or cells include an 80090, 52874, 52880, 63497, or 33425 transgene, e.g., a heterologous form of an 80090, 52874, 52880, 63497, or 33425, e.g., a gene derived from humans (in the case of a non-human cell). The 80090, 52874, 52880, 63497, or 33425 transgene can be misexpressed, e.g., overexpressed or underexpressed. In other preferred embodiments, the cell or cells include a gene which misexpress an endogenous 80090, 52874, 52880, 63497, or 33425, e.g., a gene the expression of which is disrupted, e.g., a knockout. Such cells can serve as a model for studying disorders which are related to mutated or mis-expressed 80090, 52874, 52880, 63497, or 33425 alleles or for use in drug screening.

In another aspect, the invention features, a human cell, e.g., a hematopoietic stem cell, transformed with nucleic acid which encodes a subject 80090, 52874, 52880, 63497, or 33425 polypeptide.

Also provided are cells or a purified preparation thereof, e.g., human cells, in which an endogenous 80090, 52874, 52880, 63497, or 33425 is under the control of a regulatory sequence that does not normally control the expression of the endogenous 80090, 52874, 52880, 63497, or 33425 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 80090, 52874, 52880, 63497, or 33425 gene. For example, an endogenous 80090, 52874, 52880, 63497, or 33425 gene, e.g., a gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published on May 16, 1991.

Transgenic Animals

The invention provides non-human transgenic animals. Such animals are useful for studying the function and/or activity of an 80090, 52874, 52880, 63497, or 33425 protein and for identifying and/or evaluating modulators of 80090, 52874, 52880, 63497, or 33425 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 80090, 52874, 52880, 63497, or 33425 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of an 80090, 52874, 52880, 63497, or 33425 protein to particular cells. A transgenic founder animal can be identified based upon the presence of an 80090, 52874, 52880, 63497, or 33425 transgene in its genome and/or expression of 80090, 52874, 52880, 63497, or 33425 mRNA in tissues or cells of the animals. A transgenic founder animal can then be used to breed additional animals carrying the transgene. Moreover, transgenic animals carrying a transgene encoding an 80090, 52874, 52880, 63497, or 33425 protein can further be bred to other transgenic animals carrying other transgenes.

80090, 52874, 52880, 63497, or 33425 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed herein.

Uses

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

The isolated nucleic acid molecules of the invention can be used, for example, to express an 80090, 52874, 52880, 63497, or 33425 protein (e.g., via a recombinant expression vector in a host cell in gene therapy applications), to detect an 80090, 52874, 52880, 63497, or 33425 mRNA (e.g., in a biological sample) or a genetic alteration in an 80090, 52874, 52880, 63497, or 33425 gene, and to modulate 80090, 52874, 52880, 63497, or 33425 activity, as described further below. The 80090, 52874, 52880, 63497, or 33425 proteins can be used to treat disorders characterized by insufficient or excessive production of an 80090, 52874, 52880, 63497, or 33425 substrate or production of 80090, 52874, 52880, 63497, or 33425 inhibitors. In addition, the 80090, 52874, 52880, 63497, or 33425 proteins can be used to screen for naturally occurring 80090, 52874, 52880, 63497, or 33425 substrates, to screen for drugs or compounds which modulate 80090, 52874, 52880, 63497, or 33425 activity, as well as to treat disorders characterized by insufficient or excessive production of 80090, 52874, 52880, 63497, or 33425 protein or production of 80090, 52874, 52880, 63497, or 33425 protein forms which have decreased, aberrant or unwanted activity compared to 80090, 52874, 52880, 63497, or 33425 wild-type protein. Such disorders include those characterized by aberrant signaling or aberrant, e.g., hyperproliferative, cell growth. Moreover, the anti-80090, 52874, 52880, 63497, or 33425 antibodies of the invention can be used to detect and isolate 80090, 52874, 52880, 63497, or 33425 proteins, regulate the bioavailability of 80090, 52874, 52880, 63497, or 33425 proteins, and modulate 80090, 52874, 52880, 63497, or 33425 activity.

A method of evaluating a compound for the ability to interact with, e.g., bind, a subject 80090, 52874, 52880, 63497, or 33425 polypeptide is provided. The method includes: contacting the compound with the subject 80090, 52874, 52880, 63497, or 33425 polypeptide; and evaluating ability of the compound to interact with, e.g., to bind or form a complex with the subject 80090, 52874, 52880, 63497, or 33425 polypeptide. This method can be performed in vitro, e.g., in a cell free system, or in vivo, e.g., in a two-hybrid interaction trap assay. This method can be used to identify naturally occurring molecules which interact with subject 80090, 52874, 52880, 63497, or 33425 polypeptide. It can also be used to find natural or synthetic inhibitors of subject 80090, 52874, 52880, 63497, or 33425 polypeptide. Screening methods are discussed in more detail below.

Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to 80090, 52874, 52880, 63497, or 33425 proteins, have a stimulatory or inhibitory effect on, for example, 80090, 52874, 52880, 63497, or 33425 expression or 80090, 52874, 52880, 63497, or 33425 activity, or have a stimulatory or inhibitory effect on, for example, the expression or activity of an 80090, 52874, 52880, 63497, or 33425 substrate. Compounds thus identified can be used to modulate the activity of target gene products (e.g., 80090, 52874, 52880, 63497, or 33425 genes) in a therapeutic protocol, to elaborate the biological function of the target gene product, or to identify compounds that disrupt normal target gene interactions.

In one embodiment, the invention provides assays for screening candidate or test compounds which are substrates of an 80090, 52874, 52880, 63497, or 33425 protein or polypeptide or a biologically active portion thereof. In another embodiment, the invention provides assays for screening candidate or test compounds which bind to or modulate the activity of an 80090, 52874, 52880, 63497, or 33425 protein or polypeptide or a biologically active portion thereof.

The test compounds of the present invention can be obtained using any of the numerous approaches in combinatorial library methods known in the art, including: biological libraries; peptoid libraries [libraries of molecules having the functionalities of peptides, but with a novel, non-peptide backbone which are resistant to enzymatic degradation but which nevertheless remain bioactive] (see, e.g., Zuckermann, R. N. et al., *J. Med. Chem.* 1994, 37: 2678–85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al., (1994) *Proc. Natl. Acad. Sci. USA* 91:11422; Zuckermann et al., (1994). *J. Med. Chem.* 37:2678; Cho et al., (1993) *Science* 261:1303; Carrell et al., (1994) *Angew. Chem. Int. Ed. Engl.* 33:2059; Carell et al., (1994) *Angew. Chem. Int. Ed. Engl.* 33:2061; and in Gallop et al., (1994) *J. Med. Chem.* 37:1233.

Libraries of compounds maybe presented in solution (e.g., Houghten, (1992) *Biotechniques* 13:412–421), or on beads (Lam, (1991) *Nature* 354:82–84), chips (Fodor, (1993) *Nature* 364:555–556), bacteria or spores (Ladner, U.S. Pat.

No. 5,223,409), plasmids (Cull et al., (1992) *Proc. Natl. Acad. Sci. USA* 89:1865–1869) or on phage (Scott and Smith, (1990) *Science* 249:386–390); (Devlin, (1990) *Science* 249:404–406); (Cwirla et al., (1990) *Proc. Natl. Acad. Sci.* 87:6378–6382); (Felici, (1991) *J. Mol. Biol.* 222:301–310); (Ladner supra.).

In one embodiment, an assay is a cell-based assay in which a cell which expresses an 80090, 52874, 52880, 63497, or 33425 protein or biologically active portion thereof is contacted with a test compound, and the ability of the test compound to modulate 80090, 52874, 52880, 63497, or 33425 activity is determined. Determining the ability of the test compound to modulate 80090, 52874, 52880, 63497, or 33425 activity can be accomplished by monitoring, for example, fucosyltransferase, 7TM receptor, or RhoGAP activity. The cell, for example, can be of mammalian origin, e.g., human. Cell homogenates, or fractions, preferably membrane containing fractions, can also be tested.

The ability of the test compound to modulate 80090, 52874, 52880, 63497, or 33425 binding to a compound, e.g., an 80090, 52874, 52880, 63497, or 33425 substrate, or to bind to 80090, 52874, 52880, 63497, or 33425 can also be evaluated. This can be accomplished, for example, by coupling the compound, e.g., the substrate, with a radioisotope or enzymatic label such that binding of the compound, e.g., the substrate, to 80090, 52874, 52880, 63497, or 33425 can be determined by detecting the labeled compound, e.g., substrate, in a complex. Alternatively, 80090, 52874, 52880, 63497, or 33425 could be coupled with a radioisotope or enzymatic label to monitor the ability of a test compound to modulate 80090, 52874, 52880, 63497, or 33425 binding to an 80090, 52874, 52880, 63497, or 33425 substrate in a complex. For example, compounds (e.g., 80090, 52874, 52880, 63497, or 33425 substrates) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., an 80090, 52874, 52880, 63497, or 33425 substrate) to interact with 80090, 52874, 52880, 63497, or 33425 with or without the labeling of any of the interactants can be evaluated. For example, a microphysiometer can be used to detect the interaction of a compound with 80090, 52874, 52880, 63497, or 33425 without the labeling of either the compound or the 80090, 52874, 52880, 63497, or 33425. McConnell, H. M. et al., (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 80090, 52874, 52880, 63497, or 33425.

In yet another embodiment, a cell-free assay is provided in which an 80090, 52874, 52880, 63497, or 33425 protein or biologically active portion thereof is contacted with a test compound and the ability of the test compound to bind to the 80090, 52874, 52880, 63497, or 33425 protein or biologically active portion thereof is evaluated. Preferred biologically active portions of the 80090, 52874, 52880, 63497, or 33425 proteins to be used in assays of the present invention include fragments which participate in interactions with non-80090, 52874, 52880, 63497, or 33425 molecules, e.g., fragments with high surface probability scores.

Soluble and/or membrane-bound forms of isolated proteins (e.g., 80090, 52874, 52880, 63497, or 33425 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl-N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

In one embodiment, assays are performed where the ability of an agent to block fucosyltransferase, 7TM receptor, or RhoGAP activity within a cell is evaluated.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 80090, 52874, 52880, 63497, or 33425 protein to bind to a target molecule can be accomplished using real-time Biomolecular Interaction Analysis (BIA) (see, e.g., Sjolander, S. and Urbaniczky, C., (1991) *Anal. Chem.* 63:2338–2345 and Szabo et al., (1995) *Curr. Opin. Struct. Biol.* 5:699–705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 80090, 52874, 52880, 63497, or 33425, an anti-80090, 52874, 52880, 63497, or 33425 antibody or its target molecule to facilitate separation of complexed from uncomplexed forms of one or both of the proteins, as well as to accommodate automation of the assay. Binding of a test compound to an 80090, 52874, 52880, 63497, or 33425 protein, or interaction of an 80090, 52874, 52880, 63497, or 33425 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/80090, 52874, 52880, 63497, or 33425 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 80090, 52874, 52880, 63497, or 33425 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 80090, 52874, 52880, 63497, or 33425 binding or activity determined using standard techniques.

Other techniques for immobilizing either an 80090, 52874, 52880, 63497, or 33425 protein or a target molecule on matrices include using conjugation of biotin and streptavidin. Biotinylated 80090, 52874, 52880, 63497, or 33425 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 80090, 52874, 52880, 63497, or 33425 protein or target molecules but which do not interfere with binding of the 80090, 52874, 52880, 63497, or 33425 protein to its target molecule. Such antibodies can be derivatized to the wells of the plate, and unbound target or 80090, 52874, 52880, 63497, or 33425 protein trapped in the wells by antibody conjugation. Methods for detecting such complexes, in addition to those described above for the GST-immobilized complexes, include immunodetection of complexes using antibodies reactive with the 80090, 52874, 52880, 63497, or 33425 protein or target molecule, as well as enzyme-linked assays which rely on detecting an enzymatic activity associated with the 80090, 52874, 52880, 63497, or 33425 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., *Trends Biochem Sci* 1993 Aug. 18(8):284–7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. Current Protocols in Molecular Biology 1999, J. Wiley: New York). Such resins and chromatographic techniques are known to one skilled in the art (see, e.g., Heegaard, N. H., *J Mol. Recognit.* 1998 Winter;11(1–6):141–8; Hage, D. S., and Tweed, S. A., *J. Chromatogr. B Biomed. Sci. Appl.* 1997 Oct. 10; 699(1–2): 499–525). Further, fluorescence energy transfer may also be conveniently utilized, as described herein, to detect binding without further purification of the complex from solution.

In a preferred embodiment, the assay includes contacting the 80090, 52874, 52880, 63497, or 33425 protein or biologically active portion thereof with a known compound which binds 80090, 52874, 52880, 63497, or 33425 to form an assay mixture, contacting the assay mixture with a test compound, and determining the ability of the test compound to interact with an 80090, 52874, 52880, 63497, or 33425 protein, wherein determining the ability of the test compound to interact with an 80090, 52874, 52880, 63497, or 33425 protein includes determining the ability of the test compound to preferentially bind to 80090, 52874, 52880, 63497, or 33425 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 80090, 52874, 52880, 63497, or 33425 genes herein identified. In an alternative embodiment, the invention provides methods for determining the ability of the test compound to modulate the activity of an 80090, 52874, 52880, 63497, or 33425 protein through modulation of the activity of a downstream effector of an 80090, 52874, 52880, 63497, or 33425 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), e.g., a substrate, a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner.

Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 80090, 52874, 52880, 63497, or 33425 proteins can be used as "bait proteins" in a two-hybrid assay or three-hybrid assay (see, e.g., U.S. Pat. No. 5,283, 317; Zervos et al., (1993) Cell 72:223–232; Madura et al., (1993) J. Biol. Chem. 268:12046–12054; Bartel et al., (1993) Biotechniques 14:920–924; Iwabuchi et al., (1993) Oncogene 8:1693–1696; and Brent WO94/10300), to identify other proteins, which bind to or interact with 80090, 52874, 52880, 63497, or 33425 ("80090, 52874, 52880, 63497, or 33425-binding proteins" or "80090, 52874, 52880, 63497, or 33425-bp") and are involved in 80090, 52874, 52880, 63497, or 33425 activity. Such 80090, 52874, 52880, 63497, or 33425-bps can be activators or inhibitors of signals by the 80090, 52874, 52880, 63497, or 33425 proteins or 80090, 52874, 52880, 63497, or 33425 targets as, for example, downstream elements of an 80090, 52874, 52880, 63497, or 33425-mediated signaling pathway.

The two-hybrid system is based on the modular nature of most transcription factors, which consist of separable DNA-binding and activation domains. Briefly, the assay utilizes two different DNA constructs. In one construct, the gene that codes for an 80090, 52874, 52880, 63497, or 33425 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 80090, 52874, 52880, 63497, or 33425 protein can be the fused to the activator domain.) If the "bait" and the "prey" proteins are able to interact, in vivo, forming an 80090, 52874, 52880, 63497, or 33425-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 80090, 52874, 52880, 63497, or 33425 protein.

In another embodiment, modulators of 80090, 52874, 52880, 63497, or 33425 expression are identified. For example, a cell or cell free mixture is contacted with a candidate compound and the expression of 80090, 52874, 52880, 63497, or 33425 mRNA or protein evaluated relative to the level of expression of 80090, 52874, 52880, 63497, or 33425 mRNA or protein in the absence of the candidate compound. When expression of 80090, 52874, 52880, 63497, or 33425 mRNA or protein is greater in the presence of the candidate compound than in its absence, the candidate compound is identified as a stimulator of 80090, 52874, 52880, 63497, or 33425 mRNA or protein expression.

Alternatively, when expression of 80090, 52874, 52880, 63497, or 33425 mRNA or protein is less (statistically significantly less) in the presence of the candidate compound than in its absence, the candidate compound is identified as an inhibitor of 80090, 52874, 52880, 63497, or 33425 mRNA or protein expression. The level of 80090, 52874, 52880, 63497, or 33425 mRNA or protein expression can be determined by methods described herein for detecting 80090, 52874, 52880, 63497, or 33425 mRNA or protein.

In another aspect, the invention pertains to a combination of two or more of the assays described herein. For example, a modulating agent can be identified using a cell-based or a cell free assay, and the ability of the agent to modulate the activity of an 80090, 52874, 52880, 63497, or 33425 protein can be confirmed in vivo, e.g., in an animal.

This invention further pertains to novel agents identified by the above-described screening assays. Accordingly, it is within the scope of this invention to further use an agent identified as described herein (e.g., an 80090, 52874, 52880, 63497, or 33425 modulating agent, an antisense 80090, 52874, 52880, 63497, or 33425 nucleic acid molecule, an 80090, 52874, 52880, 63497, or 33425-specific antibody, or an 80090, 52874, 52880, 63497, or 33425-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 80090, 52874, 52880, 63497, or 33425 with a disease; (ii) identify an individual from a minute biological sample (tissue typing); and (iii) aid in forensic identification of a biological sample. These applications are described in the subsections below.

Chromosome Mapping

The 80090, 52874, 52880, 63497, or 33425 nucleotide sequences or portions thereof can be used to map the location of the 80090, 52874, 52880, 63497, or 33425 genes on a chromosome. This process is called chromosome mapping. Chromosome mapping is useful in correlating the 80090, 52874, 52880, 63497, or 33425 sequences with genes associated with disease.

Briefly, 80090, 52874, 52880, 63497, or 33425 genes can be mapped to chromosomes by preparing PCR primers (preferably 15–25 bp in length) from the 80090, 52874, 52880, 63497, or 33425 nucleotide sequences. These primers can then be used for PCR screening of somatic cell hybrids containing individual human chromosomes. Only those hybrids containing the human gene corresponding to the 80090, 52874, 52880, 63497, or 33425 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al., (1983) *Science* 220:919–924).

Other mapping strategies e.g., in situ hybridization (described in Fan, Y. et al., (1990) *Proc. Natl. Acad. Sci. USA*, 87:6223–27), pre-screening with labeled flow-sorted chromosomes, and pre-selection by hybridization to chromosome specific cDNA libraries can be used to map 80090, 52874, 52880, 63497, or 33425 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al., (1987) *Nature*, 325:783–787.

Moreover, differences in the DNA sequences between individuals affected and unaffected with a disease associated with the 80090, 52874, 52880, 63497, or 33425 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing 80090, 52874, 52880, 63497, or 33425 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 80090, 52874, 52880, 63497, or 33425 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, 4, 7, 10, or 13 can provide positive individual identification with a panel of perhaps 10 to 1,000 primers which each yield a noncoding amplified sequence of 100 bases. If predicted coding sequences, such as those in SEQ ID NO:3, 6, 9, 12, or 15 are used, a more appropriate number of primers for positive individual identification would be 500–2,000.

If a panel of reagents from 80090, 52874, 52880, 63497, or 33425 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 80090, 52874, 52880, 63497, or 33425 Sequences in Forensic Biology DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1, 4, 7, 10, or 13 (e.g., fragments derived from the noncoding regions of SEQ ID NO:1, 4, 7, 10, or 13 having a length of at least 20 bases, preferably at least 30 bases) are particularly appropriate for this use.

The 80090, 52874, 52880, 63497, or 33425 nucleotide sequences described herein can further be used to provide polynucleotide reagents, e.g., labeled or labelable probes which can be used in, for example, an in situ hybridization technique, to identify a specific tissue, e.g., a tissue containing fucosyltransferase, 7TM receptor, or RhoGAP activity. This can be very useful in cases where a forensic pathologist is presented with a tissue of unknown origin. Panels of such 80090, 52874, 52880, 63497, or 33425 probes can be used to identify tissue by species and/or by organ type.

In a similar fashion, these reagents, e.g., 80090, 52874, 52880, 63497, or 33425 primers or probes can be used to screen tissue culture for contamination (i.e. screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 80090, 52874, 52880, 63497, or 33425.

Such disorders include, e.g., a disorder associated with the misexpression of 80090, 52874, 52880, 63497, or 33425, or lipid metabolism related disorder.

The method includes one or more of the following: detecting, in a tissue of the subject, the presence or absence of a mutation which affects the expression of the 80090, 52874, 52880, 63497, or 33425 gene, or detecting the presence or absence of a mutation in a region which controls the expression of the gene, e.g., a mutation in the 5' control region; detecting, in a tissue of the subject, the presence or absence of a mutation which alters the structure of the 80090, 52874, 52880, 63497, or 33425 gene; detecting, in a tissue of the subject, the misexpression of the 80090, 52874, 52880, 63497, or 33425 gene, at the mRNA level, e.g., detecting a non-wild type level of a mRNA; detecting, in a tissue of the subject, the misexpression of the gene, at the protein level, e.g., detecting a non-wild type level of an 80090, 52874, 52880, 63497, or 33425 polypeptide.

In preferred embodiments the method includes: ascertaining the existence of at least one of: a deletion of one or more nucleotides from the 80090, 52874, 52880, 63497, or 33425 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1 naturally occurring mutants thereof or 5' or 3' flanking sequences naturally associated with the 80090, 52874, 52880, 63497, or 33425 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 80090, 52874, 52880, 63497, or 33425 gene; the presence of a non-wild type splicing pattern of a messenger RNA transcript of the gene; or a non-wild type level of 80090, 52874, 52880, 63497, or 33425.

Methods of the invention can be used prenatally or to determine if a subject's offspring will be at risk for a disorder.

In preferred embodiments the method includes determining the structure of an 80090, 52874, 52880, 63497, or 33425 gene, an abnormal structure being indicative of risk for the disorder.

In preferred embodiments the method includes contacting a sample form the subject with an antibody to the 80090, 52874, 52880, 63497, or 33425 protein or a nucleic acid, which hybridizes specifically with the gene. These and other embodiments are discussed below.

Diagnostic and Prognostic Assays

The presence, level, or absence of 80090, 52874, 52880, 63497, or 33425 protein or nucleic acid in a biological sample can be evaluated by obtaining a biological sample from a test subject and contacting the biological sample with a compound or an agent capable of detecting 80090, 52874, 52880, 63497, or 33425 protein or nucleic acid (e.g., mRNA, genomic DNA) that encodes 80090, 52874, 52880, 63497, or 33425 protein such that the presence of 80090, 52874, 52880, 63497, or 33425 protein or nucleic acid is detected in the biological sample. The term "biological sample" includes tissues, cells and biological fluids isolated from a subject, as well as tissues, cells and fluids present within a subject. A preferred biological sample is serum. The level of expression of the 80090, 52874, 52880, 63497, or 33425 gene can be measured in a number of ways, including, but not limited to: measuring the mRNA encoded by the 80090, 52874, 52880, 63497, or 33425 genes; measuring the amount of protein encoded by the 80090, 52874, 52880, 63497, or 33425 genes; or measuring the activity of the protein encoded by the 80090, 52874, 52880, 63497, or 33425 genes.

The level of mRNA corresponding to the 80090, 52874, 52880, 63497, or 33425 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 80090, 52874, 52880, 63497, or 33425 nucleic acid, such as the nucleic acid of SEQ ID NO:1, or a portion thereof, such as an oligonucleotide of at least 7, 15, 30, 50, 100, 250 or 500 nucleotides in length and sufficient to specifically hybridize under stringent conditions to 80090, 52874, 52880, 63497, or 33425 mRNA or genomic DNA. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA encoded by the 80090, 52874, 52880, 63497, or 33425 genes.

The level of mRNA in a sample that is encoded by one of 80090, 52874, 52880, 63497, or 33425 can be evaluated with nucleic acid amplification, e.g., by rtPCR (Mullis, 1987, U.S. Pat. No. 4,683,202), ligase chain reaction (Barany, 1991, *Proc. Natl. Acad. Sci. USA* 88:189–193), self sustained sequence replication (Guatelli et al., 1990, *Proc. Natl. Acad. Sci. USA* 87:1874–1878), transcriptional amplification system (Kwoh et al., 1989, *Proc. Natl. Acad. Sci. USA* 86:1173–1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 80090, 52874, 52880, 63497, or 33425 gene being analyzed.

In another embodiment, the methods further contacting a control sample with a compound or agent capable of detecting 80090, 52874, 52880, 63497, or 33425 mRNA, or genomic DNA, and comparing the presence of 80090, 52874, 52880, 63497, or 33425 mRNA or genomic DNA in the control sample with the presence of 80090, 52874, 52880, 63497, or 33425 mRNA or genomic DNA in the test sample.

A variety of methods can be used to determine the level of protein encoded by 80090, 52874, 52880, 63497, or 33425. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 80090, 52874, 52880, 63497, or 33425 protein in a biological sample in vitro as well as in vivo. In vitro techniques for detection of 80090, 52874, 52880, 63497, or 33425 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 80090, 52874, 52880, 63497, or 33425 protein include introducing into a subject a labeled anti-80090, 52874, 52880, 63497, or 33425 antibody. For example, the antibody can be labeled with a radioactive marker whose presence and location in a subject can be detected by standard imaging techniques.

In another embodiment, the methods further include contacting the control sample with a compound or agent capable of detecting 80090, 52874, 52880, 63497, or 33425 protein, and comparing the presence of 80090, 52874, 52880, 63497, or 33425 protein in the control sample with the presence of 80090, 52874, 52880, 63497, or 33425 protein in the test sample.

The invention also includes kits for detecting the presence of 80090, 52874, 52880, 63497, or 33425 in a biological sample. For example, the kit can include a compound or agent capable of detecting 80090, 52874, 52880, 63497, or 33425 protein or mRNA in a biological sample; and a standard. The compound or agent can be packaged in a suitable container. The kit can further comprise instructions for using the kit to detect 80090, 52874, 52880, 63497, or 33425 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein-stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 80090, 52874, 52880, 63497, or 33425 expression or activity. As used herein, the term "unwanted" includes an unwanted phenomenon involved in a biological response such as pain or deregulated cell proliferation.

In one embodiment, a disease or disorder associated with aberrant or unwanted 80090, 52874, 52880, 63497, or 33425 expression or activity is identified. A test sample is obtained from a subject and 80090, 52874, 52880, 63497, or 33425 protein or nucleic acid (e.g., mRNA or genomic DNA) is evaluated, wherein the level, e.g., the presence or absence, of 80090, 52874, 52880, 63497, or 33425 protein or nucleic acid is diagnostic for a subject having or at risk of developing a disease or disorder associated with aberrant or unwanted 80090, 52874, 52880, 63497, or 33425 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 80090, 52874, 52880, 63497, or 33425 expression or activity. For example, such methods can be used to determine whether a subject can be effectively treated with an agent for a cellular growth related disorder.

The methods of the invention can also be used to detect genetic alterations in an 80090, 52874, 52880, 63497, or 33425 gene, thereby determining if a subject with the altered gene is at risk for a disorder characterized by misregulation in 80090, 52874, 52880, 63497, or 33425 protein activity or nucleic acid expression, such as a cellular growth related disorder. In preferred embodiments, the methods include detecting, in a sample from the subject, the presence or absence of a genetic alteration characterized by at least one of an alteration affecting the integrity of a gene encoding an 80090, 52874, 52880, 63497, or 33425-protein, or the misexpression of the 80090, 52874, 52880, 63497, or 33425 gene. For example, such genetic alterations can be detected by ascertaining the existence of at least one of 1) a deletion of one or more nucleotides from an 80090, 52874, 52880, 63497, or 33425 gene; 2) an addition of one or more nucleotides to an 80090, 52874, 52880, 63497, or 33425 gene; 3) a substitution of one or more nucleotides of an 80090, 52874, 52880, 63497, or 33425 gene, 4) a chromosomal rearrangement of an 80090, 52874, 52880, 63497, or 33425 gene; 5) an alteration in the level of a messenger RNA transcript of an 80090, 52874, 52880, 63497, or 33425 gene, 6) aberrant modification of an 80090, 52874, 52880, 63497, or 33425 gene, such as of the methylation pattern of the genomic DNA, 7) the presence of a non-wild type splicing pattern of a messenger RNA transcript of an 80090, 52874, 52880, 63497, or 33425 gene, 8) a non-wild type level of an 80090, 52874, 52880, 63497, or 33425-protein, 9) allelic loss of an 80090, 52874, 52880, 63497, or 33425 gene, and 10) inappropriate post-translational modification of an 80090, 52874, 52880, 63497, or 33425-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 80090, 52874, 52880, 63497, or 33425-gene. This method can include the steps of collecting a sample of cells from a subject, isolating nucleic acid (e.g., genomic, mRNA or both) from the sample, contacting the nucleic acid sample with one or more primers which specifically hybridize to an 80090, 52874, 52880, 63497, or 33425 gene under conditions such that hybridization and amplification of the 80090, 52874, 52880, 63497, or 33425-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al., (1988) *Bio-Technology* 6:1197), or other nucleic acid amplification methods, followed by the detection of the amplified molecules using techniques known to those of skill in the art.

In another embodiment, mutations in an 80090, 52874, 52880, 63497, or 33425 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 80090, 52874, 52880, 63497, or 33425 can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. The arrays can have a high density of addresses, e.g., can contain hundreds or thousands of oligonucleotides probes (Cronin, M. T. et al., (1996) *Human Mutation* 7: 244–255; Kozal, M. J. et al., (1996) *Nature Medicine* 2:753–759). For example, genetic mutations in 80090, 52874, 52880, 63497, or 33425 can be identified in two dimensional arrays containing light-generated DNA probes as described in Cronin, M. T. et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 80090, 52874, 52880, 63497, or 33425 gene and detect mutations by comparing the sequence of the sample 80090, 52874, 52880, 63497, or 33425 with the corresponding wild-type (control) sequence. Automated sequencing procedures can be utilized when performing the diagnostic assays ((1995) *Biotechniques* 19:448), including sequencing by mass spectrometry.

Other methods for detecting mutations in the 80090, 52874, 52880, 63497, or 33425 gene include methods in which protection from cleavage agents is used to detect mismatched bases in RNA/RNA or RNA/DNA heteroduplexes (Myers et al., (1985) *Science* 230:1242; Cotton et al., (1988) *Proc. Natl. Acad. Sci. USA* 85:4397; Saleeba et al., (1992) *Methods Enzymol.* 217:286–295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 80090, 52874, 52880, 63497, or 33425 cDNAs obtained from samples of cells. For example, the mutY enzyme of *E. coli* cleaves A at G/A mismatches and the thymidine DNA glycosylase from HeLa cells cleaves T at G/T mismatches (Hsu et al., (1994) *Carcinogenesis* 15:1657–1662; U.S. Pat. No. 5,459,039).

In other embodiments, alterations in electrophoretic mobility will be used to identify mutations in 80090, 52874, 52880, 63497, or 33425 genes. For example, single strand conformation polymorphism (SSCP) may be used to detect differences in electrophoretic mobility between mutant and wild type nucleic acids (Orita et al., (1989) *Proc. Natl. Acad. Sci. USA*: 86:2766, see also Cotton, (1993) *Mutat. Res.* 285:125–144; and Hayashi, (1992) *Genet. Anal. Tech. Appl.* 9:73–79). Single-stranded DNA fragments of sample and control 80090, 52874, 52880, 63497, or 33425 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al., (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al., (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner, (1987) *Biophys. Chem.* 265:12753).

Examples of other techniques for detecting point mutations include, but are not limited to, selective oligonucleotide hybridization, selective amplification, or selective primer extension (Saiki et al., (1986) *Nature* 324:163); Saiki et al., (1989) *Proc. Natl. Acad. Sci. USA* 86:6230).

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al., (1989) *Nucleic Acids Res.* 17:2437–2448) or at the extreme 3' end of one primer where, under appropriate conditions, mismatch can prevent, or reduce polymerase extension (Prossner, (1993) *Tibtech* 11:238). In addition it may be desirable to introduce a novel restriction site in the region of the mutation to create cleavage-based detection (Gasparini et al., (1992) *Mol. Cell Probes* 6:1). It is anticipated that in certain embodiments amplification may also be performed using Taq ligase for amplification (Barany, (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an 80090, 52874, 52880, 63497, or 33425 gene.

Use of 80090, 52874, 52880, 63497, or 33425 Molecules as Surrogate Markers

The 80090, 52874, 52880, 63497, or 33425 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 80090, 52874, 52880, 63497, or 33425 molecules of the invention may be detected, and may be correlated with one or more biological states in vivo. For example, the 80090, 52874, 52880, 63497, or 33425 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258–264; and James (1994) *AIDS Treatment News Archive* 209.

The 80090, 52874, 52880, 63497, or 33425 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., an 80090, 52874, 52880, 63497, or 33425 marker) transcription or expression, the amplified marker may be in a quantity which is more readily detectable than the drug itself. Also, the marker may be more easily detected due to the nature of the marker itself; for example, using the methods described herein, anti-80090, 52874, 52880, 63497, or 33425 antibodies may be employed in an immune-based detection system for an 80090, 52874, 52880, 63497, or 33425 protein marker, or 80090, 52874, 52880, 63497, or 33425-specific radiolabeled probes may be used to detect an 80090, 52874, 52880, 63497, or 33425 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229–238; Schentag (1999) *Am. J. Health-Syst. Pharm.* 56 Suppl. 3: S21–S24; and Nicolau (1999) *Am, J. Health-Syst. Pharm.* 56 Suppl. 3: S16–S20.

The 80090, 52874, 52880, 63497, or 33425 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35(12): 1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 80090, 52874, 52880, 63497, or 33425 protein or RNA) for specific tumor markers in a subject, a drug or course of treatment may be selected that is optimized for the treatment of the specific tumor likely to be present in the subject. Similarly, the presence or absence of a specific sequence mutation in 80090, 52874, 52880, 63497, or 33425 DNA may correlate 80090, 52874, 52880, 63497, or 33425 drug response. The use of pharmacogenomic markers therefore permits the application of the most appropriate treatment for each subject without having to administer the therapy.

Pharmaceutical Compositions

The nucleic acid and polypeptides, fragments thereof, as well as anti-80090, 52874, 52880, 63497, or 33425 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al., ((1997) *J. Acquired Immune Deficiency Syndromes and Human Retrovirology* 14:193).

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, .alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al., (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

The present invention provides for both prophylactic and therapeutic methods of treating a subject at risk of (or susceptible to) a disorder or having a disorder associated with aberrant or unwanted 80090, 52874, 52880, 63497, or 33425 expression or activity. With regards to both prophylactic and therapeutic methods of treatment, such treatments may be specifically tailored or modified, based on knowledge obtained from the field of pharmacogenomics. "Treatment", as used herein, is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 80090, 52874, 52880, 63497, or 33425 molecules of the present invention or 80090, 52874, 52880, 63497, or 33425 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 80090, 52874, 52880, 63497, or 33425 expression or activity, by administering to the subject an 80090, 52874, 52880, 63497, or 33425 or an agent which modulates 80090, 52874, 52880, 63497, or 33425 expression or at least one 80090, 52874, 52880, 63497, or 33425 activity. Subjects at risk for a disease which is caused or contributed to by aberrant or unwanted 80090, 52874, 52880, 63497, or 33425 expression or activity can be identified by, for example, any or a combination of diagnostic or prognostic assays as described herein. Administration of a prophylactic agent can occur prior to the manifestation of symptoms characteristic of the 80090, 52874, 52880, 63497, or 33425 aberrance, such that a disease or disorder is prevented or, alternatively, delayed in its progression. Depending on the type of 80090, 52874, 52880, 63497, or 33425 aberrance, for example, an 80090, 52874, 52880, 63497, or 33425, 80090, 52874, 52880, 63497, or 33425 agonist or 80090, 52874, 52880, 63497, or 33425 antagonist agent can be used for treating the subject. The appropriate agent can be determined based on screening assays described herein.

It is possible that some 80090, 52874, 52880, 63497, or 33425 disorders can be caused, at least in part, by an abnormal level of gene product, or by the presence of a gene product exhibiting abnormal activity. As such, the reduction in the level and/or activity of such gene products would bring about the amelioration of disorder symptoms.

As discussed, successful treatment of 80090, 52874, 52880, 63497, or 33425 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 80090, 52874, 52880, 63497, or 33425 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and FAb, F(ab')$_2$ and FAb expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by 80090, 52874, 52880, 63497, or 33425 expression is through the use of aptamer molecules specific for 80090, 52874, 52880, 63497, or 33425 protein. Aptamers are nucleic acid molecules having a tertiary structure which permits them to specifically bind to protein ligands (see, e.g., Osborne, et al., Curr. Opin. Chem. Biol. 1997, 1(1): 5–9; and Patel, D. J., Curr. Opin. Chem. Biol. 1997 June;1(1):32–46). Since nucleic acid molecules may in many cases be more conveniently introduced into target cells than therapeutic protein molecules may be, aptamers may offer a method by which 80090, 52874, 52880, 63497, or 33425 protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of 80090, 52874, 52880, 63497, or 33425 disorders. For a description of antibodies, see the Antibody section above.

In circumstances wherein injection of an animal or a human subject with an 80090, 52874, 52880, 63497, or 33425 protein or epitope for stimulating antibody production is harmful to the subject, it is possible to generate an immune response against 80090, 52874, 52880, 63497, or 33425 through the use of anti-idiotypic antibodies (see, for example, Herlyn, D., Ann. Med. 1999;31(1):66–78; and Bhattacharya-Chatterjee, M., and Foon, K. A., Cancer Treat. Res. 1998;94:51–68). If an anti-idiotypic antibody is introduced into a mammal or human subject, it should stimulate the production of anti-anti-idiotypic antibodies, which should be specific to the 80090, 52874, 52880, 63497, or 33425 protein. Vaccines directed to a disease characterized by 80090, 52874, 52880, 63497, or 33425 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al., (1993, Proc. Natl. Acad. Sci. USA 90:7889–7893).

The identified compounds that inhibit target gene expression, synthesis and/or activity can be administered to a patient at therapeutically effective doses to prevent, treat or ameliorate 80090, 52874, 52880, 63497, or 33425 disorders. A therapeutically effective dose refers to that amount of the compound sufficient to result in amelioration of symptoms of the disorders.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC$_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate 80090, 52874, 52880, 63497, or 33425 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell, R. J. et al., (1996) *Current Opinion in Biotechnology* 7:89–94 and in Shea, K. J., (1994) *Trends in Polymer Science* 2:166–173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al., (1993) *Nature* 361:645–647. Through the use of isotope-labeling, the "free" concentration of compound which modulates the expression or activity of 80090, 52874, 52880, 63497, or 33425 can be readily monitored and used in calculations of IC$_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual IC$_{50}$. A rudimentary example of such a "biosensor" is discussed in Kriz, D. et al., (1995) *Analytical Chemistry* 67:2142–2144.

Another aspect of the invention pertains to methods of modulating 80090, 52874, 52880, 63497, or 33425 expression or activity for therapeutic purposes. Accordingly, in an exemplary embodiment, the modulatory method of the invention involves contacting a cell with an 80090, 52874, 52880, 63497, or 33425 or agent that modulates one or more of the activities of 80090, 52874, 52880, 63497, or 33425 protein activity associated with the cell. An agent that modulates 80090, 52874, 52880, 63497, or 33425 protein activity can be an agent as described herein, such as a nucleic acid or a protein, a naturally-occurring target molecule of an 80090, 52874, 52880, 63497, or 33425 protein (e.g., an 80090, 52874, 52880, 63497, or 33425 substrate or receptor), an 80090, 52874, 52880, 63497, or 33425 antibody, an 80090, 52874, 52880, 63497, or 33425 agonist or antagonist, a peptidomimetic of an 80090, 52874, 52880, 63497, or 33425 agonist or antagonist, or other small molecule.

In one embodiment, the agent stimulates one or more 80090, 52874, 52880, 63497, or 33425 activities. Examples of such stimulatory agents include active 80090, 52874, 52880, 63497, or 33425 protein and a nucleic acid molecule encoding 80090, 52874, 52880, 63497, or 33425. In another embodiment, the agent inhibits one or more 80090, 52874, 52880, 63497, or 33425 activities. Examples of such inhibitory agents include antisense 80090, 52874, 52880, 63497, or 33425 nucleic acid molecules, anti-80090, 52874, 52880, 63497, or 33425 antibodies, and 80090, 52874, 52880, 63497, or 33425 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of an 80090, 52874, 52880, 63497, or 33425 protein or nucleic acid molecule. In one embodiment, the method involves administering an agent (e.g., an agent identified by a screening assay described herein), or combination of agents that modulates (e.g., upregulates or downregulates) 80090, 52874, 52880, 63497, or 33425 expression or activity. In another embodiment, the method involves administering an 80090, 52874, 52880, 63497, or 33425 protein or nucleic acid molecule as therapy to compensate for reduced, aberrant, or unwanted 80090, 52874, 52880, 63497, or 33425 expression or activity.

Stimulation of 80090, 52874, 52880, 63497, or 33425 activity is desirable in situations in which 80090, 52874, 52880, 63497, or 33425 is abnormally downregulated and/or in which increased 80090, 52874, 52880, 63497, or 33425 activity is likely to have a beneficial effect. For example, stimulation of 80090, 52874, 52880, 63497, or 33425 activity is desirable in situations in which an 80090, 52874, 52880, 63497, or 33425 is downregulated and/or in which increased 80090, 52874, 52880, 63497, or 33425 activity is likely to have a beneficial effect. Likewise, inhibition of 80090, 52874, 52880, 63497, or 33425 activity is desirable in situations in which 80090, 52874, 52880, 63497, or 33425 is abnormally upregulated and/or in which decreased 80090, 52874, 52880, 63497, or 33425 activity is likely to have a beneficial effect.

The 80090, 52874, 52880, 63497, or 33425 molecules can act as novel diagnostic targets and therapeutic agents for controlling one or more of cellular proliferative and/or differentiative disorders, heart disorders, cardiovascular disorders, including endothelial cell disorders, hematopoietic disorders, blood vessel disorders, brain disorders, pain and metabolic disorders, liver disorders and platelet disorders, as described above, as well as disorders associated with bone metabolism or viral diseases.

Aberrant expression and/or activity of 80090, 52874, 52880, 63497, or 33425 molecules may mediate disorders associated with bone metabolism. "Bone metabolism" refers to direct or indirect effects in the formation or degeneration of bone structures, e.g., bone formation, bone resorption, etc., which may ultimately affect the concentrations in serum of calcium and phosphate. This term also includes activities mediated by 80090, 52874, 52880, 63497, or 33425 molecules effects in bone cells, e.g. osteoclasts and osteoblasts, that may in turn result in bone formation and degeneration. For example, 80090, 52874, 52880, 63497, or 33425 molecules may support different activities of bone resorbing osteoclasts such as the stimulation of differentiation of monocytes and mononuclear phagocytes into osteoclasts. Accordingly, 80090, 52874, 52880, 63497, or 33425 molecules that modulate the production of bone cells can influence bone formation and degeneration, and thus may be used to treat bone disorders. Examples of such disorders include, but are not limited to, osteoporosis, osteodystrophy, osteomalacia, rickets, osteitis fibrosa cystica, renal osteodystrophy, osteosclerosis, anti-convulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

Additionally, 80090, 52874, 52880, 63497, or 33425 molecules may play an important role in the etiology of certain viral diseases, including but not limited to, Hepatitis B, Hepatitis C and Herpes Simplex Virus (HSV). Modulators of 80090, 52874, 52880, 63497, or 33425 activity could be used to control viral diseases. The modulators can be used in the treatment and/or diagnosis of viral infected tissue or virus-associated tissue fibrosis, especially liver and liver fibrosis. Also, 80090, 52874, 52880, 63497, or 33425 modulators can be used in the treatment and/or diagnosis of virus-associated carcinoma, especially hepatocellular cancer.

Pharmacogenomics

The 80090, 52874, 52880, 63497, or 33425 molecules of the present invention, as well as agents, or modulators which have a stimulatory or inhibitory effect on 80090, 52874, 52880, 63497, or 33425 activity (e.g., 80090, 52874, 52880, 63497, or 33425 gene expression) as identified by a screening assay described herein can be administered to individuals to treat (prophylactically or therapeutically) 80090, 52874, 52880, 63497, or 33425 associated disorders (e.g., cellular growth related disorders) associated with aberrant or unwanted 80090, 52874, 52880, 63497, or 33425 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer an 80090, 52874, 52880, 63497, or 33425 molecule or 80090, 52874, 52880, 63497, or 33425 modulator as well as tailoring the dosage and/or therapeutic regimen of treatment with an 80090, 52874, 52880, 63497, or 33425 molecule or 80090, 52874, 52880, 63497, or 33425 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11):983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high-resolution map can be generated from a combination of some ten million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., an 80090, 52874, 52880, 63497, or 33425 protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., an 80090, 52874, 52880, 63497, or 33425 molecule or 80090, 52874, 52880, 63497, or 33425 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with an 80090, 52874, 52880, 63497, or 33425 molecule or 80090, 52874, 52880, 63497, or 33425 modulator, such as a modulator identified by one of the exemplary screening assays described herein.

The present invention further provides methods for identifying new agents, or combinations, that are based on identifying agents that modulate the activity of one or more of the gene products encoded by one or more of the 80090, 52874, 52880, 63497, or 33425 genes of the present invention, wherein these products may be associated with resistance of the cells to a therapeutic agent. Specifically, the activity of the proteins encoded by the 80090, 52874, 52880, 63497, or 33425 genes of the present invention can be used as a basis for identifying agents for overcoming agent resistance. By blocking the activity of one or more of the resistance proteins, target cells, e.g., cancer cells, will become sensitive to treatment with an agent that the unmodified target cells were resistant to.

Monitoring the influence of agents (e.g., drugs) on the expression or activity of an 80090, 52874, 52880, 63497, or 33425 protein can be applied in clinical trials. For example, the effectiveness of an agent determined by a screening assay as described herein to increase 80090, 52874, 52880, 63497, or 33425 gene expression, protein levels, or upregulate 80090, 52874, 52880, 63497, or 33425 activity, can be monitored in clinical trials of subjects exhibiting decreased 80090, 52874, 52880, 63497, or 33425 gene expression, protein levels, or downregulated 80090, 52874, 52880, 63497, or 33425 activity. Alternatively, the effectiveness of an agent determined by a screening assay to decrease 80090, 52874, 52880, 63497, or 33425 gene expression, protein levels, or downregulate 80090, 52874, 52880, 63497, or 33425 activity, can be monitored in clinical trials of subjects exhibiting increased 80090, 52874, 52880, 63497, or 33425 gene expression, protein levels, or upregulated 80090, 52874, 52880, 63497, or 33425 activity. In such clinical trials, the expression or activity of an 80090, 52874, 52880, 63497, or 33425 gene, and preferably, other genes that have been implicated in, for example, an 80090, 52874, 52880, 63497, or 33425-associated disorder can be used as a "read out" or markers of the phenotype of a particular cell.

Other Embodiments

In another aspect, the invention features, a method of analyzing a plurality of capture probes. The method can be used, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence; contacting the array with an 80090, 52874, 52880, 63497, or 33425, preferably purified, nucleic acid, preferably purified, polypeptide, preferably purified, or antibody, and thereby evaluating the plurality of capture probes. Binding, e.g., in the case of a nucleic acid, hybridization with a capture probe at an address of the plurality, is detected, e.g., by signal generated from a label attached to the 80090, 52874, 52880, 63497, or 33425 nucleic acid, polypeptide, or antibody.

The capture probes can be a set of nucleic acids from a selected sample, e.g., a sample of nucleic acids derived from a control or non-stimulated tissue or cell.

The method can include contacting the 80090, 52874, 52880, 63497, or 33425 nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of 80090, 52874, 52880, 63497, or 33425. Such methods can be used to diagnose a subject, e.g., to evaluate risk for a disease or disorder, to evaluate suitability of a selected treatment for a subject, to evaluate whether a subject has a disease or disorder. 80090, 52874, 52880, 63497, or 33425 is associated with fucosyltransferase, 7TM receptor, or RhoGAP activity, thus it is useful for disorders associated with abnormal fucosyltransferase, 7TM receptor, or RhoGAP activity.

The method can be used to detect SNPs, as described above.

In another aspect, the invention features, a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express or mis express 80090, 52874, 52880, 63497, or 33425 or from a cell or subject in which an 80090, 52874, 52880, 63497, or 33425 mediated response has been elicited, e.g., by contact of the cell with 80090, 52874, 52880, 63497, or 33425 nucleic acid or protein, or administration to the cell or subject 80090, 52874, 52880, 63497, or 33425 nucleic acid or protein; contacting the array with one or more inquiry probe, wherein an inquiry probe can be a nucleic acid, polypeptide, or antibody (which is preferably other than 80090, 52874, 52880, 63497, or 33425 nucleic acid, polypeptide, or antibody); providing a two dimensional array having a plurality of addresses, each address of the plurality being positionally distinguishable from each other address of the plurality, and each address of the plurality having a unique capture probe, e.g., wherein the capture probes are from a cell or subject which does not express 80090, 52874, 52880, 63497, or 33425 (or does not express as highly as in the case of the 80090, 52874, 52880, 63497, or 33425 positive plurality of capture probes) or from a cell or subject which in which an 80090, 52874, 52880, 63497, or 33425 mediated response has not been elicited (or has been elicited to a lesser extent than in the first sample); contacting the array with one or more inquiry probes (which is preferably other than an 80090, 52874, 52880, 63497, or 33425 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features, a method of analyzing 80090, 52874, 52880, 63497, or 33425, e.g., analyzing structure, function, or relatedness to other nucleic acid or amino acid sequences. The method includes: providing an 80090, 52874, 52880, 63497, or 33425 nucleic acid or amino acid sequence; comparing the 80090, 52874, 52880, 63497, or 33425 sequence with one or more preferably a plurality of sequences from a collection of sequences, e.g., a nucleic acid or protein sequence database; to thereby analyze 80090, 52874, 52880, 63497, or 33425.

Preferred databases include GenBank™. The method can include evaluating the sequence identity between an 80090, 52874, 52880, 63497, or 33425 sequence and a database sequence. The method can be performed by accessing the database at a second site, e.g., over the internet.

In another aspect, the invention features, a set of oligonucleotides, useful, e.g., for identifying SNP's, or identifying specific alleles of 80090, 52874, 52880, 63497, or 33425. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with different labels, such that an oligonucleotides which hybridizes to one allele provides a signal that is distinguishable from an oligonucleotides which hybridizes to a second allele.

This invention is further illustrated by the following examples which should not be construed as limiting. The contents of all references, patents and published patent applications cited throughout this application are incorporated herein by reference.

EXAMPLES

Example 1

Identification and Characterization of Human 80090, 52874, 52880, 63497, or 33425 cDNAs The human 80090 sequence (FIG. 1; SEQ ID NO:1), which is approximately 1669 nucleotides long including untranslated regions, contains a predicted methionine-initiated coding sequence of about 1461 nucleotides (nucleotides 163–1623 of SEQ ID NO:1; SEQ ID NO:3), including the terminal codon. The coding sequence encodes a 486 amino acid protein (SEQ ID NO:2).

The human 52874 sequence (FIGS. 7A–B; SEQ ID NO:4), which is approximately 1420 nucleotides long including untranslated regions, contains a predicted methionine-initiated coding sequence of about 1386 nucleotides (nucleotides 32–1417 of SEQ ID NO:4; SEQ ID NO:6), including the terminal codon. The coding sequence encodes a 461 amino acid protein (SEQ ID NO:5).

The human 52880 sequence (FIG. 13; SEQ ID NO:7), which is approximately 1352 nucleotides long including untranslated regions, contains a predicted methionine-initiated coding sequence of about 1092 nucleotides (nucleotides 210–1301 of SEQ ID NO:7; SEQ ID NO:9), including the terminal codon. The coding sequence encodes a 363 amino acid protein (SEQ ID NO:8).

The human 63497 sequence (FIG. 20; SEQ ID NO:10), which is approximately 1178 nucleotides long including untranslated regions, contains a predicted methionine-initiated coding sequence of about 906 nucleotides (nucleotides 152–1057 of SEQ ID NO:10; SEQ ID NO:12), including the terminal codon. The coding sequence encodes a 301 amino acid protein (SEQ ID NO:11).

The human 33425 sequence (FIGS. 24A–C; SEQ ID NO:13), which is approximately 3492 nucleotides long including untranslated regions, contains a predicted methionine-initiated coding sequence of about 1992 nucleotides (nucleotides 73–2764 of SEQ ID NO:13; SEQ ID NO:15), including the terminal codon. The coding sequence encodes a 663 amino acid protein (SEQ ID NO:14).

Example 2

Tissue Distribution of 80090, 52874, 52880, 63497, or 33425 mRNA

Northern blot hybridizations with various RNA samples can be performed under standard conditions and washed under stringent conditions, i.e., 0.2×SSC at 65° C. A DNA probe corresponding to all or a portion of the 80090, 52874, 52880, 63497, or 33425 cDNA (SEQ ID NO:1) or 80090, 52874, 52880, 63497, or 33425 cDNA (SEQ ID NO:4) can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 3

Gene Expression Analysis

Total RNA was prepared from various human tissues by a single step extraction method using RNA STAT-60 according to the manufacturer's instructions (TelTest, Inc). Each RNA preparation was treated with DNase I (Ambion) at 37° C. for 1 hour. DNAse I treatment was determined to be complete if the sample required at least 38 PCR amplification cycles to reach a threshold level of fluorescence using β-2 microglobulin as an internal amplicon reference. The integrity of the RNA samples following DNase I treatment was confirmed by agarose gel electrophoresis and ethidium bromide staining. After phenol extraction cDNA was prepared from the sample using the SUPERSCRIPT™ Choice System following the manufacturer's instructions (GibcoBRL). A negative control of RNA without reverse transcriptase was mock reverse transcribed for each RNA sample.

Human 52880 or 33425 expression was measured by TaqMan® quantitative PCR (Perkin Elmer Applied Biosystems) in cDNA prepared from a variety of normal and diseased (e.g., cancerous) human tissues or cell lines.

Probes were designed by PrimerExpress software (PE Biosystems) based on the sequence of the human 52880 or 33425 gene. Each human 52880 or 33425 gene probe was labeled using FAM (6-carboxyfluorescein), and the β2-microglobulin reference probe was labeled with a different fluorescent dye, VIC. The differential labeling of the target gene and internal reference gene thus enabled measurement in same well. Forward and reverse primers and the probes for both β2-microglobulin and target gene were added to the TaqMan® Universal PCR Master Mix (PE Applied Biosystems). Although the final concentration of primer and probe could vary, each was internally consistent within a given experiment. A typical experiment contained 200 nM of forward and reverse primers plus 100 nM probe for β-2 microglobulin and 600 nM forward and reverse primers plus 200 nM probe for the target gene. TaqMan matrix experiments were carried out on an ABI PRISM 7700 Sequence Detection System (PE Applied Biosystems). The thermal cycler conditions were as follows: hold for 2 min at 50° C. and 10 min at 95° C., followed by two-step PCR for 40 cycles of 95° C. for 15 sec followed by 60° C. for 1 min.

The following method was used to quantitatively calculate human 52880 or 33425 gene expression in the various tissues relative to β-2 microglobulin expression in the same tissue. The threshold cycle (Ct) value is defined as the cycle at which a statistically significant increase in fluorescence is detected. A lower Ct value is indicative of a higher mRNA concentration. The Ct value of the human 52880 or 33425 gene is normalized by subtracting the Ct value of the β-2 microglobulin gene to obtain a ΔCt value using the following formula: $\Delta Ct = Ct_{human\ 59914\ and\ 59921} - Ct_{\beta\text{-}2\ microglobulin}$. Expression is then calibrated against a cDNA sample showing a comparatively low level of expression of the human 52880 or 33425 gene. The ΔCt value for the calibrator sample is then subtracted from ΔCt for each tissue sample according to the following formula: $\Delta\Delta Ct = \Delta Ct_{sample} - \Delta Ct_{calibrator}$. Relative expression is then calculated using the arithmetic formula given by 2–ΔΔCt. Expression of the target human 52880 or 33425 gene in each of the tissues tested is then graphically represented as discussed in more detail below.

TaqMan real-time quantitative RT-PCR is used to detect the presence of RNA transcript corresponding to human 52880 relative to a no template control in a panel of human tissues or cells. Table 1 indicates expression levels below detectable level compared to controls for a panel of different cell and tissue types.

TABLE 1

| Tissue Type | Mean | β 2 Mean | ∂∂ Ct | Expression |
|---|---|---|---|---|
| Artery normal | 40 | 21.15 | 18.85 | 0 |
| Aorta diseased | 40 | 23.27 | 16.73 | 0 |
| Vein normal | 40 | 20.57 | 19.43 | 0 |
| Coronary SMC | 40 | 21.22 | 18.78 | 0 |
| HUVEC | 39.83 | 21.25 | 18.57 | 0 |
| Hemangioma | 40 | 20.09 | 19.91 | 0 |
| Heart normal | 40 | 20.66 | 19.34 | 0 |
| Heart CHF | 40 | 21.48 | 18.52 | 0 |
| Kidney | 39.77 | 21.2 | 18.57 | 0 |
| Skeletal Muscle | 40 | 22.64 | 17.36 | 0 |
| Liver normal | 40 | 20.28 | 19.72 | 0 |
| Small intestine normal | 40 | 20.97 | 19.03 | 0 |
| Adipose normal | 40 | 20.07 | 19.93 | 0 |
| Pancreas | 40 | 22.66 | 17.34 | 0 |
| primary osteoblasts | 38.4 | 20.17 | 18.23 | 0 |
| Bladder-Female normal | 36.76 | 20.31 | 16.45 | 0 |
| Adrenal Gland normal | 40 | 19.86 | 20.14 | 0 |
| Pituitary Gland normal | 40 | 20.55 | 19.45 | 0 |
| Spinal cord normal | 39.77 | 21.54 | 18.24 | 0 |
| Brain Cortex normal | 36.58 | 23.23 | 13.35 | 0 |
| Brain Hypothalamus normal | 36.59 | 21.57 | 15.03 | 0 |
| Nerve | 40 | 21.19 | 18.81 | 0 |
| DRG (Dorsal Root Ganglion) | 39.33 | 21.66 | 17.68 | 0 |
| Breast normal | 40 | 21.35 | 18.65 | 0 |
| Breast tumor/IDC | 40 | 20.17 | 19.83 | 0 |
| Ovary normal | 40 | 20.59 | 19.41 | 0 |
| Ovary Tumor | 37.01 | 20.23 | 16.78 | 0 |
| Prostate BPH | 40 | 20.22 | 19.79 | 0 |
| Prostate Adenocarcinoma | 39.56 | 21 | 18.57 | 0 |
| Colon normal | 40 | 19.77 | 20.23 | 0 |
| Colon Adenocarcinoma | 38.85 | 22.23 | 16.63 | 0 |
| Lung normal | 39.87 | 18.84 | 21.02 | 0 |
| Lung tumor | 39.43 | 21.26 | 18.17 | 0 |
| Lung COPD | 40 | 19.25 | 20.75 | 0 |
| Colon IBD | 40 | 20.93 | 19.07 | 0 |
| Synovium | 39.99 | 19.73 | 20.25 | 0 |
| Tonsil normal | 35.88 | 19.07 | 16.81 | 0 |
| Lymph node normal | 40 | 20.64 | 19.36 | 0 |
| Liver fibrosis | 40 | 21.31 | 18.7 | 0 |
| Spleen normal | 39.92 | 19.15 | 20.77 | 0 |
| Macrophages | 40 | 17.35 | 22.65 | 0 |
| Progenitors (erythroid, megakaryocyte, neutrophil) | 40 | 20.25 | 19.75 | 0 |
| Megakaryocytes | 40 | 19.8 | 20.2 | 0 |
| Activated PBMC | 40 | 17.39 | 22.61 | 0 |
| Neutrophils | 39.86 | 19.04 | 20.82 | 0 |
| Erytbroid | 40 | 21.93 | 18.07 | 0 |
| positive control | 28.41 | 22.07 | 6.33 | 12.4303 |

TaqMan real-time quantitative RT-PCR is used to detect the presence of RNA transcript corresponding to human 52880 relative to a no template control in a panel of human tissues or cells. Table 2 indicates expression of 52880 in normal brain cortex and tonsil.

TABLE 2

| Tissue Type | Mean | β 2 Mean | ∂∂ Ct | Expression |
|---|---|---|---|---|
| Artery normal | 37.73 | 22.72 | 16.27 | 0 |
| Aorta diseased | 39.38 | 22.14 | 18.5 | 0 |
| Vein normal | 38.69 | 20.4 | 19.55 | 0 |
| Coronary SMC | 39.26 | 23.09 | 17.43 | 0 |
| HUVEC | 37.8 | 21.3 | 17.75 | 0 |
| Hemangioma | 39.45 | 19.73 | 20.97 | 0 |
| Heart normal | 39.46 | 20.44 | 20.27 | 0 |
| Heart CHF | 38 | 19.59 | 19.66 | 0 |
| Kidney | 37.3 | 20.07 | 18.48 | 0 |
| Skeletal Muscle | 38.66 | 22.11 | 17.82 | 0 |
| Adipose normal | 39.55 | 20.5 | 20.3 | 0 |
| Pancreas | 40 | 21.61 | 19.64 | 0 |
| primary osteoblasts | 38.23 | 20.54 | 18.95 | 0 |
| Osteoclasts (diff) | 39.09 | 17.46 | 22.88 | 0 |

TABLE 2-continued

| Tissue Type | Mean | β 2 Mean | ∂∂ Ct | Expression |
|---|---|---|---|---|
| Skin normal | 40 | 22.19 | 19.07 | 0 |
| Spinal cord normal | 37.22 | 20.9 | 17.57 | 0 |
| Brain Cortex normal | 34.04 | 22.47 | 12.82 | 0.1378 |
| Brain Hypothalamus normal | 38.31 | 22.07 | 17.49 | 0 |
| Nerve | 40 | 21.8 | 19.46 | 0 |
| DRG (Dorsal Root Ganglion) | 38.31 | 21.77 | 17.8 | 0 |
| Breast normal | 39.84 | 20.65 | 20.45 | 0 |
| Breast tumor | 39.05 | 20.89 | 19.41 | 0 |
| Ovary normal | 39.4 | 20.11 | 20.55 | 0 |
| Ovary Tumor | 36.2 | 20.36 | 17.11 | 0 |
| Prostate Normal | 39.52 | 19.85 | 20.93 | 0 |
| Prostate Tumor | 38.74 | 20.06 | 19.95 | 0 |
| Salivary glands | 37.49 | 19.66 | 19.09 | 0 |
| Colon normal | 40 | 18.37 | 22.89 | 0 |
| Colon Tumor | 37.08 | 19.05 | 19.29 | 0 |
| Lung normal | 39.26 | 17.97 | 22.55 | 0 |
| Lung tumor | 37.87 | 20.16 | 18.96 | 0 |
| Lung COPD | 39.38 | 18.32 | 22.31 | 0 |
| Colon IBD | 39.42 | 17.8 | 22.88 | 0 |
| Liver normal | 38.09 | 20.07 | 19.27 | 0 |
| Liver fibrosis | 37.48 | 21.73 | 17.02 | 0 |
| Spleen normal | 39.77 | 21.32 | 19.7 | 0 |
| Tonsil normal | 34.3 | 17.27 | 18.28 | 0.0031 |
| Lymph node normal | 38.19 | 18.9 | 20.55 | 0 |
| Small intestine normal | 40 | 20.15 | 21.11 | 0 |
| Skin-Decubitus | 39.07 | 20.78 | 19.55 | 0 |
| Synovium | 38.92 | 19.75 | 20.43 | 0 |
| BM-MNC | 39.28 | 18.69 | 21.85 | 0 |
| Activated PBMC | 39.55 | 17.7 | 23.09 | 0 |
| Neutrophils | 39.36 | 19.03 | 21.59 | 0 |
| Megakaryocytes | 38.58 | 18.57 | 21.26 | 0 |
| Erythroid | 37.78 | 21.5 | 17.55 | 0 |

TaqMan real-time quantitative RT-PCR is used to detect the presence of RNA transcript corresponding to human 52880 relative to a no template control in a panel of human tissues or cells. Table 3 indicates highest 52880 expression in placenta and brain.

TABLE 3

| Tissue | 52880 Mean | β2M803 Mean | ∂ Ct | Expression |
|---|---|---|---|---|
| Adrenal Gland | 39.11 | 19.38 | 19.73 | 0.001 |
| Brain | 32.72 | 20.21 | 12.51 | 0.107 |
| Heart | 36.30 | 18.45 | 17.85 | 0.003 |
| Kidney | 39.76 | 18.31 | 21.45 | 0.000 |
| Liver | 38.73 | 19.33 | 19.40 | 0.001 |
| Lung | 39.16 | 16.23 | 22.94 | 0.000 |
| Mammary Gland | 40.00 | 17.73 | 22.27 | 0.000 |
| Pancreas | 39.80 | 21.89 | 17.92 | 0.003 |
| Placenta | 27.02 | 18.50 | 8.52 | 0.2 |
| Prostate | 37.12 | 17.91 | 19.22 | 0.001 |
| Salivary Gland | 38.28 | 18.31 | 19.97 | 0.001 |
| Muscle | 40.00 | 20.45 | 19.56 | 0.001 |
| Sm. Intestine | 38.13 | 18.46 | 19.67 | 0.001 |
| Spleen | 39.30 | 15.63 | 23.67 | 0.000 |
| Stomach | 39.11 | 17.32 | 21.79 | 0.000 |
| Teste | 37.59 | 19.18 | 18.42 | 0.002 |
| Thymus | 36.79 | 16.85 | 19.94 | 0.001 |
| Trachea | 39.89 | 18.54 | 21.35 | 0.000 |
| Uterus | 39.37 | 18.42 | 20.95 | 0.000 |
| Spinal Cord | 39.57 | 18.69 | 20.88 | 0.000 |
| Skin | 35.98 | 16.95 | 19.03 | 0.001 |
| DRG | 39.45 | 18.48 | 20.97 | 0.000 |

TaqMan real-time quantitative RT-PCR is used to detect the presence of RNA transcript corresponding to human 33425 relative to a no template control in a panel of human tissues or cells. Table 4 indicates the highest level of 33425 expression is seen in human umbilical vein endothelial cells (HUVEC), with relatively high expression in megakaryocytes, pancreas, kidney and erythroid cells. Table 4 also shows that there is upregulated expression of 33425 in diseased aorta, prostate tumor, and colon tumor, as compared to normal aorta, prostate, and colon tissue. Also, there is downregulated expression of 33425 in heart with congestive heart failure, and ovary tumor, as compared to normal heart and ovary tissue.

TABLE 4

| Tissue Type | Mean | β 2 Mean | ∂∂ Ct | Expression |
|---|---|---|---|---|
| Artery normal | 29.5 | 24.48 | 3.88 | 67.92 |
| Aorta diseased | 28.06 | 24.78 | 2.13 | 227.67 |
| Vein normal | 30.23 | 22.65 | 6.44 | 11.52 |
| Coronary SMC | 26.59 | 23.21 | 2.25 | 210.95 |
| HUVEC | 23.86 | 23.64 | −0.93 | 1898.68 |
| Hemangioma | 25.75 | 22.2 | 2.42 | 187.50 |
| Heart normal | 27.18 | 23.25 | 2.79 | 144.09 |
| Heart CHF | 29.75 | 23.23 | 5.38 | 24.01 |
| Kidney | 24.61 | 22.61 | 0.86 | 550.95 |
| Skeletal Muscle | 27.41 | 24.36 | 1.92 | 264.25 |
| Adipose normal | 28.8 | 23.11 | 4.54 | 42.84 |
| Pancreas | 25.78 | 24.4 | 0.24 | 846.75 |
| primary osteoblasts | 29.35 | 23.04 | 5.17 | 27.68 |
| Osteoclasts (diff) | 32.1 | 19.87 | 11.09 | 0.46 |
| Skin normal | 30.98 | 24.54 | 5.3 | 25.30 |
| Spinal cord normal | 29.5 | 23.4 | 4.97 | 31.91 |
| Brain Cortex normal | 28.94 | 24.61 | 3.19 | 109.58 |
| Brain Hypothalamus normal | 28.82 | 24.88 | 2.81 | 142.60 |
| Nerve | 29.45 | 24.52 | 3.78 | 72.80 |
| DRG (Dorsal Root Ganglion) | 27.48 | 24.02 | 2.31 | 200.96 |
| Breast normal | 27.97 | 23.34 | 3.48 | 89.62 |
| Breast tumor | 28.57 | 23.13 | 4.3 | 50.59 |
| Ovary normal | 27.79 | 22.38 | 4.26 | 52.01 |
| Ovary Tumor | 29.26 | 21.1 | 7.02 | 7.70 |
| Prostate Normal | 30.82 | 21.91 | 7.76 | 4.60 |
| Prostate Tumor | 27.61 | 22.84 | 3.64 | 80.21 |
| Salivary glands | 30.55 | 21.97 | 7.45 | 5.74 |
| Colon normal | 28.41 | 21.08 | 6.2 | 13.65 |
| Colon Tumor | 26.76 | 23.74 | 1.88 | 271.68 |
| Lung normal | 25.15 | 20.56 | 3.45 | 91.51 |
| Lung tumor | 27.89 | 22.7 | 4.04 | 60.58 |
| Lung COPD | 26.77 | 20.95 | 4.68 | 39.01 |
| Colon TBD | 31.59 | 19.97 | 10.48 | 0.70 |
| Liver normal | 33.76 | 22.31 | 10.31 | 0.79 |
| Liver fibrosis | 29.98 | 23.11 | 5.72 | 18.91 |
| Spleen normal | 30.18 | 20.91 | 8.13 | 3.56 |
| Tonsil normal | 30.18 | 20.89 | 8.15 | 3.52 |
| Lymph node normal | 31.65 | 22.41 | 8.1 | 3.66 |
| Small intestine normal | 29.62 | 22.62 | 5.86 | 17.22 |
| Macrophages | 33.41 | 19.18 | 13.09 | 0.12 |
| Synovium | 27.9 | 22.14 | 4.62 | 40.67 |
| BM-MNC | 31.19 | 21.2 | 8.85 | 2.17 |
| Activated PBMC | 34.27 | 20.25 | 12.88 | 0.13 |
| Neutrophils | 29.81 | 20.34 | 8.32 | 3.12 |
| Megakaryocytes | 22.48 | 21.36 | −0.01 | 1010.45 |
| Erythroid | 25.26 | 23.06 | 1.06 | 479.63 |
| positive control | 24.93 | 22.72 | 1.06 | 477.97 |

TaqMan real-time quantitative RT-PCR is used to detect the presence of RNA transcript corresponding to human 33425 relative to a no template control in a panel of human tissues or cells. Table 5 indicates the highest level of 33425 expression is seen in human umbilical vein endothelial cells (HUVEC), megakaryocytes, pancreas, kidney and erythroid cells. There is also relatively high expression in coronary smooth muscle cell, hemangioma, skeletal muscle cell and dorsal root ganglia. Table 5 also shows that there is upregulated expression of 33425 in diseased aorta, prostate tumor, colon tumor, and fibrotic liver, as compared to normal aorta, prostate, colon and liver tissue. Also, there is downregulated expression of 33425 in heart with congestive heart failure, breast tumor, and ovary tumor, as compared to normal heart, breast, and ovary tissue.

TABLE 5

| Tissue Type | Mean | β 2 Mean | ∂∂ Ct | Expression |
|---|---|---|---|---|
| Artery normal | 29.91 | 21.59 | 8.33 | 3.1076 |
| Aorta diseased | 28.63 | 22.41 | 6.21 | 13.5084 |
| Vein normal | 29.7 | 19.66 | 10.04 | 0.9532 |
| Coronary SMC | 26.9 | 20.43 | 6.46 | 11.3199 |
| HUVEC | 23.01 | 20.45 | 2.56 | 168.9889 |
| Heart normal | 27.02 | 20.56 | 6.46 | 11.3199 |
| Heart CHF | 29.98 | 20.12 | 9.86 | 1.0798 |
| Kidney | 24.82 | 19.87 | 4.95 | 32.4643 |
| Skeletal Muscle | 27.9 | 21.47 | 6.43 | 11.5577 |
| Adipose normal | 28.04 | 19.31 | 8.73 | 2.3551 |
| Pancreas | 25.98 | 21.95 | 4.04 | 61.002 |
| primary osteoblasts | 26.41 | 19.25 | 7.16 | 7.0167 |
| Skin normal | 28.9 | 21.31 | 7.59 | 5.1902 |
| Spinal cord normal | 29.36 | 20.24 | 9.13 | 1.791 |
| Brain Cortex normal | 29.37 | 21.64 | 7.73 | 4.7102 |
| Brain Hypothalamus normal | 30.27 | 22.02 | 8.25 | 3.2848 |
| Nerve | 29.01 | 20.93 | 8.08 | 3.6955 |
| DRG (Dorsal Root Ganglion) | 27.32 | 20.63 | 6.7 | 9.6183 |
| Breast normal | 28 | 20.23 | 7.76 | 4.5973 |
| Breast tumor | 27.95 | 19.94 | 8.01 | 3.8793 |
| Ovary normal | 27.98 | 19.41 | 8.57 | 2.6313 |
| Ovary Tumor | 32.35 | 17.85 | 14.5 | 0.0432 |
| Prostate Normal | 29.14 | 19.15 | 9.99 | 0.9834 |
| Prostate Tumor | 26.79 | 19.63 | 7.17 | 6.9682 |
| Salivary glands | 28.2 | 19.48 | 8.71 | 2.388 |
| Colon normal | 26.31 | 18.6 | 7.71 | 4.7759 |
| Colon Tumor | 26.36 | 21.39 | 4.97 | 31.9066 |
| Lung tumor | 27.34 | 20.11 | 7.24 | 6.6152 |
| Lung COPD | 25.16 | 18.11 | 7.04 | 7.5726 |
| Colon IBD | 30.36 | 17.47 | 12.89 | 0.1317 |
| Liver normal | 32.44 | 19.55 | 12.89 | 0.1322 |
| Liver fibrosis | 30.23 | 20.11 | 10.12 | 0.8986 |
| Spleen normal | 33.47 | 18.09 | 15.38 | 0.0235 |
| Tonsil normal | 28.63 | 18.18 | 10.45 | 0.7149 |
| Lymph node normal | 30 | 19.77 | 10.23 | 0.8327 |
| Small intestine normal | 28.72 | 19.43 | 9.29 | 1.5919 |
| Macrophages | 31.95 | 16.4 | 15.56 | 0.0208 |
| Synovium | 29.61 | 18.07 | 11.54 | 0.337 |
| BM-MNC | 36.78 | 17.76 | 19.02 | 0 |
| Activated PBMC | 32.38 | 17.42 | 14.96 | 0.0315 |
| Neutrophils | 28.95 | 17.18 | 11.77 | 0.2873 |
| Megakaryocytes | 21.45 | 18.04 | 3.42 | 93.7524 |
| Erythroid | 24.81 | 20.07 | 4.75 | 37.2917 |
| positive control | 26.73 | 20.75 | 5.99 | 15.7337 |
| Hemangioma | 27.82 | 19.11 | 8.71 | 2.3797 |
| Osteoclasts (diff) | 30.41 | 17.11 | 13.3 | 0.0995 |
| Lung normal | 25.91 | 17.86 | 8.06 | 3.7471 |

As seen by these results, 33425 molecules have been found to be overexpressed or underexpressed in some tumor or diseased cells. As such, 33425 molecules may serve as specific and novel identifiers of such tumor cells. Further, modulators of the 33425 molecules are useful for the treatment of diseases. Activators of the 33425 molecules are useful for the treatment of cancer, preferably breast or ovarian cancer, or a heart disorder where 33425 is downregulated and useful as a diagnostic. Inhibitors of the 33425 molecules are useful for the treatment of diseases or cancer, where 33425 expression is upregulated, such as blood vessel disorders, colon or prostate cancer, or liver fibrosis and also useful as a diagnostic.

Example 4

Recombinant Expression of 80090, 52874, 52880, 63497, or 33425 in Bacterial Cells In this example, 80090, 52874, 52880, 63497, or 33425 is expressed as a recombinant glutathione-S-transferase (GST) fusion polypeptide in *E. Coli* and the fusion polypeptide is isolated and characterized. Specifically, 80090, 52874, 52880, 63497, or 33425 is fused to GST and this fusion polypeptide is expressed in *E. coli*, e.g., strain PEB199.

Expression of the GST-80090, 52874, 52880, 63497, or 33425 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 5

Expression of Recombinant 80090, 52874, 52880, 63497, or 33425 Protein in COS Cells To express the 80090, 52874, 52880, 63497, or 33425 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 80090, 52874, 52880, 63497, or 33425 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 80090, 52874, 52880, 63497, or 33425 DNA sequence is amplified by PCR using two primers. The 5' primer contains the restriction site of interest followed by approximately twenty nucleotides of the 80090, 52874, 52880, 63497, or 33425 coding sequence starting from the initiation codon; the 3' end sequence contains complementary sequences to the other restriction site of interest, a translation stop codon, the HA tag or FLAG tag and the last 20 nucleotides of the 80090, 52874, 52880, 63497, or 33425 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 80090, 52874, 52880, 63497, or 33425 gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 80090, 52874, 52880, 63497, or 33425-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual.* 2nd, ed., Cold Spring Harbor Laboratory. Cold Spring Harbor Laboratory Press, Cold Spring Harbor, N.Y., 1989. The expression of the 80090, 52874, 52880, 63497, or 33425 polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 80090, 52874, 52880, 63497, or 33425 coding sequence is cloned directly into the polylinker of the pCDNA/Amp vector using the appropriate restriction sites. The resulting plasmid is transfected into COS cells in the manner described above, and the expression of the 80090, 52874, 52880, 63497, or 33425 polypeptide is detected by radiolabelling and immunoprecipitation using an 80090, 52874, 52880, 63497, or 33425 specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule selected from the group consisting of:
   a) a nucleic acid molecule comprising the nucleic acid sequence of SEQ ID NO:1 or SEQ ID NO:3, or a full complement thereof; and
   b) a nucleic acid molecule which encodes a polypeptide comprising the amino acid sequence of SEQ ID NO:2, or a full complement of the nucleic acid.

2. An isolated nucleic acid molecule selected from the group consisting of:
   a) a nucleic acid molecule consisting of the nucleic acid sequence of SEQ ID NO:1 or SEQ ID NO:3, or a full complement thereof; and
   b) a nucleic acid molecule which encodes a polypeptide consisting of the amino acid sequence of SEQ ID NO:2, or a full complement of the nucleic acid.

3. A vector comprising the nucleic acid molecule of claim 1.

4. A vector comprising the nucleic acid molecule of claim 2.

5. The nucleic acid molecule of claim 1, further comprising a nucleic acid sequences encoding a heterologous polypeptide.

6. The nucleic acid molecule of claim 2, further comprising a nucleic acid sequences encoding a heterologous polypeptide.

7. An isolated host cell which contains the nucleic acid molecule of claim 3.

8. The host cell of claim 7 which is a mammalian host cell.

9. An isolated host cell which contains the nucleic acid molecule of claim 4.

10. The host cell of claim 9 which is a mammalian host cell.

11. A method for producing a polypeptide, comprising culturing the host cell of claim 7 under conditions in which the polypeptide encoded by the nucleic acid molecule is expressed.

12. A method for producing a polypeptide, comprising culturing the host cell of claim 9 under conditions in which the polypeptide encoded by the nucleic acid molecule is expressed.

* * * * *